US012091446B1

(12) United States Patent
Harmon et al.

(10) Patent No.: US 12,091,446 B1
(45) Date of Patent: Sep. 17, 2024

(54) SARS-COV-2 VARIANT NANOBODIES AND CONSTRUCTS COMPRISING SUCH NANOBODIES

(71) Applicant: National Technology & Engineering Solutions of Sandia, LLC, Albuquerque, NM (US)

(72) Inventors: Brooke Nicole Harmon, Livermore, CA (US); Le Thanh Mai Pham, Berkeley, CA (US); Peter Riches McIlroy, Livermore, CA (US); Yooli Kim Light, Pleasanton, CA (US)

(73) Assignee: National Technology & Engineering Solutions of Sandia, LLC., Albuquerque, NM (US)

( * ) Notice: Subject to any disclaimer, the term of this patent is extended or adjusted under 35 U.S.C. 154(b) by 0 days.

(21) Appl. No.: 17/849,928

(22) Filed: Jun. 27, 2022

(51) Int. Cl.
*C07K 16/10* (2006.01)

(52) U.S. Cl.
CPC ........ *C07K 16/10* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2022/0089693 A1 * 3/2022 Chen ...................... C07K 16/10

OTHER PUBLICATIONS

Almagro JC, Fransson J. Humanization of antibodies. Front Biosci. Jan. 1, 2008;13:1619-33. (Year: 2008).*

Muyldermans S. Nanobodies: natural single-domain antibodies. Annu Rev Biochem. 2013;82:775-97. doi: 10.1146/annurev-biochem-063011-092449. Epub Mar. 13, 2013. (Year: 2013).*

Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

Kussie et al. A single engineered amino acid substitution changes antibody fine specificity.J Immunol. Jan. 1, 1994;152(1):146-52. (Year: 1994).*

Edwards et al. The remarkable flexibility of the human antibody repertoire;isolation of over one thousand different antibodies to a single protein,BLyS. J Mol Biol Nov. 14, 2003;334(1):103-18. (Year: 2003).*

Stefan, M. A. et al., Development of potent and effective synthetic SARS-CoV-2 neutralizing nanobodies; ISSN: (Print) (Online) Journal homepage: https://www.tandfonline.com/loi/kmab20; Aug. 4, 2021, MABS 13(1):e1958663, 14 pages.

Koenig, P.-A. et al., Structure-guided multivalent nanobodies block SARS-CoV-2 infection and suppress mutational escape; Science 371, 691 (2021) Feb. 12, 2021, 17 pages.

Schoff, M. et al., An ultrapotent synthetic nanobody neutralizes SARS-CoV-2 by stabilizing inactive Spike; Science 370, 1473-1479 (2020) Dec. 18, 2020.

Ziang, Y. et al., Versatile and multivalent nanobodies efficiently neutralize SARS-CoV-2; Science 370, 1479-1484 (2020) Dec. 18, 2020.

* cited by examiner

*Primary Examiner* — Aurora M Fontainhas
*Assistant Examiner* — Jennifer A Benavides
(74) *Attorney, Agent, or Firm* — Escheweiler & Potashnik, LLC.; Samantha Updegraff

(57) ABSTRACT

A large and highly diverse nanobody library was constructed and screened against multiple variants of SARS-COV-2 to find nanobodies with high sensitivity and specificity for the variants. Four rounds of positive selection against a panel of six diverse SARS-COV-2 variant RBDs was performed with our high-diversity. At least 59 of these nanobodies were found to work well against Alpha, Beta, Gamma, Delta, Kappa, Lambda and Mu with some overlap efficacy against other variants. These nanobodies have efficacy as stand-alone nanobodies and as a construct comprising nanobodies linked to the human IgG1 constant fragment (Fc) (nanobody-hFc constructions or nb-hFcs) to make enhanced humanized sdAbs with all the attributes of nanobodies with improved half-life and optimized effector functions. Several promising nanobodies that neutralize the original SARS-COV-2 and several of its variants have been identified, including Delta, with high efficacy. In particular, a subset of these nanobodies bind to the Omicron RBD.

20 Claims, 30 Drawing Sheets

Specification includes a Sequence Listing.

| Nb_Fc or ACE2 | kD (nM) |
|---|---|
| BP2A6 | 0.0766 |
| KP1C9 | 0.1189 |
| AP1C3 | 0.1333 |
| EP2G4 | 0.1827 |
| BP1B1 | 0.2657 |
| BP2A3 | 0.3153 |
| KP1G11 | 0.4913 |
| BP1A10 | 0.5478 |
| AP1B6 | 0.5848 |
| KP1B5 | 0.9396 |
| AP1D4 | 1.0885 |
| AP1A5 | 1.2892 |
| KP2C6 | 4.4574 |
| DP4F2 | 9.5128 |
| huACE2-Fc | 1.3342 |

| Nb_Fc | EC50 (nM) |
|---|---|
| BP2A6 | 0.7657 |
| AP1C3 | 1.0321 |
| AP1C5 | 1.3961 |
| KP1C9 | 2.8940 |
| AP1B6 | 3.3199 |
| BP1B1 | 4.1288 |
| AP1D4 | 6.6497 |
| BP1A10 | 8.3837 |
| AP1A5 | 11.9368 |
| BP3B3 | 12.2737 |
| BP2A3 | 53.6669 |
| KP2C6 | 516.7942 |
| U-huFc | 0.2031 |

| Nb_Fc or ACE2 | kD (nM) |
|---|---|
| EP2G4 | 0.46 |
| KP1G11 | 2.35 |
| BP2A6 | 12.73 |
| BP1B1 | 12.88 |
| KP2C6 | 32.36 |
| AP1A5 | 35.50 |
| BP2A3 | 43.36 |
| BP1A10 | 46.85 |
| AP1D4 | 48.27 |
| DP4F2 | 49.81 |
| huACE2-Fc | 44.44 |

| Nb_Fc | EC50 (nM) |
|---|---|
| AP1B6 | 0.12 |
| BP2A6 | 0.34 |
| BP2H9 | 0.21 |
| BP1B1 | 3.50 |
| BP2A3 | 4.44 |
| BP1A10 | 4.32 |
| BP3B3 | 75.37 |
| AP1A5 | 197.65 |
| KP1C9 | 202.95 |
| KP2A7 | 247.31 |
| KP1G11 | 308.88 |
| AP1C3 | 332.96 |
| KP2C6 | 410.81 |
| U-huFc | 1.62 |

| Nb_Fc or ACE2 | kD (nM) |
|---|---|
| BP1B1 | 0.03 |
| BP2A3 | 0.06 |
| BP2A6 | 0.06 |
| AP1B6 | 0.07 |
| EP2G4 | 0.07 |
| BP2H9 | 0.10 |
| BP1A10 | 0.17 |
| KP1G11 | 0.22 |
| KP1B5 | 0.89 |
| KP2C6 | 9.14 |
| AP1D4 | 20.85 |
| AP1A5 | 35.01 |
| KP1C9 | 61.14 |
| AP1C3 | 66.30 |
| huACE2-Fc | 3.60 |

| Nb_Fc | EC50 (nM) |
|---|---|
| AP1B6 | 0.26 |
| BP2A6 | 0.63 |
| BP2H9 | 0.26 |
| BP1A10 | 3.95 |
| BP1B1 | 3.68 |
| BP2A3 | 3.73 |
| KP1C9 | 60.23 |
| BP3B3 | 176.86 |
| U-huFc | 0.54 |

| Nb_Fc or ACE2 | kD (nM) |
|---|---|
| EP2G4 | 1.90 |
| DP4F2 | 1.91 |
| KP1G11 | 16.66 |
| KP1C9 | 25.48 |
| AP1C3 | 33.28 |
| KP2C6 | 62.64 |
| KP1B5 | 119.19 |
| BP2H9 | 215.31 |
| AP1A5 | N.B |
| AP1B6 | N.B |
| AP1D4 | N.B |
| BP2A3 | N.B |
| BP2A6 | N.B |
| BP1B1 | N.B |
| huACE2-Fc | 23.57 |

| Nb_Fc | EC50 (nM) |
|---|---|
| AP1C3 | 1.04 |
| KP1C9 | 1.22 |
| AP1D4 | 8.24 |
| KP2C6 | 18.34 |
| KP1B4 | 28.06 |
| KP2A7 | 112.50 |
| KP1G11 | 275.25 |
| KP1B5 | 323.91 |
| KP2B10 | 338.46 |
| AP1B6 | 586.11 |
| BP3C5 | 622.66 |
| EP2G4 | 865.96 |
| BP2A6 | 874.54 |
| BP2H9 | 1828.37 |
| U-huFc | 0.22 |

| Nb_Fc or ACE2 | kD (nM) |
|---|---|
| AP1C3 | 0.66 |
| EP2G4 | 1.82 |
| KP1G11 | 4.52 |
| BP2A3 | 17.81 |
| KP1B5 | 33.23 |
| BP2A6 | 74.97 |
| BP1A10 | 234.38 |
| BP1B1 | 334.38 |
| AP1A5 | 354.22 |
| KP2C6 | 393.44 |
| BP2H9 | 565.63 |
| AP1B6 | N.B |
| AP1D4 | N.B |
| DP4F2 | N.B |
| huACE2-Fc | 5.34 |

| Nb_Fc | EC50 (nM) |
|---|---|
| AP1C3 | 0.02 |
| KP1C9 | 0.13 |
| AP1B6 | 413.69 |
| KP1B5 | 471.85 |
| EP2G4 | 477.40 |
| AP1D4 | 485.48 |
| KP2B10 | 569.79 |
| KP2C6 | 611.96 |
| KP1B4 | 752.08 |
| BP3C5 | 763.12 |
| KP2A7 | 790.27 |
| KP1G11 | 834.07 |
| BP2A6 | 983.12 |
| BP3H9 | 1060.28 |
| DP4F2 | N.N |
| U-huFc | 0.21 |

| Nb_Fc or ACE2 | kD (nM) |
|---|---|
| EP2G4 | 3.21 |
| BP2A3 | 7.67 |
| BP2A6 | 9.02 |
| AP1B6 | 13.11 |
| KP1G11 | 13.19 |
| BP1B1 | 17.41 |
| BP1A10 | 29.53 |
| KP2C6 | 48.11 |
| AP1D4 | 67.52 |
| AP1C3 | 143.13 |
| KP1C9 | 321.09 |
| AP1A5 | 475.47 |
| KP1B5 | N.B |
| BP2H9 | N.B |
| huACE2-Fc | 12.94 |

| Nb_Fc | EC50 (nM) |
|---|---|
| AP1C3 | 0.80 |
| AP1B6 | 1.54 |
| AP1D4 | 1.96 |
| KP1C9 | 2.02 |
| BP2A6 | 2.53 |
| BP1B1 | 6.97 |
| AP1A5 | 7.18 |
| AP1C5 | 7.91 |
| AP3G8 | 17.90 |
| BP1A10 | 26.14 |
| BP3B3 | 33.56 |
| AP1B5 | 142.93 |
| BP2A3 | 465.58 |
| U-huFc | 0.28 |

| NB_Fc or ACE2 | kD (nM) |
|---|---|
| EP2G4 | 0.22 |
| KP1G11 | 0.77 |
| BP2A6 | 3.32 |
| BP1B1 | 5.13 |
| AP1B6 | 9.38 |
| KP1C9 | 29.71 |
| AP1C3 | 30.51 |
| KP1B5 | 66.88 |
| AP1A5 | 253.25 |
| BP2A3 | 349.50 |
| DP4F2 | 967.75 |
| BP1A10 | 1701.25 |
| AP1D4 | 1722.50 |
| BP2H9 | 2026.25 |
| KP2C6 | 2472.50 |
| huACE2-Fc | 2.20 |

| Nb_Fc | EC50 (nM) |
|---|---|
| BP1B1 | 402.74 |
| BP2A6 | 43.31 |
| AP1C3 | N.N |
| AP1A5 | N.N |
| AP1D4 | N.N |
| BP1A10 | N.N |
| AP1B6 | N.N |
| KP1C9 | N.N |
| EP2G4 | N.N |
| BP2H9 | N.N |
| KP1G11 | N.N |
| KP1B5 | N.N |
| DP4F2 | N.N |
| BP2A3 | N.N |
| KP2C6 | N.N |
| U-Fc | N.N |

| SEQ ID NO. | CDR1 | SEQ ID NO. | CDR2 | SEQ ID NO. | CDR3 | Secondary Identifier |
|---|---|---|---|---|---|---|
| 1 | GTSGEYD | 60 | HWDGKATAY | 119 | ARLDDEIDF | EP1B6 |
| 2 | QSFSTYY | 61 | AFGAGEQYY | 120 | AYTTTTVPQ | EP1B2 |
| 3 | FSDGRFH | 62 | QTTDEDTYY | 121 | AYTTTTVPQ | EP1F3 |
| 4 | SPFDHYV | 63 | AGDGAASYY | 122 | IFDNIRASLQDP | BP1G6 |
| 5 | TTDSQYD | 64 | SWADTTVSY | 123 | IQSRKQVGF | KP3F12 |
| 6 | FYFSGQY | 65 | TAYDGETYY | 124 | LKDPVRIIDAIW | EP3F2 |
| 7 | HTFGFSH | 66 | AGDGAASYY | 125 | LWPYSDDRLDSY | BP1D8 |
| 8 | RTFSGYI | 67 | HGDSYASYY | 126 | LYDINTVPY | BP1G4 |
| 9 | FIFGDLQ | 68 | AWYDDTTQY | 127 | PYFGEADIA | DP1E5 |
| 10 | QAFSQYH | 69 | SQAGATTQY | 128 | VWYGHTDPQHDR | KP3G12 |
| 11 | RYSQDYR | 70 | DRGGTTTDY | 129 | YFQHREPFL | BP1B10 |
| 12 | RTSQDYR | 71 | AWSGDSFRY | 130 | AFGPAQDGKGRW | AP1F10 |
| 13 | RTYDHTA | 72 | STQGRTVRY | 131 | AIDRWNTRV | AP3D12 |
| 14 | HAFDQDR | 73 | TWAGDSARY | 132 | HLPLVRGKN | AP2F4 |
| 15 | FYFSAHR | 74 | AGDGAASYY | 133 | LYNQSVRPWFTH | AP3F2 |
| 16 | RSFHDYR | 75 | DRGGTTTYY | 134 | YFQHREPFL | BP1G10 |
| 17 | GPFGTYR | 76 | SWSGGSARY | 135 | SWFVDQSDAHTSIFR | DP4B4 |
| 18 | TTYSERV | 77 | SGQSDQTYY | 136 | PFAGDANLPREW | DP4F2 |
| 19 | TFDQRSR | 78 | AWGGGSAKY | 137 | SWILDANTFLQE | DP3C8 |
| 20 | RTSGQYR | 79 | SWSGGSAR | 138 | AWKSDIAEW | AP1C5 |
| 21 | RTFRAYT | 80 | GGTGEATY | 139 | AYTTTTVPQ | BP3B3 |
| 22 | RTFTSFH | 81 | SGDDGTQY | 140 | AYTTTTVPQ | KP2C6 |
| 23 | GSFGAYI | 82 | TTTDAEYY | 141 | AYTTTTVPY | KP1B4 |
| 24 | SYFDRRW | 83 | SAYGFATY | 142 | EIEAWGHREVRP | BP3A10 |
| 25 | RTFSAYS | 84 | AGDGAASY | 143 | HYYTTSATLDYA | BP2A3 |
| 26 | TSFDDQP | 85 | GGGDKSTW | 144 | IAQDRFRNP | AP3B8 |
| 27 | QTFRSLT | 86 | SGDGGPTY | 145 | IFQQRAVPI | KP2A7 |
| 28 | QTFSHYI | 87 | AGQGHATY | 146 | KYQDTIAPL | BP2A6 |
| 29 | SSFGIRR | 88 | RWSDWAVW | 147 | KYWTGKYDRQWW | BP1C8 |
| 30 | RTFDAYS | 89 | SWSDDWTA | 148 | LQNTKEDRL | KP1C9 |

*Fig. 13A*

| SEQ ID NO. | CDR1 | SEQ ID NO. | CDR2 | SEQ ID NO. | CDR3 | Secondary Identifier |
|---|---|---|---|---|---|---|
| 31 | HTFGFNH | 90 | PGDCAASY | 149 | LWACSDDPLDSY | BP3C5 |
| 32 | RTFSGYI | 91 | QGDSYASY | 150 | LYDINTVPY | BP1B1 |
| 33 | GAFSDYG | 92 | TAGSWYTY | 151 | NKETWNTHW | EP1F4 |
| 34 | RFFTDRT | 93 | DRSGKHTY | 152 | PFAGDANLPREW | AP1B5 |
| 35 | HYFGEYR | 94 | SWSGGSAR | 153 | PLVGPEDSGLIR | AP1D5 |
| 36 | FMFTDVA | 95 | SWAGGRSL | 154 | PYFEVDDNP | KP2A10 |
| 37 | RYDDFQV | 96 | DGYQESTA | 155 | PYFGEADEHIKS | KP2B10 |
| 38 | STYDQYV | 97 | DRGGTTTD | 156 | PYFGEADPYPDA | EP3C11 |
| 39 | QAFQSYR | 98 | AGDGAASY | 157 | QFHQSPIDKGLR | BP3F2 |
| 40 | GTDTGYV | 99 | GQSGHTTL | 158 | QGDWGRHPT | EP2G4 |
| 41 | RTADHHV | 100 | AQAGGSSA | 159 | QGDWGRHPT | KP1G11 |
| 42 | HTFDAHR | 101 | SWGQSSTY | 160 | QTDEGNQYV | AP1D4 |
| 43 | RAFRIYT | 102 | AGDGAASY | 161 | QYWQSINPI | BP3D5 |
| 44 | TTFSDHT | 103 | QSDGWDTY | 162 | TFNHSLASKLFNDIK | AP1A10 |
| 45 | RTFDAYS | 104 | TQSGYSTY | 163 | TFNHSLASKLFNDIK | AP3G8 |
| 46 | QPSDRYI | 105 | QGAANKTA | 164 | THFNWQNYS | BP1A10 |
| 47 | RFFSWYA | 106 | GASGFQTY | 165 | TSGKAALPFVSK | AP2A12 |
| 48 | FTFDWSA | 107 | SSTSESTT | 166 | TYYGGKTVEQDF | KP1B5 |
| 49 | FPFSSHW | 108 | DWRDHKTY | 167 | VAFGIHWFAPHSDHI | AP1B1 |
| 50 | SAFQIYA | 109 | STDSETDH | 168 | VNGFDYAHSKAGPQV | AP1B6 |
| 51 | SIFTHVP | 110 | HANGGSQT | 169 | WAYDHFNN | BP2G12 |
| 52 | HTFTHYR | 111 | GAGGTSFY | 170 | WAYDQFNWN | BP2D3 |
| 53 | QTFTHVP | 112 | DTSGFETY | 171 | WAYDQFNWN | BP2H9 |
| 54 | RTYRGYS | 113 | SWSDDWTA | 172 | WQYIDEIQY | AP1C3 |
| 55 | STASHYT | 114 | SGRDHAKQ | 173 | YEEINATQKDTL | AP1A5 |
| 56 | FTAQEYS | 115 | TFAGHDKQ | 174 | YEINADPHGSI | BP3C3 |
| 57 | HTFSFWR | 116 | SGYGGSSK | 175 | YLSQERTPV | AP2D12 |
| 58 | RTFQDFA | 117 | RFTGWSTD | 176 | YQTHNNEWV | AP1C7 |
| 59 | SYFRWYY | 118 | SGRAERTY | 177 | YWNPVAYRFRFPTPT | KP1D5 |

*Fig. 13B*

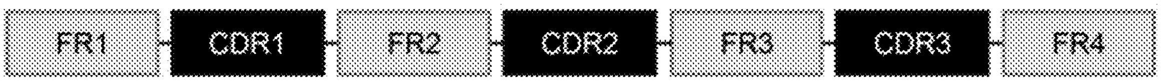

*Fig. 14*

| SEQ ID NO | **Full nanobody sequences: FR1:CDR1:FR2:CDR2:FR3:CDR3:FR4** | Secondary Identifier |
|---|---|---|
| 340 | EVQLQASGGGFVQPGGSLRLSCAASG**GTSGEYD**MGWFRQAPGKEREFVSAIS**HWDGKATAY**YADSVKGRFTISRDNSKNTVYLQMNSLRAEDTATYYCA**ARLDDEIDF**YWGQGTQVTVSSA | EP1B6 |
| 341 | EVQLQASGGGFVQPGGSLRLSCAASG**QSFSTYY**MGWFRQAPGKEREFVSAIS**AFGAGEQYY**YADSVKGRFTISRDNSKNTVYLQMNSLRAEDTATYYCA**AYTTTTVPQ**YWGQGTQVTVSSA | EP1B2 |
| 342 | EVQLQASGGGFVQPGGSLRLSCAASG**FSDGRFH**MGWFRQAPGKEREFVSAIS**QTTDEDTYY**YADSVKGRFTISRDNSKNTVYLQMNSLRAEDTATYYCA**AYTTTTVPQ**YWGQGTQVTVSSA | EP1F3 |
| 343 | EVQLQASGGGFVQPGGSLRLSCAASG**SPFDHYV**MGWFRQAPGKEREFVSAIS**AGDGAASYY**YADSVKGRFTISRDNSKNTVYLQMNSLRAEDTATYYCA**IFDNIRASLQDP**YWGQGTQVTVSSA | BP1G6 |
| 344 | EVQLQASGGGFVQPGGSLRLSCAASG**TTDSQYD**MGWFRQAPGKEREFVSAIS**SWADTTVSY**YADSVKGRFTISRDNSKNTVYLQMNSLRAEDTATYYCA**IQSRKQVGF**YWGQGTQVTVSSA | KP3F12 |
| 345 | EVQLQASGGGFVQPGGSLRLSCAASG**FYFSGQY**MGWFRQAPGKEREFVSAIS**TAYDGETYY**YADSVKGRFTISRDNSKNTVYLQMNSLRAEDTATYYCA**LKDPVRIIDAIW**YWGQGTQVTVSSA | EP3F2 |
| 346 | EVQLQASGGGFVQPGGSLRLSCAASG**HTFGFSH**MGWFRQAPGKEREFVSAIS**AGDGAASYY**YADSVKGRFTISRDNSKNTVYLQMNSLRAEDTATYYCA**LWPYSDDRLDSY**YWGQGTQVTVSSA | BP1D8 |
| 347 | EVQLQASGGGFVQPGGSLRLSCAASG**RTFSGYI**MGWFRQAPGKEREFVSAIS**HGDSYASYY**YADSVKGRFTISRDNSKNTVYLQMNSLRAEDTATYYCA**LYDINTVPY**YWGQGTQVTVSSA | BP1G4 |
| 348 | EVQLQASGGGFVQPGGSLRLSCAASG**FIFGDLQ**MGWFRQAPGKEREFVSAIS**AWYDDTTQY**YADSVKGRFTISRDNSKNTVYLQMNSLRAEDTATYYCA**PYFGEADIA**YWGQGTQVTVSSA | DP1E5 |
| 349 | EVQLQASGGGFVQPGGSLRLSCAASG**QAFSQYH**MGWFRQAPGKEREFVSAIS**SQAGATTQY**YADSVKGRFTISRDNSKNTVYLQMNSLRAEDTATYYCA**VWYGHTDPQHDR**YWGQGTQVTVSSA | KP3G12 |

*Fig. 15A*

| | | |
|---|---|---|
| 350 | EVQLQASGGGFVQPGGSLRLSCAASG**RYSQDYR**MGWFRQAPGKEREFVSAIS**DRGGTTTDY**YADSVKGRFTISRDNSKNTVYLQMNSLRAEDTATYYCA**YFQHREPFL**YWGQGTQVTVSSA | BP1B10 |
| 351 | EVQLQASGGGFVQPGGSLRLSCAASG**RTSQDYR**MGWFRQAPGKEREFVSAIS**AWSGDSFRY**YADSVKGRFTISRDNSKNTVYLQMNSLRAEDTATYYCA**AFGPAQDGKGRW**YWGQGTQVTVSSA | AP1F10 |
| 352 | EVQLQASGGGFVQPGGSLRLSCAASG**RTYDHTA**MGWFRQAPGKEREFVSAIS**STQGRTVRY**YADSVKGRFTISRDNSKNTVYLQMNSLRAEDTATYYCA**AIDRWNTRV**YWGQGTQVTVSSA | AP3D12 |
| 353 | EVQLQASGGGFVQPGGSLRLSCAASG**HAFDQDR**MGWFRQAPGKEREFVSAIS**TWAGDSAR**YYADSVKGRFTISRDNSKNTVYLQMNSLRAEDTATYYCA**HLPLVRGKN**YWGQGTQVTVSSA | AP2F4 |
| 354 | EVQLQASGGGFVQPGGSLRLSCAASG**FYFSAHR**MGWFRQAPGKEREFVSAIS**AGDGAASYY**YADSVKGRFTISRDNSKNTVYLQMNSLRAEDTATYYCA**LYNQSVRPWFTH**YWGQGTQVTVSSA | AP3F2 |
| 355 | EVQLQASGGGFVQPGGSLRLSCAASG**RSFHDYR**MGWFRQAPGKEREFVSAIS**DRGGTTTYY**YADSVKGRFTISRDNSKNTVYLQMNSLRAEDTATYYCA**YFQHREPFL**YWGQGTQVTVSSA | BP1G10 |
| 356 | EVQLQASGGGFVQPGGSLRLSCAASG**GPFGTYR**MGWFRQAPGKEREFVSAIS**SWSGGSARY**YADSVKGRFTISRDNSKNTVYLQMNSLRAEDTATYYCA**SWFVDQSDAHTSIFR**YWGQGTQVTVSSA | DP4B4 |
| 357 | EVQLQASGGGFVQPGGSLRLSCAASG**TTYSERV**MGWFRQAPGKEREFVSAIS**SGQSDQTYY**YADSVKGRFTISRDNSKNTVYLQMNSLRAEDTATYYCA**PFAGDANLPREW**YWGQGTQVTVSSA | DP4F2 |
| 358 | EVQLQASGGGFVQPGGSLRLSCAASG**TFDQRSR**MGWFRQAPGKEREFVSAIS**AWGGGSAKY**YADSVKGRFTISRDNSKNTVYLQMNSLRAEDTATYYCA**SWILDANTFLQE**YWGQGTQVTVSSA | DP3C8 |
| 359 | EVQLQASGGGFVQPGGSLRLSCAASG**RTSGQYR**MGWFRQAPGKEREFVSAIS**SWSGGSAR**YADSVKGRFTISRDNSKNTVYLQMNSLRAEDTATYYCA**AWKSDIAEW**YWGQGTQVTVSS | AP1C5 |
| 360 | EVQLQASGGGFVQPGGSLRLSCAASG**RTFRAYT**MGWFRQAPGKEREFVSAIS**GGTGEATY**YADSVKGRFTISRDNSKNTVYLQMNSLRAEDTATYYCA**AYTTTTVPQ**YWGQGTQVTVSS | BP3B3 |
| 361 | EVQLQASGGGFVQPGGSLRLSCAASG**RTFTSFH**MGWFRQAPGKEREFVSAIS**SGDDGTQY**YADSVKGRFTISRDNSKNTVYLQMNSLRAEDTATYYCA**AYTTTTVPQ**YWGQGTQVTVSS | KP2C6 |
| 362 | EVQLQASGGGFVQPGGSLRLSCAASG**GSFGAYI**MGWFRQAPGKEREFVSAIS**TTTDAEYY**YADSVKGRFTISRDNSKNTVYLQMNSLRAEDTATYYCA**AYTTTTVPY**YWGQGTQVTVSS | KP1B4 |

*Fig. 15B*

| | | |
|---|---|---|
| 363 | EVQLQASGGGFVQPGGSLRLSCAASG**SYFDRRW**MGWFRQAPGKEREFVSAIS**SAYGFATY**YADSVKGRFTISRDNSKNTVYLQMNSLRAEDTATYYCA**EIEAWGHREVR**PYWGQGTQVTVSS | BP3A10 |
| 364 | EVQLQASGGGFVQPGGSLRLSCAASG**RTFSAYS**MGWFRQAPGKEREFVSAIS**AGDGAASY**YADSVKGRFTISRDNSKNTVYLQMNSLRAEDTATYYCAHYYTTSATLDYAYWGQGTQVTVSS | BP2A3 |
| 365 | EVQLQASGGGFVQPGGSLRLSCAASG**TSFDDQP**MGWFRQAPGKEREFVSAIS**GGGDKSTW**YADSVKGRFTISRDNSKNTVYLQMNSLRAEDTATYYCA**IAQDRFRNP**YWGQGTQVTVSS | AP3B8 |
| 366 | EVQLQASGGGFVQPGGSLRLSCAASG**QTFRSLT**MGWFRQAPGKEREFVSAIS**SGDGGPTY**YADSVKGRFTISRDNSKNTVYLQMNSLRAEDTATYYCA**IFQQRAVP**IYWGQGTQVTVSS | KP2A7 |
| 367 | EVQLQASGGGFVQPGGSLRLSCAASG**QTFSHYI**MGWFRQAPGKEREFVSAIS**AGQGHATY**YADSVKGRFTISRDNSKNTVYLQMNSLRAEDTATYYCA**KYQDTIAPL**YWGQGTQVTVSS | BP2A6 |
| 368 | EVQLQASGGGFVQPGGSLRLSCAASG**SSFGIRR**MGWFRQAPGKEREFVSAIS**RWSDWAVW**YADSVKGRFTISRDNSKNTVYLQMNSLRAEDTATYYCA**KYWTGKYDRQWW**YWGQGTQVTVSS | BP1C8 |
| 369 | EVQLQASGGGFVQPGGSLRLSCAASG**RTFDAYS**MGWFRQAPGKEREFVSAIS**SWSDDWTA**YADSVKGRFTISRDNSKNTVYLQMNSLRAEDTATYYCA**LQNTKEDRL**YWGQGTQVTVSS | KP1C9 |
| 370 | EVQLQASGGGFVQPGGSLRLSCAASG**HTFGFNH**MGWFRQAPGKEREFVSAIS**PGDCAASY**YADSVKGRFTISRDNSKNTVYLQMNSLRAEDTATYYCA**LWACSDDPLDSY**YWGQGTQVTVSS | BP3C5 |
| 371 | EVQLQASGGGFVQPGGSLRLSCAASG**RTFSGYI**MGWFRQAPGKEREFVSAIS**QGDSYASY**YADSVKGRFTISRDNSKNTVYLQMNSLRAEDTATYYCA**LYDINTVPY**YWGQGTQVTVSS | BP1B1 |
| 372 | EVQLQASGGGFVQPGGSLRLSCAASG**GAFSDYG**MGWFRQAPGKEREFVSAIS**TAGSWYTY**YADSVKGRFTISRDNSKNTVYLQMNSLRAEDTATYYCA**NKETWNTHW**YWGQGTQVTVSS | EP1F4 |
| 373 | EVQLQASGGGFVQPGGSLRLSCAASG**RFFTDRT**MGWFRQAPGKEREFVSAIS**DRSGKHTY**YADSVKGRFTISRDNSKNTVYLQMNSLRAEDTATYYCA**PFAGDANLPREW**YWGQGTQVTVSS | AP1B5 |
| 374 | EVQLQASGGGFVQPGGSLRLSCAASG**HYFGEYR**MGWFRQAPGKEREFVSAIS**SWSGGSAR**YADSVKGRFTISRDNSKNTVYLQMNSLRAEDTATYYCA**PLVGPEDSGLIR**YWGQGTQVTVSS | AP1D5 |
| 375 | EVQLQASGGGFVQPGGSLRLSCAASG**FMFTDVA**MGWFRQAPGKEREFVSAIS**SWAGGRSL**YADSVKGRFTISRDNSKNTVYLQMNSLRAEDTATYYCA**PYFEVDDNP**YWGQGTQVTVSS | KP2A10 |
| 376 | EVQLQASGGGFVQPGGSLRLSCAASG**RYDDFQV**MGWFRQAPGKEREFVSAIS**DGYQESTA**YADSVKGRFTISRDNSKNTVYLQMNSLRAEDTATYYCA**PYFGEADEHIKS**YWGQGTQVTVSS | KP2B10 |

*Fig. 15C*

| | | |
|---|---|---|
| 377 | EVQLQASGGGFVQPGGSLRLSCAASG**STYDQYV**MGWFRQAPGKEREFVSAIS**DRGGTTTD**YADSVKGRFTISRDNSKNTVYLQMNSLRAEDTATYYCA**PYFGEADPYPDA**YWGQGTQVTVSS | EP3C11 |
| 378 | EVQLQASGGGFVQPGGSLRLSCAASG**QAFQSYR**MGWFRQAPGKEREFVSAIS**AGDGAASY**YADSVKGRFTISRDNSKNTVYLQMNSLRAEDTATYYCA**QFHQSPIDKGLR**YWGQGTQVTVSS | BP3F2 |
| 379 | EVQLQASGGGFVQPGGSLRLSCAASG**GTDTGYV**MGWFRQAPGKEREFVSAIS**GQSGHTTL**YADSVKGRFTISRDNSKNTVYLQMNSLRAEDTATYYCA**QGDWGRHPT**YWGQGTQVTVSS | EP2G4 |
| 380 | EVQLQASGGGFVQPGGSLRLSCAASG**RTADHHV**MGWFRQAPGKEREFVSAIS**AQAGGSSA**YADSVKGRFTISRDNSKNTVYLQMNSLRAEDTATYYCA**QGDWGRHPT**YWGQGTQVTVSS | KP1G11 |
| 381 | EVQLQASGGGFVQPGGSLRLSCAASG**HTFDAHR**MGWFRQAPGKEREFVSAIS**SWGQSSTY**YADSVKGRFTISRDNSKNTVYLQMNSLRAEDTATYYCA**QTDEGNQYV**YWGQGTQVTVSS | AP1D4 |
| 382 | EVQLQASGGGFVQPGGSLRLSCAASG**RAFRIYT**MGWFRQAPGKEREFVSAIS**AGDGAASY**YADSVKGRFTISRDNSKNTVYLQMNSLRAEDTATYYCA**QYWQSINPI**YWGQGTQVTVSS | BP3D5 |
| 383 | EVQLQASGGGFVQPGGSLRLSCAASG**TTFSDHT**MGWFRQAPGKEREFVSAIS**QSDGWDTY**YADSVKGRFTISRDNSKNTVYLQMNSLRAEDTATYYCA**TFNHSLASKLFNDIK**YWGQGTQVTVSS | AP1A10 |
| 384 | EVQLQASGGGFVQPGGSLRLSCAASG**RTFDAYS**MGWFRQAPGKEREFVSAIS**TQSGYSTY**YADSVKGRFTISRDNSKNTVYLQMNSLRAEDTATYYCA**TFNHSLASKLFNDIK**YWGQGTQVTVSS | AP3G8 |
| 385 | EVQLQASGGGFVQPGGSLRLSCAASG**QPSDRYI**MGWFRQAPGKEREFVSAIS**QGAANKTA**YADSVKGRFTISRDNSKNTVYLQMNSLRAEDTATYYCA**THFNWQNYS**YWGQGTQVTVSS | BP1A10 |
| 386 | EVQLQASGGGFVQPGGSLRLSCAASG**RFFSWYA**MGWFRQAPGKEREFVSAIS**GASGFQTY**YADSVKGRFTISRDNSKNTVYLQMNSLRAEDTATYYCA**TSGKAALPFVSK**YWGQGTQVTVSS | AP2A12 |
| 387 | EVQLQASGGGFVQPGGSLRLSCAASG**FTFDWSA**MGWFRQAPGKEREFVSAIS**SSTSESTT**YADSVKGRFTISRDNSKNTVYLQMNSLRAEDTATYYCA**TYYGGKTVEQDF**YWGQGTQVTVSS | KP1B5 |
| 388 | EVQLQASGGGFVQPGGSLRLSCAASG**FPFSSHW**MGWFRQAPGKEREFVSAIS**DWRDHKTY**YADSVKGRFTISRDNSKNTVYLQMNSLRAEDTATYYCA**VAFGIHWFAPHSDHI**YWGQGTQVTVSS | AP1B1 |
| 389 | EVQLQASGGGFVQPGGSLRLSCAASG**SAFQIYA**MGWFRQAPGKEREFVSAIS**STDSETDH**YADSVKGRFTISRDNSKNTVYLQMNSLRAEDTATYYCA**VNGFDYAHSKAGPQV**YWGQGTQVTVSS | AP1B6 |

*Fig. 15D*

| | | |
|---|---|---|
| 390 | EVQLQASGGGFVQPGGSLRLSCAASG**SIFTHVP**MGWFRQAPGKEREFVSAIS**HANGGSQT**YADSV<br>KGRFTISRDNSKNTVYLQMNSLRAEDTATYYCA**WAYDHFNN**YWGQGTQVTVSS | BP2G12 |
| 391 | EVQLQASGGGFVQPGGSLRLSCAASG**HTFTHYR**MGWFRQAPGKEREFVSAIS**GAGGTSFY**YADSVK<br>GRFTISRDNSKNTVYLQMNSLRAEDTATYYCA**WAYDQFNWN**YWGQGTQVTVSS | BP2D3 |
| 392 | EVQLQASGGGFVQPGGSLRLSCAASG**QTFTHVP**MGWFRQAPGKEREFVSAIS**DTSGFETY**YADSVK<br>GRFTISRDNSKNTVYLQMNSLRAEDTATYYCA**WAYDQFNWN**YWGQGTQVTVSS | BP2H9 |
| 393 | EVQLQASGGGFVQPGGSLRLSCAASG**RTYRGYS**MGWFRQAPGKEREFVSAIS**SWSDDWTA**YADS<br>VKGRFTISRDNSKNTVYLQMNSLRAEDTATYYCA**WQYIDEIQY**YWGQGTQVTVSS | AP1C3 |
| 394 | EVQLQASGGGFVQPGGSLRLSCAASG**STASHYT**MGWFRQAPGKEREFVSAIS**SGRDHAKQ**YADSV<br>KGRFTISRDNSKNTVYLQMNSLRAEDTATYYCA**YEEINATQKDTL**YWGQGTQVTVSS | AP1A5 |
| 395 | EVQLQASGGGFVQPGGSLRLSCAASG**FTAQEYS**MGWFRQAPGKEREFVSAIS**TFAGHDKQ**YADSV<br>KGRFTISRDNSKNTVYLQMNSLRAEDTATYYCA**YEINADPHGSI**YWGQGTQVTVSS | BP3C3 |
| 396 | EVQLQASGGGFVQPGGSLRLSCAASG**HTFSFWR**MGWFRQAPGKEREFVSAIS**SGYGGSSK**YADSV<br>KGRFTISRDNSKNTVYLQMNSLRAEDTATYYCA**YLSQERTPV**YWGQGTQVTVSS | AP2D12 |
| 397 | EVQLQASGGGFVQPGGSLRLSCAASG**RTFQDFA**MGWFRQAPGKEREFVSAIS**RFTGWSTD**YADSV<br>KGRFTISRDNSKNTVYLQMNSLRAEDTATYYCA**YQTHNNEWV**YWGQGTQVTVSS | AP1C7 |
| 398 | EVQLQASGGGFVQPGGSLRLSCAASG**SYFRWYY**MGWFRQAPGKEREFVSAIS**SGRAERTY**YADSV<br>KGRFTISRDNSKNTVYLQMNSLRAEDTATYYCA**YWNPVAYRFRFPTPT**YWGQGTQVTVSS | KP1D5 |

*Fig. 15E*

| SEQ ID NOs | |
|---|---|
| | FR1 |
| 405 | EVQLQASGGGFVQPGGSLRLSCAASG |
| | FR2 |
| 406 | MGWFRQAPGKEREFVSAIS |
| | FR3 |
| 407 | YADSVKGRFTISRDNSKNTVYLQMNSLRAEDTATYYCA |
| | FR4 |
| 408 | YWGQGTQVTVSS |

*Fig. 16*

XVQLXXSGXXXXXXXXXLXLXCXXSGXXXX~CDR1~XXWXXXXXXXXXXXXXXXX~CDR2~
XXXXXXXXXXXXXXDXXXXXXXXXXXXXXXXXXDXXXYXCXX~CDR3~XXGXGTXXXVSX (SEQ ID NO:180)

XXXLXXXGXXXXXFXXXXXXXCXXXX~CDR1~XXWXXXXXXXXXEXXXXXX~CDR2~
XXXXXXXXXXXXXXXXXXXDXXXXXXXXXXXXXDXXXYXXXX~CDR3~XWGXXXXXXVSX (SEQ ID NO:181)

XVXLXXSGGGXXXXGXSLXLSCAASG~CDR1~XXWXRXXPXXXXXXXXXXX~CDR2~
XYXXXXXXRFXXSXDXXXXXXXXLXXXXXXXXDTXXYXCAX~CDR3~XXGXGTXVTVSX (SEQ ID NO:182)

EVQLQASGGGFVQPGGSLRLSCAASG~CDR1~MGWFRQAPGKEREFVSAIS~CDR2~
YADSVKGRFTISRDNSKNTVYLQMNSLRAEDTATYYCA~CDR3~YWGQGTQVTVSS (SEQ ID NO:183)

EVQLQASGGGFVQPGGSLRLSCAASG~CDR1~MGWFRQAPGKEREFVSAIS~CDR2~
YADSVKGRFTISRDNSKNTVYLQMNSLRAEDTATYYCA~CDR3~YWGQGTQVTVSS (SEQ ID NO:184)

EVQLQASGGGFVQAGGSLRLSCAASG~CDR1~MGWFRQAPGKEREFVAAIS~CDR2~
YYADSVKGRFTISRDNAKNTVYLQMNSLKPEDTATYYCA~CDR3~YWGQGTQVTVSS (SEQ ID NO:185)

EVQLQASGGGFVQAGGSLRLSCAASG~CDR1~MGWFRQAPGKEREFVAAIS~CDR2~
YYADSVKGRFTISRDNAKNTVYLQMNSLKPEDTATYYCA~CDR3~YWGQGTQVTVSS (SEQ ID NO:186)

| | |
|---|---|
| EVQLQASGGGFVQAGGSLRLSCAASG | (SEQ ID NO:190) |
| EVQLQASGGGFVQPGGSLRLSCAASG | (SEQ ID NO:191) |
| QVQLVESGGGSVQAGGSLRLSCTASGGSEY | (SEQ ID NO:192) |
| QVQLVESGGGSVQAGGSLRLSCTASG | (SEQ ID NO:193) |
| QVQLVESGGGSVQAGGSLRLSCTASGFSRE | (SEQ ID NO:194) |
| QVQLQESGPSLVRPSQTLSLTCTISGFSRE | (SEQ ID NO:195) |
| QVQLQESGPSLVRPSQTLSLTCTISG | (SEQ ID NO:196) |
| QVQLVESGGNLVQPGGSLRLSCAASGFTFG | (SEQ ID NO:197) |
| QVQLVESGGNLVQPGGSLRLSCAASG | (SEQ ID NO:198) |
| QVQLVESGGALVQPGGSLRLSCAASGFPVN | (SEQ ID NO:199) |
| QVQLVESGGALVQPGGSLRLSCAASGFTFG | (SEQ ID NO:200) |
| QVQLVESGGGLVQPGGSLRLSCAASGFTFG | (SEQ ID NO:201) |
| QVQLVESGGALVQPGGSLRLSCAASG | (SEQ ID NO:202) |
| QVQLVESGGGLVQAGGSLRLSCAASG | (SEQ ID NO:203) |
| QVQLVESGGGLMQAGGSLRLSCAVSG | (SEQ ID NO:204) |
| QVQLQESGGGLVQAGGSLRLSCAASG | (SEQ ID NO:205) |
| HVQLVESGGGLVQAGGSLRLSCAASG | (SEQ ID NO:206) |
| DVQLVESGGGLVQAGGSLRLSCAASG | (SEQ ID NO:207) |
| EVQLVESGGGLVQAGGSLRLSCAASG | (SEQ ID NO:208) |
| EVQLVESGGGVVQPGRSLRLSCAASGFTFD | (SEQ ID NO:209) |
| EVQLVESGGGVVQPGRSLRLSCAASG | (SEQ ID NO:210) |
| DVQLQASGGGLVQAGGSLRLSCAASGFKIT | (SEQ ID NO:211) |
| DVQLQASGGGLVQAGGSLRLSCAASG | (SEQ ID NO:212) |
| | |
| XVQLXXSGXXXXXXXXXLXLXCXXSGXXXX | (SEQ ID NO:213) |
| XXXLXXXGXXXXXXXXXXXXCXXXX | (SEQ ID NO:214) |
| XVQLXXSGXXXXXXXXXLXLXCXXSG | (SEQ ID NO:215) |
| QVQLVESGGGLVQXGGSLRLSCAASGXXXX | (SEQ ID NO:216) |
| QVQLVESGGGLVQXGGSLRLSCAASG | (SEQ ID NO:217) |

| | |
|---|---|
| MGWFRQAPGKEREFVAAIS | (SEQ ID NO:220) |
| MGWFRQAPGKEREFVSAIS | (SEQ ID NO:221) |
| --WFRQAPGQEREAVA | (SEQ ID NO:222) |
| --WFRQAPGQEREAVAAIA | (SEQ ID NO:223) |
| --WVRQAPGKALEWLG | (SEQ ID NO:224) |
| --WVRQAPGKALEWLGRI | (SEQ ID NO:225) |
| --WFRQAPGQEREWLG | (SEQ ID NO:226) |
| --WFRQAPGQEREWLGRI | (SEQ ID NO:227) |
| --WVRQAPGGGLEWVA | (SEQ ID NO:228) |
| --WYRQATGKEREWVA | (SEQ ID NO:229) |
| MSWYRQATGKEREWVA | (SEQ ID NO:230) |
| MGWFRQAPGKEREFVAAIR | (SEQ ID NO:231) |
| MGWFRQAPGKEREFVAAI | (SEQ ID NO:232) |
| MGWFRQAPGKEREFVA | (SEQ ID NO:233) |
| MGWYRQAPGKERELVA | (SEQ ID NO:234) |
| MGWYRQAPGKERELVAA | (SEQ ID NO:235) |
| MGWYRQAPGKERELVAAID | (SEQ ID NO:236) |
| MGWYRQAPGKERELVAVIS | (SEQ ID NO:237) |
| MGWFRQAPGKEREGVA | (SEQ ID NO:238) |
| --WFRQAPGKEREGVA | (SEQ ID NO:239) |
| MGWFRQAPGKEREFVA | (SEQ ID NO:240) |
| --WFRQAPGKEREFVA | (SEQ ID NO:241) |
| --WVRQAPGKGPEWVA | (SEQ ID NO:242) |
| --WFRQAPGKEREFVS | (SEQ ID NO:243) |
| | |
| XXWXXXXXXXXXXXXXXXX | (SEQ ID NO:244) |
| XXWXRQAXGXXXEXXXXXX | (SEQ ID NO:245) |
| XXWXRQAXGXXXEXXX | (SEQ ID NO:246) |
| MXWFRQAPGKEREWVAXXX | (SEQ ID NO:247) |
| MXWFRQAPGKEREWVA | (SEQ ID NO:248) |

| | |
|---|---|
| -YADSVKGRFTISRDNAKNTVYLQMNSLKPEDTATYYCA- | (SEQ ID NO:250) |
| YYADSVKGRFTISRDNAKNTVYLQMNSLKPEDTATYYCA- | (SEQ ID NO:251) |
| -YADSVKGRFTISRDNSKNTVYLQMNSLRAEDTATYYCA- | (SEQ ID NO:252) |
| YYADSVKGRFTISRDNSKNTVYLQMNSLRAEDTATYYCA- | (SEQ ID NO:253) |
| --------RFTISRDNAKNTVTLQMNNLKPEDTAIYYCA- | (SEQ ID NO:254) |
| --------RFTISRDNAKNTVTLQMNNLKPEDTAIYYCAA | (SEQ ID NO:255) |
| --------RLTITRDISKSQVSLSLSSVTLEDTAEYYCV- | (SEQ ID NO:256) |
| --------RLTITRDISKSQVSLSLSSVTLEDTAEYYCVY | (SEQ ID NO:257) |
| --------RFTISRDIAKNTVTLQMNNLKPEDTAIYYVY- | (SEQ ID NO:258) |
| --------RFTISRDIAKNTVTLQMNNLKPEDTAIYYVYA | (SEQ ID NO:259) |
| YYADSVKGRFTISRDNAKNTVTLQMNNLKPEDTAIYYCA- | (SEQ ID NO:260) |
| YYADSVKGRFTISRDNAKNTVTLQMNNLKPEDTAIYYCAA | (SEQ ID NO:261) |
| -YEDSVKGRFCISRDDAKNTVYLQMNSLKPEDTAVYYCNV | (SEQ ID NO:262) |
| -YEDSVKGRFCISRDDAKNTVYLQMNSLKPEDTAVYYCN- | (SEQ ID NO:263) |
| -YADSVKGRFTISRDNAKNSVYLQMNSLKVEDTAVYYCAR | (SEQ ID NO:264) |
| -YADSVKGRFTISRDNAKNSVYLQMNSLRVEDTAVYYCA- | (SEQ ID NO:265) |
| -YADSVKGRFTISRDNAKNTVYLQMNSLKPEDTAVYYCAR | (SEQ ID NO:266) |
| -YADSVKGRFTISRDNAKNTVYLQMNSLKPEDTAVYYCA- | (SEQ ID NO:267) |
| -YADSVKGRFTISRDNAKNTVYLQMNSLKPEDTAVYYCAR | (SEQ ID NO:268) |
| --------RFTISRDNAKNTVYLQMNSLKPEDTAVYYCAR | (SEQ ID NO:269) |
| -YADSVKGRFTISRDKGKNTVYLQMDSLKPEDTATYYCAA | (SEQ ID NO:270) |
| --------RFTISRDKGKNTVYLQMDSLKPEDTATYYCAA | (SEQ ID NO:271) |
| -YADSVKGRFTISRDKGKNTVYLQMDSLKPEDTATYYCA- | (SEQ ID NO:272) |
| --------RFTISRDKGKNTVYLQMDSLKPEDTATYYCA- | (SEQ ID NO:273) |
| YYADSVKGRFTISRDKAKNTVYLQMNSLKYEDTAVYYCA- | (SEQ ID NO:274) |
| -YADSVKGRFTISRDKAKNTVYLQMNSLKYEDTAVYYCA- | (SEQ ID NO:275) |
| YYADSVKGRFTISRDNAKNTVYLQMNSLKPEDTAVYYCA- | (SEQ ID NO:276) |
| LHNPALKSRLTITRDISKSQVSLSLSSVTLEDTAEYYCV- | (SEQ ID NO:277) |
| LHNPALKSRLTITRDISKSQVSLSLSSVTLEDTAEYYCVY | (SEQ ID NO:278) |
| LHNPALKSRFTISRDIAKNTVTLQMNNLKPEDTAIYYVYA | (SEQ ID NO:279) |
| -YADSVKGRFTISRDNAKNTVYLQMNSLKPEDTAVYYCAA | (SEQ ID NO:280) |
| -YADSVKGRFTISRDNAKNTVYLQMNSLKPEDTAVYYCA- | (SEQ ID NO:281) |
| YYADSVKGRFTISRDNAKNTVYLQMNSLKPEDTAVYYCAA | (SEQ ID NO:282) |
| --------RFTISRDNSKNTLYLQMNSLRAEDTAVYYCAK | (SEQ ID NO:283) |
| --------RFTISRDNAKNTVYLQMNSLKPEDTADYYCAA | (SEQ ID NO:284) |
| | |
| XXXXXXXXXXXXXDXXXXXXXXXXXXXXXXDXXXYXCXX | (SEQ ID NO:285) |
| XXXXXXXXRXXIXRDXXXXXVXLXXXXXXXEDTAXYYXXX | (SEQ ID NO:286) |
| XXXXXXXXRXXIXRDXXXXXVXLXXXXXXXEDTAXYYXX | (SEQ ID NO:287) |
| XYADSVKGRFTISRDNAKNTVYLQMNSLKPEDTAVYYCAX | (SEQ ID NO:288) |
| XYADSVKGRFTISRDNAKNTVYLQMNSLKPEDTAVYYCA | (SEQ ID NO:289) |

| | |
|---|---|
| YWGQGTQVTVSS | (SEQ ID NO:290) |
| -WGQGTQVTVSS | (SEQ ID NO:291) |
| VWGPGLLLTVSS | (SEQ ID NO:292) |
| -WGPGLLLTVSS | (SEQ ID NO:293) |
| -WGQGTLVTVS- | (SEQ ID NO:294) |
| -WGQGTLVTVSS | (SEQ ID NO:295) |
| -WGQGTQVTVS- | (SEQ ID NO:296) |
| -WGQGTQVTVSS | (SEQ ID NO:297) |
| QWGQGTQVTVSS | (SEQ ID NO:298) |
| YWGQGTQVTVS- | (SEQ ID NO:299) |
| -WGQGTTVVVSS | (SEQ ID NO:300) |
| -WGKGTQVTVSS | (SEQ ID NO:301) |
| XWGXGXXXTVSX | (SEQ ID NO:302) |
| XWGXGXXXTVS | (SEQ ID NO:303) |
| WGXGXXXTVSX | (SEQ ID NO:304) |
| XXGXGTXXXVSX | (SEQ ID NO:305) |
| XWGQGTQVTVSS | (SEQ ID NO:306) |
| XWGQGTQVTVS | (SEQ ID NO:307) |

*Fig. 18D*

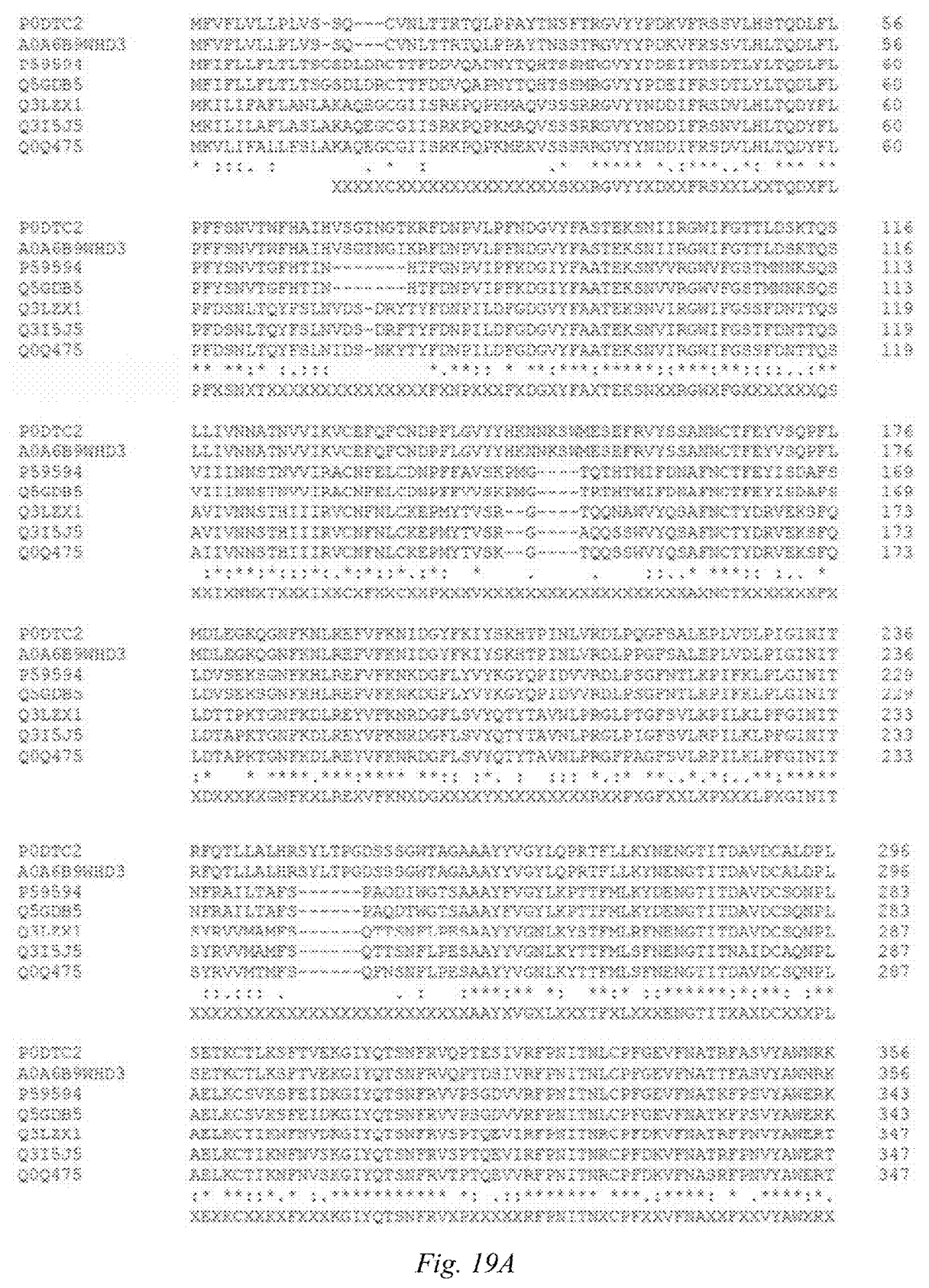

```
P0DTC2        MFVFLVLLPLVS-SQ---CVNLTTRTQLPPAYTNSFTRGVYYPDKVFRSSVLHSTQDLFL   56
A0A6B9WHD3    MFVFLVLLPLVS-SQ---CVNLTTRTQLPPAYTNSSTRGVYYPDKVFRSSVLHLTQDLFL   56
P59594        MFIFLLFLTLTSGSDLDRCTTFDDVQAPNYTQHTSSMRGVYYPDEIFRSDTLYLTQDLFL   60
Q5GDB5        MFIFLLFLTLTSGSDLDRCTTFDDVQAPNYTQHTSSMRGVYYPDEIFRSDTLYLTQDLFL   60
Q3LZX1        MKILIFAFLANLAKAQEGCGIISRKPQPKMAQVSSSRRGVYYNDDIFRSDVLHLTQDYFL   60
Q3I5J5        MKILILAFLASLAKAQEGCGIISRKPQPKMAQVSSSRRGVYYNDDIFRSNVLHLTQDYFL   60
Q0Q475        MKVLIFALLFSLAKAQEGCGIISRKPQPKMEKVSSSRRGVYYNDDIFRSDVLHLTQDYFL   60
              * :::. :          . *  :               .*  ***** *.:***..*: *** **
                    XXXXXCXXXXXXXXXXXXXXSXXRGVYYXDXXFRSXXLXXTQDXFL

P0DTC2        PFFSNVTWFHAIHVSGTNGTKRFDNPVLPFNDGVYFASTEKSNIIRGWIFGTTLDSKTQS   116
A0A6B9WHD3    PFFSNVTWFHAIHVSGTNGIKRFDNPVLPFNDGVYFASTEKSNIIRGWIFGTTLDSKTQS   116
P59594        PFYSNVTGFHTIN-------HTFGNPVIPFKDGIYFAATEKSNVVRGWVFGSTMNNKSQS   113
Q5GDB5        PFYSNVTGFHTIN-------HTFDNPVIPFKDGIYFAATEKSNVVRGWVFGSTMNNKSQS   113
Q3LZX1        PFDSNLTQYFSLNVDS-DRYTYFDNPILDFGDGVYFAATEKSNVIRGWIFGSSFDNTTQS   119
Q3I5J5        PFDSNLTQYFSLNVDS-DRFTYFDNPILDFGDGVYFAATEKSNVIRGWIFGSTFDNTTQS   119
Q0Q475        PFDSNLTQYFSLNIDS-NKYTYFDNPILDFGDGVYFAATEKSNVIRGWIFGSSFDNTTQS   119
              ** **:* :.:::          *.**:: * **:***:*****::***:**:::..:**
              PFXSNXTXXXXXXXXXXXXXXFXNPXXXFXDGXYFAXTEKSNXXRGWXFGXXXXXXXQS

P0DTC2        LLIVNNATNVVIKVCEFQFCNDPFLGVYYHKNNKSWMESEFRVYSSANNCTFEYVSQPFL   176
A0A6B9WHD3    LLIVNNATNVVIKVCEFQFCNDPFLGVYYHKNNKSWMESEFRVYSSANNCTFEYVSQPFL   176
P59594        VIIINNSTNVVIRACNFELCDNPFFAVSKPMG-----TQTHTMIFDNAFNCTFEYISDAFS   169
Q5GDB5        VIIINNSTNVVIRACNFELCDNPFFVVSKPMG-----TRTHTMIFDNAFNCTFEYISDAFS   169
Q3LZX1        AVIVNNSTHIIIRVCNFNLCKEPMYTVSR--G-----TQQNAWVYQSAFNCTYDRVEKSFQ   173
Q3I5J5        AVIVNNSTHIIIRVCNFNLCKEPMYTVSR--G-----AQQSSWVYQSAFNCTYDRVEKSFQ   173
Q0Q475        AIIVNNSTHIIIRVCNFNLCKEPMYTVSK--G-----TQQSSWVYQSAFNCTYDRVEKSFQ   173
               :*:**:*::*:*:.*:*::*.:*:  *    .     .     ::..* ***:: :. . *
              XXIXNNXTXXXIXXCXFXXCXXPXXXVXXXXXXXXXXXXXXXXXXXXXXAXNCTXXXXXXXFX

P0DTC2        MDLEGKQGNFKNLREFVFKNIDGYFKIYSKHTPINLVRDLPQGFSALEPLVDLPIGINIT   236
A0A6B9WHD3    MDLEGKQGNFKNLREFVFKNIDGYFKIYSKHTPINLVRDLPPGFSALEPLVDLPIGINIT   236
P59594        LDVSEKSGNFKHLREFVFKNKDGFLYVYKGYQPIDVVRDLPSGFNTLKPIFKLPLGINIT   229
Q5GDB5        LDVSEKSGNFKHLREFVFKNKDGFLYVYKGYQPIDVVRDLPSGFNTLKPIFKLPLGINIT   229
Q3LZX1        LDTTPKTGNFKDLREYVFKNRDGFLSVYQTYTAVNLPRGLPTGFSVLKPILKLPFGINIT   233
Q3I5J5        LDTAPKTGNFKDLREYVFKNRDGFLSVYQTYTAVNLPRGLPIGFSVLRPILKLPFGINIT   233
Q0Q475        LDTAPKTGNFKDLREYVFKNRDGFLSVYQTYTAVNLPRGFPAGFSVLRPILKLPFGINIT   233
              :*    * ****.***:****  **::  :*.  :    ::: *.:*  **..*.*:..**:*****
              XDXXXKXGNFKXLREXVFKNXDGXXXXYXXXXXXXXXRXXPXGFXXLXPXXXLPXGINIT

P0DTC2        RFQTLLALHRSYLTPGDSSSGWTAGAAAYYVGYLQPRTFLLKYNENGTITDAVDCALDPL   296
A0A6B9WHD3    RFQTLLALHRSYLTPGDSSSGWTAGAAAYYVGYLQPRTFLLKYNENGTITDAVDCALDPL   296
P59594        NFRAILTAFS-------PAQDIWGTSAAAYFVGYLKPTTFMLKYDENGTITDAVDCSQNPL   283
Q5GDB5        NFRAILTAFS-------PAQDTWGTSAAAYFVGYLKPTTFMLKYDENGTITDAVDCSQNPL   283
Q3LZX1        SYRVVMAMFS-------QTTSNFLPESAAYYVGNLKYSTFMLRFNENGTITDAVDCSQNPL   287
Q3I5J5        SYRVVMAMFS-------QTTSNFLPESAAYYVGNLKYTTFMLSFNENGTITNAIDCAQNPL   287
Q0Q475        SYRVVMTMFS-------QFNSNFLPESAAYYVGNLKYTTFMLSFNENGTITDAVDCSQNPL   287
               ::.::: .            . :    :****:** *:   **:*  ::******:*:**: :**
              XXXXXXXXXXXXXXXXXXXXXXXXXXAAYXVGXLXXXTFXLXXXENGTITXAXDCXXXPL

P0DTC2        SETKCTLKSFTVEKGIYQTSNFRVQPTESIVRFPNITNLCPFGEVFNATRFASVYAWNRK   356
A0A6B9WHD3    SETKCTLKSFTVEKGIYQTSNFRVQPTDSIVRFPNITNLCPFGEVFNATTFASVYAWNRK   356
P59594        AELKCSVKSFEIDKGIYQTSNFRVVPSGDVVRFPNITNLCPFGEVFNATKFPSVYAWERK   343
Q5GDB5        AELKCSVKSFEIDKGIYQTSNFRVVPSGDVVRFPNITNLCPFGEVFNATKFPSVYAWERK   343
Q3LZX1        AELKCTIKNFNVDKGIYQTSNFRVSPTQEVIRFPNITNRCPFDKVFNATRFPNVYAWERT   347
Q3I5J5        AELKCTIKNFNVSKGIYQTSNFRVSPTQEVIRFPNITNRCPFDKVFNATRFPNVYAWERT   347
Q0Q475        AELKCTIKNFNVSKGIYQTSNFRVTPTQEVVRFPNITNRCPFDKVFNASRFPNVYAWERT   347
              :*  **::*.* :.************ *:  .::******* ***.:*****: *  .****:*.
              XEXKCXXKXFXXXKGIYQTSNFRVXPXXXXXRFPNITNXCPFXXVFNAXXFXXVYAWXRX
```

*Fig. 19A*

```
P0DTC2        RISNCVADYSVLYNSASFSTFKCYGVSPTKLNDLCFTNVYADSFVIRGDEVRQIAPGQTG   416
A0A6B9WHD3    RISNCVADYSVLYNSTSFSTFKCYGVSPTKLNDLCFTNVYADSFVITGDEVRQIAPGQTG   416
P59594        KISSCVADYSVLYNSTFFSTFKCYCVSATKLNDLCFSNVYADSFVVKGDDVRQIAPGQTG   403
Q5GDB5        KISSCVADYSVLYNSTSFSTFKCYGVSATKLNDLCFSNVYADSFVVKGDDVRQIAPGQTG   403
Q3LZX1        KISDCVADYTVLYNSTSFSTFKCYGVSPSKLIDLCFTSVYADTFLIRSSEVRQVAPGETG   407
Q3I5J5        KISDCVADYTVLYNSTSFSTFKCYGVSPSKLIDLCFTSVYADTFLIRSSEVRQVAPGETG   407
Q0Q475        KISDCVADYTVLYNSTSFSTFKCYGVSPSKLIDLCFTSVYADTFLIRSSEVRQVAPGETG   407
              :**:*****:*****: **********  :** ****:.****:*:: ..:***:***:**
              XISXCVADYXVLYNSXXFSTFKCYGVSXXKLXDLCFXXVYADXFXXXXXVRQXAPGXTG

P0DTC2        KIADYNYKLPDDFTGCVIAWNSNNLDSKVGGNYNYLYRLFRKSNLKPFERDISTEIYQAG   476
A0A6B9WHD3    KIADYNYKLPDDFTGCVIAWNSKHIDAKEGGNFNYLYRLFRKANLKPFERDISTEIYQAG   476
P59594        VIADYNYKLPDDFMGCVLAWNTRNIDATSTGNYNYKYRYLRHGKLRPFERDISNVPFSPD   463
Q5GDB5        VIADYNYKLPDDFMGCVLAWNTRNIDATSTGNYNYKYRYLRHGKLRPFERDISNVPFSPD   463
Q3LZX1        VIADYNYKLPDDFTGCVIAWNTAKHDT----G--NYYYRSHRKTKLKPFERDLSSDD---   458
Q3I5J5        VIADYNYKLPDDFTGCVIAWNTAKQDQ----G--QYYYRSHRKTKLKPFERDLSSD----   457
Q0Q475        VIADYNYKLPDDFTGCVIAWNTAQQDQ----G--QYYYRSYRKEKLKPFERDLSSD----   457
               ************ ***:****: : *    *   :* **  *: :*:*****:*.
              XIADYNYKLPDDFXGCVXAWNXXXXDXXXXGXXXYXYRXXRXXXLXPFERDXSXXXXXX

P0DTC2        STPCNGVEGFNCYFPLQSYGFQPTNGVGYQPYRVVVLSFELLHAPATVCGPKKSTNLVKN   536
A0A6B9WHD3    SKPCNGQTGLNCYYPLYRYGFYPTDGVGHQPYRVVVLSFELLNAPATVCGPKKSTNLVKN   536
P59594        GKPCTPP-ALNCYWPLNDYGFYTTTGIGYQPYRVVVLSFELLNAPATVCGPKLSTDLIKN   522
Q5GDB5        GKPCTPP-APNCYWPLNGYGFYTTSGIGYQPYRVVVLSFELLNAPATVCGPKLSTDLIKN   522
Q3LZX1        ---------GNGVYTLSTYDFYPNVPVAYQATRVVVLSFELLNAPATVCGPKLSTELVKN   509
Q3I5J5        ---------ENGVRTLSTYDFYPSVPVAYQATRVVVLSFELLNAPATVCGPKLSTQLVKN   508
Q0Q475        ---------ENGVYTLSTYDFYPSIPVEYQATRVVVLSFELLNAPATVCGPKLSTQLVKN   508
                        *    *  *.*  .  : :*  **********:********** **:*:**
              XXXXXXXXXXNXXXXLXXYXFXXXXXXXXQXXRVVVLSFELLXAPATVCGPKXSTXLXKN

P0DTC2        KCVNFNFNGLTGTGVLTESNKKFLPFQQFGRDIADTTDAVRDPQTLEILDITPCSFGGVS   596
A0A6B9WHD3    KCVNFNFNGLTGTGVLTESNKKFLPFQQFGRDIADTTDAVRDPQTLEILDITPCSFGGVS   596
P59594        QCVNFNFNGLTGTGVLTPSSKRFQPFQQFGRDVSDFTDSVRDPKTSEILDISPCSFGGVS   582
Q5GDB5        QCVNFNFNGLTGTGVLTPSSKRFQPFQQFGRDVSDFTDSVRDPKTSEILDISPCSFGGVS   582
Q3LZX1        QCVNFNFNGLKGTGVLTSSSKRFQSFQQFGRDTSDFTDSVRDPQTLEILDISPCSFGGVS   569
Q3I5J5        QCVNFNFNGLKGTGVLTESSKRFQSFQQFGRDTSDFTDSVRDPQTLEILDISPCSFGGVS   568
Q0Q475        QCVNFNFNGLRGTGVLTTSSKRFQSFQQFGRDTSDFTDSVRDPQTLEILDISPCSFGGVS   568
              :********* ****** *.*:*  ******* :* **:****:* *****:********
              XCVNFNFNGLXGTGVLTXSXKXFXXFQQFGRDXXDXTDXVRDPXTXEILDIXPCSFGGVS

P0DTC2        VITPGTNTSNQVAVLYQDVNCTEVPVAIHADQLTPTWRVYSTGSNVFQTRAGCLIGAEHV   656
A0A6B9WHD3    VITPGTNASNQVAVLYQDVNCTEVPVAIHADQLTPTWRVYSTGSNVFQTRAGCLIGAEHV   656
P59594        VITPGTNASSEVAVLYQDVNCTDVSTAIHADQLTPAWRIYSTGNNVFQTQAGCLIGAEHV   642
Q5GDB5        VITPGTNASSEVAVLYQDVNCTDVSTLIHAEQLTPAWRIYSTGNNVFQTQAGCLIGAEHV   642
Q3LZX1        VITPGTNASSEVAVLYQDVNCTDVPTAIRADQLTPAWRVYSTGVNVFQTQAGCLIGAEHV   629
Q3I5J5        VITPGTNASSEVAVLYQDVNCTDVPAAIHADQLTPAWRVYSTGTNVFQTQAGCLIGAEHV   628
Q0Q475        VITPGTNASSEVAVLYQDVNCTDVPTSIHADQLTPAWRVYSTGVNVFQTQAGCLIGAEHV   628
              *******:*.:***********:* . *:*:****:**:**** *****:**********
              VITPGTNXSXXVAVLYQDVNCTXVXXXIXAXQLTPXWRXYSTGXNVFQTXAGCLIGAEHV

P0DTC2        NNSYECDIPIGAGICASYQTQTNSPRRARSVASQSIIAYTMSLGAENSVAYSNNSIAIPT   716
A0A6B9WHD3    NNSYECDIPIGAGICASYQTQTNS----RSVASQSIIAYTMSLGAENSVAYSNNSIAIPT   712
P59594        DTSYECDIPIGAGICASYHTVS----LLRSTSQKSIVAYTMSLGADSSIAYSNNTIAIPT   698
Q5GDB5        DTSYECDIPIGAGICASYHTVS----SLRSTSQKSIVAYTMSLGADSSIAYSNNTIAIPT   698
Q3LZX1        NASYECDIPIGAGICASYHTAS----VLRSTGQKSIVAYTMSLGAENSIAYANNSIAIPT   685
Q3I5J5        NASYECDIPIGAGICASYHTAS----TLRSVGQKSIVAYTMSLGAENSIAYANNSIAIPT   684
Q0Q475        NASYECDIPIGAGICASYHTAS----VLRSTGQKSIVAYTMSLGAENSIAYANNSIAIPT   684
              : ***************:* :      **...:**:********:.*:**:**:*****
              XXSYECDIPIGAGICASYXTXXXXXXXXRSXXXXSIXAYTMSLGAXXSXAYXNNXIAIPT
```

*Fig. 19B*

```
P0DTC2        NFTISVTTEILPVSMTKTSVDCTMYICGDSTECSNLLLQYGSFCTQLNRALTGIAVEQDK   776
A0A6B9WHD3    NFTISVTTEILPVSMTKTSVDCTMYICGDSTECSNLLLQYGSFCTQLNRALTGIAVEQDK   772
P59594        NFSISITTEVMPVSMAKTSVDCNMYICGDSTECANLLLQYGSFCTQLNRALSGIAAEQDR   758
Q5GDB5        NFSISITTEVMPVSMAKTSVDCNMYICGDSTECANLLLQYGSFCRQLNRALSGIAAEQDR   758
Q3LZX1        NFSISVTTEVMPVSMAKTAVDCTMYICGDSLECSNLLLQYGSFCTQLNRALTGIAIEQDK   745
Q3I5J5        NFSISVTTEVMPVSMAKTSVDCTMYICGDSLECSNLLLQYGSFCTQLNRALSGIAIEQDK   744
Q0Q475        NFSISVTTEVMPVSIAKTSVDCTMYICGDSLECSNLLLQYGSFCTQLNRALTGIAIEQDK   744
              **:**:***::***::**:***.******* **:********** ******:*** ***:
              NFXISXTTEXXPVSXXKTXVDCXMYICGDSXECXNLLLQYGSFCXQLNRALXGIAXEQDX

P0DTC2        NTQEVFAQVKQIYKTPPIKDFGGFNFSQILPDPSKPSKRSFIEDLLFNKVTLADAGFIKQ   836
A0A6B9WHD3    NTQEVFAQVKQIYKTPPIKDFGGFNFSQILPDPSKPSKRSFIEDLLFNKVTLADAGFIKQ   832
P59594        NTREVFAQVKQMYKTPTLKYFGGFNFSQILPDPLKPTKRSFIEDLLFNKVTLADAGFMKQ   818
Q5GDB5        NTREVFVQVKQMYKTPTLKDFGGFNFSQILPDPLKPTKRSFIEDLLFNKVTLADAGFMKQ   818
Q3LZX1        NTQEVFAQVKQMYKTPAIKDFGGFNFSQILPDPSKPTKRSFIEDLLFNKVTLADAGFMKQ   805
Q3I5J5        NTQEVFAQVKQMYKTPAIKDFGGFNFSQILPDPSKPTKRSFIEDLLFNKVTLADAGFMKQ   804
Q0Q475        NTQEVFAQVKQMYKTPAIKDFGGFNFSQILPDPSKPTKRSFIEDLLFNKVTLADAGFMKQ   804
              **:***.****:****  :* ************* **:********************:**
              NTXEVFXQVKQXYKTPXXKXFGGFNFSQILPDPXKPXKRSFIEDLLFNKVTLADAGFXKQ

P0DTC2        YGDCLGDIAARDLICAQKFNGLTVLPPLLTDEMIAQYTSALLAGTITSGWTFGAGAALQI   896
A0A6B9WHD3    YGDCLGDIAARDLICAQKFNGLTVLPPLLTDEMIAQYTSALLAGTITSGWTFGAGAALQI   892
P59594        YGECLGDINARDLICAQKFNGLTVLPPLLTDDMIAAYTAALVSGTATAGWTFGAGAALQI   878
Q5GDB5        YGECLGDINARDLICAQKFNGLTVLPPLLTDDMIAAYTAALVSGTATAGWTFGAGAALQI   878
Q3LZX1        YGDCLGDVSARDLICAQKFNGLTVLPPLLTDEMVAAYTAALVSGTATAGWTFGAGAALQI   865
Q3I5J5        YGECLGDISARDLICAQKFNGLTVLPPLLTDEMIAAYTAALVSGTATAGWTFGAGSALQI   864
Q0Q475        YGECLGDISARDLICAQKFNGLTVLPPLLTDEMIAAYTAALVSGTATAGWTFGAGSALQI   864
              **:****: **********************:*:* **:**::** *:*******:****
              YGXCLGDXXARDLICAQKFNGLTVLPPLLTDXMXAXYTXALXXGTXTXGWTFGAGXALQI

P0DTC2        PFAMQMAYRFNGIGVTQNVLYENQKLIANQFNSAIGKIQDSLSSTASALGKLQDVVNQNA   956
A0A6B9WHD3    PFAMQMAYRFNGIGVTQNVLYENQKLIANQFNSAIGKIQDSLSSTASALGKLQDVVNQNA   952
P59594        PFAMQMAYRFNGIGVTQNVLYENQKQIANQFNKAISQIQESLTTTSTALGKLQDVVNQNA   938
Q5GDB5        PFAMQMAYRFNGIGVTQNVLYENQKQIANQFNKAISQIQESLTTTSTALGKLQDVVNQNA   938
Q3LZX1        PFAMQMAYRFNGIGVTQNVLYENQKLIANQFNSAIGKIQESLSSTASALGKLQDVVNQNA   925
Q3I5J5        PFAMQMAYRFNGIGVTQNVLYENQKQIANQFNKAISQIQESLTTTSTALGKLQDVVNQNA   924
Q0Q475        PFAMQMAYRFNGIGVTQNVLYENQKQIANQFNKAISQIQESLTTTSTALGKLQDVVNDNA   924
              ************************* ******.**.:**:**::*::**********:**
              PFAMQMAYRFNGIGVTQNVLYENQKXIANQFNXAIXXIQXSLXXTXXALGKLQDVVNXNA

P0DTC2        QALNTLVKQLSSNFGAISSVLNDILSRLDKVEAEVQIDRLITGRLQSLQTYVTQQLIRAA   1016
A0A6B9WHD3    QALNTLVKQLSSNFGAISSVLNDILSRLDKVEAEVQIDRLITGRLQSLQTYVTQQLIRAA   1012
P59594        QALNTLVKQLSSNFGAISSVLNDILSRLDKVEAEVQIDRLITGRLQSLQTYVTQQLIRAA   998
Q5GDB5        QALNTLVKQLSSNFGAISSVLNDILSRLDKVEAEVQIDRLITGRLQSLQTYVTQQLIRAA   998
Q3LZX1        QALNTLVKQLSSNFGAISSVLNDILSRLDKVEAEVQIDRLITGRLQSLQTYVTQQLIRAA   985
Q3I5J5        QALNTLVKQLSSNFGAISSVLNDILSRLDKVEAEVQIDRLITGRLQSLQTYVTQQLIRAA   984
Q0Q475        QALNTLVKQLSSNFGAISSVLNDILSRLDKVEAEVQIDRLITGRLQSLQTYVTQQLIRAA   984
              ************************************************************
              QALNTLVKQLSSNFGAISSVLNDILSRLDKVEAEVQIDRLITGRLQSLQTYVTQQLIRAA

P0DTC2        EIRASANLAATKMSECVLGQSKRVDFCGKGYHLMSFPQSAPHGVVFLHVTYVPAQEKNFT   1076
A0A6B9WHD3    EIRASANLAATKMSECVLGQSKRVDFCGKGYHLMSFPQSAPHGVVFLHVTYVPAQEKNFT   1072
P59594        EIRASANLAATKMSECVLGQSKRVDFCGKGYHLMSFPQAAPHGVVFLHVTYVPSQERNFT   1058
Q5GDB5        EIRASANLAATKMSECVLGQSKRVDFCGKGYHLMSFPQAAPHGVVFLHVTYVPSQERNFT   1058
Q3LZX1        EIRASANLAATKMSECVLGQSKRVDFCGKGYHLMSFPQSAPHGVVFLHVTYVPSQERNFT   1045
Q3I5J5        EIRASANLAATKMSECVLGQSKRVDFCGKGYHLMSFPQAAPHGVVFLHVTYVPSQERNFT   1044
Q0Q475        EIRASANLAATKMSECVLGQSKRVDFCGKGYHLMSFPQAAPHGVVFLHVTYVPSQERNFT   1044
              **************************************:**************:**:***
              EIRASANLAATKMSECVLGQSKRVDFCGKGYHLMSFPQXAPHGVVFLHVTYVPXQEXNFT
```

*Fig. 19C*

```
P0DTC2          TAPAICHDGKAHFPREGVFVSNGTHWFVTQRNFYEPQIITTDNTFVSGNCDVVIGIVNNT    1136
A0A6B9WHD3      TAPAICHDGKAHFPREGVFVSNGTHWFVTQRNFYEPQIITTDNTFVSGSCDVVIGIVNNT    1132
P59594          TAPAICHEGKAYFPREGVFVFNGTSWFITQRNFFSPQIITTDNTFVSGNCDVVIGIINNT    1118
Q5GDB5          TAPAICHEGKAYFPREGVFVFNGTSWFITQRNFFSPQIITTDNTFVSGNCDVVIGIINNT    1118
Q3LZX1          TAPAICHEGKAYFPREGVFVSNGTSWFITQRNFYSPQLITTDNTFVSGNCDVVIGIINNT    1105
Q3I5J5          TAPAICHEGKAYFPREGVFVSNGTSWFITQRNFYSPQIITTDNTFVAGSCDVVIGIINNT    1104
Q0Q475          TAPAICHEGKAYFPREGVFVSNGTSWFITQRNFYSPQIITTDNTFVAGNCDVVIGIINNT    1104
                *******:***:******** *** **:*****:.**:*********:*.*******:***
                TAPAICHXGKAXFPREGVFVXNGTXWFXTQRNFXXPQXITTDNTFVXGXCDVVIGIXNNT

P0DTC2          VYDPLQPELDSFKEELDKYFKNHTSPDVDLGDISGINASVVNIQKEIDRLNEVAKNLNES    1196
A0A6B9WHD3      VYDPLQPELDSFKEELDKYFKNHTSPDVDLGDISGINASVVNIQKEIDRLNEVAKNLNES    1192
P59594          VYDPLQPELDSFKEELDKYFKNHTSPDVDLGDISGINASVVNIQKEIDRLNEVAKNLNES    1178
Q5GDB5          VYDPLQPELDSFKEELDKYFKNHTSPDVDLGDISGINASVVNIQEEIDRLNEVAKNLNES    1178
Q3LZX1          VYDPLQPELDSFKEELDKYFKNHTSPDVDLGDISGINASVVNIQKEIDRLNEVAKNLNES    1165
Q3I5J5          VYDPLQPELDSFKEELDKYFKNHTSPDVDLGDISGINASVVNIQKEIDRLNEVAKNLNES    1164
Q0Q475          VYDPLQPELDSFKEELDKYFKNHTSPDVDLGDISGINASVVNIQKEIDRLNEVAKNLNES    1164
                ********************************************:***************
                VYDPLQPELDSFKEELDKYFKNHTSPDVDLGDISGINASVVNIQXEIDRLNEVAKNLNES

P0DTC2          LIDLQELGKYEQYIKWPWYIWLGFIAGLIAIVMVTIMLCCMTSCCSCLKGCCSCGSCCKF    1256
A0A6B9WHD3      LIDLQELGKYEQYIKWPWYIWLGFIAGLIAIIMVTIMLCCMTSCCSCLKGCCSCGSCCKF    1252
P59594          LIDLQELGKYEQYIKWPWYVWLGFIAGLIAIVMVTILLCCMTSCCSCLKGACSCGSCCKF    1238
Q5GDB5          LIDLQELGKYEQYIKWPWYVWLGFIAGLIAIVMVTILLCCMTSCCSCLKGACSCGSCCKF    1238
Q3LZX1          LIDLQELGKYEQYIKWPWYVWLGFIAGLIAIVMVTILLCCMTSCCSCLKGACSCGSCCKF    1225
Q3I5J5          LIDLQELGKYEQYIKWPWYVWLGFIAGLIAIVMVTILLCCMTSCCSCLKGACSCGSCCKF    1224
Q0Q475          LIDLQELGKYEQYIKWPWYVWLGFIAGLIAIVMVTILLCCMTSCCSCLKGACSCGSCCKF    1224
                *******************:***********:****:*************.*********
                LIDLQELGKYEQYIKWPWYXWLGFIAGLIAIXMVTIXLCCMTSCCSCLKGXCSCGSCCKF

P0DTC2          DEDDSEPVLKGVKLHYT     1273          (SEQ ID NO:320)
A0A6B9WHD3      DEDDSEPVLKGVKLHYT     1269          (SEQ ID NO:321)
P59594          DEDDSEPVLKGVKLHYT     1255          (SEQ ID NO:322)
Q5GDB5          DEDDSEPVLKGVKLHYT     1255          (SEQ ID NO:323)
Q3LZX1          DEDDSEPVLKGVKLHYT     1242          (SEQ ID NO:324)
Q3I5J5          DEDDSEPVLKGVKLHYT     1241          (SEQ ID NO:325)
Q0Q475          DEDDSEPVLKGVKLHYT     1241          (SEQ ID NO:326)
                *****************
                DEDDSEPVLKGVKLHYT                   (SEQ ID NO:327)
```

*Fig. 19D*

```
P0DTC2          RVQPTESIVRFPNITNLCPFGEVFNATRFASVYAWNRKRISNCVADYSVLYNSASFSTFK   378
A0A6B9WHD3      RVQPTDSIVRFPNITNLCPFGEVFNATTFASVYAWNRKRISNCVADYSVLYNSTSFSTFK   378
P59594          RVVPSGDVVRFPNITNLCPFGEVFNATKFPSVYAWERKKISNCVADYSVLYNSTFFSTFK   365
Q5GDB5          RVVPSGDVVRFPNITNLCPFGEVFNATKFPSVYAWERKKISNCVADYSVLYNSTSFSTFK   365
Q3LZX1          RVSPTQEVIRFPNITNRCPFDKVFNATRFPNVYAWERTKISDCVADYTVLYNSTSFSTFK   369
Q3I5J5          RVSPTQEVIRFPNITNRCPFDKVFNATRFPNVYAWERTKISDCVADYTVLYNSTSFSTFK   369
Q0Q475          RVTPTQEVVRFPNITNRCPFDKVFNASRFPNVYAWERTKISDCVADYTVLYNSTSFSTFK   369
                ** *: .::******** ***.:*****: * .****:*.:**:*****:*****: *****
                RVXPXXXXXRFPNITNXCPFXXXFNAXXFXXVYAWXRXXISXCVADYXVLYNSXXFSTFK

P0DTC2          CYGVSPTKLNDLCFTNVYADSFVIRGDEVRQIAPGQTGKIADYNYKLPDDFTGCVIAWNS   438
A0A6B9WHD3      CYGVSPTKLNDLCFTNVYADSFVITGDEVRQIAPGQTGKIADYNYKLPDDFTGCVIAWNS   438
P59594          CYGVSATKLNDLCFSNVYADSFVVKGDDVRQIAPGQTGVIADYNYKLPDDFMGCVLAWNT   425
Q5GDB5          CYGVSATKLNDLCFSNVYADSFVVKGDDVRQIAPGQTGVIADYNYKLPDDFMGCVLAWNT   425
Q3LZX1          CYGVSPSKLIDLCFTSVYADTFLIRSSEVRQVAPGETGVIADYNYKLPDDFTGCVIAWNT   429
Q3I5J5          CYGVSPSKLIDLCFTSVYADTFLIRSSEVRQVAPGETGVIADYNYKLPDDFTGCVIAWNT   429
Q0Q475          CYGVSPSKLIDLCFTSVYADTFLIRSSEVRQVAPGETGVIADYNYKLPDDFTGCVIAWNT   429
                ***** :** ****:.****:*:: ..:***:***:** ************ ***:***:
                CYGVSXXKLXDLCFXXVYADXFXXXXXXVRQXAPGXTGXIADYNYKLPDDFXGCVXXWNX
                                                                          NX

P0DTC2          NNLDSKVGGNYNYLYRLFRKSNLKPFERDISTEIYQAGSTPCNGVEGFNCYFPLQSYGFQ   498
A0A6B9WHD3      KHIDAKEGGNFNYLYRLFRKANLKPFERDISTEIYQAGSKPCNGQTGLNCYYPLYRYGFY   498
P59594          RNIDATSTGNYNYKYRYLRHGKLRPFERDISNVPFSPDGKPCTPP-ALNCYWPLNDYGFY   484
Q5GDB5          RNIDATSTGNYNYKYRYLRHGKLRPFERDISNVPFSPDGKPCTPP-APNCYWPLNGYGFY   484
Q3LZX1          AKHDT---G--NYYYRSHRKTKLKPFERDLSSDD--------------GNGVYTLSTYDFN   471
Q3I5J5          AKQDQ---G--QYYYRSHRKTKLKPFERDLSSD---------------ENGVRTLSTYDFY   470
Q0Q475          AQQDQ---G--QYYYRSYRKEKLKPFERDLSSD---------------ENGVYTLSTYDFY   470
                 : *    *  :* **  *: :*:*****:*.                *    *  *:*
                XXXDXXXXGXXXYXYRXXRXXXLXPFERDXSXXXXXXXXXXXXXXXXXXXNXXXXLXXYXFX
                XXXDXXXXGXXXYXYRXXRXXXLXPFERDXSXXXXXXXXXXXXXXXXXXXNXXXXLXXYXFX

P0DTC2          PTNGVGYQPYRVVVLSFELLHAPATVCGPKKSTNLVKNKCVNF    541 (SEQ ID NO:328)
A0A6B9WHD3      PTDGVGHQPYRVVVLSFELLNAPATVCGPKKSTNLVKNKCVNF    541 (SEQ ID NO:329)
P59594          TTTGIGYQPYRVVVLSFELLNAPATVCGPKLSTDLIKNQCVNF    527 (SEQ ID NO:330)
Q5GDB5          TTSGIGYQPYRVVVLSFELLNAPATVCGPKLSTDLIKNQCVNF    527 (SEQ ID NO:331)
Q3LZX1          PNVPVAYQATRVVVLSFELLNAPATVCGPKLSTELVKNQCVNF    514 (SEQ ID NO:332)
Q3I5J5          PSVPVAYQATRVVVLSFELLNAPATVCGPKLSTQLVKNQCVNF    513 (SEQ ID NO:333)
Q0Q475          PSIPVEYQATRVVVLSFELLNAPATVCGPKLSTQLVKNQCVNF    513 (SEQ ID NO:334)
                 .   : :*  **********:********** **:*:**:****
                XXXXXXXQXXRVVVLSFELLXAPATVCGPKXSTXLXKNXCVNF        (SEQ ID NO:335)
                XXXXXXXQXX                                         (SEQ ID NO:336)
```

*Fig. 20*

SARS-COV-2 VARIANT NANOBODIES AND CONSTRUCTS COMPRISING SUCH NANOBODIES

STATEMENT OF GOVERNMENT INTEREST

This invention was made with Government support under Contract No. DE-NA0003525 awarded by the United States Department of Energy/National Nuclear Security Administration. The U.S. Government has certain rights in the invention.

REFERENCE TO A SEQUENCE LISTING APPENDIX

A sequence listing appendix including an ASCII formatted file accompanies this application. The appendix includes a file named "SD-16033_ST25.txt," created on Jun. 3, 2022 (size of 291 kilobytes), which is hereby incorporated by reference in its entirety.

FIELD OF THE INVENTION

The present disclosure relates to nanobodies, a portion of an antibody including a heavy chain portion and having a binding domain that binds to a coronavirus (e.g., SARS-COV-2 or a portion thereof). Methods of using such antibodies are also described herein, such as methods of treating, prophylactically treating, or delaying the progression of a disease associated with a coronavirus.

BACKGROUND

The novel respiratory virus, severe acute respiratory syndrome coronavirus 2 (SARS-CoV-2), has infected hundreds of millions and killed millions of people worldwide, causing the worst global health crisis since the 1918-1919 influenza pandemic. In addition to the lives lost to COVID-19, this virus has wreaked havoc on the global economy and highlighted the threat that emerging diseases pose to global security. Work is ongoing to develop effective vaccines for pre-exposure prophylaxis, and to create new treatments to prevent and mitigate severe disease.

Viral neutralizing antibodies are an effective therapeutic intervention for COVID-19, as the current pandemic response has shown. High titer convalescent plasma has been used for the treatment of hospitalized patients early in the disease course and/or with impaired humoral immunity; however, batch-to-batch variability results in various levels of success, limiting its reliability as a treatment. Monoclonal antibody therapies, like convalescent plasma, block cell entry, the first step of virus infection, but consist only of highly neutralizing antibodies with high target specificity, and more favorable pharmacokinetics. Recently, promising clinical trial data demonstrated that a single intravenous infusion of monoclonal antibody (mAb) cocktail significantly reduced COVID-19 related hospitalization and death in comparison to placebo. Methods for improved development and characterization of novel neutralizing antibodies can be part of a toolset to combat the COVID-19 pandemic and future epidemics, by providing lower cost, easier manufacturability, and diverse functionality, including response to emerging variants.

SUMMARY

This disclosure relates to use of an isolated or purified nanobody, or a construct comprising such nanobody, that binds to a SARS-COV-2 variant or a portion thereof (e.g., the spike protein or receptor-binding domain (RBD) of the spike protein). These nanobodies were identified through data mining and testing samples from a library screening process of a highly diverse library of nanobodies. This process is also very rapid in comparison to other techniques, which makes it effective in quickly finding therapeutics to SARS-COV-2 variants or other viruses.

Once the protein sequence, or genetic coding, of a virus has been identified, a nanobody-based countermeasure can be developed within 90 days. Speeding up the discovery of neutralizing antibodies could reduce the impact of future viral outbreaks.

Under current practice, virologists rely upon patients' blood samples to build an antibody library that we can then screen for potential treatments. This means researchers have to wait, either for people to become infected or for those who are vaccinated to build an immune response. With the approach utilized herein, researchers can begin to screen for extremely potent neutralizing nanobodies as soon as the genetic coding of a virus has been identified.

Neutralizing nanobodies represent an attractive strategy due to their ability to work effectively against an entire family of viruses or variants. Virus families tend to interact with immune response in the same way. Thus, nanobody treatments can be rapidly adaptable to all variants of a virus.

In an embodiment, the nanobody constructs disclosed herein for SARS-COV-2 are modular and can be engineered to bind to multiple different places on the virus and induce a more effective immune response. Modular nanobodies can be combined with other nanobodies to increase their ability to bind to the virus or target specific tissues. Nanobodies can also be produced as smaller versions of conventional antibodies with the ability to engage the immune response. That is they may include the heavy chain component of an antibody and also include the Fc chain component.

Additionally, due to the small size of the nanobodies, they can be released into the blood and penetrate tissues more thoroughly than conventional antibodies. Nanobody therapies can also target an infection site directly, decreasing the dose needed and increasing efficacy.

Nanobodies can also be administered via aerosol, so they can be given to a patient orally or in an inhalable form. Conventional antibody treatments are less versatile and must be received through injection only.

These qualities and features of nanobodies make nanobody therapies potentially much more effective than current solutions. These treatments are also easier and cheaper to manufacture.

In particular, in an embodiment provided herein is a nanobody or construct comprising a nanobody that comprises: a first binding domain, wherein the first binding domain comprises: a first complementarity determining region comprising a polypeptide sequence having at least 90% sequence identity to any one of SEQ ID NOs: 1-59; a second complementarity determining region comprising a polypeptide sequence having at least 90% sequence identity to any one of SEQ ID NOs: 60-118; and a third complementarity determining region comprising a polypeptide sequence having at least 90% sequence identity to any one of SEQ ID NOs: 119-177.

In an embodiment, a construct comprises: a nanobody and an Fc domain and hinge region of human IgG1 protein, the construct comprising: a nanobody comprising a first framework region (FR1) coupled to a first complementarity determining region (CDR1), a second framework region (FR2) coupled to the first complementarity determining region (CDR1) and a second complementarity determining region (CDR2), a third framework region (FR3) coupled to the second complementarity determining region (CDR2) and a third complementarity determining region (CDR3), and a fourth framework region (FR4) coupled to the third complementary determining region (CDR3); the first complementarity determining region comprising a polypeptide sequence having at least 90% sequence identity to any one of SEQ ID NOs: 1-59; the second complementarity determining region comprising a polypeptide sequence having at least 90% sequence identity to any one of SEQ ID NOs: 60-118; and the third complementarity determining region comprising a polypeptide sequence having at least 90% sequence identity to any one of SEQ ID NOs: 119-177; and the nanobody is coupled to the hinge region of the Fc domain.

In an embodiment, a method for treating or prophylactically treating a SARS-Cov-2 viral infection, comprises the steps of: administering a pharmaceutically acceptable composition comprising an isolated or purified nanobody or a construct comprising the nanobody to a patient in need thereof. The nanobody comprises: a first complementarity determining region comprising a polypeptide sequence having at least 90% sequence identity to any one of SEQ ID NOs: 1-59; a second complementarity determining region comprising a polypeptide sequence having at least 90% sequence identity to any one of SEQ ID NOs: 60-118; and a third complementarity determining region comprising a polypeptide sequence having at least 90% sequence identity to any one of SEQ ID NOs: 119-177.

In some embodiments, the nanobody or construct comprising the nanobody further includes: a first framework region attached to an N-terminus of the first complementarity determining region; a second framework region disposed between the first and second complementarity determining regions; a third framework region disposed between the second and third complementarity determining regions; and a fourth framework region attached to a C-terminus of the third complementarity determining region.

In other embodiments, the first framework region includes a polypeptide sequence having at least 90% sequence identity to any one of SEQ ID NOs: 213-217. In yet other embodiments, the second framework region includes a polypeptide sequence having at least 90% sequence identity to any one of SEQ ID NOs: 244-248. In other embodiments, the third framework region includes a polypeptide sequence having at least 90% sequence identity to any one of SEQ ID NOs: 285-289. In yet other embodiments, the fourth framework region includes a polypeptide sequence having at least 90% sequence identity to any one of SEQ ID NOs: 302-307.

In an embodiment, the nanobody comprises a polypeptide sequence having at least 90% sequence identity to any one of SEQ ID NOs: 340-398.

In some embodiments, the antibody or construct comprising such further includes a linker disposed between the first and second binding domains. Non-limiting linkers include any described herein, such as SEQ ID NOs: 310-319.

In any embodiment herein, the nanobody or construct comprising such further includes a therapeutic agent or a diagnostic agent attached directly or indirectly to the first binding domain.

In a second aspect, the present disclosure features a method of treating or prophylactically treating a viral infection. In some embodiments, the method includes: administering an isolated or purified nanobody or construct comprising such (e.g., any described herein) to a subject in need thereof. In other embodiments, the isolated or purified antibody or construct comprising such is provided as a pharmaceutical composition having a pharmaceutically acceptable carrier (e.g., as described herein). Such a composition can be provided as a medication (e.g., a vaccine optionally including any useful adjuvant).

In some embodiments, the viral infection includes an infection from a coronavirus. In other embodiments, the coronavirus is SARS-COV-2 or a variant thereof. A variant as used herein includes mutated versions.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified." as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Examples of stringent conditions are described in detail in Tijssen (1993), Laboratory Techniques In Biochemistry And Molecular Biology-Hybridization With Nucleic Acid Probes Part 1. Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T. "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9.

By "protein," "peptide," or "polypeptide." as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" means a portion of a nucleic acid or a polypeptide that is at least one nucleotide or one amino acid shorter than the reference sequence. This portion contains, preferably, at least about 85%, 95%, or 99% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 90%, about 95%, about 97%, about 98%, about 99%, or about 100%) identical to any of the sequences described herein. In certain embodiments, a polypeptide disclosed herein includes 2, 3, 4, 5, 6, 7, 8, 9, 10, or more mutations (e.g., one or more conservative amino acid substitutions, as described herein). In yet another example, any nucleic acid fragment can include a stretch of at least about 5, about 10, about 28, about 30, or more nucleotides that are at least about 80%, about 90%, about 95%, about 87%, about 98%, about 99%, or about 100% identical to any of the sequences described herein.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val. V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined within the skill in the art, for instance, by the BLAST (Basic Local Alignment Search Tool; Altschul S F et al., J. Mol. Biol. 1990; 215:403-10). This algorithm is accessible using publicly available computer software such as "Best Fit" (Smith T F et al., Adv. Appl. Math. 1981; 2(4):482-9) as incorporated into GeneMatcher Plus TM. In addition, those skilled in the art can determine appropriate parameters for measuring alignment, including any algorithms needed to achieve optimal alignment over the length of the sequences being compared. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an antiviral agent, an effective amount of an agent is, for example, an amount sufficient to achieve a reduction in viral load or a mitigation of a symptom related to a viral infection or a delay in a symptom related to a viral infection, as compared to the response obtained without administration of the agent.

By "subject" or "patient" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and/or remission (whether partial or total), whether detectable or undetectable.

By "attached," "attaching." "attachment," or related word forms is meant any covalent or non-covalent bonding interaction between two components. Non-covalent bonding interactions include, without limitation, hydrogen bonding, ionic interactions, halogen bonding, electrostatic interactions, $\pi$ bond interactions, hydrophobic interactions, inclusion complexes, clathration, van der Waals interactions, and combinations thereof.

The term "EC50" means the amount to obtain a response effectiveness that is 50% of maximal response.

The term "RBD" means a receptor-binding domain (RBD). An RBD is a short immunogenic fragment from a virus that binds to a specific endogenous receptor sequence to gain entry into host cells. It refers to a part of the 'spike' glycoprotein (S-domain) that is needed to interact with endogenous receptors to facilitate membrane fusion and delivery to the cytoplasm. Typically, the S-domain is also the site of neutralizing antibodies.

"Binding affinity" is measured and reported herein by the equilibrium dissociation constant (KD), which is used to evaluate and rank order strengths of bimolecular interactions. The smaller the KD value, the greater the binding affinity of the ligand for its target.

BRIEF DESCRIPTION OF THE DRAWINGS

FIGS. 13A and 13B provides example sequences for CDRs, including sequences for complementarity determining region 1 (CDR1, SEQ ID NOs: 1-59), complementarity determining region 2 (CDR2, SEQ ID NOs:60-118), and complementarity determining region 3 (CDR3, SEQ ID NOs: 119-177).

FIG. 14 is an example schematic of an antibody having framework regions (FRs) interspersed with complementarity determining regions (CDRs), in which a nanobody can include framework regions 1-4 (FR1, FR2, FR3, and FR4) with interspersed CDR1, CDR2, and CDR3.

FIGS. 15A-15E provides example nanobody sequences corresponding to SEQ ID NOs: 340-398.

FIG. 16 lists sequences for framework regions FR1, FR2, FR3, and FR4 (SEQ ID NOS. 405-408, respectively), FIG. 17 provides additional example sequences for framework regions FR1, FR2, FR3, and FR4.

FIGS. 18A-18D provide (A) a sequence alignment of example FR1 sequences (SEQ ID NOs: 190-212) and example consensus sequences (SEQ ID NOs:213-217); (B) a sequence alignment of example FR2 sequences (SEQ ID NOs:220-243) and example consensus sequences (SEQ ID NOs:244-248); (C) a sequence alignment of example FR3 sequences (SEQ ID NOs:250-284) and example consensus sequences (SEQ ID NOs:285-289); and (D) a sequence alignment of example FR4 sequences (SEQ ID NOs:290-301) and example consensus sequences (SEQ ID NOs:302-307).

FIGS. 19A-19D show a sequence alignment of example sequences for spike glycoproteins (SEQ ID NOs: 320-326) and an example consensus sequence (SEQ ID NOs: 327).

FIG. 20 shows a sequence alignment of example sequences for RBDs of spike glycoproteins (SEQ ID NOs: 328-334) and example consensus sequences (SEQ ID NOs: 335-336).

DETAILED DESCRIPTION

This disclosure relates to an isolated or purified nanobody or a construct comprising such nanobody that binds to SARS-COV-2, particularly a variant thereof, or a portion thereof (e.g., the spike protein or receptor-binding domain (RBD) of the spike protein). In an embodiment, the nanobody is bound to a humanized Fc.

From a large and highly diverse synthetic library that was designed to find highly potent nanobodies that are both easier to manufacture and more accessible to certain proteins and smaller tissues than conventional antibodies, the nanobodies disclosed herein were identified and tested.

The large and highly diverse nanobody library was constructed and screened against multiple variants of SARS-COV-2 to find nanobodies with high sensitivity and specificity for the variants. Four rounds of positive selection against a panel of six diverse SARS-COV-2 variant RBDs was performed with our high-diversity. At least 59 of these nanobodies were found to work well against Alpha, Beta, Gamma, Delta, Kappa, Lambda and Mu with some overlap efficacy against other variants. These nanobodies have efficacy as stand-alone nanobodies and as a construct comprising nanobodies linked to the human IgG1 constant fragment (Fc) (nanobody-huFc constructions or nb-huFcs) to make enhanced humanized sdAbs with all the attributes of nanobodies with improved half-life and optimized effector functions.

The binding affinity and specificity of the nanobody-huFc constructs was evaluated and a subset of nanobodies with significant and specific affinity for their respective RBD were tested for neutralization of VSV-SARS-COV-2 GFP with Spike from the original Wuhan, Alpha, Beta, Gamma, Delta, Lambda and Mu variants.

Several nanobody-hFcs were tested by ELISA for binding affinity to the Omicron RBD and two of these demonstrated significant affinity for the Omicron variant RBD and neutralization of VSV-SARS-COV-2 GFP with Spike from Omicron variant.

Thus far, several promising nanobodies that neutralize the original SARS-COV-2 and several of its variants have been identified, including Delta and Omicron, with high efficacy.

As disclosed herein, CDRs were identified that provide enhanced efficacy, as determined by reducing infectivity of a coronavirus and/or exhibiting binding to the coronavirus. Such CDRs can be provided in an antibody having a useful format, such as a nanobody, either separate or joined to a human Fc or other forms described herein.

Figure 1:
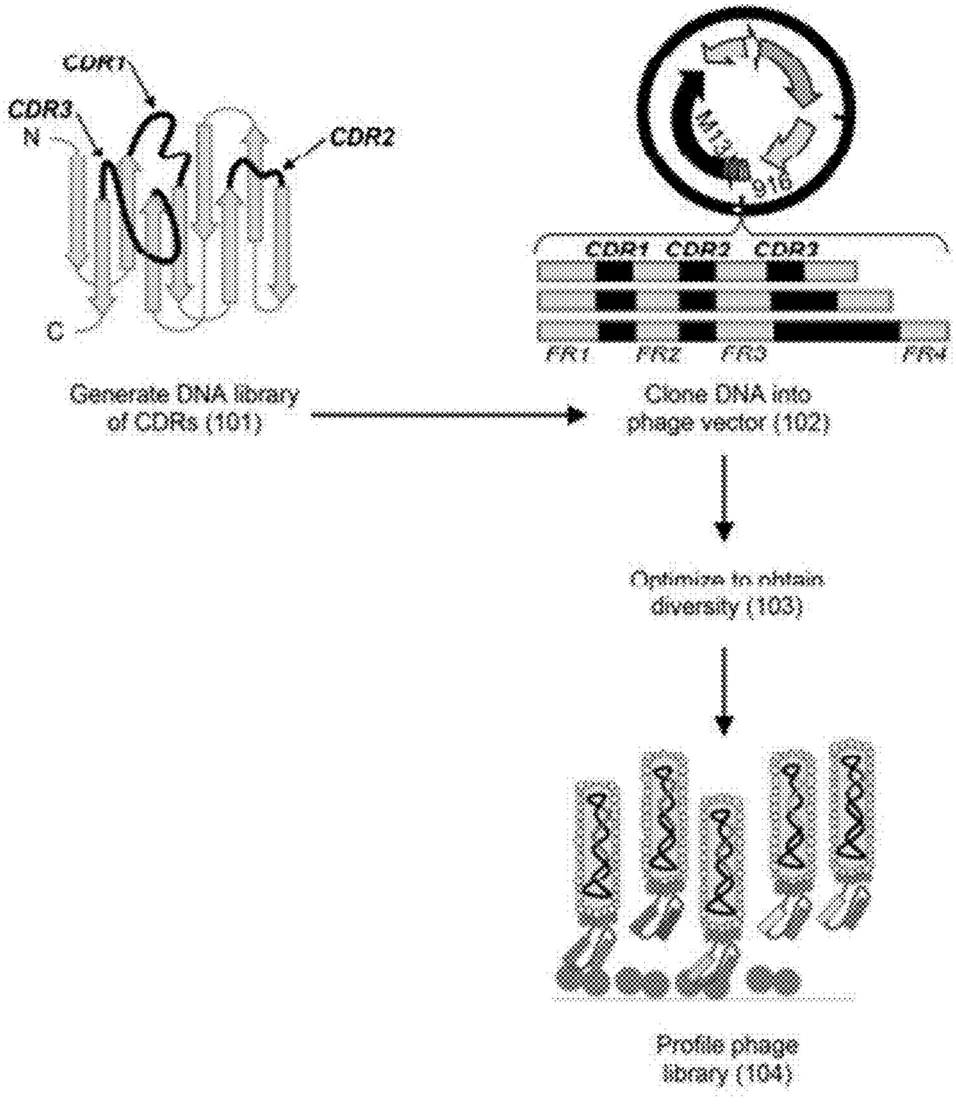
FIG. 1 is a schematic of an example method for developing a library of nanobodies.

CDRs for the nanobody were identified starting with a using a phage library (FIG. 1). FIG. 1 shows a description of how the library was constructed. The library incorporated both the diversity and prevalence of amino acids at key positions in each of the CDR1 and CDR2 derived from a single domain antibody (sdAb) database. This database contained sequences of validated sdAbs or nanobodies from both synthetic and natural sources from both naïve and immune repertoires. Components of the database were curated using sequences derived from existing databases (Protein Data Bank and NCBI) and publications.

Such a library can be constructed by generating 101 a DNA library of CDRs with high diversity, cloning 102 the DNA into a phage vector to express nanobodies as fusion proteins with the phage coat protein, optimizing 103 the transformation to obtain phages having sufficient diversity, and profiling 104 the phage library by sequencing. Diversity can include distribution in both the amino acid content and the length of the CDRs.

The selections from the phage library can be screened. Such screening can include testing by various assays, including a competition enzyme-linked immunosorbent assay (ELISA), a binding assay with the coronavirus or a portion thereof (e.g., SARS-COV-2, the spike protein of SARS-COV-2, or the RBD of SARS-COV-2), a competition assay including the coronavirus (or a portion thereof) and a target of the coronavirus (e.g., human ACE2 or another receptor that binds to SARS-COV-2), and/or a neutralization assay including coronavirus-expressing cells.

Further information on the library is disclosed in the Examples section and in the publication Stefan M A, Light Y K, Schwedler J L, McIlroy P R, Courtney C M, Saada E A, Thatcher C E, Phillips A M, Bourguet F A, Mageeney C M, McCloy S A, Collette N M, Negrete O A, Schoeniger J S, Weilhammer D R, Harmon B. *Development of potent and effective synthetic SARS-COV-*2 *neutralizing nanobodies*. MAbs. 2021 January-December; 13(1):1958663 (published online Aug. 4, 2021), incorporated herein by reference.

The CDRs from the screening process can be provided in the form of an antibody. The antibody can have a useful form, such as one or more of the following domains: a single variable domain (VHH) or nanobody, a variable heavy domain (VH), a variable light domain (VL), a single-chain variable-fragment (scFv) antibody, a monoclonal antibody (mAb), an antigen-binding fragment (Fab), a fragment crystallizable region (Fc region), a heavy-chain only antibody (HcAb), an Immunoglobulin G (IgG) antibody, as well as bivalent, trivalent, tetravalent, multivalent, biparatropic, bispecific, multispecific chimeric, and humanized forms thereof. Any of the forms can include a linker between a first amino acid sequence (any domain herein, e.g., such as VH) and a second amino acid sequence (any domain herein, e.g. such as VL).

The constructs herein can be employed as a nanobody, alone or bound to a human Fc domain or humanized Fc domain. In some embodiments, the nanobody can include a single VHH domain. In other embodiments, the nanobody can include a plurality of VHH domains, in which each VHH domain can be the same or different. Furthermore, each VHH domain can bind to the same target, the same portion of the same target, different targets, or different portions of the same target. Non-limiting targets are described herein.

Fc Domains and Hinge One or more VHH domains can be fused to a useful amino acid sequence, such as a Fc domain or a humanized Fc domain. The VHH domains can be fused to other humanized forms of constant domains, such as Fc, CH1, CH2, CH3, and CL domains. Such VHH domains can also be fused to other forms, such as IgG1, IgG3, IgA, or IgM.

Yet other forms can include an Fc region and a Fab; or an Fc region and a VHH. The Fc region can include heavy chains present in any useful isotype (A, E, G, or M), such as Immunoglobulin G (e.g., IgG1, IgG2a, or lgG3). The Fab region can include domains from the heavy chains, including the variable heavy (VH) domains. Within the VH domain, CDRs can be configured to bind to a target of interest. The VHH domain can include CDRs configured to bind to a target of interest.

The Fc region of the constructs herein can include a native immunoglobulin, i.e., as formed by the dimeric association of the respective Fc domains (or Fc moieties) of its two heavy chains, in which a native Fc region is homodimeric and comprises two polypeptide chains; or a genetically-fused Fc region or a single-chain Fc region (scFc region), in which a synthetic dimeric Fc region comprised of Fc domains (or Fc moieties) are genetically linked within a single polypeptide chain (i.e., encoded in a single contiguous genetic sequence) as described. In one embodiment, the construct includes a complete Fc region, whether present as one polypeptide chain (an scFc molecule) or in the wild-type form as two polypeptide chains.

The Fc region can include a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In an embodiment, the Fc region includes an upper hinge, a core, and a lower hinge, connected in that order. The upper hinge is connected to the FR4 region of the nanobody and the lower hinge is connected to the human Fc region. These components may have the following sequences presented in Table 1, or a sequence having at least 90% sequence identity, such as at least 95%, or at least 98% sequence identity. In an exemplary embodiment, a nanobody coupled to a human Fc region is in accordance with SEQ ID NO. 400. In SEQ ID No. 400, the upper hinge corresponds to SEQ ID No. 401, the core is SEQ ID NO. 402, the lower hinge corresponds to SEQ ID NO. 403, and the human Fc region is SEQ ID No. 404.

TABLE 1

| Description | SEQ ID No. | Sequence |
|---|---|---|
| Example Nanobody coupled to human Fc Region | 400 | EVQLQASGGGFVQPGGSLRLSCAASGGTSG EYDMGWFRQAPGKEREFVSAISHWDGKATA YYADSVKGRFTISRDNSKNTVYLQMNSLRA EDTATYYCAARLDDEIDFYWGQGTQVTVSS AEPKSCDKTHTCPPCPAPELLGGPSVFLFP PKPKDTLMISRTPEVTCVVVDVSHEDPEVK FNWYVDGVEVHNAKTKPREEQYNSTYRVVS VLTVLHQDWLNGKEYKCKVSNKALPAPIEK TISKAKGQPREPQVYTLPPSRDELTKNQVS |

TABLE 1-continued

| Description | SEQ ID No. | Sequence |
|---|---|---|
| | | LTCLVKGFYPSDIAVEWESNGQPENNYKTT PPVLDSDGSFFLYSKLTVDKSRWQQGNVFS CSVMHEALHNHYTQKSLSLSPGK |
| Upper Hinge | 401 | EPKSCDKTHT |
| Core | 402 | CPPC |
| Lower Hinge | 403 | PAPELLGGP |
| Human Fc Region | 404 | SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYTLPPSRDEL TKNQVSLTCLVKGFYPSDIAVEWESNGQPE NNYKTTPPVLDSDGSFFLYSKLTVDKSRWQ QGNVFSCSVMHEALHNHYTQKSLSLSPGK |

The Fc domains or moieties of a polypeptide may be from any isotype (A, E, G, or M) and may be derived from different immunoglobulin molecules. For example, an Fc domain or moiety of a polypeptide may comprise a CH2 and/or CH3 domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

The constructs herein can be modified antibodies, which includes synthetic forms of antibodies which are altered such that they are not naturally occurring, e.g., antibodies that comprise at least two heavy chain portions but not two complete heavy chains (such as, domain deleted antibodies or minibodies); engineered antibodies having synthetic linkers, such as any described herein; and multispecific forms of antibodies (e.g., bispecific, trispecific, etc., forms of any antibody, such as a nanobody) altered to bind to two or more different antigens, e.g., to the RBD of a coronavirus and another therapeutically relevant target binding site.

Modified antibodies can include other types of modifications, such as chemical modification (e.g., pegylation, glycosylation, lipidation, etc.), attachment to a particle or liposome, or bonding to a protein (e.g., a serum protein, a cytokine) or a cell (e.g., a CAR-T cell).

The constructs herein can be "chimeric" or "fusion" proteins. Such proteins comprise a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created using methods well known in the art, for example, by chemical synthesis, or by creating and translating a polynucleotide in which the peptide regions are encoded in the desired relationship.

Linkers

Such forms or fusions can include a linker disposed between any number of domains, in which non-limiting linkers are described herein. Any useful linker can be employed, such as a peptide linker that can be cleavable or non-cleavable. Linkers can include or consist of a sequence according to the formula $[(Gly)_m(Ser)]_n(Gly)_p$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. Alternatively, the linker sequence includes or consists of a sequence according to the formula $(Gly)_p[(Ser)(Gly)_m]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In another embodiment, the linker sequence includes or consists of a sequence according to the formula $[(Gly)_m(Ser)(Gly)_p]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p-0, 1, 2, 3, or 4. Further non-limiting linkers include any described herein, such as in SEQ ID NOs: 310-319 (Table 2).

TABLE 2

Example linkers

| Name | Sequence | SEQ ID NO: |
|---|---|---|
| $G_3$ | GGG | 310 |
| $G_3S$ | GGGS | 311 |
| $G_4$ | GGGG | 312 |
| $G_4S$ | GGGGS | 313 |
| $G_2SG$ | GGSG | 314 |
| $(G_4S)_2$ | GGGGSGGGGS | 315 |
| $(G_4S)_3$ | GGGGSGGGGSGGGGS | 316 |
| $(G_4S)_4$ | GGGGSGGGGSGGGGSGGGGS | 317 |
| $(G_2SG)_2$ | GGSGGGSG | 318 |
| $(G_2SG)_3$ | GGSGGGSGGGSG | 319 |

The constructs can include other variations. Such variations can include one or more amino acids that facilitate humanization of an initial sequence. Humanization can include use of one or more amino acids present in a human form of the constant or variable regions (e.g., frameworks regions or CDRs). In other embodiments, the variation can include a sequence that lacks Cys and Met residues. In yet other embodiments, the CDR can have an altered length, such as a length from about 4-9 amino acids, 9-12 amino acids, or 12-15 amino acids.

In an embodiment, the nanobody or construct comprising the nanobody can bind a target (e.g., any described herein), in which such binding can be characterized by titration enzyme-linked immunosorbent assay (ELISA) resulting in a dissociation constant ($K_d$) of about 0.05 nM to 1 μM, such as 0.05 nM to 3.25 nM for binding with SARS-COV-2 Beta RBD, or 0.2 to 3.31 nM. In an embodiment, the nanobody or construct comprising the nanobody can bind a target (e.g., any described herein) and this binding can be characterized by in vitro neutralization assay against SARS-COV spike pseudotyped virus resulting in a half maximal effective concentration (EC50) of about 0.025-100 nM, such as 0.1 to 10 nM for SARS-COV Beta spike pseudotyped virus, or 1.0 nM to 14.6 for SARS-COV Delta spike pseudotyped virus.

In an embodiment, a nanobody disclosed herein or a nanobody construct including a nanobody disclosed herein has an EC50 against a coronavirus, such as SARS-COV-2, including variants thereof of 10 micrograms/mL or less, such as, for example, 1.3 micrograms/mL or less, or 0.15 micrograms/mL, or less than 0.1 micrograms/mL. In an embodiment, a nanobody disclosed herein has a molecular weight of 20 kDa to 10 kDa, such as 16 kDa to 12 kDa, or 15 kDa to 11 kDa.

Test conditions are incorporated by reference herein from the same or similar tests reported in Stefan M A, Light Y K. Schwedler J L, McIlroy P R. Courtney C M, Saada E A, Thatcher C E. Phillips A M, Bourguet F A. Mageeney C M, McCloy S A, Collette N M, Negrete O A, Schoeniger J S, Weilhammer D R, Harmon B. *Development of potent and effective synthetic SARS-COV-2 neutralizing nanobodies*. MAbs. 2021 January-December; 13(1): 1958663 (published online Aug. 4, 2021).

Through the library screening process and testing disclosed herein, 59 nanobodies comprising 177 CDRs were identified as being active against one or more SARS-COV-2 variants.

In one embodiment, the binding domain includes or is a polypeptide sequence having at least 80% sequence identity to any one of SEQ ID NOs: 1-177 (FIGS. 13A-13B), such as at least 85%, or at least 90% sequence identity. Examples of fragments can include a polypeptide that is one amino acid shorter than the reference sequence of SEQ ID NOs: 1-177. In an embodiment, the omitted amino acid can be removed from the C-terminus. This omission or others can also be covered as an absent amino acid under a percent sequence identity calculation.

In an embodiment, a nanobody or construct comprising a nanobody, comprises a first binding domain, wherein the first binding domain comprises: a first complementarity determining region comprising a polypeptide sequence having at least 80% sequence identity to any one of SEQ ID NOs: 1-59; a second complementarity determining region comprising a polypeptide sequence having at least 80% sequence identity to any one of SEQ ID NOs: 60-118; and a third complementarity determining region comprising a polypeptide sequence having at least 80% sequence identity to any one of SEQ ID NOs: 119-177.

The construct can include one or more binding domains. The binding domain can also be characterized by its binding affinity to a binding sequence. The terms “binding sequence,” “binding domain,” or “binding site”, as used herein, refer to the portion, region, or site of polypeptide that mediates specific binding with a target molecule (e.g., a SARS-COV-2 as the target, including the spike protein or RBD thereof). Exemplary binding domains include an antigen binding site (e.g., a VHH or VH domain) or molecules comprising such a binding site (e.g., an antibody or a single domain antibody). A plurality of CDRs can be taken together to form a binding domain for the nanobody or construct, such as CDR1, CDR2, and CDR3.

In an embodiment, within the variable domain of the nanobody, three CDRs can be present. The CDRs can include a first CDR, a second CDR, and a third CDR. Any of these CDRs can be a polypeptide sequence having at least 80% sequence identity to any of SEQ ID NOs: 1-177 (FIGS. 13A and 13B), such as 85%, or 90% sequence identity. A fragment can be covered by the at least 80% sequence identity, for example, including a polypeptide that is one, two, or three amino acids shorter than the reference sequence of any of SEQ ID NOs: 1-177. The omitted amino acid(s) can be removed from the C-terminus and/or the N-terminus. Omitted amino acid(s) can also be included under the sequence identity percentage.

The nanobodies can be arranged in a structure including the CDRs disclosed herein, and corresponding to the structure disclosed in FIG. 14. Such nanobody sequences include framework regions FR1, FR2, FR3, and FR4, and CDR1, CDR2, and CDR3. In an embodiment, a nanobody construct comprises CDRs and framework regions (FRs). As can be seen, each CDR can be disposed between two FRs. An exemplary construct can include framework region 1 (FR1) attached to an N-terminus of CDR1; FR2 disposed between CDR1 and CD2; FR3 disposed between CDR2 and CDR3; and FR4 attached to a C-terminus of CDR3. Examples of sequences for CDR1, CDR2, and CDR3 include, e.g., any sequences for first CDR, second CDR, and third CDR, respectively, as described herein.

In an embodiment, the nanobody has a structure corresponding to FIG. 14 and comprises a polypeptide sequence having at least 90% sequence identity (such as at least 95% or at least 98%) to any one of SEQ ID NOs: 340-398 (FIGS. 15A-15E). In another embodiment, the FR regions of the nanobody can be selected from those disclosed below, but the CDR regions are selected from those in any one of SEQ ID NOs: 340-398 (CDRs are shown in bold). Such nanobodies have usefulness as being active against a coronavirus, such as, SARS-COV-2, including the original Wuhan strain, and subsequent variants, Alpha, Beta, Gamma, Delta, Lambda, Mu, and Omicron.

In an embodiment, the nanobodies disclosed herein are active against the SARS-COV-2 Omicron variant, and the nanobody is a polypeptide sequence having at least 90% sequence identity (such as at least 95% or at least 98%) to any one of SEQ ID NOs. 350-354, 367, 369, 371, 374, 375, 379, 385, 387, 388, or 393.

In an embodiment, the nanobodies disclosed herein are active against the SARS-COV-2 Delta variant, and the nanobody is a polypeptide sequence having at least 90% sequence identity (such as at least 95% or at least 98%) to any one of SEQ ID Nos. 359 to 398.

In an embodiment, the nanobodies disclosed herein are active against the SARS-COV-2 Gamma variant, and the nanobody is a polypeptide sequence having at least 90% sequence identity (such as at least 95% or at least 98%) to any one of SEQ ID Nos. 364, 367, 371, 385, 389, or 392.

In an embodiment, the nanobodies disclosed herein are active against the SARS-COV-2 Mu variant, and the nanobody is a polypeptide sequence having at least 90% sequence identity (such as at least 95% or at least 98%) to any one of SEQ ID Nos. 350, 367, 369, 381, 385, 389, 393, or 394.

In an embodiment, the nanobodies disclosed herein are active against the SARS-COV-2 Alpha strain, and the nanobody is a polypeptide sequence having at least 90% sequence identity (such as at least 95% or at least 98%) to any one of SEQ ID Nos. 350, 360-362, 364, 367, 369, 371, 379, 380, 381, 385, 389, 393, or 394.

In an embodiment, the nanobodies disclosed herein are active against the SARS-COV-2 Beta variant, and the nanobody is a polypeptide sequence having at least 90% sequence identity (such as at least 95% or at least 98%) to any one of SEQ ID Nos. 360, 364, 367, 369, 385, 389, 392, or 393.

In an embodiment, the nanobodies disclosed herein are active against the SARS-COV-2 Lambda variant, and the nanobody is a polypeptide sequence having at least 90% sequence identity (such as at least 95% or at least 98%) to any one of SEQ ID NOs. 359, 361-369, 373, 374, 376, or 379-398.

In an embodiment, a nanobody is part of a construct comprising: a nanobody and an Fc domain and hinge region of human IgG1 protein. The nanobody comprises a first framework region coupled to a first complementarity determining region, a second framework region coupled to the first complementarity determining region and a second complementarity determining region, a third framework region coupled to the second complementarity determining region and a third complementarity determining region, and a fourth framework region coupled to the third complementary determining region. The first complementarity determining region comprises a polypeptide sequence having at least 80% sequence identity (such as at least 85% or at least 90%) to any one of SEQ ID NOs: 1-59; the second complementarity determining region comprising a polypeptide sequence having at least 80% sequence identity (such as at least 85% or at least 90%) to any one of SEQ ID NOs: 60-118; and the third complementarity determining region comprising a polypeptide sequence having at least 80% sequence identity (such as at least 85% or at least 90%) to any one of SEQ ID NOs: 119-177. The nanobody is coupled to the hinge region of the Fc domain.

FIG. 16 lists sequences for framework regions FR1, FR2, FR3, and FR4 (SEQ ID NOs. 405-408, respectively), which are disposed adjacent and/or between the regions indicated as CDR1, CDR2, and CDR3 as shown in FIG. 14. These framework regions are utilized in the examples herein.

FIG. 17 lists additional sequences for framework regions FR1, FR2, FR3, and FR4, which are disposed adjacent and/or between regions indicated as CDR1, CDR2, and CDR3 as shown in FIG. 14. SEQ ID NOs: 180-182 provide consensus sequences, in which each X in SEQ ID NOS: 180-182 can be an amino acid in any one of SEQ ID NOs: 183-186 when any one of the sequences in SEQ ID NOs: 183-186 is used as a reference sequence to be optimally aligned with one of SEQ ID NOs: 180-182.

In some embodiments, the nanobody construct includes or is a polypeptide sequence having at least 90% sequence identity (or at least 95%, or 98% sequence identity) to SEQ ID NO:180:

$X_1VQLX_5X_6SGX_9X_{10}X_{11}X_{12}X_{13}X_{14}X_{15}X_{16}X_{17}LX_{19}LX_{21}CX_{23}X_{24}SGX_{27}X_{28}X_{29}X_{30}$-CDR1-$X_{31}X_{32}WX_{34}X_{35}X_{36}X_{37}X_{38}X_{39}X_{40}X_{41}X_{42}X_{43}X_{44}X_{45}X_{46}X_{47}X_{48}X_{49}$-CDR2-$X_{50}X_{51}X_{52}X_{53}X_{54}X_{55}X_{56}X_{57}X_{58}X_{59}X_{60}X_{61}X_{62}X_{63}DX_{65}X_{66}X_{67}X_{68}X_{69}X_{70}X_{71}X_{72}X_{73}X_{74}X_{75}X_{76}X_{77}X_{78}X_{79}X_{80}DX_{82}X_{83}X_{84}YX_{86}X_{87}X_{88}X_{89}$-CDR3-$X_{90}X_{91}GX_{93}GX_{95}X_{96}X_{97}X_{98}VSX_{101}$, wherein:

$X_1$ is A, V, I, L, D, E, R, H, K, N, or Q (e.g., A, D, E, H, or Q);
$X_5$ is A, V, I, L, N, or Q (e.g., V, L, or Q);
$X_6$ is A, V, I, L, D, E, N, or Q (e.g., A, E, or Q);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{14}$ is A, V, I, L, F, Y, or P (e.g., A or P);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{19}$ is R, H, K, S, or T (e.g., R, K, S, or T);
$X_{21}$ is S, T, N, or Q (e.g., S or T);
$X_{23}$ is G, A, V, I, L, R, H, K, S, or T (e.g., A, V, K, or T);
$X_{24}$ is A, V, I, L, F, Y, or W (e.g., A, V, I, or F);
$X_{27}$ is G, F, Y, W, or absent (e.g., G, F, or absent);
$X_{28}$ is R, H, K, S, T, P, F, Y, W, or absent (e.g., K, S, T, P, or absent);
$X_{29}$ is A, V, I, L, D, E, R, H, K, F, Y, W, or absent (e.g., V, I, E, R, F, or absent);
$X_{30}$ is G, D, E, N, Q, S, T, F, Y, W, or absent (e.g., G, D, E, N, T, Y, or absent);
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{35}$ is R, H, or K (e.g., R or K);
$X_{36}$ is R, H, K, N, or Q (e.g., R or Q);
$X_{37}$ is A, V, I, L, R, H, K, P, F, Y, or W (e.g., A, V, R, or P);
$X_{38}$ is R, H, K, S, T, P, F, Y, or W (e.g., H, S, T, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{43}$ is D, E, S or T (e.g., D or E);
$X_{44}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent);
$X_{49}$ is A, V, I, L, D, E, R, H, K, M, S, T, or absent (e.g., A, D, R, S, or absent);
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);
$X_{73}$ is D, E, R, H, K, N, Q, S, T, F, Y, or W (e.g., E, R, K, Q, S, or F);

$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{82}$ is C, S, or T (e.g., S or T);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{87}$ is A, V, I, L, C, or M (e.g., V or C);
$X_{88}$ is A, V, I, L, N, Q, S, T, F, Y, W, or absent (e.g., A, V, N, Q, T, Y, or absent);
$X_{89}$ is G, A, V, I, L, R, H, K, F, Y, W, or absent (e.g., G, A, V, R, K, Y, or absent);
$X_{90}$ is any amino acid or absent (e.g., V, H, Q, S, F, Y, or absent);
$X_{91}$ is R, H, K, F, Y, or W (e.g., R or W);
$X_{93}$ is R, H, K, N, Q, P, F, Y, or W (e.g., R, K, Q, or P);
$X_{95}$ is A, V, I, L, S, or T (e.g., L or T);
$X_{96}$ is A, V, I, L, C, M, N, Q, S, or T (e.g., L, M, Q, S, or T);
$X_{97}$ is A, V, I, or L (e.g., V or L);
$X_{98}$ is A, V, I, L, S, or T (e.g., V or T);
$X_{101}$ is S, T, or absent (e.g., S or absent);
CDR1 is any CDR described herein (e.g., SEQ ID NOs: 40-73 and 150-155);
CDR2 is any CDR described herein (e.g., SEQ ID NOs: 74-107 and 160-167); and
CDR3 is any CDR described herein (e.g., SEQ ID NOs: 108-141 and 170-175).

CDR1, CDR2, and CDR3 are defined based on the relative location on the nanobody (VH) chain. Rearranging their locations in the chain, may produce useful and bioactive sequences, e.g., if sequences disclosed to be located at CDR1 are put on a CDR1 location.

In an embodiment, the nanobody construct includes or is a polypeptide sequence having at least 90% sequence identity (or at least 95%, or 98% sequence identity) to SEQ ID NO: 181:

$X_1X_2X_3LX_5X_6X_7GX_9X_{10}X_{11}X_{12}X_{13}PX_{15}X_{16}X_{17}X_{18}X_{19}X_{20}X_{21}CX_{23}X_{24}X_{25}X_{26}$-CDR1-$X_{31}X_{32}WX_{34}X_{35}X_{36}X_{37}X_{38}X_{39}X_{40}X_{41}X_{42}EX_{44}X_{45}X_{46}X_{47}X_{48}X_{49}$-CDR2-$X_{50}X_{51}X_{52}X_{53}X_{54}X_{55}X_{56}X_{57}X_{58}X_{59}X_{60}X_{61}X_{62}X_{63}X_{64}X_{65}X_{66}X_{67}X_{68}X_{69}X_{70}X_{71}X_{72}X_{73}X_{74}X_{75}X_{76}X_{77}X_{78}X_{79}X_{80}DX_{82}X_{83}X_{84}YX_{86}X_{87}X_{88}X_{89}$-CDR3-$X_{90}WGX_{93}X_{94}X_{95}X_{96}X_{97}X_{98}VSX_{101}$, wherein:
$X_1$ is A, V, I, L, D, E, R, H, K, N, or Q (e.g., A, D, E, H, or Q);
$X_2$ is A, V, I, or L (e.g., V or L);
$X_3$ is N, Q, S, or T (Q or T);
$X_5$ is A, V, I, L, N, or Q (e.g., V, L, or Q);
$X_6$ is A, V, I, L, D, E, N, or Q (e.g., A, E, or Q);
$X_7$ is S, T, P, F, Y, or W (e.g., S, T, or P);
$X_9$ is G, A, V, I, L, P, F, Y, or W (e.g., G, A, or P);
$X_{10}$ is G, A, V, I, L, D, E, N, Q, S, or T (e.g., G, A, E, N, or S);
$X_{11}$ is A, V, I, L, S, T, F, Y, or W (e.g., V, L, S, or F);
$X_{12}$ is A, V, I, L, R, H, K, M, S, or T (e.g., V, K, or M);
$X_{13}$ is R, H, K, N, or Q (e.g., R, K, or Q);
$X_{15}$ is G, S, or T (e.g., G or S);
$X_{16}$ is G, A, V, I, L, D, E, R, H, K, N, Q, S, or T (e.g., G, A, D, E, R, Q, or S);
$X_{17}$ is S, T, N, or Q (e.g., S or T);
$X_{18}$ is A, V, I, or L (e.g., V, I, or L);
$X_{19}$ is R, H, K, S, or T (e.g., R, K, S, or T);
$X_{20}$ is A, V, I, or L (e.g., V, I, or L);
$X_{21}$ is S, T, N, or Q (e.g., S or T);
$X_{23}$ is G, A, V, I, L, R, H, K, S, or T (e.g., A, V, K, or T);
$X_{24}$ is A, V, I, L, F, Y, or W (e.g., A, V, I, or F);
$X_{25}$ is S or T;
$X_{26}$ is G, A, V, I, L, D, E, R, H, K, or absent (e.g., G, A, E, R, or absent);
$X_{31}$ is A, V, I, L, M, S, T, F, Y, W, or absent (e.g., I, V, M, W, or absent);
$X_{32}$ is G, A, V, I, L, N, Q, R, H, K, or absent (e.g., G, A, N, H, or absent);
$X_{34}$ is A, V, I, L, P, F, Y or W (e.g., I, V, F, or Y);
$X_{35}$ is R, H, or K (e.g., R or K);
$X_{36}$ is R, H, K, N, or Q (e.g., R or Q);
$X_{37}$ is A, V, I, L, R, H, K, P, F, Y, or W (e.g., A, V, R, or P);
$X_{38}$ is R, H, K, S, T, P, F, Y, or W (e.g., H, S, T, or P);
$X_{39}$ is G, D, or E (e.g., G or E);
$X_{40}$ is G, R, H, K, N, or Q (e.g., G, R, K, N, or Q);
$X_{41}$ is G, A, V, I, L, D, E, R, H, K, N, or Q (e.g., G, A, E, R, or Q);
$X_{42}$ is A, V, I, L, R, H, K, P, F, Y, or W (e.g., L, R, P, or F);
$X_{44}$ is G, A, V, I, L, P, F, Y, or W (e.g., G, A, L, F, or W);
$X_{45}$ is A, V, I, L, M, S, or T (e.g., V, I, L, or M);
$X_{46}$ is G, A, V, I, L, S, or T (e.g., G, A, V, or S);
$X_{47}$ is A, V, I, L, R, H, K, M, S, T, or absent (e.g., A, V, I, R, S, T, or absent);
$X_{48}$ is A, V, I, L, M, S, T, or absent (e.g., V, I, L, M, or absent);
$X_{49}$ is A, V, I, L, D, E, R, H, K, M, S, T, or absent (e.g., A, D, R, S, or absent);
$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{64}$ is D or E;
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);

$X_{73}$ is D, E, R, H, K, N, Q, S, T, F, Y, or W (e.g., E, R, K, Q, S, or F);

$X_{74}$ is A, V, I, L, C, or M (e.g., L or M);

$X_{75}$ is D, E, N, Q, S, or T (e.g., D, N, or S);

$X_{76}$ is R, H, K, N, Q, S, or T (e.g., R, N, or S);

$X_{77}$ is A, V, I, or L (e.g., V or L);

$X_{78}$ is R, H, K, N, Q, S, or T (e.g., R, K, Q, or T);

$X_{79}$ is A, V, I, L, R, H, K, S, T, P, F, Y, or W (e.g., A, V, L, R, S, T, P, or Y);

$X_{80}$ is A, V, I, L, D, or E (e.g., A, D, or E);

$X_{82}$ is C, S, or T (e.g., S or T);

$X_{83}$ is G, A, V, I, or L (e.g., G or A);

$X_{84}$ is A, V, I, L, C, M, D, E, S or T (e.g., V, I, M, D, E, or T);

$X_{86}$ is S, T, F, Y, or W (e.g., T, F, or Y);

$X_{87}$ is A, V, I, L, C, or M (e.g., V or C);

$X_{88}$ is A, V, I, L, N, Q, S, T, F, Y, W, or absent (e.g., A, V, N, Q, T, Y, or absent);

$X_{89}$ is G, A, V, I, L, R, H, K, F, Y, W, or absent (e.g., G, A, V, R, K, Y, or absent);

$X_{90}$ is any amino acid or absent (e.g., V, H, Q, S, F, Y, or absent);

$X_{93}$ is R, H, K, N, Q, P, F, Y, or W (e.g., R, K, Q, or P);

$X_{94}$ is G, A, V, I, or L (e.g., G);

$X_{95}$ is A, V, I, L, S, or T (e.g., L or T);

$X_{96}$ is A, V, I, L, C, M, N, Q, S, or T (e.g., L, M, Q, S, or T);

$X_{97}$ is A, V, I, or L (e.g., V or L);

$X_{98}$ is A, V, I, L, S, or T (e.g., V or T);

$X_{101}$ is S, T, or absent (e.g., S or absent);

CDR1 is any CDR described herein (e.g., SEQ ID NOs: 40-73 and 150-155);

CDR2 is any CDR described herein (e.g., SEQ ID NOs: 74-107 and 160-167); and

CDR3 is any CDR described herein (e.g., SEQ ID NOs: 108-141 and 170-175).

In an embodiment, the nanobody construct includes or is a polypeptide sequence having at least 90% sequence identity (or at least 95%, or 98% sequence identity) to SEQ ID NO: 182:

$X_1VX_3LX_5X_6SGGGX_{11}X_{12}X_{13}X_{14}GX_{16}SLX_{19}LSCAASG$-CDR1-$X_{31}X_{32}WX_{34}RX_{36}X_{37}PX_{39}X_{40}X_{41}X_{42}$ $X_{43}X_{44}X_{45}X_{46}X_{47}X_{48}X_{49}$-CDR2-$X_{50}YX_{52}X_{53}X_{54}X_{55}X_{56}X_{57}RFX_{60}X_{61}SX_{63}DX_{65}X_{66}X_{67}X_{68}X_{69}X_{70}X_{71}LX_{73}X_{74}X_{75}X_{76}X_{77}X_{78}X_{79}X_{80}DTX_{83}X_{84}YX_{86}CAX_{89}$-CDR3-$X_{90}X_{91}GX_{93}GTX_{96}VTVSX_{101}$, wherein:

$X_1$ is A, V, I, L, D, E, R, H, K, N, or Q (e.g., A, D, E, H, or Q);

$X_3$ is N, Q, S, or T (Q or T);

$X_5$ is A, V, I, L, N, or Q (e.g., V, L, or Q);

$X_6$ is A, V, I, L, D, E, N, or Q (e.g., A, E, or Q);

$X_{11}$ is A, V, I, L, S, T, F, Y, or W (e.g., V, L, S, or F);

$X_{12}$ is A, V, I, L, R, H, K, M, S, or T (e.g., V, K, or M);

$X_{13}$ is R, H, K, N, or Q (e.g., R, K, or Q);

$X_{14}$ is A, V, I, L, F, Y, or P (e.g., A or P);

$X_{16}$ is G, A, V, I, L, D, E, R, H, K, N, Q, S, or T (e.g., G, A, D, E, R, Q, or S);

$X_{19}$ is R, H, K, S, or T (e.g., R, K, S, or T);

$X_{31}$ is A, V, I, L, M, S, T, F, Y, W, or absent (e.g., I, V, M, W, or absent);

$X_{32}$ is G, A, V, I, L, N, Q, R, H, K, or absent (e.g., G, A, N, H, or absent);

$X_{34}$ is A, V, I, L, P, F, Y or W (e.g., I, V, F, or Y);

$X_{36}$ is R, H, K, N, or Q (e.g., R or Q);

$X_{37}$ is A, V, I, L, R, H, K, P, F, Y, or W (e.g., A, V, R, or P);

$X_{39}$ is G, D, or E (e.g., G or E);

$X_{40}$ is G, R, H, K, N, or Q (e.g., G, R, K, N, or Q);

$X_{41}$ is G, A, V, I, L, D, E, R, H, K, N, or Q (e.g., G, A, E, R, or Q);

$X_{42}$ is A, V, I, L, R, H, K, P, F, Y, or W (e.g., L, R, P, or F);

$X_{43}$ is D or E;

$X_{44}$ is G, A, V, I, L, P, F, Y, or W (e.g., G, A, L, F, or W);

$X_{45}$ is A, V, I, L, M, S, or T (e.g., V, I, L, or M);

$X_{46}$ is G, A, V, I, L, S, or T (e.g., G, A, V, or S);

$X_{47}$ is A, V, I, L, R, H, K, M, S, T, or absent (e.g., A, V, I, R, S, T, or absent);

$X_{48}$ is A, V, I, L, M, S, T, or absent (e.g., V, I, L, M, or absent);

$X_{49}$ is A, V, I, L, D, E, R, H, K, M, S, T, or absent (e.g., A, D, R, S, or absent);

$X_{50}$ is A, V, I, L, D, E, R, H, K, N, Q, S, T, F, Y, W, or absent (e.g., L, D, R, N, T, Y, or absent);

$X_{52}$ is G, A, V, I, L, D, E, R, H, K, N, Q, S, T, or absent (e.g., G, A, V, L, D, E, R, N, T, or absent);

$X_{53}$ is G, D, E, N, Q, S, T, P, F, Y, W, or absent (e.g., G, D, E, Q, S, P, or absent);

$X_{54}$ is A, V, I, L, R, H, K, S, T, F, Y, W, or absent (e.g., A, K, S, F, or absent);

$X_{55}$ is A, V, I, L, M, S, T, F, Y, W, or absent (e.g., A, V, L, M, F, or absent);

$X_{56}$ is D, E, R, H, K, N, Q, or absent (e.g., E, R, K, Q, or absent);

$X_{57}$ is G, D, E, S, T, or absent (e.g., G, D, S, or absent);

$X_{60}$ is A, V, I, L, C, M, S, or T (e.g., A, C, S, or T);

$X_{61}$ is A, V, I, L, C, M, S, T, F, Y, or W (e.g., A, I, L, M, S, or F);

$X_{63}$ is A, V, I, L, R, H, K, N, or Q (e.g., A, V, R, K, or Q);

$X_{65}$ is A, V, I, L, D, E, R, H, K, N, Q, S, or T (e.g., I, D, R, K, N, S, or T);

$X_{66}$ is G, A, V, I, L, D, E, R, H, K, N, Q, S, or T (e.g., G, A, D, R, K, N, or S);

$X_{67}$ is A, V, I, L, R, H, K, S, or T (e.g., A, R, K, S, or T);

$X_{68}$ is R, H, K, N, Q, S, or T (e.g., K, N, S, or T);

$X_{69}$ is A, V, I, L, C, M, N, Q, S, or T (e.g., A, L, M, Q, S, or T);

$X_{70}$ is A, V, I, L, C, M, F, Y, or W (e.g., A, V, L, M, or F);

$X_{71}$ is S, T, F, Y, or W (e.g., S, T, F, or Y);

$X_{73}$ is D, E, R, H, K, N, Q, S, T, F, Y, or W (e.g., E, R, K, Q, S, or F);

$X_{74}$ is A, V, I, L, C, or M (e.g., L or M);

$X_{75}$ is D, E, N, Q, S, or T (e.g., D, N, or S);

$X_{76}$ is R, H, K, N, Q, S, or T (e.g., R, N, or S);

$X_{77}$ is A, V, I, or L (e.g., V or L);

$X_{78}$ is R, H, K, N, Q, S, or T (e.g., R, K, Q, or T);

$X_{79}$ is A, V, I, L, R, H, K, S, T, P, F, Y, or W (e.g., A, V, L, R, S, T, P, or Y);

$X_{80}$ is A, V, I, L, D, or E (e.g., A, D, or E);

$X_{83}$ is G, A, V, I, or L (e.g., G or A);

$X_{84}$ is A, V, I, L, C, M, D, E, S or T (e.g., V, I, M, D, E, or T);

$X_{86}$ is S, T, F, Y, or W (e.g., T, F, or Y);

$X_{89}$ is G, A, V, I, L, R, H, K, F, Y, W, or absent (e.g., G, A, V, R, K, Y, or absent);

$X_{90}$ is any amino acid or absent (e.g., V, H, Q, S, F, Y, or absent);

$X_{91}$ is F, Y, or W (e.g., W);

$X_{93}$ is R, H, K, N, Q, P, F, Y, or W (e.g., R, K, Q, or P);

$X_{96}$ is A, V, I, L, C, M, N, Q, S, or T (e.g., L, M, Q, S, or T);

$X_{101}$ is S, T, or absent (e.g., S or absent);

CDR1 is any CDR described herein (e.g., SEQ ID NOs: 40-73 and 150-155);

CDR2 is any CDR described herein (e.g., SEQ ID NOs: 74-107 and 160-167); and

CDR3 is any CDR described herein (e.g., SEQ ID NOs: 108-141 and 170-175).

In some embodiments, the construct includes or is a polypeptide sequence having at least 90% (such as at least 95% or at least 98%) sequence identity to SEQ ID NOs: 183-186.

In an embodiment, the nanobody constructs herein include FRs described herein. FIG. 18A provides non-limiting FR1 sequences. In some embodiments, the first FR includes or is a polypeptide sequence having at least 90% (such as at least 95% or at least 98%) sequence identity to SEQ ID NOs: 190-212. In other embodiments, the first FR includes or is a polypeptide sequence having at least 90% (such as at least 95% or at least 98%) sequence identity to SEQ ID NO: 213:

$X_1VQLX_5X_6SGX_9X_{10}X_{11}X_{12}X_{13}X_{14}X_{15}X_{16}X_{17}LX_{19}LX_{21}CX_{23}X_{24}SGX_{27}X_{28}X_{29}X_{30}$, wherein:

$X_1$ is A, V, I, L, D, E, R, H, K, N, or Q (e.g., A, D, E, H, or Q);

$X_5$ is A, V, I, L, N, or Q (e.g., V, L, or Q);

$X_6$ is A, V, I, L, D, E, N, or Q (e.g., A, E, or Q);

$X_9$ is G, A, V, I, L, P, F, Y, or W (e.g., G, A, or P);

$X_{10}$ is G, A, V, I, L, D, E, N, Q, S, or T (e.g., G, A, E, N, or S);

$X_{11}$ is A, V, I, L, S, T, F, Y, or W (e.g., V, L, S, or F);

$X_{12}$ is A, V, I, L, R, H, K, M, S, or T (e.g., V, K, or M);

$X_{13}$ is R, H, K, N, or Q (e.g., R, K, or Q);

$X_{14}$ is A, V, I, L, F, Y, or P (e.g., A or P);

$X_{15}$ is G, S, or T (e.g., G or S);

$X_{16}$ is G, A, V, I, L, D, E, R, H, K, N, Q, S, or T (e.g., G, A, D, E, R, Q, or S);

$X_{17}$ is S, T, N, or Q (e.g., S or T);

$X_{19}$ is R, H, K, S, or T (e.g., R, K, S, or T);

$X_{21}$ is S, T, N, or Q (e.g., S or T);

$X_{23}$ is G, A, V, I, L, R, H, K, S, or T (e.g., A, V, K, or T);

$X_{24}$ is A, V, I, L, F, Y, or W (e.g., A, V, I, or F);

$X_{27}$ is G, F, Y, W, or absent (e.g., G, F, or absent);

$X_{28}$ is R, H, K, S, T, P, F, Y, W, or absent (e.g., K, S, T, P, or absent);

$X_{29}$ is A, V, I, L, D, E, R, H, K, F, Y, W, or absent (e.g., V, I, E, R, F, or absent); and $X_{30}$ is G, D, E, N, Q, S, T, F, Y, W, or absent (e.g., G, D, E, N, T, Y, or absent).

In some embodiments, each X in SEQ ID NO: 213 can be an amino acid in any one of SEQ ID NOs: 190-212 when any one of the sequences in SEQ ID NOs: 190, 191, 193, 196, 198, 202-208, 210, and 212 is used as a reference sequence to be optimally aligned with SEQ ID NO: 213.

In other embodiments, the first FR includes or is a polypeptide sequence having at least 90% (such as at least 95% or at least 98%) sequence identity to SEQ ID NO: 214:

$X_1X_2X_3LX_5X_6X_7GX_9X_{10}X_{11}X_{12}X_{13}X_{14}X_{15}X_{16}X_{17}X_{18}X_{19}X_{20}X_{21}CX_{23}X_{24}X_{25}X_{26}$, wherein:

$X_1$ is A, V, I, L, D, E, R, H, K, N, or Q (e.g., A, D, E, H, or Q);

$X_2$ is A, V, I, or L (e.g., V or L);

$X_3$ is N, Q, S, or T (Q or T);

$X_5$ is A, V, I, L, N, or Q (e.g., V, L, or Q);

$X_6$ is A, V, I, L, D, E, N, or Q (e.g., A, E, or Q);

$X_7$ is S, T, P, F, Y, or W (e.g., S, T, or P);

$X_9$ is G, A, V, I, L, P, F, Y, or W (e.g., G, A, or P);

$X_{10}$ is G, A, V, I, L, D, E, N, Q, S, or T (e.g., G, A, E, N, or S);

$X_{11}$ is A, V, I, L, S, T, F, Y, or W (e.g., V, L, S, or F);

$X_{12}$ is A, V, I, L, R, H, K, M, S, or T (e.g., V, K, or M);

$X_{13}$ is R, H, K, N, or Q (e.g., R, K, or Q);

$X_{14}$ is A, V, I, L, F, Y, or P (e.g., A or P);

$X_{15}$ is G, S, or T (e.g., G or S);

$X_{16}$ is G, A, V, I, L, D, E, R, H, K, N, Q, S, or T (e.g., G, A, D, E, R, Q, or S);

$X_{17}$ is S, T, N, or Q (e.g., S or T);

$X_{18}$ is A, V, I, or L (e.g., V, I, or L);

$X_{19}$ is R, H, K, S, or T (e.g., R, K, S, or T);

$X_{20}$ is A, V, I, or L (e.g., V, I, or L);

$X_{21}$ is S, T, N, or Q (e.g., S or T);

$X_{23}$ is G, A, V, I, L, R, H, K, S, or T (e.g., A, V, K, or T);

$X_{24}$ is A, V, I, L, F, Y, or W (e.g., A, V, I, or F);

$X_{25}$ is S or T; and $X_{26}$ is G, A, V, I, L, D, E, R, H, K, or absent (e.g., G, A, E, R, or absent).

In some embodiments, each X in SEQ ID NO: 214 can be an amino acid in any one of SEQ ID NOs: 190-212 when any one of the sequences in SEQ ID NOs: 190-212 is used as a reference sequence to be optimally aligned with SEQ ID NO: 214.

In yet other embodiments, the first FR includes or is a polypeptide sequence having at least 90% (such as at least 95% or at least 98%) sequence identity to SEQ ID NO: 215:

$X_1VQLX_5X_6SGX_9X_{10}X_{11}X_{12}X_{13}X_{14}X_{15}X_{16}X_{17}LX_{19}LX_{21}CX_{23}X_{24}SG$, wherein:

$X_1$ is A, V, I, L, D, E, R, H, K, N, or Q (e.g., A, D, E, H, or Q);

$X_5$ is A, V, I, L, N, or Q (e.g., V, L, or Q);

$X_6$ is A, V, I, L, D, E, N, or Q (e.g., A, E, or Q);

$X_9$ is G, A, V, I, L, P, F, Y, or W (e.g., G, A, or P);

$X_{10}$ is G, A, V, I, L, D, E, N, Q, S, or T (e.g., G, A, E, N, or S);

$X_{11}$ is A, V, I, L, S, T, F, Y, or W (e.g., V, L, S, or F);

$X_{12}$ is A, V, I, L, R, H, K, M, S, or T (e.g., V, K, or M);

$X_{13}$ is R, H, K, N, or Q (e.g., R, K, or Q);

$X_{14}$ is A, V, I, L, F, Y, or P (e.g., A or P);

$X_{15}$ is G, S, or T (e.g., G or S);

$X_{16}$ is G, A, V, I, L, D, E, R, H, K, N, Q, S, or T (e.g., G, A, D, E, R, Q, or S);

$X_{17}$ is S, T, N, or Q (e.g., S or T);

$X_{19}$ is R, H, K, S, or T (e.g., R, K, S, or T);

$X_{21}$ is S, T, N, or Q (e.g., S or T);

$X_{23}$ is G, A, V, I, L, R, H, K, S, or T (e.g., A, V, K, or T); and $X_{24}$ is A, V, I, L, F, Y, or W (e.g., A, V, I, or F).

In some embodiments, each X in SEQ ID NO: 215 can be an amino acid in any one of SEQ ID NOs: 190-212 when any one of the sequences in SEQ ID NOs: 190-212 is used as a reference sequence to be optimally aligned with SEQ ID NO: 215.

In some embodiments, the first FR includes or is a polypeptide sequence having at least 90% (such as at least 95% or at least 98%) sequence identity to SEQ ID NO:216:

$QVQLVESGGGLVQX_{14}GGSLRLSCAASGX_{27}X_{28}X_{29}X_{30}$, wherein:

$X_{14}$ is A, V, I, L, F, Y, or P (e.g., A or P);

$X_{27}$ is G, F, Y, W, or absent (e.g., G, F, or absent);

$X_{28}$ is R, H, K, S, T, P, F, Y, W, or absent (e.g., K, S, T, P, or absent);

$X_{29}$ is A, V, I, L, D, E, R, H, K, F, Y, W, or absent (e.g., V, I, E, R, F, or absent); and $X_{30}$ is G, D, E, N, Q, S, T, F, Y, W, or absent (e.g., G, D, E, N, T, Y, or absent).

In other embodiments, each X in SEQ ID NO: 216 can be an amino acid in any one of SEQ ID NOs: 190-212 when any one of the sequences in SEQ ID NOs: 192, 194, 195, 197, and 199-201 is used as a reference sequence to be optimally aligned with SEQ ID NO: 216.

In yet other embodiments, the first FR includes or is a polypeptide sequence having at least 90% (such as 95% or 98%) sequence identity to SEQ ID NO:217:

QVQLVESGGGLVQ$X_{14}$GGSLRLSCAASG, wherein:

$X_{14}$ is A, V, I, L, F, Y, or P (e.g., A or P).

FIG. 18B provides non-limiting FR2 sequences. In some embodiments, the second FR includes or is a polypeptide sequence having at least 90% (such as at least 95% or at least 98%) sequence identity to SEQ ID NOs: 220-243. In other embodiments, the second FR includes or is a polypeptide sequence having at least 90% (such as at least 95% or at least 98%) sequence identity to SEQ ID NO: 244:

$X_{31}X_{32}WX_{34}X_{35}X_{36}X_{37}X_{38}X_{39}X_{40}X_{41}X_{42}X_{43}X_{44}X_{45}X_{46}X_{47}X_{48}X_{49}$, wherein:

$X_{31}$ is A, V, I, L, M, S, T, F, Y, W, or absent (e.g., I, V, M, W, or absent);

$X_{32}$ is G, A, V, I, L, N, Q, R, H, K, or absent (e.g., G, A, N, H, or absent);

$X_{34}$ is A, V, I, L, P, F, Y or W (e.g., I, V, F, or Y);

$X_{35}$ is R, H, or K (e.g., R or K);

$X_{36}$ is R, H, K, N, or Q (e.g., R or Q);

$X_{37}$ is A, V, I, L, R, H, K, P, F, Y, or W (e.g., A, V, R, or P);

$X_{38}$ is R, H, K, S, T, P, F, Y, or W (e.g., H, S, T, or P);

$X_{39}$ is G, D, or E (e.g., G or E);

$X_{40}$ is G, R, H, K, N, or Q (e.g., G, R, K, N, or Q);

$X_{41}$ is G, A, V, I, L, D, E, R, H, K, N, or Q (e.g., G, A, E, R, or Q);

$X_{42}$ is A, V, I, L, R, H, K, P, F, Y, or W (e.g., L, R, P, or F);

$X_{43}$ is D, E, S or T (e.g., D or E);

$X_{44}$ is G, A, V, I, L, P, F, Y, or W (e.g., G, A, L, F, or W);

$X_{45}$ is A, V, I, L, M, S, or T (e.g., V, I, L, or M);

$X_{46}$ is G, A, V, I, L, S, or T (e.g., G, A, V, or S);

$X_{47}$ is A, V, I, L, R, H, K, M, S, T, or absent (e.g., A, V, I, R, S, T, or absent);

$X_{48}$ is A, V, I, L, M, S, T, or absent (e.g., V, I, L, M, or absent); and $X_{49}$ is A, V, I, L, D, E, R, H, K, M, S, T, or absent (e.g., A, D, R, S, or absent).

In yet other embodiments, each X in SEQ ID NO: 244 can be an amino acid in any one of SEQ ID NOs: 220-243 when any one of the sequences in SEQ ID NOs: 220-243 is used as a reference sequence to be optimally aligned with SEQ ID NO: 244.

In some embodiments, the second FR includes or is a polypeptide sequence having at least 90% (such as at least 95% or at least 98%) sequence identity to SEQ ID NO: 245:

$X_{31}X_{32}WX_{34}RQAX_{38}GX_{40}X_{41}X_{42}EX_{44}X_{45}X_{46}X_{47}X_{48}X_{49}$, wherein:

$X_{31}$ is A, V, I, L, M, S, T, F, Y, W, or absent (e.g., I, V, M, W, or absent);

$X_{32}$ is G, A, V, I, L, N, Q, R, H, K, or absent (e.g., G, A, N, H, or absent);

$X_{34}$ is A, V, I, L, P, F, Y or W (e.g., I, V, F, or Y);

$X_{38}$ is R, H, K, S, T, P, F, Y, or W (e.g., H, S, T, or P);

$X_{40}$ is G, R, H, K, N, or Q (e.g., G, R, K, N, or Q);

$X_{41}$ is G, A, V, I, L, D, E, R, H, K, N, or Q (e.g., G, A, E, R, or Q);

$X_{42}$ is A, V, I, L, R, H, K, P, F, Y, or W (e.g., L, R, P, or F);

$X_{44}$ is G, A, V, I, L, P, F, Y, or W (e.g., G, A, L, F, or W);

$X_{45}$ is A, V, I, L, M, S, or T (e.g., V, I, L, or M);

$X_{46}$ is G, A, V, I, L, S, or T (e.g., G, A, V, or S);

$X_{47}$ is A, V, I, L, R, H, K, M, S, T, or absent (e.g., A, V, I, R, S, T, or absent);

$X_{48}$ is A, V, I, L, M, S, T, or absent (e.g., V, I, L, M, or absent); and $X_{49}$ is A, V, I, L, D, E, R, H, K, M, S, T, or absent (e.g., A, D, R, S, or absent).

In other embodiments, each X in SEQ ID NO: 245 can be an amino acid in any one of SEQ ID NOs: 220-243 when any one of the sequences in SEQ ID NOs: 220-243 is used as a reference sequence to be optimally aligned with SEQ ID NO: 245.

In some embodiments, the second FR includes or is a polypeptide sequence having at least 90% (such as at least 95% or at least 98%) sequence identity to SEQ ID NO: 246:

$X_{31}X_{32}WX_{34}RQAX_{38}GX_{40}X_{41}X_{42}EX_{44}X_{45}X_{46}$, wherein:

$X_{31}$ is A, V, I, L, M, S, T, F, Y, W, or absent (e.g., I, V, M, W, or absent);

$X_{32}$ is G, A, V, I, L, N, Q, R, H, K, or absent (e.g., G, A, N, H, or absent);

$X_{34}$ is A, V, I, L, P, F, Y or W (e.g., I, V, F, or Y);

$X_{38}$ is R, H, K, S, T, P, F, Y, or W (e.g., H, S, T, or P);

$X_{40}$ is G, R, H, K, N, or Q (e.g., G, R, K, N, or Q);

$X_{41}$ is G, A, V, I, L, D, E, R, H, K, N, or Q (e.g., G, A, E, R, or Q);

$X_{42}$ is A, V, I, L, R, H, K, P, F, Y, or W (e.g., L, R, P, or F);

$X_{44}$ is G, A, V, I, L, P, F, Y, or W (e.g., G, A, L, F, or W);

$X_{45}$ is A, V, I, L, M, S, or T (e.g., V, I, L, or M); and $X_{46}$ is G, A, V, I, L, S, or T (e.g., G, A, V, or S).

In other embodiments, each X in SEQ ID NO: 246 can be an amino acid in any one of SEQ ID Nos: 220-243 when any one of the sequences in SEQ ID NOs: 222, 224, 226, 228-230, 233, 234, 238-243 is used as a reference sequence to be optimally aligned with SEQ ID NO: 246.

In some embodiments, the second FR includes or is a polypeptide sequence having at least 90% (such as at least 95% or at least 98%) sequence identity to SEQ ID NO: 247:

$MX_{32}WFRQAPGKEREWVAX_{47}X_{48}X_{49}$, wherein:

$X_{32}$ is G, A, V, I, L, N, Q, R, H, K, or absent (e.g., G, A, N, H, or absent);

$X_{47}$ is A, V, I, L, R, H, K, M, S, T, or absent (e.g., A, V, I, R, S, T, or absent);

$X_{48}$ is A, V, I, L, M, S, T, or absent (e.g., V, I, L, M, or absent); and $X_{49}$ is A, V, I, L, D, E, R, H, K, M, S, T, or absent (e.g., A, D, R, S, or absent).

In other embodiments, each X in SEQ ID NO: 247 can be an amino acid in any one of SEQ ID NOs: 220-243 when any one of the sequences in SEQ ID NOs: 228-230 or 242 is used as a reference sequence to be optimally aligned with SEQ ID NO: 247.

In yet other embodiments, the second FR includes or is a polypeptide sequence having at least 90% (such as at least 95% or at least 98%) sequence identity to SEQ ID NO: 230:

$MX_{32}WFRQAPGKEREWVA$, wherein:

$X_{32}$ is G, A, V, I, L, N, Q, R, H, K, or absent (e.g., G, A, N, H, or absent).

FIG. 18C provides non-limiting FR3 sequences. In some embodiments, the third FR includes or is a polypeptide sequence having at least 90% (such as at least 95% or at least 98%) sequence identity to SEQ ID NOs: 250-284. In other embodiments, the third FR includes or is a polypeptide sequence having at least 90% (such as at least 95% or at least 98%) sequence identity to SEQ ID NO: 285:

$X_{50}X_{51}X_{52}X_{53}X_{54}X_{55}X_{56}X_{57}X_{58}X_{59}X_{60}X_{61}X_{62}X_{63}DX_{65}X_{66}X_{67}X_{68}X_{69}X_{70}X_{71}X_{72}X_{73}X_{74}X_{75}X_{76}X_{77}X_{78}X_{79}X_{80}DX_{82}X_{83}X_{84}YX_{86}CX_{88}X_{89}$, wherein:

$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{58}$ is R, H, or K (e.g., R or K);
$X_{59}$ is A, V, I, L, F, Y, or W (e.g., A, V, L, or F);
$X_{60}$ is A, V, I, L, C, M, S, or T (e.g., A, C, S, or T);
$X_{61}$ is A, V, I, L, C, M, S, T, F, Y, or W (e.g., A, I, L, M, S, or F);
$X_{62}$ is C, M, S, or T (e.g., S or T);
$X_{63}$ is A, V, I, L, R, H, K, N, or Q (e.g., A, V, R, K, or Q);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{70}$ is A, V, I, L, C, M, F, Y, or W (e.g., A, V, L, M, or F);
$X_{71}$ is S, T, F, Y, or W (e.g., S, T, F, or Y);
$X_{72}$ is A, V, I, L, C, or M (e.g., L or M);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{80}$ is A, V, I, L, D, or E (e.g., A, D, or E);
$X_{82}$ is C, S, or T (e.g., S or T);
$X_{83}$ is G, A, V, I, or L (e.g., G or A);
$X_{84}$ is A, V, I, L, C, M, D, E, S or T (e.g., V, I, M, D, E, or T);
$X_{86}$ is S, T, F, Y, or W (e.g., T, F, or Y);
$X_{88}$ is A, V, I, L, N, Q, S, T, F, Y, W, or absent (e.g., A, V, N, Q, T, Y, or absent); and
$X_{89}$ is G, A, V, I, L, R, H, K, F, Y, W, or absent (e.g., G, A, V, R, K, Y, or absent).

In other embodiments, each X in SEQ ID NO: 285 can be an amino acid in any one of SEQ ID NOs: 250-284 when any one of the sequences in SEQ ID NOs: 250-284 is used as a reference sequence to be optimally aligned with SEQ ID NO: 285.

In some embodiments, the third FR includes or is a polypeptide sequence having at least 90% sequence identity to SEQ ID NO: 286:

$X_{50}X_{51}X_{52}X_{53}X_{54}X_{55}X_{56}X_{57}RX_{59}X_{60}IX_{62}RDX_{65}X_{66}X_{67}X_{68}X_{69}VX_{71}LX_{73}X_{74}X_{75}X_{76}X_{77}X_{78}X_{79}EDTAX_{84}YYX_{87}X_{88}X_{89}$, wherein:

$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);
$X_{52}$ is G, A, V, I, L, D, E, R, H, K, N, Q, S, T, or absent (e.g., G, A, V, L, D, E, R, N, T, or absent);
$X_{53}$ is G, D, E, N, Q, S, T, P, F, Y, W, or absent (e.g., G, D, E, Q, S, P, or absent);
$X_{54}$ is A, V, I, L, R, H, K, S, T, F, Y, W, or absent (e.g., A, K, S, F, or absent);
$X_{55}$ is A, V, I, L, M, S, T, F, Y, W, or absent (e.g., A, V, L, M, F, or absent);
$X_{56}$ is D, E, R, H, K, N, Q, or absent (e.g., E, R, K, Q, or absent);
$X_{57}$ is G, D, E, S, T, or absent (e.g., G, D, S, or absent);
$X_{59}$ is A, V, I, L, F, Y, or W (e.g., A, V, L, or F);
$X_{60}$ is A, V, I, L, C, M, S, or T (e.g., A, C, S, or T);
$X_{62}$ is C, M, S, or T (e.g., S or T);
$X_{65}$ is A, V, I, L, D, E, R, H, K, N, Q, S, or T (e.g., I, D, R, K, N, S, or T);
$X_{66}$ is G, A, V, I, L, D, E, R, H, K, N, Q, S, or T (e.g., G, A, D, R, K, N, or S);
$X_{67}$ is A, V, I, L, R, H, K, S, or T (e.g., A, R, K, S, or T);
$X_{68}$ is R, H, K, N, Q, S, or T (e.g., K, N, S, or T);
$X_{69}$ is A, V, I, L, C, M, N, Q, S, or T (e.g., A, L, M, Q, S, or T);
$X_{71}$ is S, T, F, Y, or W (e.g., S, T, F, or Y);
$X_{73}$ is D, E, R, H, K, N, Q, S, T, F, Y, or W (e.g., E, R, K, Q, S, or F);
$X_{74}$ is A, V, I, L, C, or M (e.g., L or M);
$X_{75}$ is D, E, N, Q, S, or T (e.g., D, N, or S);
$X_{76}$ is R, H, K, N, Q, S, or T (e.g., R, N, or S);
$X_{77}$ is A, V, I, or L (e.g., V or L);
$X_{78}$ is R, H, K, N, Q, S, or T (e.g., R, K, Q, or T);
$X_{79}$ is A, V, I, L, R, H, K, S, T, P, F, Y, or W (e.g., A, V, L, R, S, T, P, or Y);
$X_{84}$ is A, V, I, L, C, M, D, E, S or T (e.g., V, I, M, D, E, or T);
$X_{87}$ is F, Y, or W (e.g., Y);
$X_{88}$ is A, V, I, L, N, Q, S, T, F, Y, W, or absent (e.g., A, V, N, Q, T, Y, or absent); and
$X_{89}$ is G, A, V, I, L, R, H, K, F, Y, W, or absent (e.g., G, A, V, R, K, Y, or absent).

In other embodiments, each X in SEQ ID NO: 286 can be an amino acid in any one of SEQ ID NOs: 250-282 and 284 when any one of the sequences in SEQ ID NOs: 250-282 and 284 is used as a reference sequence to be optimally aligned with SEQ ID NO: 286.

In some embodiments, the third FR includes or is a polypeptide sequence having at least 90% sequence identity to SEQ ID NO:287:

$X_{50}X_{51}X_{52}X_{53}X_{54}X_{55}X_{56}X_{57}RX_{59}X_{60}IX_{62}RDX_{65}X_{66}X_{67}X_{68}X_{69}VX_{71}LX_{73}X_{74}X_{75}X_{76}X_{77}X_{78}X_{79}EDTAX_{84}YYX_{87}X_{88}$, wherein:

$X_{50}$ is A, V, I, L, D, E, R, H, K, N, Q, S, T, F, Y, W, or absent (e.g., L, D, R, N, T, Y, or absent);
$X_{51}$ is R, H, K, S, T, F, Y, W, or absent (e.g., H, S, F, Y, or absent);

$X_{52}$ is G, A, V, I, L, D, E, R, H, K, N, Q, S, T, or absent (e.g., G, A, V, L, D, E, R, N, T, or absent);

$X_{53}$ is G, D, E, N, Q, S, T, P, F, Y, W, or absent (e.g., G, D, E, Q, S, P, or absent);

$X_{54}$ is A, V, I, L, R, H, K, S, T, F, Y, W, or absent (e.g., A, K, S, F, or absent);

$X_{55}$ is A, V, I, L, M, S, T, F, Y, W, or absent (e.g., A, V, L, M, F, or absent);

$X_{56}$ is D, E, R, H, K, N, Q, or absent (e.g., E, R, K, Q, or absent);

$X_{57}$ is G, D, E, S, T, or absent (e.g., G, D, S, or absent);

$X_{59}$ is A, V, I, L, F, Y, or W (e.g., A, V, L, or F);

$X_{60}$ is A, V, I, L, C, M, S, or T (e.g., A, C, S, or T);

$X_{62}$ is C, M, S, or T (e.g., S or T);

$X_{65}$ is A, V, I, L, D, E, R, H, K, N, Q, S, or T (e.g., I, D, R, K, N, S, or T);

$X_{66}$ is G, A, V, I, L, D, E, R, H, K, N, Q, S, or T (e.g., G, A, D, R, K, N, or S);

$X_{67}$ is A, V, I, L, R, H, K, S, or T (e.g., A, R, K, S, or T);

$X_{68}$ is R, H, K, N, Q, S, or T (e.g., K, N, S, or T);

$X_{69}$ is A, V, I, L, C, M, N, Q, S, or T (e.g., A, L, M, Q, S, or T);

$X_{71}$ is S, T, F, Y, or W (e.g., S, T, F, or Y);

$X_{73}$ is D, E, R, H, K, N, Q, S, T, F, Y, or W (e.g., E, R, K, Q, S, or F);

$X_{74}$ is A, V, I, L, C, or M (e.g., L or M);

$X_{75}$ is D, E, N, Q, S, or T (e.g., D, N, or S);

$X_{76}$ is R, H, K, N, Q, S, or T (e.g., R, N, or S);

$X_{77}$ is A, V, I, or L (e.g., V or L);

$X_{78}$ is R, H, K, N, Q, S, or T (e.g., R, K, Q, or T);

$X_{79}$ is A, V, I, L, R, H, K, S, T, P, F, Y, or W (e.g., A, V, L, R, S, T, P, or Y);

$X_{84}$ is A, V, I, L, C, M, D, E, S or T (e.g., V, I, M, D, E, or T);

$X_{87}$ is F, Y, or W (e.g., Y); and $X_{88}$ is A, V, I, L, N, Q, S, T, F, Y, W, or absent (e.g., A, V, N, Q, T, Y, or absent).

In other embodiments, each X in SEQ ID NO: 287 can be an amino acid in any one of SEQ ID NOs: 250-284 when any one of the sequences in SEQ ID NOs: 250-282, and 284 is used as a reference sequence to be optimally aligned with SEQ ID NO: 287.

In some embodiments, the third FR includes or is a polypeptide sequence having at least 90% (such as at least 95% or at least 98%) sequence identity to SEQ ID NO: 288:

$X_{50}$YADSVKGRFTISRDNAKNTVYLQMNSLKPED-TAVYYCA$X_{89}$, wherein:

$X_{50}$ is A, V, I, L, D, E, R, H, K, N, Q, S, T, F, Y, W, or absent (e.g., L, D, R, N, T, Y, or absent); and $X_{89}$ is G, A, V, I, L, R, H, K, F, Y, W, or absent (e.g., G, A, V, R, K, Y, or absent).

In other embodiments, each X in SEQ ID NO: 288 can be an amino acid in any one of SEQ ID NOs: 250-284 when any one of the sequences in SEQ ID NOs: 250, 251, 260-263, 266-268, 270, 272, 276, and 280-282 is used as a reference sequence to be optimally aligned with SEQ ID NO: 288.

In other embodiments, the third FR includes or is a polypeptide sequence having at least 90% (such as at least 95% or at least 98%) sequence identity to SEQ ID NO: 289:

$X_{50}$YADSVKGRFTISRDNAKNTVYLQMNSLKPED-TAVYYCA, wherein:

$X_{50}$ is A, V, I, L, D, E, R, H, K, N, Q, S, T, F, Y, W, or absent (e.g., L, D, R, N, T, Y, or absent).

In other embodiments, each X in SEQ ID NO: 289 can be an amino acid in any one of SEQ ID NOs: 250-284 when any one of the sequences in SEQ ID NOs: 250, 251, 260, 267, 272, 276, and 281 is used as a reference sequence to be optimally aligned with SEQ ID NO: 289.

FIG. 18D provides non-limiting FR4 sequences. In some embodiments, the fourth FR includes or is a polypeptide sequence having at least 90% (such as at least 95% or at least 98%) sequence identity to SEQ ID NOs: 290-301. In other embodiments, the fourth FR includes or is a polypeptide sequence having at least 90% (such as at least 95% or at least 98%) sequence identity to SEQ ID NO: 302:

$X_{90}$WG$X_{93}$G$X_{95}X_{96}X_{97}$TVS$X_{101}$, wherein:

$X_{90}$ is A, V, I, L, R, H, K, N, Q, S, T, F, Y, W, or absent (e.g., V, H, Q, S, F, Y, or absent);

$X_{93}$ is R, H, K, N, Q, P, F, Y, or W (e.g., R, K, Q, or P);

$X_{95}$ is A, V, I, L, S, or T (e.g., L or T);

$X_{96}$ is A, V, I, L, C, M, N, Q, S, or T (e.g., L, M, Q, S, or T);

$X_{97}$ is A, V, I, or L (e.g., V or L); and $X_{101}$ is S, T, or absent (e.g., S or absent).

In other embodiments, each X in SEQ ID NO: 302 can be an amino acid in any one of SEQ ID NOs: 290-301 when any one of the sequences in SEQ ID NOs: 290-299, and 301 is used as a reference sequence to be optimally aligned with SEQ ID NO: 302.

In some embodiments, the fourth FR includes or is a polypeptide sequence having at least 90% (such as at least 95% or at least 98%) sequence identity to SEQ ID NO:303:

$X_{90}$WG$X_{93}$G$X_{95}X_{96}X_{97}$TVS, wherein:

$X_{90}$ is A, V, I, L, R, H, K, N, Q, S, T, F, Y, W, or absent (e.g., V, H, Q, S, F, Y, or absent);

$X_{93}$ is R, H, K, N, Q, P, F, Y, or W (e.g., R, K, Q, or P);

$X_{95}$ is A, V, I, L, S, or T (e.g., L or T);

$X_{96}$ is A, V, I, L, C, M, N, Q, S, or T (e.g., L, M, Q, S, or T); and $X_{97}$ is A, V, I, or L (e.g., V or L).

In other embodiments, each X in SEQ ID NO: 303 can be an amino acid in any one of SEQ ID NOs: 290-301 when any one of the sequences in SEQ ID NOs: 290-293, 295, 297, 298, 300, and 301 is used as a reference sequence to be optimally aligned with SEQ ID NO: 303.

In some embodiments, the fourth FR includes or is a polypeptide sequence having at least 90% (such as at least 95% or at least 98%) sequence identity to SEQ ID NO: 304:

WG$X_{93}$G$X_{95}X_{96}X_{97}$TVS$X_{101}$, wherein:

$X_{93}$ is R, H, K, N, Q, P, F, Y, or W (e.g., R, K, Q, or P);

$X_{95}$ is A, V, I, L, S, or T (e.g., L or T);

$X_{96}$ is A, V, I, L, C, M, N, Q, S, or T (e.g., L, M, Q, S, or T);

$X_{97}$ is A, V, I, or L (e.g., V or L); and $X_{101}$ is S, T, or absent (e.g., S or absent).

In other embodiments, each X in SEQ ID NO: 304 can be an amino acid in any one of SEQ ID NOs: 290-301 when any one of the sequences in SEQ ID NOs: 291, 293-297, 300, and 301 is used as a reference sequence to be optimally aligned with SEQ ID NO: 304.

In some embodiments, the fourth FR includes or is a polypeptide sequence having at least 90% sequence identity to SEQ ID NO: 305:

$X_{90}X_{91}$G$X_{93}$GT$X_{96}X_{97}X_{98}$VS$X_{101}$, wherein:

$X_{90}$ is A, V, I, L, R, H, K, N, Q, S, T, F, Y, W, or absent (e.g., V, H, Q, S, F, Y, or absent);

$X_{91}$ is P, F, Y, or W (e.g., W);

$X_{93}$ is R, H, K, N, Q, P, F, Y, or W (e.g., R, K, Q, or P);

$X_{96}$ is A, V, I, L, C, M, N, Q, S, or T (e.g., L, M, Q, S, or T);

$X_{97}$ is A, V, I, or L (e.g., V or L);

$X_{98}$ is S or T; and $X_{101}$ is S, T, or absent (e.g., S or absent).

In other embodiments, each X in SEQ ID NO: 305 can be an amino acid in any one of SEQ ID NOs: 290-301 when any one of the sequences in SEQ ID NOs: 290, 291, 294-301 is used as a reference sequence to be optimally aligned with SEQ ID NO: 305.

In some embodiments, the fourth FR includes or is a polypeptide sequence having at least 90% (such as at least 95% or at least 98%) sequence identity to SEQ ID NO:306:

$X_{90}$WGQGTQVTVSS, wherein:

$X_{90}$ is A, V, I, L, R, H, K, N, Q, S, T, F, Y, W, or absent (e.g., V, H, Q, S, F, Y, or absent).

In other embodiments, each X in SEQ ID NO: 306 can be an amino acid in any one of SEQ ID NOs: 290-301 when any one of the sequences in SEQ ID NOs: 290, 291, 296, 297, 298, 299, and 301 is used as a reference sequence to be optimally aligned with SEQ ID NO: 306.

In other embodiments, the fourth FR includes or is a polypeptide sequence having at least 90% (such as at least 95% or at least 98%) sequence identity to SEQ ID NO: 307:

$X_{90}$WGQGTQVTVS, wherein:

$X_{90}$ is A, V, I, L, R, H, K, N, Q, S, T, F, Y, W, or absent (e.g., V, H, Q, S, F, Y, or absent).

In other embodiments, each X in SEQ ID NO: 307 can be an amino acid in any one of SEQ ID NOs: 290-301 when any one of the sequences in SEQ ID NOs: 296 and 299 is used as a reference sequence to be optimally aligned with SEQ ID NO: 307.

Targets

A target can be an antigen that can be bound by any construct described herein. Non-limiting targets include a coronavirus or a portion thereof. Non-limiting portions of a coronavirus, such as SARS-Cov-2, includes a spike protein (e.g., a S-glycoprotein) or a receptor-binding domain (RBD). Non-limiting sequences for such spike proteins and RBDs include one or more of the following: UniProtKB No. P0DTC2 (amino acids 13-1273 for the spike glycoprotein, amino acids 13-685 for the spike protein 1, amino acids 319-541 for the RBD, or amino acids 437-508 for a receptor-binding motif that binds to human ACE2); UniProtKB No. A0A6B9WHD3 (amino acids 31-1228 for the spike glycoprotein, amino acids 31-592 for the spike protein 1, or amino acids 349-526 for the RBD); UniProtKB No. P59594 (amino acids 14-1255 for the spike glycoprotein, amino acids 14-667 for the spike protein S1, amino acids 306-527 for the RBD, or amino acids 424-494 for a receptor-binding motif that binds to human ACE2); UniProtKB No. Q5GDB5 (amino acids 14-667 for spike protein S1, amino acids 306-527 for the RBD, or amino acids 335-512 for the RBD); UniProtKB No. Q3LZX1 (amino acids 14-1242 for the spike glycoprotein, amino acids 14-654 for the spike protein S1, or amino acids 310-514 for the RBD); UniProtKB No. Q315J5 (amino acids 14-1241 for the spike glycoprotein, amino acids 14-653 for the spike protein S1, or amino acids 310-513 for the RBD); and UniProtKB No. Q0Q475 (amino acids 14-1241 for the spike glycoprotein, amino acids 14-653 for the spike protein S1, or amino acids 310-513 for the RBD).

Targets can also include a polypeptide sequence having at least 90% (such as at least 95% or at least 98%) sequence identity to any one of SEQ ID NOs: 320-327 (FIGS. 19A-19D) or a fragment thereof. In other embodiments, each X in SEQ ID NO: 327 can be an amino acid in any one of SEQ ID NOs: 320-326 when any one of the sequences in SEQ ID NOs: 320-326 is used as a reference sequence to be optimally aligned with SEQ ID NO: 327.

In yet other embodiments, the target can include the following one or more mutations: L5F. V341I, K417N, K417T, A435S, N439K, L452R, K458R, 1472V, E484K, N501Y, D614G, H655Y, R682Q, D936Y, S939F. S943T, and/or any other mutations listed herein using the numbering provided for SEQ ID NO: 320 or for another sequence that is optimally aligned with SEQ ID NO: 320.

Targets can also include a polypeptide sequence having at least 90% (such as at least 95% or at least 98%) sequence identity to any one of SEQ ID NOs: 328-336 (FIG. 20) or a fragment thereof. In other embodiments, each X in SEQ ID NO: 335 can be an amino acid in any one of SEQ ID NOs: 328-334 when any one of the sequences in SEQ ID NOs: 328-334 is used as a reference sequence to be optimally aligned with SEQ ID NO: 335. In yet other embodiments, each X in SEQ ID NO: 336 can be an amino acid in any one of SEQ ID NOs: 328-334 when any one of the sequences in SEQ ID NOs: 328-334 is used as a reference sequence to be optimally aligned with SEQ ID NO: 336.

In some embodiments, the target is or includes a polypeptide sequence having at least 90% (such as at least 95% or at least 98%) sequence identity to SEQ ID NO: 335:

$RVX_{321}PX_{323}X_{324}X_{325}X_{326}X_{327}RFPNITNX_{335}$
$CPFX_{339}X_{340}X_{341}FNAX_{345}X_{346}FX_{348}X_{349}VYA$-
$WX_{354}RX_{356}X_{357}ISX_{360}CVADYX_{366}VLYNSX_{372}$
$X_{373}FSTFKCYGVSX_{384}X_{385}KLX_{388}DLCFX_{393}$
$X_{394}VYADX_{399}FX_{401}X_{402}X_{403}X_{404}X_{405}X_{406}VR$-
$QX_{410}APGX_{414}TGX_{417}IADYNYKLPDDFX_{430}GC$-
$VX_{434}X_{435}WNX_{438}X_{439}X_{440}X_{441}DX_{443}X_{444}X_{445}$
$X_{446}GX_{448}X_{449}X_{450}YX_{452}YRX_{455}X_{456}RX_{458}X_{459}$
$X_{460}$ $LX_{462}PFERDX_{468}SX_{470}X_{471}X_{472}X_{473}X_{474}X_{475}$
$X_{476}X_{477}X_{478}X_{479}X_{480}X_{481}X_{482}X_{483}X_{484}X_{485}X_{486}$
$NX_{488}X_{489}X_{490}X_{491}LX_{493}X_{494}YX_{496}FX_{498}X_{499}X_{500}$
$X_{501}X_{502}X_{503}X_{504}X_{505}QX_{507}X_{508}RVVVLSFEL$-
$LX_{519}APATVCGPKX_{529}S$ $TX_{532}LX_{534}KNX_{537}CVNF$ wherein:

$X_{321}$ is A, V, I, L, N, Q, S, or T (e.g., V, Q, S, or T);

$X_{323}$, $X_{345}$, $X_{366}$, $X_{385}$, $X_{393}$, $X_{399}$, $X_{404}$, and $X_{438}$ is, independently, G, S, or T (e.g., S or T);

$X_{324}$, $X_{339}$, $X_{354}$, $X_{360}$, $X_{414}$, and $X_{532}$ is, independently, G, D, E, N or Q (e.g., G, D, E, or Q; E or N; D or N; or E or Q);

$X_{325}$ and $X_{405}$ is, independently, D, E, S, or T (e.g., D, E, or S);

$X_{326}$, $X_{327}$, $X_{341}$, $X_{401}$, $X_{402}$, $X_{410}$, $X_{434}$, $X_{468}$, $X_{503}$, and $X_{534}$ is, independently, A, V, I, or L (e.g., V or I; or V or L);

$X_{335}$ and $X_{529}$ is, independently, A, V, I, L, R, H, or K (e.g., L or R; or V or K);

$X_{340}$ is D, E, R, H, or K (e.g., E or K);

$X_{346}$, $X_{356}$, and $X_{403}$ is, independently, R, H, K, S, or T (e.g., R, K, or T);

$X_{348}$, $X_{384}$, $X_{489}$, $X_{502}$, and $X_{507}$ is, independently, G, A, V, I, L, P, F, Y, or W (e.g., A or P; V or W; G or P; G or W);

$X_{349}$, $X_{394}$, $X_{470}$, and $X_{500}$ is, independently, N, Q, S, or T (e.g., N or S);

$X_{357}$, $X_{458}$, and $X_{462}$ is, independently, R, H, or K (e.g., R or K);

$X_{372}$ and $X_{435}$ is, independently, A, V, I, L, S, or T (e.g., A or T; or A or S);

$X_{373}$, $X_{491}$, and $X_{499}$ is, independently, S, T, P, F, Y, or W (e.g., S or F; or T or P);

$X_{388}$ is A, V, I, L, N, or Q (e.g., I or N);

$X_{406}$, $X_{496}$, and $X_{504}$ is, independently, G, A, V, I, L, D, or E (e.g., D or E; or G, A, or E);

$X_{417}$, $X_{439}$, $X_{441}$, and $X_{443}$ is, independently, A, V, I, L, R, H, K, N, Q, S, or T (e.g., V, K, N, or T; A, R, K, or N; A, Q, S, or T; or L, I, H, or Q);

$X_{430}$ is L, C, M, S, or T (e.g., M or T);

$X_{440}$, $X_{450}$, $X_{460}$, $X_{519}$, and $X_{537}$ is, independently, R, H, K, N or Q (e.g., N, K, or Q);

$X_{444}$, $X_{446}$, and $X_{478}$ is, independently, G, R, H, K, S, T, or absent (e.g., K, T, or absent; or G, T, or absent; or K, T, or absent);

$X_{445}$, $X_{459}$, $X_{471}$, $X_{476}$, $X_{477}$, and $X_{485}$ is, independently, G, A, V, I, L, D, E, S, T, or absent (e.g., V, E, S, or absent; G, A, E, S, or T; V, D, or E; G, D, E, or absent; G, S, or absent; E, T, or absent; or G, A, or absent);

$X_{448}$ is N, Q, or absent (e.g., N or absent);

$X_{449}$, $X_{473}$, $X_{479}$, and $X_{482}$ is, independently, G, P, F, Y, W, or absent (e.g., F, Y, or absent; P or absent; or G, P, or absent);

$X_{452}$, $X_{456}$, $X_{490}$, and $X_{505}$ is, independently, A, V, I, L, R, H, K, F, Y, or W (e.g., L, R, K or Y; or L, H, F, or Y; or R, F, Y, or W; or H or Y);

$X_{455}$ and $X_{508}$ is, independently, A, V, I, L, S, T, F, Y, or W (e.g., L, S, or Y; or T or Y);

$X_{472}$, $X_{475}$, and $X_{483}$ is, independently, A, V, I, L, D, E, N, Q, P, or absent (e.g., V, I, D, P, or absent; A, P, or absent; or V, Q, P, or absent);

$X_{474}$ and $X_{481}$ is, independently, N, Q, S, T, or absent (e.g., Q. S, or absent; N, T, or absent);

$X_{480}$ and $X_{488}$ is, independently, G, C, M, or absent (e.g., C or absent);

$X_{486}$ is G, A, V, I, L, D, E, P, F, Y, or W (e.g., G, L, E, P, or F);

$X_{493}$ and $X_{498}$ is, independently, N, Q, S, T, F, Y, or W (e.g., N, Q, S, or Y; or N, Q, or Y)

$X_{484}$ and $X_{494}$ is, independently, G, D, E, R, H, K, S, T, or absent (e.g., G, D, R, S, or T; or E, K, T, or absent); and $X_{501}$ is any amino acid, such as A, V, I, L, D, E, N, Q, S, T, F, Y, or W (e.g., V, I, D, N, S, T, or Y).

In yet other embodiments, the target can include the following one or more mutations: V341I, K417N, K417T, A435S, N439K, L452R, K458R, 1472V, E484K, N501Y and/or any other mutations listed herein, using the numbering provided for SEQ ID NOs: 335-336 or for another sequence that is optimally aligned with one of SEQ ID NOs: 335-336.

Therapeutic or Diagnostic Agents

The present disclosure also encompasses a construct that can be directly or indirectly attached to one or more therapeutic or diagnostic agents. Such agents can include a therapeutic antibody, a complementarity determining region (CDR), a small molecule, a chemotherapeutic agent, an antiviral agent, an antibacterial agent, an anti-inflammatory agent, a scavenging agent, an imaging agent, a marker, a dye, a detectable moiety, or a label.

However, in an embodiment, the nanobody or construct comprising a nanobody is not attached directly, or indirectly to any therapeutic, delivery, or diagnostic agent. In fact, the small size and water solubility of the nanobody are advantageous without additional attachments to promote delivery to the body, targeting certain tissues, and circulation within the body. The nanobody attached to a humanized Fc still provides solubility and targeting benefits, but also promotes signaling the body's own immune response and keeping the nanobody circulating in the blood stream without being filtered out by the kidneys.

Any of the constructs herein (e.g., nanobodies, nanobodies bound to humanized Fc) can be employed to bind to a target. Binding can be accomplished, e.g., by using CDRs specific for that target, such as those disclosed herein. In one embodiment, the construct includes one or more CDRs for viral targets. Exemplary targets include a virus, such as Coronaviridae (e.g., severe acute respiratory syndrome-related coronavirus (SARS-COV), severe acute respiratory syndrome coronavirus 2 (SARS-COV-2), or variants thereof); or a portion of a virus, such as a spike protein or a receptor-binding domain (RBD) of a coronavirus.

Other non-limiting therapeutic or diagnostic agents include a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; or a lipopolysaccharide.

Non-limiting detectable moieties for diagnostic agents may be a radioisotope (e.g., 32P), a fluorescent or chemiluminescent compound such as rhodamine or luciferin, or an enzyme, such as alkaline phosphatase or horseradish peroxidase. Non-limiting labels include a radiolabel, an isotope, a visible or near-infrared fluorescent label, a reporter molecule, or biotin.

The therapeutic or diagnostic agent can be a peptide, an enzyme (e.g., horseradish peroxidase, alkaline phosphatase, glucose-6-phosphatase or Beta-galactosidase), a nucleic acid, a virus, a fluorophore (e.g., green fluorescent protein (GFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or dyes excited with far-red light (e.g., Cy5) to be visualized with electronic detectors (CCD cameras, photomultipliers)), a heavy metal (including chelates thereof, such as those including europium, lanthanum or yttrium), a chemical entity, or a radioisotope (e.g., [$^{18}$F] fluorodeoxy glucose, $^{11}$C—, $^{125}$I—, $^{131}$I—, $^{3}$H—, $^{14}$C—, $^{35}$S—, or $^{99}$Tc— labelled compounds).

The therapeutic or diagnostic agent can include a drug, an antigen binding fragment of an antibody molecule or portion thereof (e.g., F(ab), scFv, a VH domain, or a VL domain) (e.g., to impart, induce or block a biological response), a ligand binding portion of a receptor or a receptor binding portion of a ligand, an enzyme, therapeutically useful amino acids, peptides, proteins, nucleic acids, including but not limited to polynucleotides, oligonucleotides, carbohydrates and lipids. Yet other exemplary agents include cytokines, neurotrophic factors, growth factors, enzymes, antibodies, neurotransmitters, neuromodulators, antibiotics, antiviral agents, antifungal agents, imaging or detectable agents, isotopes, and chemotherapeutic agents, and the like. The therapeutic or diagnostic agents can also include drugs, prodrugs, and precursors that can be activated when the therapeutic agent is delivered to the target tissue.

Methods

The present disclosure also encompasses methods that employ any construct described herein. In particular embodiments, the methods include method of treatment or prophylaxis of one or more diseases or conditions. Non-limiting diseases and conditions include a viral infection.

Methods can also include use of the construct as a therapeutic or diagnostic agent, which can be administered to a subject (a mammal or a human) by inhalation, oral, nasal, injection, intravenous, intraperitoneal, intramuscular or subcutaneous injection. The constructs herein (e.g., with a therapeutic or diagnostic agent) can be used in imaging or in diagnosing viral spread.

Methods can also include providing a construct or a pharmaceutical composition thereof (e.g., as described herein) for use in the treatment of viral infections or any disorder or condition herein. A pharmaceutical composition can include any construct, described herein either with a therapeutic or diagnostic agent, and a pharmaceutically acceptable carrier.

As used herein, "pharmaceutically acceptable carrier" is intended to include pharmaceutically acceptable salts, adjuvants, dispersion media, coatings, antibacterial and antifungal agents, isotonic and absorption delaying agents, and the like, compatible with pharmaceutical administration. Pharmaceutically acceptable salts include the acid addition salts (formed with the free amino groups of the polypeptide or antibody molecule) which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Suitable carriers include those disclosed in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

EXAMPLES

Example 1: Nanobody Development and Library

A high-diversity synthetic nanobody phage library was used to identify 59 humanized nanobodies that show nanomolar to low picomolar efficacy in preventing cell infection by replicating VSV-SARSCOV-2 virus. In particular, a high diversity humanized nanobody library (more than $3\times10^{10}$ nanobody variants) was developed and designed to have three different CDR3 lengths and incorporated the natural prevalence of amino acids at specific CDR positions for CDR1 and CDR2 derived from numerous effective nanobodies. For CDR3, all amino acids were used with the exception of cysteine and methionine. The sequence used for the framework to house the custom made CDRs, hs2dAb, was derived from Moutel et al. In this framework, multiple residues are changed such that the framework more closely mirrors germline human VH3 immunoglobin. To obtain sufficient diversity coverage for the library (i.e., transformants), 150 electroporations were performed yielding approximately $3.38\times10^{10}$ transformants. To determine the level of success for the ligation of the library into the vector backbone, colony PCR was performed. Of the 408 colonies selected, 395 contained the correct size amplified DNA fragment (95.9%). This value was used to adjust the calculated value for library diversity to $3.24\times10^{10}$. Finally, library diversity, quality, and the distribution of CDR3 lengths were assessed by NGS from a total of 39,870,360 reads. The 9-amino acid CDR3 was the most prevalent at 40%, followed by 12-amino acid CDR3 at 34%, and lastly the 15-amino acid CDR3 at 25% of the observed diversity. Overall, there was good coverage of all represented CDR3s. Approximately 1% of sequences contained a stop codon and 99% of reads were unique sequences (38,592,027 reads). Roughly 1% of reads were duplicates, and 0.01% (1,095 sequences) were present in triplicate. With these corrections, the adjusted diversity for this nanobody library is $3.18\times10^{10}$.

FIG. 1 discloses a method of constructing a nanobody phage library. In particular, the library was constructed using novel DNA synthesis technology, thereby ensuring high quality and full length nanobodies with low incidence of stop codons. These attributes allowed for the identification of highly potent binders to desired targets with femtomolar to nanomolar dissociation constants. This library was cloned into the pADL20c M13 phagemid vector, which allows for expression of nanobodies as a fusion protein to coat protein gIIIp of M13 phage.

Example 2

Figure 2:
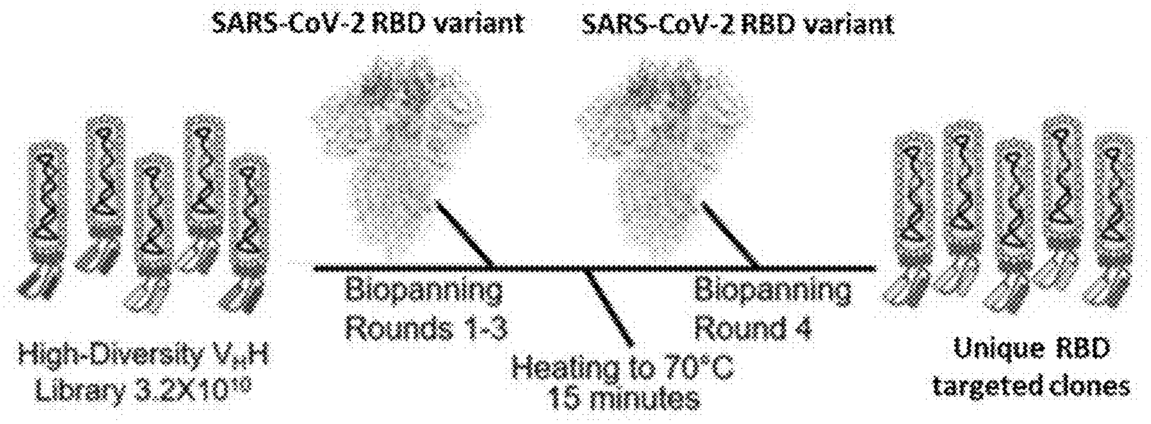
FIG. 2 is a schematic of further details for developing the library of nanobodies.

FIG. 2 shows a further process in which the library of Example 1 was screened against mutated variants of full length soluble SARS-COV-2 stabilized spike protein for one to three rounds, followed by a single round against mutated variants of the SARS-COV-2 receptor-binding domain (RBD) to determine binding affinity for the SARS-COV-2 variants. For the first three rounds, full-length soluble purified SARS-COV-2 S protein confirmed as a trimer was used, ensuring that conformational integrity of the RBD was maintained for initial selection. A 15-minute heat denaturing step at 70° C. was used to remove unstable sequences and a final round of biopanning against SARS-COV-2 RBD was conducted to identify therapeutically relevant VHH antibodies. Enrichment of phage against SARS-COV-2 S was observed over the initial three rounds of biopanning and there was a significant loss in phage recovered when the antigen was shifted to RBD (0.0005% compared to 0.004%).

In particular, the SARS-COV-2 variants that the library was screened for were for those mutations identified in Table 3 for each variant.

TABLE 3

| 20I (Alpha, V1) (B.1.1.7) | 20H (Beta, V2) (B.1.351) | 20J (Gamma, V3) (P.1) | 21A (Delta) (B.1.617.2) | 21B (Kappa) (B.1.617.1) | 21K (Omicron) (BA.1) | 21G (Lambda) (C.37) | 21H (Mu) (B.1.621) |
|---|---|---|---|---|---|---|---|
| Shared mutations | | | | | | | |
| S:D614G | S:D614G | S:D614G | S:D614G | S:D614G | S:D614G | S:D614G | S:D614G |
| | S:E484K | S:E484K | | S:E484Q | S:E484A | | S:E484K |
| S:N501Y | S:N501Y | S:N501Y | | | S:N501Y | | S:N501Y |
| S:P681H | | | S:P681R | S:P681R | S:P681H | | S:P681H |
| S:Y144- | | | | | S:Y144- | | S:Y144S |
| | S:K417N | S:K417T | | | S:K417N | | |
| | | | S:T478K | | S:T478K | | |
| | | S:H655Y | | | S:H655Y | | |
| | | | | | S:Y145D | | S:Y145N |
| | | | S:L452R | S:L452R | | S:L452Q | |
| | | | | | S:T95I | | S:T95I |
| S: V70- | | | | | S:V70- | | |
| S:H69- | | | | | S:H69- | | |
| Other Mutations | | | | | | | |
| S:A570D | S:A701V | S:L18F | S:D950N | S:E154K | S:N764K | S:D253N | S:D950N |
| S:T716I | S:L18F | S:P26S | S:T19R | S:Q1071H | S:Q493R | S:G75V | S:R346K |
| S:S982A | S:D80A | S:T20N | S:E156- | | S:D796Y | S:T76I | |
| S:D1118H | S:D215G | S:D138Y | S:F157- | | S:N679K | S:R246- | |
| | S:L241- | S:R190S | S:R158G | | S:Y505H | S:S247- | |
| | S:L242- | S:T1027I | | | S:Q498R | S:Y248- | |
| | S:A243- | S:V1176F | | | S:Q954H | S:L249- | |
| | | | | | S:S477N | S:T250- | |
| | | | | | S:N440K | S:P251- | |
| | | | | | S:S375F | S:G252- | |
| | | | | | S:S373P | S:F490S | |
| | | | | | S:S371L | S:T859N | |
| | | | | | S:G339D | | |
| | | | | | S:V143- | | |
| | | | | | S:G142- | | |
| | | | | | S:A67V | | |
| | | | | | S:N969K | | |
| | | | | | S:N211- | | |
| | | | | | S:L212I | | |
| | | | | | S:G446S | | |

Figure 3:
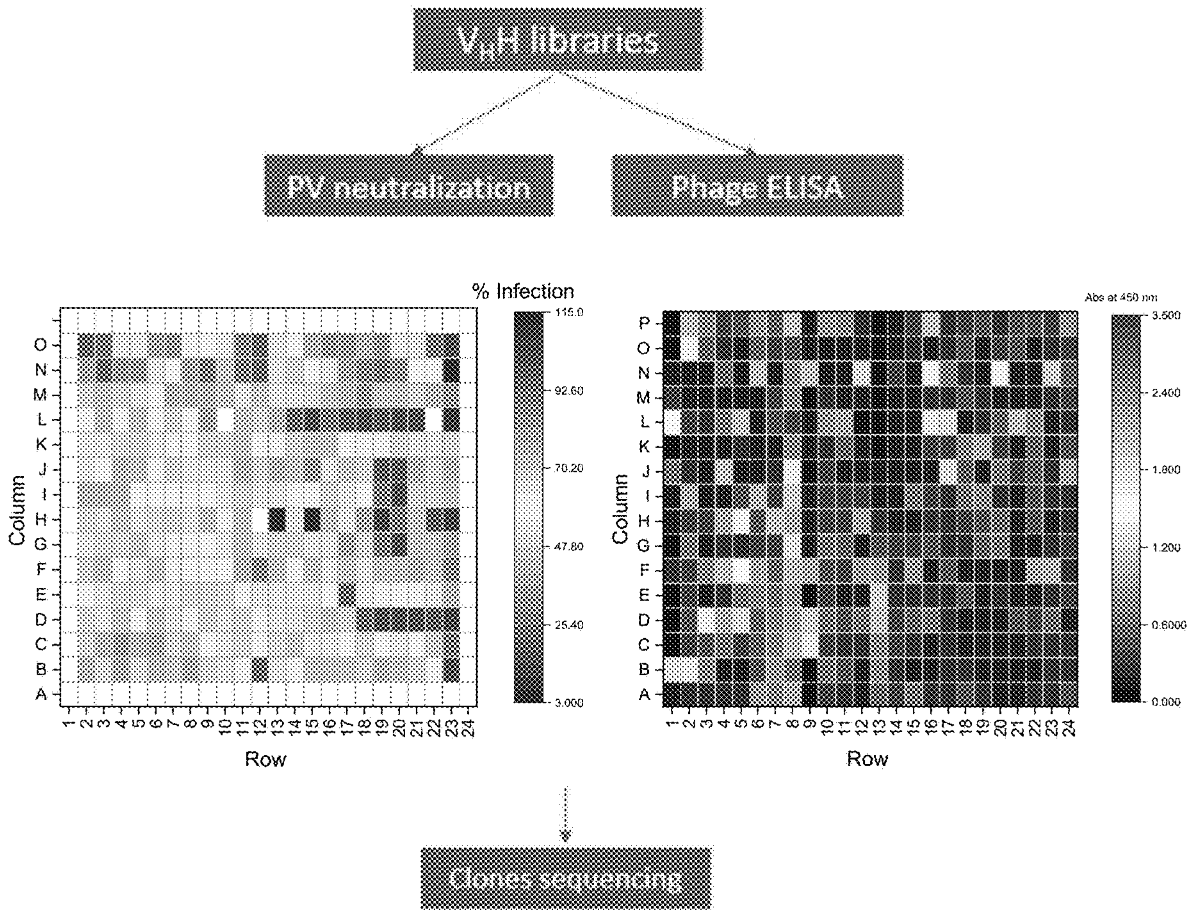
FIG. 3 is another schematic of further details for screening the library of nanobodies.

FIG. 3 is a diagram showing more detail on the screening campaign for the SARS-COV-2 RBD variants binding VHHs from the library. This shows the screening of the VHH library through phage enzyme-linked immunosorbent assay (ELISA) and neutralization of VSC-SARS-COV GFP viral infection. The data is from experimental conditions performed in triplicate; the error is the standard deviation from the mean. From the biopanning campaigns, numerous potential candidate nanobodies were identified.

The phage obtained after the fourth round of selection with RBD from Delta, Lambda, Alpha, Beta, Epsilon and Kappa were singly isolated. The binding affinity and specificity of the nanobody-hock constructs was evaluated and a subset of nanobodies with significant and specific affinity for their respective RBD were tested for neutralization of VSV-SARS-COV-2 GFP pseudotype virus with Spike from the original, Beta, Gamma, Delta, Lambda, Mu and Omicron variants.

Several nanobody-huFcs were tested by ELISA for binding affinity to the Omicron RBD and two of these demonstrated significant affinity for the Omicron variant RBD, comparable to human ACE2. These nanobody-huFcs were also tested for neutralization of VSV SARS-COV-2 GFP pseudotype virus with Spike from Omicron variant.

Thus far, several promising nanobodies that neutralize the original SARS-COV-2 and several of its variants have been identified, including Delta, with high efficacy. A subset of these nanobodies bind to the Omicron RBD.

Example 3

Nanobody constructs comprising three CDRs interspersed between four framework regions and bound to hu-Fc were made from the potential candidate nanobodies identified above. These humanized VHH-huFc antibodies were produced as a fusion of the nanobodies to the hinge region and the Fc domain of human IgG1. This was done by Evitria of Zurich, Switzerland.

This construct combines the advantages of the VHH with the improved half-life and effector functions of human IgG1 while reducing the overall size by half that of a conventional antibody, improving circulation and increasing their ability to penetrate target tissues in the body. These were further tested against SARS-COV-2 variants to determine their binding affinities in competition assays and neutralization assays.

Example 4

Figure 4A:
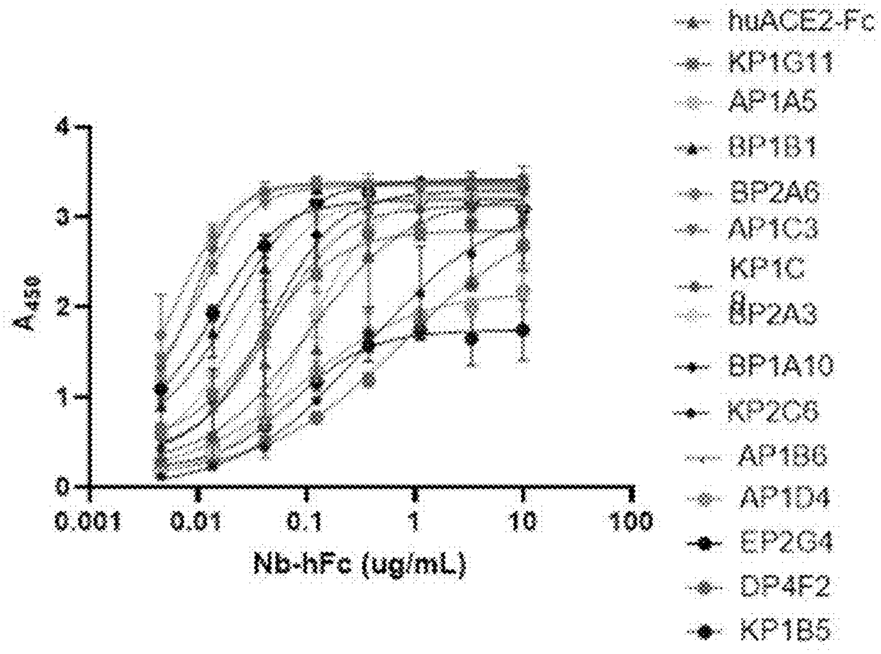
FIGS. 4A-4B are charts showing characterization of selected Nb-huFcs against the Wuhan variant.
Figure 4B:
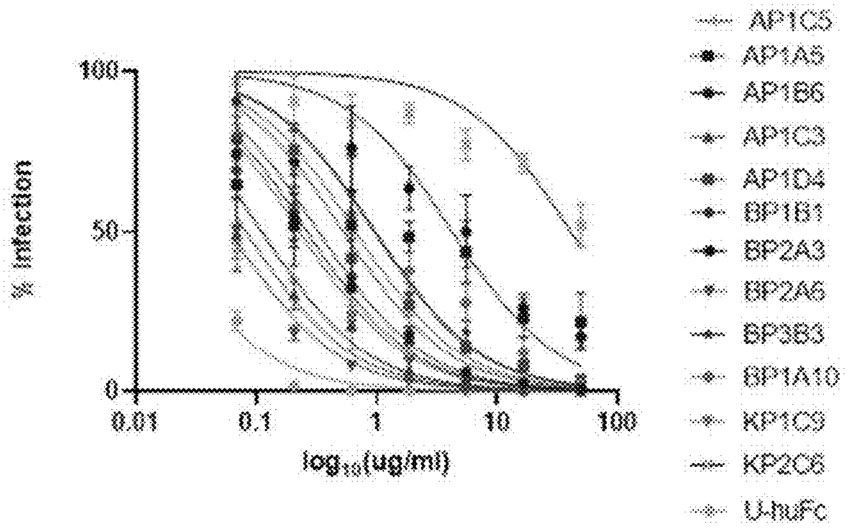

FIGS. 4A-4B are charts showing characterization of selected Nb-huFcs against the Wuhan variant. FIG. 4A shows several Nb-huFcs with their binding affinity to SARS-COV-2 RBD Wuhan variant along with a comparison to ACE2; the effectiveness is measured in kD (nM). FIG. 4B shows neutralization efficacy in preventing cell infection by a VSV-SARS-COV-2 Wuhan variant. The data shows the data normalized to the infection rate in the absence of the antibody. Neutralization effectiveness is measured in EC50 (nM) in FIG. 4B. FIG. 4B also shows a comparison to the U-huFc disclosed in Koenig P A, Das H, Liu H, Kümmerer B M, Gohr F N, Jenster L M, Schiffelers L D J, Tesfamariam Y M, Uchima M, Wuerth J D, Gatterdam K, Ructalo N, Christensen M H, Fandrey C I, Normann S, Todtmann J M P, Pritzl S, Hanke L, Boos J, Yuan M, Zhu X, Schmid-Burgk J L, Kato H, Schindler M, Wilson I A, Geyer M, Ludwig K U, Hällberg B M, Wu N C, Schmidt F I. Structure-guided multivalent nanobodies block SARS-COV-2 infection and suppress mutational escape. Science. 2021 Feb. 12; 371 (6530):cabe6230. doi: 10.1126/science.abc6230. Epub 2021 Jan. 12. PMID: 33436526; PMCID: PMC7932109. The data are from experimental conditions performed in triplicate, the error is the standard deviation from the mean. The nanobody constructs were bound to huFc and are identified by an internal name on the right hand side of the absorbance graph. A key matching the internal names of the nanobody constructs to the Sequence I.D.s is provided in the FIGS.

Example 5

Figure 5A:
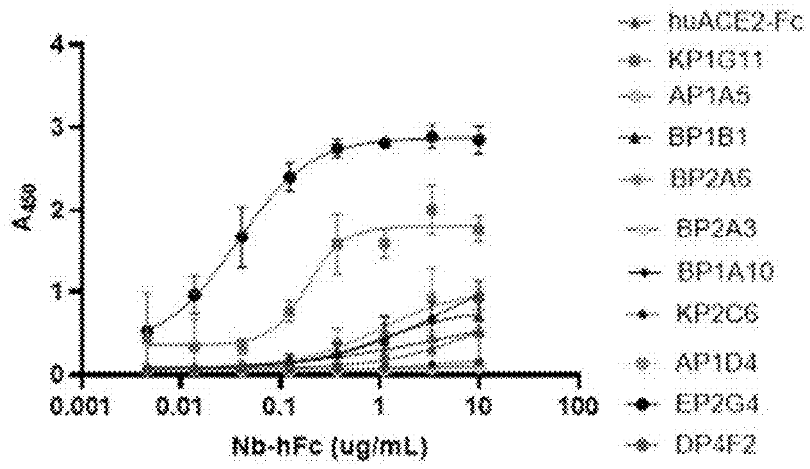
FIGS. 5A-5B are charts showing characterization of selected Nb-huFcs against the Beta variant.
Figure 5B:
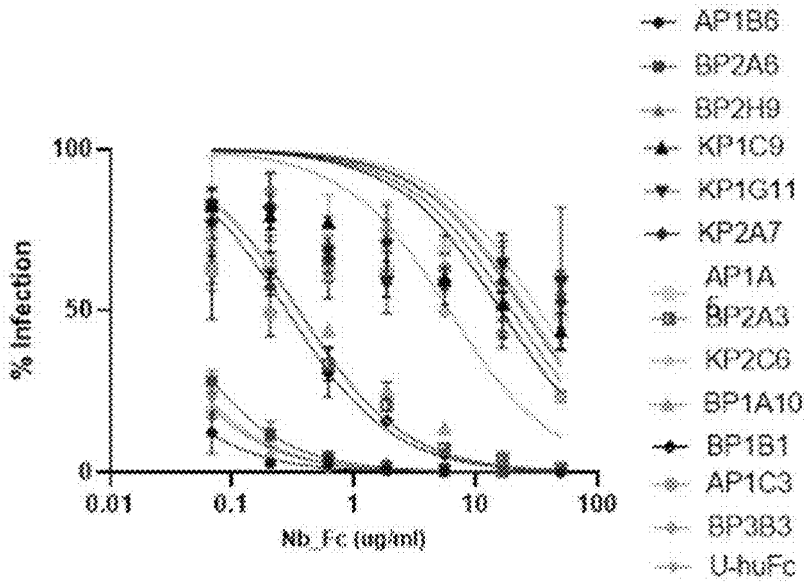

FIGS. 5A-5B are charts showing characterization of selected Nb-huFcs against the Beta variant. FIG. 5A shows several Nb-huFcs with their binding affinity to SARS-COV-2 RBD Beta variant along with a comparison to ACE2; the effectiveness is measured in kD (nM). FIG. 5B shows neutralization efficacy in preventing cell infection by a VSV-SARS-COV-2 Beta variant. The data shows the data normalized to the infection rate in the absence of the antibody. Effectiveness is measured in EC50 (nM) in FIG. 5B. FIG. 5B also shows a comparison to the U-huFc.

Example 6

Figure 6A:
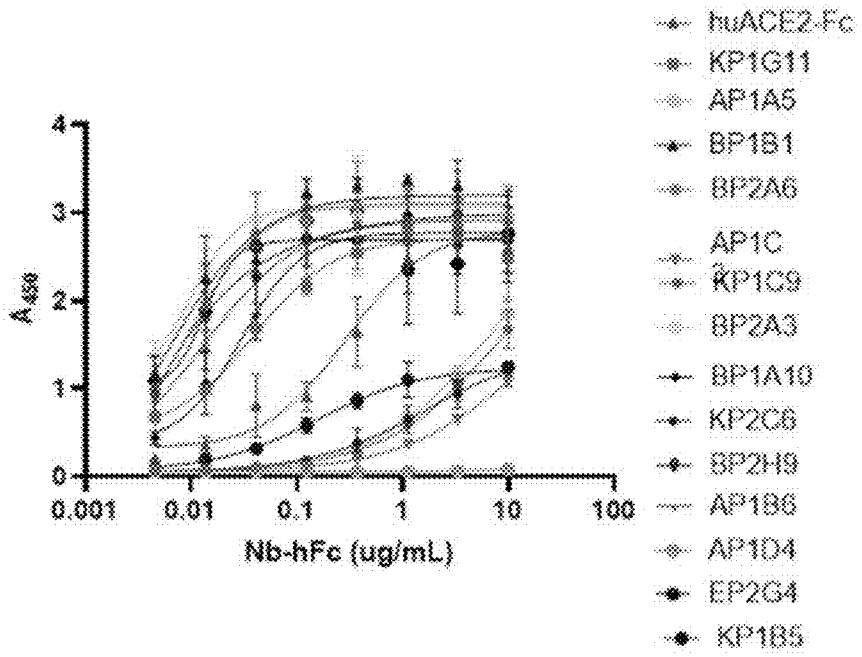
FIGS. 6A-6B are charts showing characterization of selected Nb-huFcs against the Gamma variant.
Figure 6B:
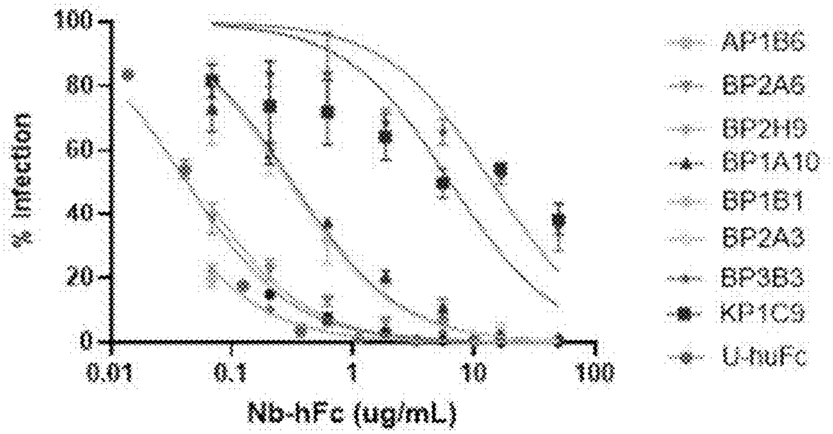

FIGS. 6A and 6B are charts showing characterization of selected Nb-huFcs against the Gamma variant. FIG. 6A shows several Nb-huFcs with their binding affinity to SARS-COV-2 RBD Gamma variant along with a comparison to ACE2; the effectiveness is measured in kD (nM). FIG. 6B shows neutralization efficacy in preventing cell infection by a VSV-SARS-COV-2 Gamma variant. The data shows the data normalized to the infection rate in the absence of the antibody. Effectiveness is measured in EC50 (nM) in FIG. 6B. FIG. 6B also shows a comparison to the U-huFc.

Example 7

Figure 7A:
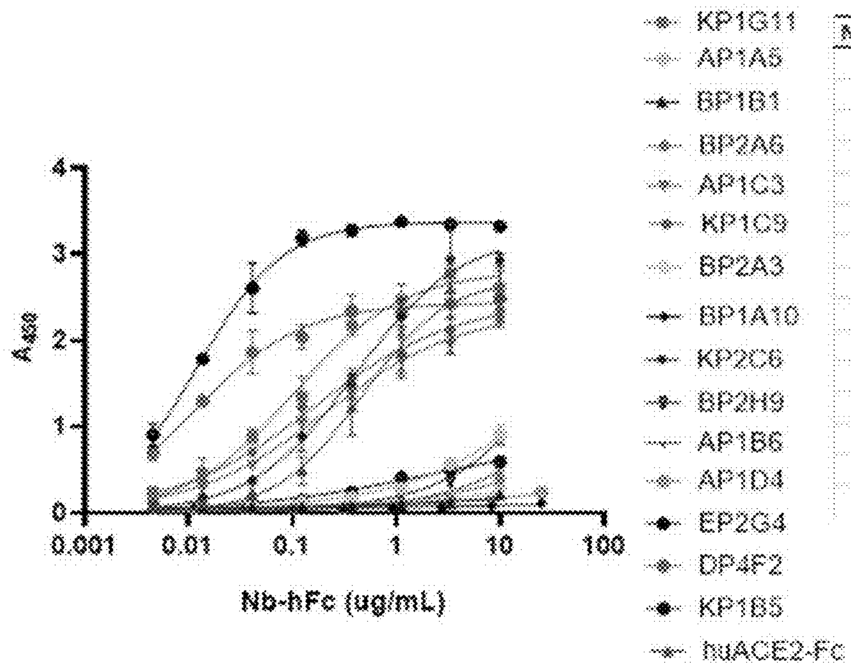
FIGS. 7A-7B are charts showing characterization of selected Nb-huFcs against the Delta variant.
Figure 7B:
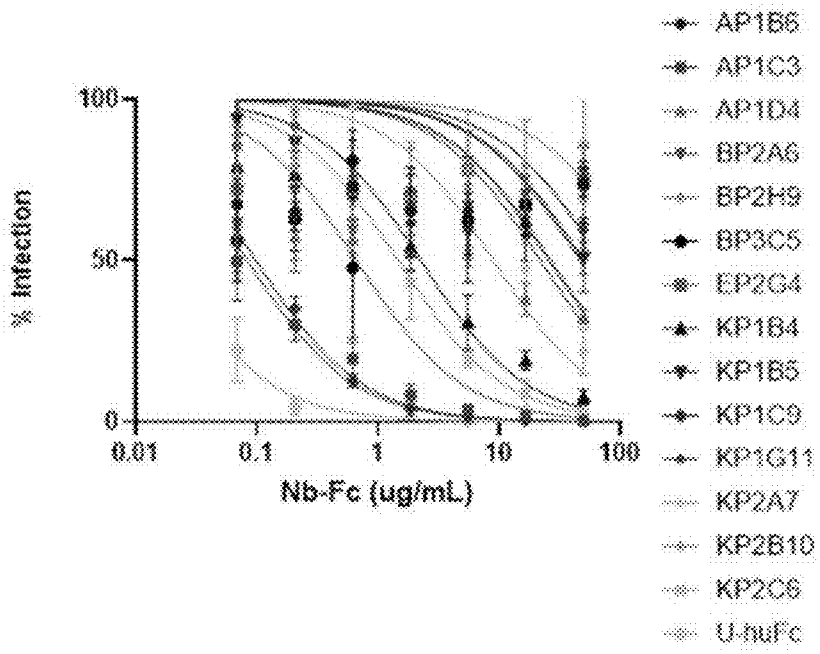

FIGS. 7A-7B are charts showing characterization of selected Nb-huFcs against the Delta variant. FIG. 7A shows several Nb-huFcs with their binding affinity to SARS-COV-2 RBD Delta variant along with a comparison to ACE2; the effectiveness is measured in kD (nM). FIG. 7B shows neutralization efficacy in preventing cell infection by a VSV-SARS-COV-2 Delta variant. The data shows the data normalized to the infection rate in the absence of the antibody. Effectiveness is measured in EC50 (nM) in FIG. 7B. FIG. 7B also shows a comparison to the U-huFc.

Example 8

Figure 8A:
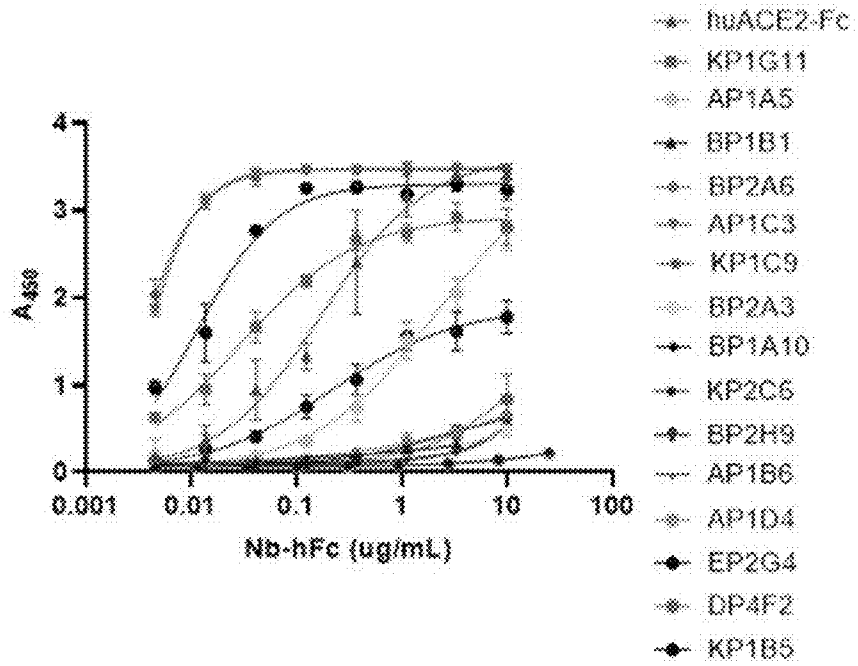
FIGS. 8A-8B are charts showing characterization of selected Nb-huFcs against the Lambda variant.
Figure 8B:
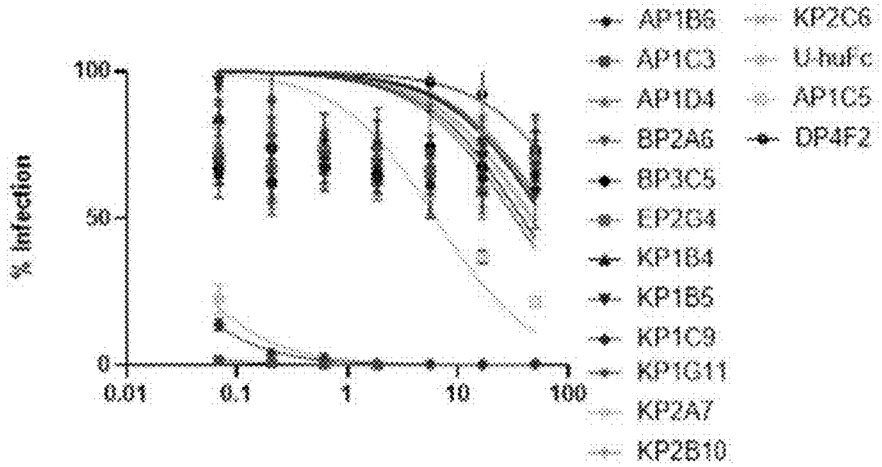

FIGS. 8A-8B are charts showing characterization of selected Nb-huFcs against the Lambda variant. FIG. 8A shows several Nb-huFcs with their binding affinity to SARS-COV-2 RBD Lambda variant along with a comparison to ACE2; the effectiveness is measured in kD (nM). FIG. 8B shows neutralization efficacy in preventing cell infection by a VSV-SARS-COV-2 Lambda variant. The data shows the data normalized to the infection rate in the absence of the antibody. Effectiveness is measured in EC50 (nM) in FIG. 8B. FIG. 8B also shows a comparison to the U-huFc. N.B: Non-binding. N.N: non-neutralization.

Example 9

Figure 9A:
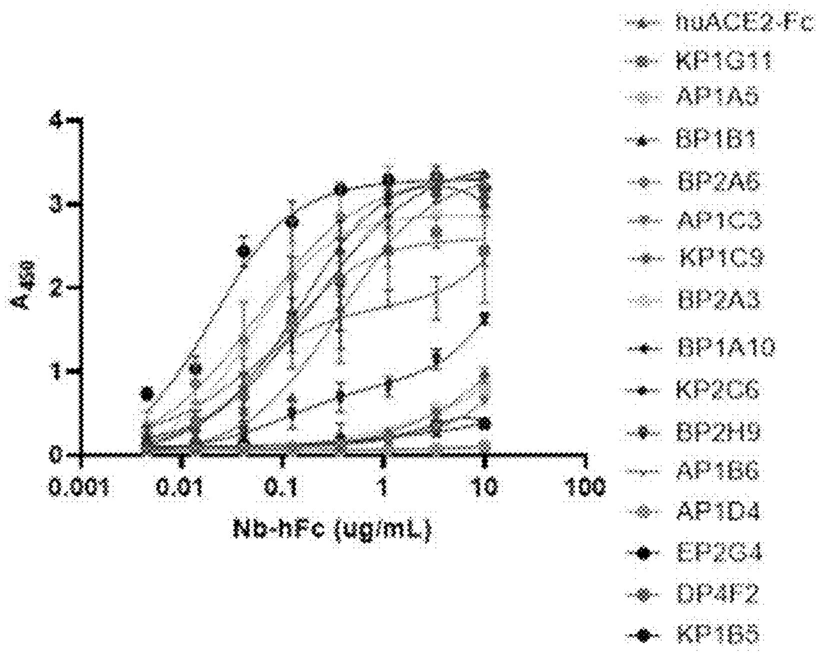
FIGS. 9A-9B are charts showing characterization of selected Nb-huFcs against the Mu variant.
Figure 9B:
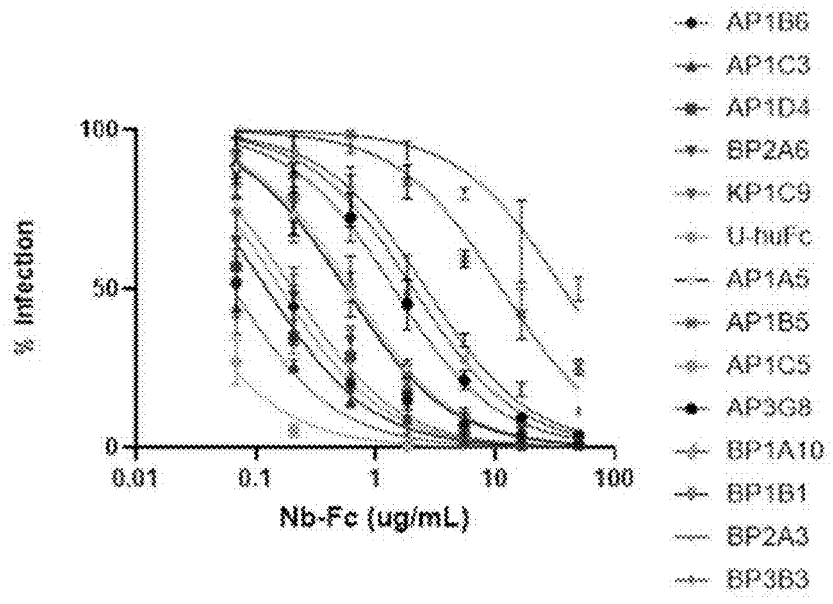

FIGS. 9A-9B are charts showing characterization of selected Nb-huFcs against the Mu variant. FIG. 9A shows several Nb-huFcs with their binding affinity to SARS-COV-2 RBD Mu variant along with a comparison to ACE2; the effectiveness is measured in kD (nM). FIG. 9B shows neutralization efficacy in preventing cell infection by a VSV-SARS-COV-2 Mu variant. The data shows the data normalized to the infection rate in the absence of the antibody. Effectiveness is measured in EC50 (nM) in FIG. 9B. FIG. 9B also shows a comparison to the U-huFc. N.B: Non-binding. N.N: non-neutralization.

Example 10

Figure 10A:
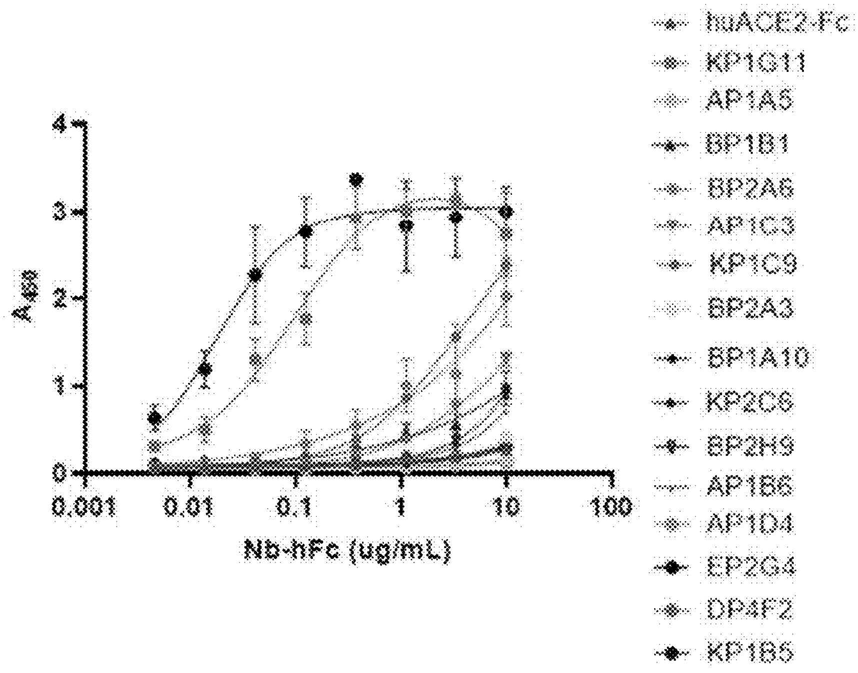
FIGS. 10A-10B are charts showing the characterization of selected Nb-huFcs against the Omicron variant.
Figure 10B:
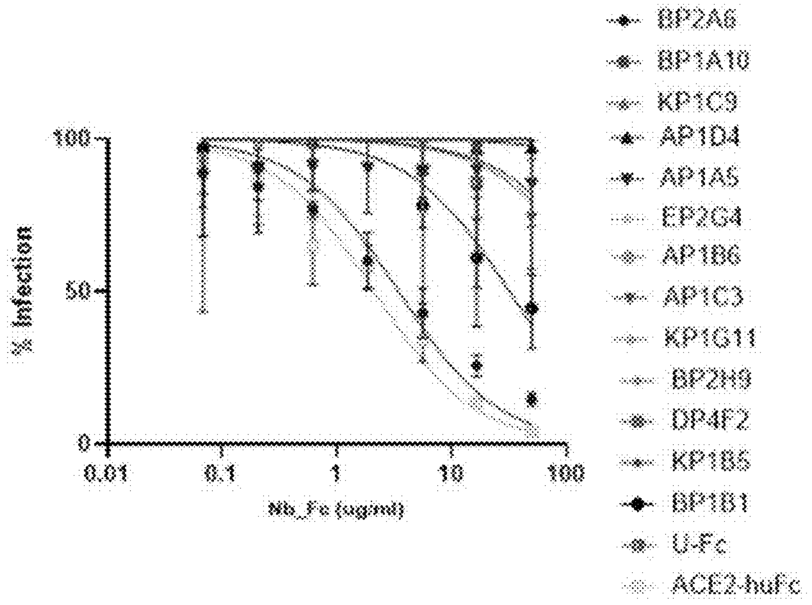
Figure 11A:
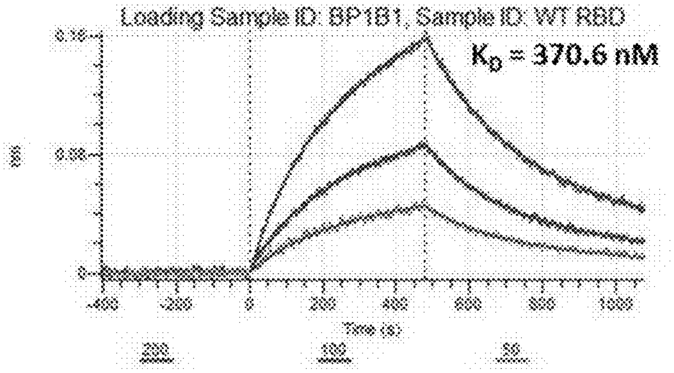
FIGS. 11A-11F are charts showing bio-layer interferometry (BLI) was performed to study the binding kinetics of each of the prepared Nb-huFc constructs against variant SARS-COV-2 spike/RBD
Figure 11B:
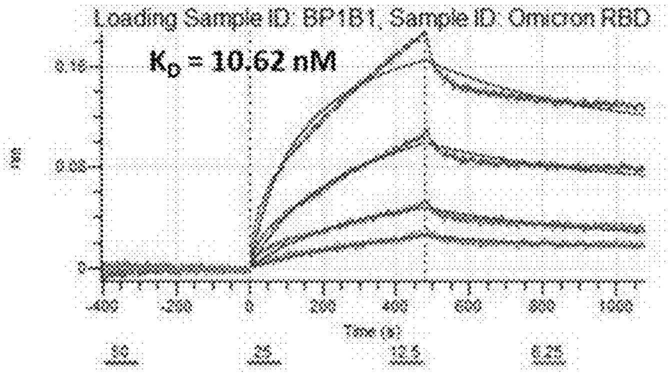
Figure 11C:
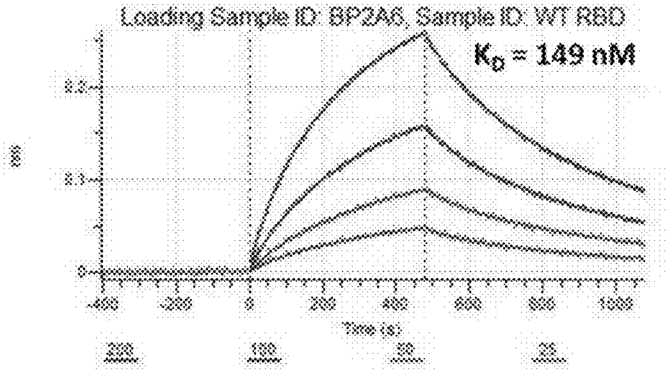
Figure 11D:
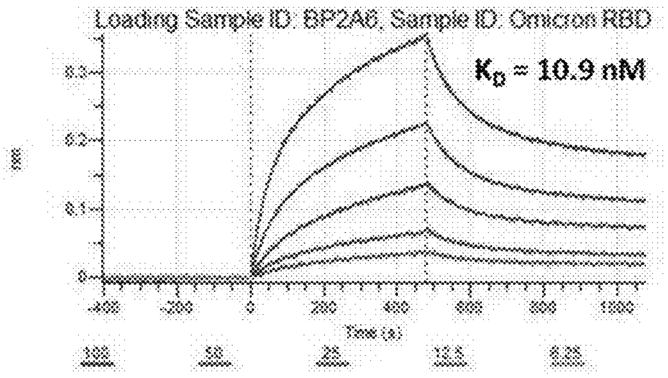
Figure 11E:
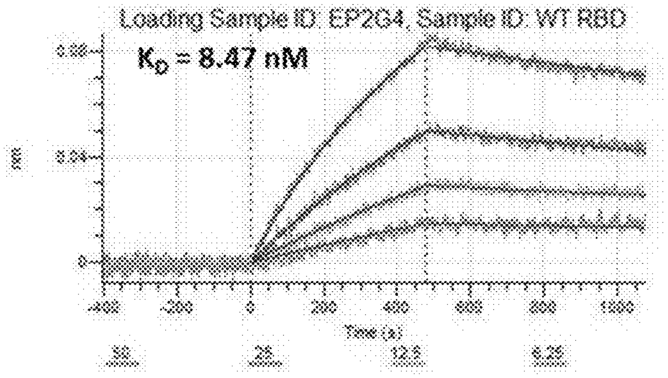
Figure 11F:
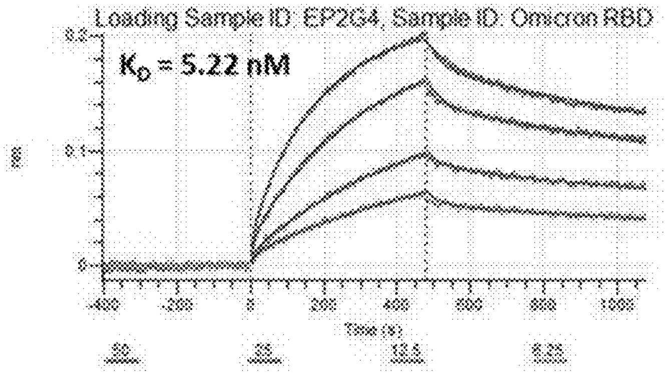

FIGS. 10A-10B are charts showing the characterization of selected Nb-huFcs against the Omicron variant. FIG. 10A shows several Nb-huFcs with their binding affinity to SARS-COV-2 RBD Omicron variant and a comparison to ACE2; the effectiveness is measured in kD (nM). FIG. 10B shows neutralization efficacy in preventing cell infection by a VSV-SARS-COV-2 Omiron variant. The data shows the data normalized to the infection rate in the absence of the antibody. Effectiveness is measured in EC50 (nM) in FIG. 10B. FIG. 10B also shows a comparison to the U-huFc. N.B: Non-binding. N.N: non-neutralization.

Example 11

Tables 4A and 4B summarize the neutralizing efficacy of selected Nb-huFc (nanobody-huFc) candidates formed and tested as discussed above against SARS-COV-2 variant spike pseudotyped virus variants. These tables summarize the EC50s in nanomolar (nM) quantities. (N.N=non-neutralization)

TABLE 4A

| Secondary Identifier | AP1A5 | AP1B6 | AP1C3 | AP1D4 | BP2A6 | BP1A10 |
|---|---|---|---|---|---|---|
| SEQ ID No. | 394 | 389 | 393 | 381 | 367 | 385 |
| Wuhan | 11.94 | 3.32 | 1.04 | 6.62 | 0.77 | 8.38 |
| Beta | 197.65 | 0.12 | 338.03 | 627.21 | 0.34 | 4.32 |
| Gamma | 533.37 | 0.26 | 1.07 | 13.53 | 0.63 | 3.95 |
| Delta | 73.26 | 586.11 | 190.70 | 758.20 | 874.54 | N.N |
| Lambda | 79.13 | 413.63 | 0.02 | 489.67 | 883.12 | N.N |
| Mu | 7.18 | 1.54 | 0.83 | 1.92 | 2.53 | 26.14 |
| Omicron | N.N | N.N | N.N | N.N | 43.31 | N.N |

TABLE 4B

| Secondary Identifier | BP1B1 | BP2A3 | BP2H9 | KP1C9 | DP4F2 | KP2C6 | KP1B5 |
|---|---|---|---|---|---|---|---|
| SEQ ID No. | 371 | 364 | 392 | 369 | 357 | 361 | 387 |
| Wuhan | 4.13 | 58.53 | N.N | 2.89 | 65.79 | 516.79 | 896.47 |
| Beta | 3.50 | 4.44 | 0.21 | 202.95 | N.N | 410.81 | 481.51 |
| Gamma | 3.68 | 3.73 | 0.26 | 80.23 | N.N | 408.39 | 213.68 |
| Delta | N.N | N.N | N.N | 1.22 | 26.83 | 18.34 | 323.91 |
| Lambda | N.N | N.N | N.N | 0.13 | N.N | 611.96 | 471.85 |
| Mu | 6.97 | 465.58 | 922.28 | 2.02 | 25.13 | 304.58 | 367.37 |
| Omicron | 402.74 | N.N | N.N | N.N | N.N | N.N | N.N |

Example 12

Bio-layer interferometry (BLI) was performed to study the binding kinetics of each of the prepared Nb-huFc constructs against variant SARS-COV-2 spike/RBD. FIGS. 11A-11F are BLI sensorgrams that show binding to SARS-COV-2 RBD of SARS-COV-2 Wuhan (WT) RBD and SARS-COV-2 Omicron RBD by Nb-huFc construct candidates BP1B1 (A, B); BP2A6 (C, D) and EP2G4 (E, F). Affinity measurements for Nb-huFc antibodies were performed using BLI with an Octet 384 Red system (Sartorius). Measurements were conducted in 10 mM phosphate (pH 7.4), 300 mM NaCl, 1 mg/mL BSA, 0.1% NP-40 (Thermo, 28,324). Nb-huFc ligands were immobilized on human Fc capturing sensors. SARS-COV-2 RBD was used as the analyte and sensorgrams were fit to a global 1:1 fit.

Example 13

Figure 12A:
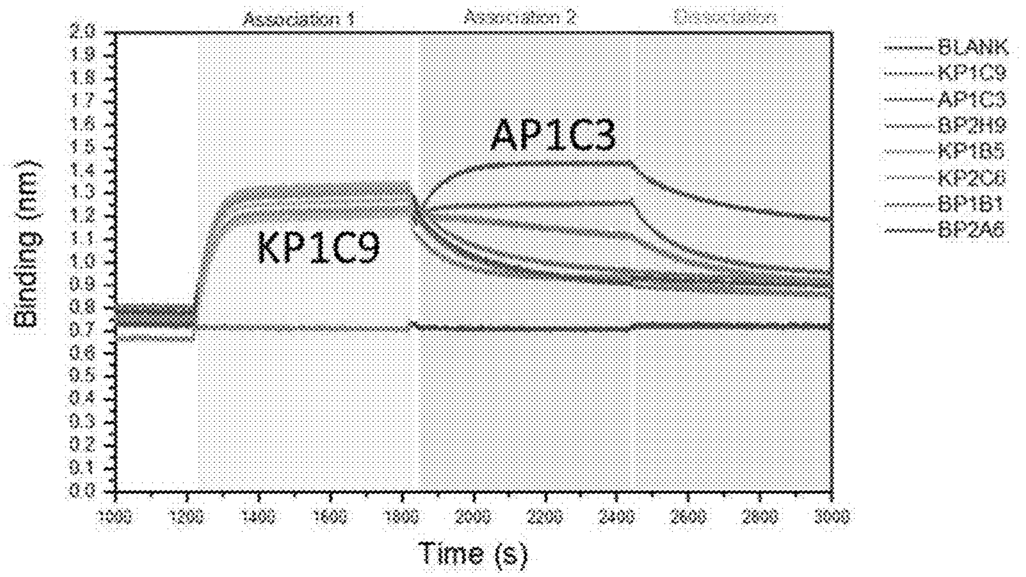
FIGS. 12A-12B are charts showing a competition assay which was conducted by using Bio-layer interferometry (BLI) to study binding against two epitopes on SARS-COV-2 RBD variants, specifically Delta and Omicron.
Figure 12B:
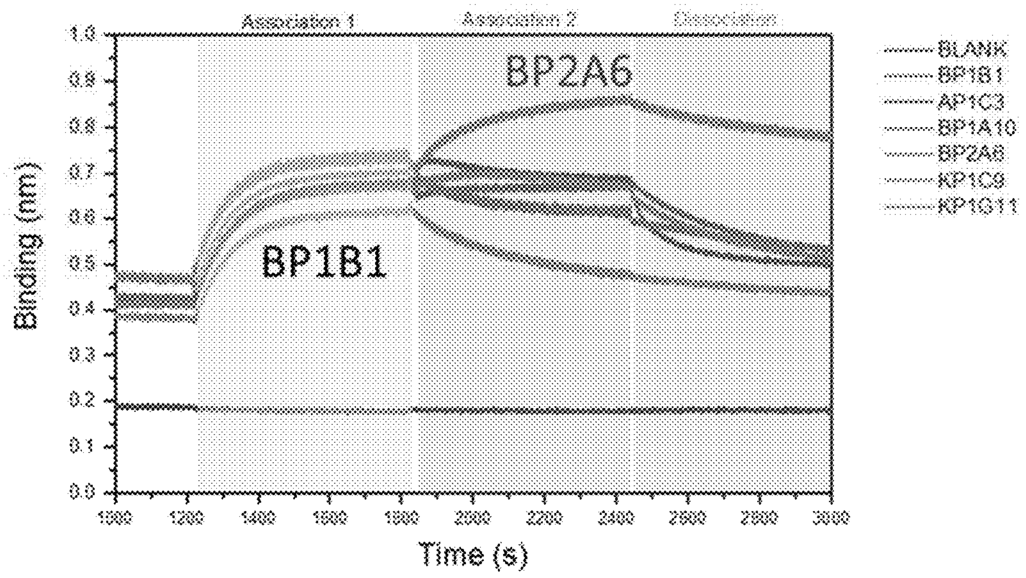

A competition assay was conducted by using Bio-layer interferometry (BLI) to study binding against two epitopes on SARS-COV-2 RBD variants, specifically Delta and Omicron. FIGS. 12A and 12B show an evaluation of Nb-huFc hits for two epitope binding. A combination of KP1C9 and AP1C3 shows synergistic increase in binding against two epitopes on SARS-COV-2 Delta RBD variant (FIG. 12A). A combination of BP2A6 and BP1B1 shows synergistic increase in binding against two epitopes on SARS-COV-2 Omicron RBD variant (FIG. 12B). Epitope binding was performed by first injecting a first Nb-huFc for 600 s, followed by injection of a second Nb-huFc for 600 s, and finally a dissociation step for 600 s.

All publications, patents, and patent applications mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

The invention claimed is:

1. A nanobody or construct comprising a nanobody that comprises a first binding domain, wherein the nanobody or construct comprising the nanobody comprises: a polypeptide sequence corresponding to any one of SEQ ID NOs: 340-398 wherein the first binding domain binds to a spike protein of a coronavirus or a receptor-binding domain of a coronavirus.

2. The nanobody or construct comprising the nanobody of claim 1, wherein the nanobody is a single variable domain antibody.

3. The nanobody or construct comprising the nanobody of claim 1, wherein the coronavirus is SARS-COV-2.

4. The nanobody or construct comprising the nanobody of claim 3, wherein the coronavirus is SARS-COV-2 Omicron variant, and the nanobody is a polypeptide sequence corresponding to any one of SEQ ID NOs. 350-354, 367, 369, 371, 374, 375, 379, 385, 387, 388, or 393.

5. The nanobody or construct comprising the nanobody of claim 3, wherein the coronavirus is SARS-COV-2 Delta variant, and the nanobody is a polypeptide sequence corresponding to any one of SEQ ID NOs. 359 to 398.

6. The nanobody or construct comprising the nanobody of claim 3, wherein the coronavirus is SARS-COV-2 Gamma variant, and the nanobody is a polypeptide sequence corresponding to any one of SEQ ID NOs. 364, 367, 371, 385, 389, or 392.

7. The nanobody or construct comprising the nanobody of claim 3, wherein the coronavirus is SARS-COV-2 Mu variant, and the nanobody is a polypeptide sequence corresponding to any one of SEQ ID NOs. 350, 367, 369, 381, 385, 389, 393, or 394.

8. The nanobody or construct comprising the nanobody of claim 3, wherein the coronavirus is SARS-COV-2 Alpha strain, and the nanobody is a polypeptide sequence corresponding to any one of SEQ ID NOs. 350, 360-362, 364, 367, 369, 371, 379, 380, 381, 385, 389, 393, or 394.

9. The nanobody or construct comprising the nanobody of claim 3, wherein the coronavirus is SARS-COV-2 Beta variant, and the nanobody is a polypeptide sequence corresponding to any one of SEQ ID NOs. 360, 364, 367, 369, 385, 389, 392, or 393.

10. The nanobody or construct comprising the nanobody of claim 3, wherein the coronavirus is SARS-COV-2 Lambda variant, and the nanobody is a polypeptide sequence corresponding to any one of SEQ ID NOs. 359, 361-369, 373, 374, 376, or 379-398.

11. The nanobody or construct comprising the nanobody of claim 3, wherein the nanobody or construct comprising the nanobody has an EC50 against SARS-COV-2 Alpha, Beta, Gamma, Delta, Mu, Lambda, or Omicron variant of 1.1 micrograms/mL or less.

12. The nanobody or construct comprising the nanobody of claim 1, wherein the spike protein comprises a polypeptide sequence having at least 90% sequence identity to any one of SEQ ID NOs: 320-327 or a fragment thereof; or wherein the receptor-binding domain comprises a polypeptide sequence having at least 90% sequence identity to any one of SEQ ID NOs: 328-336 or a fragment thereof.

13. A construct comprising:

a nanobody, an Fc domain and hinge region of human IgG1 protein, the nanobody coupled to the hinge region of the Fc domain;

the nanobody comprising a first framework region coupled to a first complementarity determining region, a second framework region coupled to the first complementarity determining region and a second complementarity determining region, a third framework region coupled to the second complementarity determining region and a third complementarity determining region, and a fourth framework region coupled to the third complementarity determining region;

wherein the nanobody comprises a polypeptide sequence corresponding to any one of SEQ ID NOs: 340-398.

14. The construct of claim 13, wherein the nanobody is a single variable domain antibody.

15. A nanobody or construct comprising a nanobody comprising: a polypeptide sequence corresponding to any one of SEQ ID NOs: 340-398.

16. The nanobody or construct comprising a nanobody of claim 15, wherein the polypeptide sequence corresponds to SEQ ID NOs: 350, 360-362, 364, 367, 369, 371, 379, 380, 381, 385, 389, 393, or 394.

17. The nanobody or construct comprising the nanobody of claim 15, wherein the nanobody is a polypeptide sequence corresponding to any one of SEQ ID NOs: 350-354, 367, 369, 371, 374, 375, 379, 385, 387, 388, or 393.

18. The nanobody or construct comprising the nanobody of claim 15, wherein the nanobody is a polypeptide sequence corresponding to any one of SEQ ID NOs: 364, 367, 371, 385, 389, or 392.

19. The nanobody or construct comprising the nanobody of claim 15, wherein the nanobody is a polypeptide sequence corresponding to any one of SEQ ID NOs: 350, 367, 369, 381, 385, 389, 393, or 394.

20. The nanobody or construct comprising the nanobody of claim 15, wherein the nanobody is a single variable domain antibody.

* * * * *

SEQUENCE LISTING

```
<160> NUMBER OF SEQ ID NOS: 408

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Gly Thr Ser Gly Glu Tyr Asp
1               5


<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Gln Ser Phe Ser Thr Tyr Tyr
1               5


<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3
```

-continued

```
Phe Ser Asp Gly Arg Phe His
1               5


<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Ser Pro Phe Asp His Tyr Val
1               5


<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Thr Thr Asp Ser Gln Tyr Asp
1               5


<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Phe Tyr Phe Ser Gly Gln Tyr
1               5


<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

His Thr Phe Gly Phe Ser His
1               5


<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Arg Thr Phe Ser Gly Tyr Ile
1               5


<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Phe Ile Phe Gly Asp Leu Gln
```

1 5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gln Ala Phe Ser Gln Tyr His
1 5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Arg Tyr Ser Gln Asp Tyr Arg
1 5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Arg Thr Ser Gln Asp Tyr Arg
1 5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Arg Thr Tyr Asp His Thr Ala
1 5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

His Ala Phe Asp Gln Asp Arg
1 5

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Phe Tyr Phe Ser Ala His Arg
1 5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Arg Ser Phe His Asp Tyr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gly Pro Phe Gly Thr Tyr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Thr Thr Tyr Ser Glu Arg Val
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Thr Phe Asp Gln Arg Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Arg Thr Ser Gly Gln Tyr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Arg Thr Phe Arg Ala Tyr Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Arg Thr Phe Thr Ser Phe His
1 5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Gly Ser Phe Gly Ala Tyr Ile
1 5

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Ser Tyr Phe Asp Arg Arg Trp
1 5

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Arg Thr Phe Ser Ala Tyr Ser
1 5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Thr Ser Phe Asp Asp Gln Pro
1 5

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Gln Thr Phe Arg Ser Leu Thr
1 5

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Gln Thr Phe Ser His Tyr Ile
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Ser Ser Phe Gly Ile Arg Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Arg Thr Phe Asp Ala Tyr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic

<400> SEQUENCE: 31

His Thr Phe Gly Phe Asn His
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Arg Thr Phe Ser Gly Tyr Ile
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Gly Ala Phe Ser Asp Tyr Gly
1               5

<210> SEQ ID NO 34

<211> LENGTH: 7
<212> TYPE: PRT
<213> ORGANISM: Artificial Sequence
<220> FEATURE:
<223> OTHER INFORMATION: Synthetic

<400> SEQUENCE: 34

Arg Phe Phe Thr Asp Arg Thr
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

His Tyr Phe Gly Glu Tyr Arg
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Phe Met Phe Thr Asp Val Ala
1 5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Arg Tyr Asp Asp Phe Gln Val
1 5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ser Thr Tyr Asp Gln Tyr Val
1 5

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Gln Ala Phe Gln Ser Tyr Arg
1 5

<210> SEQ ID NO 40
<211> LENGTH: 7

<212> TYPE: PRT
<213> ORGANISM: Artificial Sequence
<220> FEATURE:
<223> OTHER INFORMATION: Synthetic

<400> SEQUENCE: 40

Gly Thr Asp Thr Gly Tyr Val
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Arg Thr Ala Asp His His Val
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic

<400> SEQUENCE: 42

His Thr Phe Asp Ala His Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Arg Ala Phe Arg Ile Tyr Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Thr Thr Phe Ser Asp His Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic

<400> SEQUENCE: 45

Arg Thr Phe Asp Ala Tyr Ser
1               5

<210> SEQ ID NO 46
<211> LENGTH: 7
<212> TYPE: PRT

<213> ORGANISM: Artificial Sequence
<220> FEATURE:
<223> OTHER INFORMATION: Synthetic

<400> SEQUENCE: 46

Gln Pro Ser Asp Arg Tyr Ile
1 5

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Arg Phe Phe Ser Trp Tyr Ala
1 5

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Phe Thr Phe Asp Trp Ser Ala
1 5

<210> SEQ ID NO 49
<211> LENGTH: 7
<212> TYPE: PRT
<213> ORGANISM: Artificial Sequence
<220> FEATURE:
<223> OTHER INFORMATION: Synthetic

<400> SEQUENCE: 49

Phe Pro Phe Ser Ser His Trp
1 5

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Ser Ala Phe Gln Ile Tyr Ala
1 5

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Ser Ile Phe Thr His Val Pro
1 5

<210> SEQ ID NO 52
<211> LENGTH: 7
<212> TYPE: PRT
<213> ORGANISM: Artificial Sequence -continued
<220> FEATURE:
<223> OTHER INFORMATION: Synthetic

<400> SEQUENCE: 52

His Thr Phe Thr His Tyr Arg
1 5

<210> SEQ ID NO 53
<211> LENGTH: 7
<212> TYPE: PRT
<213> ORGANISM: Artificial Sequence
<220> FEATURE:
<223> OTHER INFORMATION: Synthetic

<400> SEQUENCE: 53

Gln Thr Phe Thr His Val Pro
1 5

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Arg Thr Tyr Arg Gly Tyr Ser
1 5

<210> SEQ ID NO 55
<211> LENGTH: 7
<212> TYPE: PRT
<213> ORGANISM: Artificial Sequence
<220> FEATURE:
<223> OTHER INFORMATION: Synthetic

<400> SEQUENCE: 55

Ser Thr Ala Ser His Tyr Thr
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Phe Thr Ala Gln Glu Tyr Ser
1 5

<210> SEQ ID NO 57
<211> LENGTH: 7
<212> TYPE: PRT
<213> ORGANISM: Artificial Sequence
<220> FEATURE:
<223> OTHER INFORMATION: Synthetic

<400> SEQUENCE: 57

His Thr Phe Ser Phe Trp Arg
1 5

<210> SEQ ID NO 58
<211> LENGTH: 7
<212> TYPE: PRT
<213> ORGANISM: Artificial Sequence
<220> FEATURE:

-continued

<223> OTHER INFORMATION: Synthetic

<400> SEQUENCE: 58

Arg Thr Phe Gln Asp Phe Ala
1 5

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59

Ser Tyr Phe Arg Trp Tyr Tyr
1 5

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

His Trp Asp Gly Lys Ala Thr Ala Tyr
1 5

<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Ala Phe Gly Ala Gly Glu Gln Tyr Tyr
1 5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Gln Thr Thr Asp Glu Asp Thr Tyr Tyr
1 5

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Ala Gly Asp Gly Ala Ala Ser Tyr Tyr
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Ser Trp Ala Asp Thr Thr Val Ser Tyr
1 5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Thr Ala Tyr Asp Gly Glu Thr Tyr Tyr
1 5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Ala Gly Asp Gly Ala Ala Ser Tyr Tyr
1 5

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

His Gly Asp Ser Tyr Ala Ser Tyr Tyr
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Ala Trp Tyr Asp Asp Thr Thr Gln Tyr
1 5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Ser Gln Ala Gly Ala Thr Thr Gln Tyr
1 5

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Asp Arg Gly Gly Thr Thr Thr Asp Tyr
1 5

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Ala Trp Ser Gly Asp Ser Phe Arg Tyr
1 5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Ser Thr Gln Gly Arg Thr Val Arg Tyr
1 5

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Thr Trp Ala Gly Asp Ser Ala Arg Tyr
1 5

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Ala Gly Asp Gly Ala Ala Ser Tyr Tyr
1 5

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Asp Arg Gly Gly Thr Thr Thr Tyr Tyr
1 5

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Ser Trp Ser Gly Gly Ser Ala Arg Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic

<400> SEQUENCE: 77

Ser Gly Gln Ser Asp Gln Thr Tyr Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Ala Trp Gly Gly Gly Ser Ala Lys Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic

<400> SEQUENCE: 79

Ser Trp Ser Gly Gly Ser Ala Arg
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic

<400> SEQUENCE: 80

Gly Gly Thr Gly Glu Ala Thr Tyr
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Ser Gly Asp Asp Gly Thr Gln Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

-continued

Thr Thr Thr Asp Ala Glu Tyr Tyr
1 5

<210> SEQ ID NO 83
<211> LENGTH: 8
<212> TYPE: PRT
<213> ORGANISM: Artificial Sequence
<220> FEATURE:
<223> OTHER INFORMATION: Synthetic

<400> SEQUENCE: 83

Ser Ala Tyr Gly Phe Ala Thr Tyr
1 5

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Ala Gly Asp Gly Ala Ala Ser Tyr
1 5

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Gly Gly Gly Asp Lys Ser Thr Trp
1 5

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ser Gly Asp Gly Gly Pro Thr Tyr
1 5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Ala Gly Gln Gly His Ala Thr Tyr
1 5

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Arg Trp Ser Asp Trp Ala Val Trp 1 5

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Ser Trp Ser Asp Asp Trp Thr Ala
1 5

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Pro Gly Asp Cys Ala Ala Ser Tyr
1 5

<210> SEQ ID NO 91
<211> LENGTH: 8
<212> TYPE: PRT
<213> ORGANISM: Artificial Sequence
<220> FEATURE:
<223> OTHER INFORMATION: Synthetic

<400> SEQUENCE: 91

Gln Gly Asp Ser Tyr Ala Ser Tyr
1 5

<210> SEQ ID NO 92
<211> LENGTH: 8
<212> TYPE: PRT
<213> ORGANISM: Artificial Sequence
<220> FEATURE:
<223> OTHER INFORMATION: Synthetic

<400> SEQUENCE: 92

Thr Ala Gly Ser Trp Tyr Thr Tyr
1 5

<210> SEQ ID NO 93
<211> LENGTH: 8
<212> TYPE: PRT
<213> ORGANISM: Artificial Sequence
<220> FEATURE:
<223> OTHER INFORMATION: Synthetic

<400> SEQUENCE: 93

Asp Arg Ser Gly Lys His Thr Tyr
1 5

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Ser Trp Ser Gly Gly Ser Ala Arg
1 5

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Ser Trp Ala Gly Gly Arg Ser Leu
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Asp Gly Tyr Gln Glu Ser Thr Ala
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Asp Arg Gly Gly Thr Thr Thr Asp
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic

<400> SEQUENCE: 98

Ala Gly Asp Gly Ala Ala Ser Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Gly Gln Ser Gly His Thr Thr Leu
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Ala Gln Ala Gly Gly Ser Ser Ala
1               5

-continued

```
<210> SEQ ID NO 101
<211> LENGTH: 8
<212> TYPE: PRT
<213> ORGANISM: Artificial Sequence
<220> FEATURE:
<223> OTHER INFORMATION: Synthetic

<400> SEQUENCE: 101

Ser Trp Gly Gln Ser Ser Thr Tyr
1               5


<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ala Gly Asp Gly Ala Ala Ser Tyr
1               5


<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Gln Ser Asp Gly Trp Asp Thr Tyr
1               5


<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

Thr Gln Ser Gly Tyr Ser Thr Tyr
1               5


<210> SEQ ID NO 105
<211> LENGTH: 8
<212> TYPE: PRT
<213> ORGANISM: Artificial Sequence
<220> FEATURE:
<223> OTHER INFORMATION: Synthetic

<400> SEQUENCE: 105

Gln Gly Ala Ala Asn Lys Thr Ala
1               5


<210> SEQ ID NO 106
<211> LENGTH: 8
<212> TYPE: PRT
<213> ORGANISM: Artificial Sequence
<220> FEATURE:
<223> OTHER INFORMATION: Synthetic

<400> SEQUENCE: 106

Gly Ala Ser Gly Phe Gln Thr Tyr
1               5
```

<210> SEQ ID NO 107
<211> LENGTH: 8
<212> TYPE: PRT
<213> ORGANISM: Artificial Sequence
<220> FEATURE:
<223> OTHER INFORMATION: Synthetic

<400> SEQUENCE: 107

Ser Ser Thr Ser Glu Ser Thr Thr
1 5

<210> SEQ ID NO 108
<211> LENGTH: 8
<212> TYPE: PRT
<213> ORGANISM: Artificial Sequence
<220> FEATURE:
<223> OTHER INFORMATION: Synthetic

<400> SEQUENCE: 108

Asp Trp Arg Asp His Lys Thr Tyr
1 5

<210> SEQ ID NO 109
<211> LENGTH: 8
<212> TYPE: PRT
<213> ORGANISM: Artificial Sequence
<220> FEATURE:
<223> OTHER INFORMATION: Synthetic

<400> SEQUENCE: 109

Ser Thr Asp Ser Glu Thr Asp His
1 5

<210> SEQ ID NO 110
<211> LENGTH: 8
<212> TYPE: PRT
<213> ORGANISM: Artificial Sequence
<220> FEATURE:
<223> OTHER INFORMATION: Synthetic

<400> SEQUENCE: 110

His Ala Asn Gly Gly Ser Gln Thr
1 5

<210> SEQ ID NO 111
<211> LENGTH: 8
<212> TYPE: PRT
<213> ORGANISM: Artificial Sequence
<220> FEATURE:
<223> OTHER INFORMATION: Synthetic

<400> SEQUENCE: 111

Gly Ala Gly Gly Thr Ser Phe Tyr
1 5

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Asp Thr Ser Gly Phe Glu Thr Tyr
1 5

<210> SEQ ID NO 113

<211> LENGTH: 8
<212> TYPE: PRT
<213> ORGANISM: Artificial Sequence
<220> FEATURE:
<223> OTHER INFORMATION: Synthetic

<400> SEQUENCE: 113

Ser Trp Ser Asp Asp Trp Thr Ala
1 5

<210> SEQ ID NO 114
<211> LENGTH: 8
<212> TYPE: PRT
<213> ORGANISM: Artificial Sequence
<220> FEATURE:
<223> OTHER INFORMATION: Synthetic

<400> SEQUENCE: 114

Ser Gly Arg Asp His Ala Lys Gln
1 5

<210> SEQ ID NO 115
<211> LENGTH: 8
<212> TYPE: PRT
<213> ORGANISM: Artificial Sequence
<220> FEATURE:
<223> OTHER INFORMATION: Synthetic

<400> SEQUENCE: 115

Thr Phe Ala Gly His Asp Lys Gln
1 5

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Ser Gly Tyr Gly Gly Ser Ser Lys
1 5

<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117

Arg Phe Thr Gly Trp Ser Thr Asp
1 5

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ser Gly Arg Ala Glu Arg Thr Tyr
1 5

<210> SEQ ID NO 119
<211> LENGTH: 9

<212> TYPE: PRT
<213> ORGANISM: Artificial Sequence
<220> FEATURE:
<223> OTHER INFORMATION: Synthetic

<400> SEQUENCE: 119

Ala Arg Leu Asp Asp Glu Ile Asp Phe
1 5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Ala Tyr Thr Thr Thr Thr Val Pro Gln
1 5

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Ala Tyr Thr Thr Thr Thr Val Pro Gln
1 5

<210> SEQ ID NO 122
<211> LENGTH: 12
<212> TYPE: PRT
<213> ORGANISM: Artificial Sequence
<220> FEATURE:
<223> OTHER INFORMATION: Synthetic

<400> SEQUENCE: 122

Ile Phe Asp Asn Ile Arg Ala Ser Leu Gln Asp Pro
1 5 10

<210> SEQ ID NO 123
<211> LENGTH: 9
<212> TYPE: PRT
<213> ORGANISM: Artificial Sequence
<220> FEATURE:
<223> OTHER INFORMATION: Synthetic

<400> SEQUENCE: 123

Ile Gln Ser Arg Lys Gln Val Gly Phe
1 5

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

Leu Lys Asp Pro Val Arg Ile Ile Asp Ala Ile Trp
1 5 10

<210> SEQ ID NO 125
<211> LENGTH: 12
<212> TYPE: PRT

<213> ORGANISM: Artificial Sequence
<220> FEATURE:
<223> OTHER INFORMATION: Synthetic

<400> SEQUENCE: 125

Leu Trp Pro Tyr Ser Asp Asp Arg Leu Asp Ser Tyr
1 5 10

<210> SEQ ID NO 126
<211> LENGTH: 9
<212> TYPE: PRT
<213> ORGANISM: Artificial Sequence
<220> FEATURE:
<223> OTHER INFORMATION: Synthetic

<400> SEQUENCE: 126

Leu Tyr Asp Ile Asn Thr Val Pro Tyr
1 5

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127

Pro Tyr Phe Gly Glu Ala Asp Ile Ala
1 5

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Val Trp Tyr Gly His Thr Asp Pro Gln His Asp Arg
1 5 10

<210> SEQ ID NO 129
<211> LENGTH: 9
<212> TYPE: PRT
<213> ORGANISM: Artificial Sequence
<220> FEATURE:
<223> OTHER INFORMATION: Synthetic

<400> SEQUENCE: 129

Tyr Phe Gln His Arg Glu Pro Phe Leu
1 5

<210> SEQ ID NO 130
<211> LENGTH: 12
<212> TYPE: PRT
<213> ORGANISM: Artificial Sequence
<220> FEATURE:
<223> OTHER INFORMATION: Synthetic

<400> SEQUENCE: 130

Ala Phe Gly Pro Ala Gln Asp Gly Lys Gly Arg Trp
1 5 10

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Ala Ile Asp Arg Trp Asn Thr Arg Val
1 5

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

His Leu Pro Leu Val Arg Gly Lys Asn
1 5

<210> SEQ ID NO 133
<211> LENGTH: 12
<212> TYPE: PRT
<213> ORGANISM: Artificial Sequence
<220> FEATURE:
<223> OTHER INFORMATION: Synthetic

<400> SEQUENCE: 133

Leu Tyr Asn Gln Ser Val Arg Pro Trp Phe Thr His
1 5 10

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

Tyr Phe Gln His Arg Glu Pro Phe Leu
1 5

<210> SEQ ID NO 135
<211> LENGTH: 15
<212> TYPE: PRT
<213> ORGANISM: Artificial Sequence
<220> FEATURE:
<223> OTHER INFORMATION: Synthetic

<400> SEQUENCE: 135

Ser Trp Phe Val Asp Gln Ser Asp Ala His Thr Ser Ile Phe Arg
1 5 10 15

<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

Pro Phe Ala Gly Asp Ala Asn Leu Pro Arg Glu Trp
1 5 10

<210> SEQ ID NO 137
<211> LENGTH: 12
<212> TYPE: PRT
<213> ORGANISM: Artificial Sequence
<220> FEATURE:

<223> OTHER INFORMATION: Synthetic

<400> SEQUENCE: 137

Ser Trp Ile Leu Asp Ala Asn Thr Phe Leu Gln Glu
1 5 10

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Ala Trp Lys Ser Asp Ile Ala Glu Trp
1 5

<210> SEQ ID NO 139
<211> LENGTH: 9
<212> TYPE: PRT
<213> ORGANISM: Artificial Sequence
<220> FEATURE:
<223> OTHER INFORMATION: Synthetic

<400> SEQUENCE: 139

Ala Tyr Thr Thr Thr Thr Val Pro Gln
1 5

<210> SEQ ID NO 140
<211> LENGTH: 9
<212> TYPE: PRT
<213> ORGANISM: Artificial Sequence
<220> FEATURE:
<223> OTHER INFORMATION: Synthetic

<400> SEQUENCE: 140

Ala Tyr Thr Thr Thr Thr Val Pro Gln
1 5

<210> SEQ ID NO 141
<211> LENGTH: 9
<212> TYPE: PRT
<213> ORGANISM: Artificial Sequence
<220> FEATURE:
<223> OTHER INFORMATION: Synthetic

<400> SEQUENCE: 141

Ala Tyr Thr Thr Thr Thr Val Pro Tyr
1 5

<210> SEQ ID NO 142
<211> LENGTH: 12
<212> TYPE: PRT
<213> ORGANISM: Artificial Sequence
<220> FEATURE:
<223> OTHER INFORMATION: Synthetic

<400> SEQUENCE: 142

Glu Ile Glu Ala Trp Gly His Arg Glu Val Arg Pro
1 5 10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

His Tyr Tyr Thr Thr Ser Ala Thr Leu Asp Tyr Ala
1 5 10

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Ile Ala Gln Asp Arg Phe Arg Asn Pro
1 5

<210> SEQ ID NO 145
<211> LENGTH: 9
<212> TYPE: PRT
<213> ORGANISM: Artificial Sequence
<220> FEATURE:
<223> OTHER INFORMATION: Synthetic

<400> SEQUENCE: 145

Ile Phe Gln Gln Arg Ala Val Pro Ile
1 5

<210> SEQ ID NO 146
<211> LENGTH: 9
<212> TYPE: PRT
<213> ORGANISM: Artificial Sequence
<220> FEATURE:
<223> OTHER INFORMATION: Synthetic

<400> SEQUENCE: 146

Lys Tyr Gln Asp Thr Ile Ala Pro Leu
1 5

<210> SEQ ID NO 147
<211> LENGTH: 12
<212> TYPE: PRT
<213> ORGANISM: Artificial Sequence
<220> FEATURE:
<223> OTHER INFORMATION: Synthetic

<400> SEQUENCE: 147

Lys Tyr Trp Thr Gly Lys Tyr Asp Arg Gln Trp Trp
1 5 10

<210> SEQ ID NO 148
<211> LENGTH: 9
<212> TYPE: PRT
<213> ORGANISM: Artificial Sequence
<220> FEATURE:
<223> OTHER INFORMATION: Synthetic

<400> SEQUENCE: 148

Leu Gln Asn Thr Lys Glu Asp Arg Leu
1 5

<210> SEQ ID NO 149
<211> LENGTH: 12
<212> TYPE: PRT
<213> ORGANISM: Artificial Sequence
<220> FEATURE:
<223> OTHER INFORMATION: Synthetic

<400> SEQUENCE: 149

Leu Trp Ala Cys Ser Asp Asp Pro Leu Asp Ser Tyr
1 5 10

<210> SEQ ID NO 150
<211> LENGTH: 9
<212> TYPE: PRT
<213> ORGANISM: Artificial Sequence
<220> FEATURE:
<223> OTHER INFORMATION: Synthetic

<400> SEQUENCE: 150

Leu Tyr Asp Ile Asn Thr Val Pro Tyr
1 5

<210> SEQ ID NO 151
<211> LENGTH: 9
<212> TYPE: PRT
<213> ORGANISM: Artificial Sequence
<220> FEATURE:
<223> OTHER INFORMATION: Synthetic

<400> SEQUENCE: 151

Asn Lys Glu Thr Trp Asn Thr His Trp
1 5

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Pro Phe Ala Gly Asp Ala Asn Leu Pro Arg Glu Trp
1 5 10

<210> SEQ ID NO 153
<211> LENGTH: 12
<212> TYPE: PRT
<213> ORGANISM: Artificial Sequence
<220> FEATURE:
<223> OTHER INFORMATION: Synthetic

<400> SEQUENCE: 153

Pro Leu Val Gly Pro Glu Asp Ser Gly Leu Ile Arg
1 5 10

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Pro Tyr Phe Glu Val Asp Asp Asn Pro
1 5

<210> SEQ ID NO 155
<211> LENGTH: 12
<212> TYPE: PRT
<213> ORGANISM: Artificial Sequence
<220> FEATURE:
<223> OTHER INFORMATION: Synthetic

<400> SEQUENCE: 155

Pro Tyr Phe Gly Glu Ala Asp Glu His Ile Lys Ser
1 5 10

<210> SEQ ID NO 156
<211> LENGTH: 12
<212> TYPE: PRT
<213> ORGANISM: Artificial Sequence
<220> FEATURE:
<223> OTHER INFORMATION: Synthetic

<400> SEQUENCE: 156

Pro Tyr Phe Gly Glu Ala Asp Pro Tyr Pro Asp Ala
1 5 10

<210> SEQ ID NO 157
<211> LENGTH: 12
<212> TYPE: PRT
<213> ORGANISM: Artificial Sequence
<220> FEATURE:
<223> OTHER INFORMATION: Synthetic

<400> SEQUENCE: 157

Gln Phe His Gln Ser Pro Ile Asp Lys Gly Leu Arg
1 5 10

<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Gln Gly Asp Trp Gly Arg His Pro Thr
1 5

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Gln Gly Asp Trp Gly Arg His Pro Thr
1 5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Thr Asp Glu Gly Asn Gln Tyr Val
1 5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

```
Gln Tyr Trp Gln Ser Ile Asn Pro Ile
1               5


<210> SEQ ID NO 162
<211> LENGTH: 15
<212> TYPE: PRT
<213> ORGANISM: Artificial Sequence
<220> FEATURE:
<223> OTHER INFORMATION: Synthetic

<400> SEQUENCE: 162

Thr Phe Asn His Ser Leu Ala Ser Lys Leu Phe Asn Asp Ile Lys
1               5                   10                  15


<210> SEQ ID NO 163
<211> LENGTH: 15
<212> TYPE: PRT
<213> ORGANISM: Artificial Sequence
<220> FEATURE:
<223> OTHER INFORMATION: Synthetic

<400> SEQUENCE: 163

Thr Phe Asn His Ser Leu Ala Ser Lys Leu Phe Asn Asp Ile Lys
1               5                   10                  15


<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Thr His Phe Asn Trp Gln Asn Tyr Ser
1               5


<210> SEQ ID NO 165
<211> LENGTH: 12
<212> TYPE: PRT
<213> ORGANISM: Artificial Sequence
<220> FEATURE:
<223> OTHER INFORMATION: Synthetic

<400> SEQUENCE: 165

Thr Ser Gly Lys Ala Ala Leu Pro Phe Val Ser Lys
1               5                   10


<210> SEQ ID NO 166
<211> LENGTH: 12
<212> TYPE: PRT
<213> ORGANISM: Artificial Sequence
<220> FEATURE:
<223> OTHER INFORMATION: Synthetic

<400> SEQUENCE: 166

Thr Tyr Tyr Gly Gly Lys Thr Val Glu Gln Asp Phe
1               5                   10


<210> SEQ ID NO 167
<211> LENGTH: 15
<212> TYPE: PRT
<213> ORGANISM: Artificial Sequence
<220> FEATURE:
<223> OTHER INFORMATION: Synthetic

<400> SEQUENCE: 167

Val Ala Phe Gly Ile His Trp Phe Ala Pro His Ser Asp His Ile
```

1 5 10 15

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Val Asn Gly Phe Asp Tyr Ala His Ser Lys Ala Gly Pro Gln Val
1 5 10 15

<210> SEQ ID NO 169
<211> LENGTH: 8
<212> TYPE: PRT
<213> ORGANISM: Artificial Sequence
<220> FEATURE:
<223> OTHER INFORMATION: Synthetic

<400> SEQUENCE: 169

Trp Ala Tyr Asp His Phe Asn Asn
1 5

<210> SEQ ID NO 170
<211> LENGTH: 9
<212> TYPE: PRT
<213> ORGANISM: Artificial Sequence
<220> FEATURE:
<223> OTHER INFORMATION: Synthetic

<400> SEQUENCE: 170

Trp Ala Tyr Asp Gln Phe Asn Trp Asn
1 5

<210> SEQ ID NO 171
<211> LENGTH: 9
<212> TYPE: PRT
<213> ORGANISM: Artificial Sequence
<220> FEATURE:
<223> OTHER INFORMATION: Synthetic

<400> SEQUENCE: 171

Trp Ala Tyr Asp Gln Phe Asn Trp Asn
1 5

<210> SEQ ID NO 172
<211> LENGTH: 9
<212> TYPE: PRT
<213> ORGANISM: Artificial Sequence
<220> FEATURE:
<223> OTHER INFORMATION: Synthetic

<400> SEQUENCE: 172

Trp Gln Tyr Ile Asp Glu Ile Gln Tyr
1 5

<210> SEQ ID NO 173
<211> LENGTH: 12
<212> TYPE: PRT
<213> ORGANISM: Artificial Sequence
<220> FEATURE:
<223> OTHER INFORMATION: Synthetic

<400> SEQUENCE: 173

Tyr Glu Glu Ile Asn Ala Thr Gln Lys Asp Thr Leu
1 5 10

<210> SEQ ID NO 174
<211> LENGTH: 11
<212> TYPE: PRT
<213> ORGANISM: Artificial Sequence
<220> FEATURE:
<223> OTHER INFORMATION: Synthetic

<400> SEQUENCE: 174

Tyr Glu Ile Asn Ala Asp Pro His Gly Ser Ile
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Synthetic

<400> SEQUENCE: 175

Tyr Leu Ser Gln Glu Arg Thr Pro Val
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Tyr Gln Thr His Asn Asn Glu Trp Val
1               5

<210> SEQ ID NO 177
<211> LENGTH: 15
<212> TYPE: PRT
<213> ORGANISM: Artificial Sequence
<220> FEATURE:
<223> OTHER INFORMATION: Synthetic

<400> SEQUENCE: 177

Tyr Trp Asn Pro Val Ala Tyr Arg Phe Arg Phe Pro Thr Pro Thr
1               5                   10                  15

<210> SEQ ID NO 178

<400> SEQUENCE: 178

000

<210> SEQ ID NO 179

<400> SEQUENCE: 179

000

<210> SEQ ID NO 180
<211> LENGTH: 104
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:

<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Can be any amino acid or amino acids (e.g., any
CDR1 described herein)
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(50)
<223> OTHER INFORMATION: Xaa can be any naturally occurring amino acid
<220> FEATURE:
<221> NAME/KEY: MISC_FEATURE
<222> LOCATION: (51)..(51)
<223> OTHER INFORMATION: Can be any amino acid or amino acids (e.g., any
CDR2 described herein)
<220> FEATURE:
<221> NAME/KEY: misc_feature
<222> LOCATION: (52)..(65)
<223> OTHER INFORMATION: Xaa can be any naturally occurring amino acid
<220> FEATURE:
<221> NAME/KEY: misc_feature
<222> LOCATION: (67)..(82)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: MISC_FEATURE
<222> LOCATION: (92)..(92)
<223> OTHER INFORMATION: Can be any amino acid or amino acids (e.g., any
CDR3 described herein)
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(101)
<223> OTHER INFORMATION: Xaa can be any naturally occurring amino acid
<220> FEATURE:

```
<221> NAME/KEY: misc_feature
<222> LOCATION: (104)..(104)
<223> OTHER INFORMATION: Xaa can be any naturally occurring amino acid

<400> SEQUENCE: 180

Xaa Val Gln Leu Xaa Xaa Ser Gly Xaa Xaa Xaa Xaa Xaa Xaa Xaa Xaa
1               5                   10                  15

Xaa Leu Xaa Leu Xaa Cys Xaa Xaa Ser Gly Xaa Xaa Xaa Xaa Xaa Xaa
            20                  25                  30

Xaa Trp Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Asp Xaa Xaa Xaa Xaa Xaa Xaa Xaa Xaa Xaa Xaa Xaa Xaa Xaa Xaa
65                  70                  75                  80

Xaa Xaa Asp Xaa Xaa Xaa Tyr Xaa Cys Xaa Xaa Xaa Xaa Xaa Gly Xaa
                85                  90                  95

Gly Thr Xaa Xaa Xaa Val Ser Xaa
            100


<210> SEQ ID NO 181
<211> LENGTH: 100
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (15)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(39)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: misc_feature
<222> LOCATION: (48)..(78)
```

<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (84)..(87)
<223> OTHER INFORMATION: Xaa can be any naturally occurring amino acid
<220> FEATURE:
<221> NAME/KEY: MISC_FEATURE
<222> LOCATION: (88)..(88)
<223> OTHER INFORMATION: Can be any amino acid or amino acids (e.g., any
      CDR3 described herein)
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 181

```
Xaa Xaa Xaa Leu Xaa Xaa Xaa Gly Xaa Xaa Xaa Xaa Xaa Pro Xaa Xaa
1               5                   10                  15

Xaa Xaa Xaa Xaa Xaa Cys Xaa Xaa Xaa Xaa Xaa Xaa Xaa Trp Xaa Xaa
            20                  25                  30

Xaa Xaa Xaa Xaa Xaa Xaa Xaa Glu Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Asp Xaa
65                  70                  75                  80

Xaa Xaa Tyr Xaa Xaa Xaa Xaa Xaa Xaa Trp Gly Xaa Xaa Xaa Xaa Xaa
                85                  90                  95

Xaa Val Ser Xaa
            100
```

<210> SEQ ID NO 182
<211> LENGTH: 100
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Can be any amino acid or amino acids (e.g., any CDR1 described herein)
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Can be any amino acid or amino acids (e.g., any CDR2 described herein)
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(55)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(69)
<223> OTHER INFORMATION: Xaa can be any naturally occurring amino acid
<220> FEATURE:
<221> NAME/KEY: misc_feature
<222> LOCATION: (71)..(78)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: MISC_FEATURE
<222> LOCATION: (88)..(88)
<223> OTHER INFORMATION: Can be any amino acid or amino acids (e.g., any CDR3 described herein)
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature

```
<222> LOCATION: (95)..(95)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 182

Xaa Val Xaa Leu Xaa Xaa Ser Gly Gly Gly Xaa Xaa Xaa Xaa Gly Xaa
1               5                   10                  15

Ser Leu Xaa Leu Ser Cys Ala Ala Ser Gly Xaa Xaa Xaa Trp Xaa Arg
            20                  25                  30

Xaa Xaa Pro Xaa Xaa Xaa Xaa Xaa Xaa Xaa Xaa Xaa Xaa Xaa Xaa Xaa
        35                  40                  45

Tyr Xaa Xaa Xaa Xaa Xaa Xaa Arg Phe Xaa Xaa Ser Xaa Asp Xaa Xaa
    50                  55                  60

Xaa Xaa Xaa Xaa Xaa Leu Xaa Xaa Xaa Xaa Xaa Xaa Xaa Xaa Asp Thr
65                  70                  75                  80

Xaa Xaa Tyr Xaa Cys Ala Xaa Xaa Xaa Xaa Gly Xaa Gly Thr Xaa Val
                85                  90                  95

Thr Val Ser Xaa
            100


<210> SEQ ID NO 183
<211> LENGTH: 98
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
      CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
      CDR2 described herein)
<220> FEATURE:
<221> NAME/KEY: MISC_FEATURE
<222> LOCATION: (86)..(86)
<223> OTHER INFORMATION: Can be any amino acid or amino acids (e.g., any
      CDR3 described herein)

<400> SEQUENCE: 183

Glu Val Gln Leu Gln Ala Ser Gly Gly Gly Phe Val Gln Pro Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ser Ala Ile Ser Xaa Tyr
        35                  40                  45

Ala Asp Ser Val Lys Gly Arg Phe Thr Ile Ser Arg Asp Asn Ser Lys
    50                  55                  60

Asn Thr Val Tyr Leu Gln Met Asn Ser Leu Arg Ala Glu Asp Thr Ala
65                  70                  75                  80

Thr Tyr Tyr Cys Ala Xaa Tyr Trp Gly Gln Gly Thr Gln Val Thr Val
                85                  90                  95

Ser Ser


<210> SEQ ID NO 184
<211> LENGTH: 98
<212> TYPE: PRT
```

<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
CDR2 described herein)
<220> FEATURE:
<221> NAME/KEY: MISC_FEATURE
<222> LOCATION: (86)..(86)
<223> OTHER INFORMATION: Can be any amino acid or amino acids (e.g., any
CDR3 described herein)

<400> SEQUENCE: 184

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ser Ala Ile Ser Xaa Tyr
        35                  40                  45

Ala Asp Ser Val Lys Gly Arg Phe Thr Ile Ser Arg Asp Asn Ser Lys
    50                  55                  60

Asn Thr Val Tyr Leu Gln Met Asn Ser Leu Arg Ala Glu Asp Thr Ala
65                  70                  75                  80

Thr Tyr Tyr Cys Ala Xaa Tyr Trp Gly Gln Gly Thr Gln Val Thr Val
                85                  90                  95

Ser Ser
```

<210> SEQ ID NO 185
<211> LENGTH: 99
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any
CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any
CDR2 described herein)
<220> FEATURE:
<221> NAME/KEY: MISC_FEATURE
<222> LOCATION: (87)..(87)
<223> OTHER INFORMATION: Can be any amino acid or amino acids (e.g., any
CDR3 described herein)

<400> SEQUENCE: 185

```
Glu Val Gln Leu Gln Ala Ser Gly Gly Gly Phe Val Gln Ala Gly Gly
1               5                   10                  15

Ser Leu Arg Leu Ser Cys Ala Ala Ser Gly Xaa Met Gly Trp Phe Arg
            20                  25                  30

Gln Ala Pro Gly Lys Glu Arg Glu Phe Val Ala Ala Ile Ser Xaa Tyr
        35                  40                  45

Tyr Ala Asp Ser Val Lys Gly Arg Phe Thr Ile Ser Arg Asp Asn Ala
    50                  55                  60

Lys Asn Thr Val Tyr Leu Gln Met Asn Ser Leu Lys Pro Glu Asp Thr
```

65 70 75 80

Ala Thr Tyr Tyr Cys Ala Xaa Tyr Trp Gly Gln Gly Thr Gln Val Thr
85 90 95

Val Ser Ser

<210> SEQ ID NO 186
<211> LENGTH: 99
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Can be any amino acid or amino acids (e.g., any CDR1 described herein)
<220> FEATURE:
<221> NAME/KEY: MISC_FEATURE
<222> LOCATION: (47)..(47)
<223> OTHER INFORMATION: Can be any amino acid or amino acids (e.g., any CDR2 described herein)
<220> FEATURE:
<221> NAME/KEY: MISC_FEATURE
<222> LOCATION: (87)..(87)
<223> OTHER INFORMATION: Can be any amino acid or amino acids (e.g., any CDR3 described herein)

<400> SEQUENCE: 186

Glu Val Gln Leu Gln Ala Ser Gly Gly Gly Phe Val Gln Ala Gly Gly
1 5 10 15

Ser Leu Arg Leu Ser Cys Ala Ala Ser Gly Xaa Met Gly Trp Phe Arg
20 25 30

Gln Ala Pro Gly Lys Glu Arg Glu Phe Val Ala Ala Ile Ser Xaa Tyr
35 40 45

Tyr Ala Asp Ser Val Lys Gly Arg Phe Thr Ile Ser Arg Asp Asn Ala
50 55 60

Lys Asn Thr Val Tyr Leu Gln Met Asn Ser Leu Lys Pro Glu Asp Thr
65 70 75 80

Ala Thr Tyr Tyr Cys Ala Xaa Tyr Trp Gly Gln Gly Thr Gln Val Thr
85 90 95

Val Ser Ser

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190
<211> LENGTH: 26
<212> TYPE: PRT
<213> ORGANISM: Artificial Sequence
<220> FEATURE:

-continued

```
<223> OTHER INFORMATION: Synthetic construct

<400> SEQUENCE: 190

Glu Val Gln Leu Gln Ala Ser Gly Gly Gly Phe Val Gln Ala Gly Gly
1               5                   10                  15

Ser Leu Arg Leu Ser Cys Ala Ala Ser Gly
            20                  25


<210> SEQ ID NO 191
<211> LENGTH: 26
<212> TYPE: PRT
<213> ORGANISM: Artificial Sequence
<220> FEATURE:
<223> OTHER INFORMATION: Synthetic construct

<400> SEQUENCE: 191

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25


<210> SEQ ID NO 192
<211> LENGTH: 30
<212> TYPE: PRT
<213> ORGANISM: Artificial Sequence
<220> FEATURE:
<223> OTHER INFORMATION: Synthetic construct

<400> SEQUENCE: 192

Gln Val Gln Leu Val Glu Ser Gly Gly Gly Ser Val Gln Ala Gly Gly
1               5                   10                  15

Ser Leu Arg Leu Ser Cys Thr Ala Ser Gly Gly Ser Glu Tyr
            20                  25                  30


<210> SEQ ID NO 193
<211> LENGTH: 26
<212> TYPE: PRT
<213> ORGANISM: Artificial Sequence
<220> FEATURE:
<223> OTHER INFORMATION: Synthetic construct

<400> SEQUENCE: 193

Gln Val Gln Leu Val Glu Ser Gly Gly Gly Ser Val Gln Ala Gly Gly
1               5                   10                  15

Ser Leu Arg Leu Ser Cys Thr Ala Ser Gly
            20                  25


<210> SEQ ID NO 194
<211> LENGTH: 30
<212> TYPE: PRT
<213> ORGANISM: Artificial Sequence
<220> FEATURE:
<223> OTHER INFORMATION: Synthetic construct

<400> SEQUENCE: 194

Gln Val Gln Leu Val Glu Ser Gly Gly Gly Ser Val Gln Ala Gly Gly
1               5                   10                  15

Ser Leu Arg Leu Ser Cys Thr Ala Ser Gly Phe Ser Arg Glu
            20                  25                  30


<210> SEQ ID NO 195
<211> LENGTH: 30
<212> TYPE: PRT
<213> ORGANISM: Artificial Sequence
```

<220> FEATURE:
<223> OTHER INFORMATION: Synthetic construct

<400> SEQUENCE: 195

Gln Val Gln Leu Gln Glu Ser Gly Pro Ser Leu Val Arg Pro Ser Gln
1               5                   10                  15

Thr Leu Ser Leu Thr Cys Thr Ile Ser Gly Phe Ser Arg Glu
            20                  25                  30

<210> SEQ ID NO 196
<211> LENGTH: 26
<212> TYPE: PRT
<213> ORGANISM: Artificial Sequence
<220> FEATURE:
<223> OTHER INFORMATION: Synthetic construct

<400> SEQUENCE: 196

Gln Val Gln Leu Gln Glu Ser Gly Pro Ser Leu Val Arg Pro Ser Gln
1               5                   10                  15

Thr Leu Ser Leu Thr Cys Thr Ile Ser Gly
            20                  25

<210> SEQ ID NO 197
<211> LENGTH: 30
<212> TYPE: PRT
<213> ORGANISM: Artificial Sequence
<220> FEATURE:
<223> OTHER INFORMATION: Synthetic construct

<400> SEQUENCE: 197

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 198
<211> LENGTH: 26
<212> TYPE: PRT
<213> ORGANISM: Artificial Sequence
<220> FEATURE:
<223> OTHER INFORMATION: Synthetic construct

<400> SEQUENCE: 198

Gln Val Gln Leu Val Glu Ser Gly Gly Asn Leu Val Gln Pro Gly Gly
1               5                   10                  15

Ser Leu Arg Leu Ser Cys Ala Ala Ser Gly
            20                  25

<210> SEQ ID NO 199
<211> LENGTH: 30
<212> TYPE: PRT
<213> ORGANISM: Artificial Sequence
<220> FEATURE:
<223> OTHER INFORMATION: Synthetic construct

<400> SEQUENCE: 199

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn
            20                  25                  30

<210> SEQ ID NO 200
<211> LENGTH: 30
<212> TYPE: PRT

-continued

<213> ORGANISM: Artificial Sequence
<220> FEATURE:
<223> OTHER INFORMATION: Synthetic construct

<400> SEQUENCE: 200

```
Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Gly
            20                  25                  30
```

<210> SEQ ID NO 201
<211> LENGTH: 30
<212> TYPE: PRT
<213> ORGANISM: Artificial Sequence
<220> FEATURE:
<223> OTHER INFORMATION: Synthetic construct

<400> SEQUENCE: 201

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30
```

<210> SEQ ID NO 202
<211> LENGTH: 26
<212> TYPE: PRT
<213> ORGANISM: Artificial Sequence
<220> FEATURE:
<223> OTHER INFORMATION: Synthetic construct

<400> SEQUENCE: 202

```
Gln Val Gln Leu Val Glu Ser Gly Gly Ala Leu Val Gln Pro Gly Gly
1               5                   10                  15

Ser Leu Arg Leu Ser Cys Ala Ala Ser Gly
            20                  25
```

<210> SEQ ID NO 203
<211> LENGTH: 26
<212> TYPE: PRT
<213> ORGANISM: Artificial Sequence
<220> FEATURE:
<223> OTHER INFORMATION: Synthetic construct

<400> SEQUENCE: 203

```
Gln Val Gln Leu Val Glu Ser Gly Gly Gly Leu Val Gln Ala Gly Gly
1               5                   10                  15

Ser Leu Arg Leu Ser Cys Ala Ala Ser Gly
            20                  25
```

<210> SEQ ID NO 204
<211> LENGTH: 26
<212> TYPE: PRT
<213> ORGANISM: Artificial Sequence
<220> FEATURE:
<223> OTHER INFORMATION: Synthetic construct

<400> SEQUENCE: 204

```
Gln Val Gln Leu Val Glu Ser Gly Gly Gly Leu Met Gln Ala Gly Gly
1               5                   10                  15

Ser Leu Arg Leu Ser Cys Ala Val Ser Gly
            20                  25
```

<210> SEQ ID NO 205
<211> LENGTH: 26

<212> TYPE: PRT
<213> ORGANISM: Artificial Sequence
<220> FEATURE:
<223> OTHER INFORMATION: Synthetic construct

<400> SEQUENCE: 205

Gln Val Gln Leu Gln Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 206
<211> LENGTH: 26
<212> TYPE: PRT
<213> ORGANISM: Artificial Sequence
<220> FEATURE:
<223> OTHER INFORMATION: Synthetic construct

<400> SEQUENCE: 206

His Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 207
<211> LENGTH: 26
<212> TYPE: PRT
<213> ORGANISM: Artificial Sequence
<220> FEATURE:
<223> OTHER INFORMATION: Synthetic construct

<400> SEQUENCE: 207

Asp Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 208
<211> LENGTH: 26
<212> TYPE: PRT
<213> ORGANISM: Artificial Sequence
<220> FEATURE:
<223> OTHER INFORMATION: Synthetic construct

<400> SEQUENCE: 208

Glu Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 209
<211> LENGTH: 30
<212> TYPE: PRT
<213> ORGANISM: Artificial Sequence
<220> FEATURE:
<223> OTHER INFORMATION: Synthetic construct

<400> SEQUENCE: 209

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp
            20                  25                  30

<210> SEQ ID NO 210

-continued

<211> LENGTH: 26
<212> TYPE: PRT
<213> ORGANISM: Artificial Sequence
<220> FEATURE:
<223> OTHER INFORMATION: Synthetic construct

<400> SEQUENCE: 210

Glu Val Gln Leu Val Glu Ser Gly Gly Gly Val Val Gln Pro Gly Arg
1 5 10 15

Ser Leu Arg Leu Ser Cys Ala Ala Ser Gly
20 25

<210> SEQ ID NO 211
<211> LENGTH: 30
<212> TYPE: PRT
<213> ORGANISM: Artificial Sequence
<220> FEATURE:
<223> OTHER INFORMATION: Synthetic construct

<400> SEQUENCE: 211

Asp Val Gln Leu Gln Ala Ser Gly Gly Gly Leu Val Gln Ala Gly Gly
1 5 10 15

Ser Leu Arg Leu Ser Cys Ala Ala Ser Gly Phe Lys Ile Thr
20 25 30

<210> SEQ ID NO 212
<211> LENGTH: 26
<212> TYPE: PRT
<213> ORGANISM: Artificial Sequence
<220> FEATURE:
<223> OTHER INFORMATION: Synthetic construct

<400> SEQUENCE: 212

Asp Val Gln Leu Gln Ala Ser Gly Gly Gly Leu Val Gln Ala Gly Gly
1 5 10 15

Ser Leu Arg Leu Ser Cys Ala Ala Ser Gly
20 25

<210> SEQ ID NO 213
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid

<400> SEQUENCE: 213

Xaa Val Gln Leu Xaa Xaa Ser Gly Xaa Xaa Xaa Xaa Xaa Xaa Xaa Xaa
1 5 10 15

Xaa Leu Xaa Leu Xaa Cys Xaa Xaa Ser Gly Xaa Xaa Xaa Xaa
20 25 30

<210> SEQ ID NO 214
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid

<400> SEQUENCE: 214

Xaa Xaa Xaa Leu Xaa Xaa Xaa Gly Xaa Xaa Xaa Xaa Xaa Xaa Xaa Xaa
1 5 10 15

Xaa Xaa Xaa Xaa Xaa Cys Xaa Xaa Xaa Xaa
20 25

<210> SEQ ID NO 215
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 215

Xaa Val Gln Leu Xaa Xaa Ser Gly Xaa Xaa Xaa Xaa Xaa Xaa Xaa Xaa
1 5 10 15

```
Xaa Leu Xaa Leu Xaa Cys Xaa Xaa Ser Gly
            20                  25


<210> SEQ ID NO 216
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid

<400> SEQUENCE: 216

Gln Val Gln Leu Val Glu Ser Gly Gly Gly Leu Val Gln Xaa Gly Gly
1               5                   10                  15

Ser Leu Arg Leu Ser Cys Ala Ala Ser Gly Xaa Xaa Xaa Xaa
            20                  25                  30


<210> SEQ ID NO 217
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(14)
<223> OTHER INFORMATION: Xaa can be any naturally occurring amino acid

<400> SEQUENCE: 217

Gln Val Gln Leu Val Glu Ser Gly Gly Gly Leu Val Gln Xaa Gly Gly
1               5                   10                  15

Ser Leu Arg Leu Ser Cys Ala Ala Ser Gly
            20                  25


<210> SEQ ID NO 218

<400> SEQUENCE: 218

000


<210> SEQ ID NO 219

<400> SEQUENCE: 219

000


<210> SEQ ID NO 220
<211> LENGTH: 19
<212> TYPE: PRT
<213> ORGANISM: Artificial Sequence
<220> FEATURE:
<223> OTHER INFORMATION: Synthetic construct

<400> SEQUENCE: 220

Met Gly Trp Phe Arg Gln Ala Pro Gly Lys Glu Arg Glu Phe Val Ala
1               5                   10                  15

Ala Ile Ser


<210> SEQ ID NO 221
```

-continued

<211> LENGTH: 19
<212> TYPE: PRT
<213> ORGANISM: Artificial Sequence
<220> FEATURE:
<223> OTHER INFORMATION: Synthetic construct

<400> SEQUENCE: 221

Met Gly Trp Phe Arg Gln Ala Pro Gly Lys Glu Arg Glu Phe Val Ser
1 5 10 15

Ala Ile Ser

<210> SEQ ID NO 222
<211> LENGTH: 14
<212> TYPE: PRT
<213> ORGANISM: Artificial Sequence
<220> FEATURE:
<223> OTHER INFORMATION: Synthetic construct

<400> SEQUENCE: 222

Trp Phe Arg Gln Ala Pro Gly Gln Glu Arg Glu Ala Val Ala
1 5 10

<210> SEQ ID NO 223
<211> LENGTH: 17
<212> TYPE: PRT
<213> ORGANISM: Artificial Sequence
<220> FEATURE:
<223> OTHER INFORMATION: Synthetic construct

<400> SEQUENCE: 223

Trp Phe Arg Gln Ala Pro Gly Gln Glu Arg Glu Ala Val Ala Ala Ile
1 5 10 15

Ala

<210> SEQ ID NO 224
<211> LENGTH: 14
<212> TYPE: PRT
<213> ORGANISM: Artificial Sequence
<220> FEATURE:
<223> OTHER INFORMATION: Synthetic construct

<400> SEQUENCE: 224

Trp Val Arg Gln Ala Pro Gly Lys Ala Leu Glu Trp Leu Gly
1 5 10

<210> SEQ ID NO 225
<211> LENGTH: 16
<212> TYPE: PRT
<213> ORGANISM: Artificial Sequence
<220> FEATURE:
<223> OTHER INFORMATION: Synthetic construct

<400> SEQUENCE: 225

Trp Val Arg Gln Ala Pro Gly Lys Ala Leu Glu Trp Leu Gly Arg Ile
1 5 10 15

<210> SEQ ID NO 226
<211> LENGTH: 14
<212> TYPE: PRT
<213> ORGANISM: Artificial Sequence
<220> FEATURE:
<223> OTHER INFORMATION: Synthetic construct

<400> SEQUENCE: 226

Trp Phe Arg Gln Ala Pro Gly Gln Glu Arg Glu Trp Leu Gly
1 5 10

<210> SEQ ID NO 227
<211> LENGTH: 16
<212> TYPE: PRT
<213> ORGANISM: Artificial Sequence
<220> FEATURE:
<223> OTHER INFORMATION: Synthetic construct

<400> SEQUENCE: 227

Trp Phe Arg Gln Ala Pro Gly Gln Glu Arg Glu Trp Leu Gly Arg Ile
1 5 10 15

<210> SEQ ID NO 228
<211> LENGTH: 14
<212> TYPE: PRT
<213> ORGANISM: Artificial Sequence
<220> FEATURE:
<223> OTHER INFORMATION: Synthetic construct

<400> SEQUENCE: 228

Trp Val Arg Gln Ala Pro Gly Gly Gly Leu Glu Trp Val Ala
1 5 10

<210> SEQ ID NO 229
<211> LENGTH: 14
<212> TYPE: PRT
<213> ORGANISM: Artificial Sequence
<220> FEATURE:
<223> OTHER INFORMATION: Synthetic construct

<400> SEQUENCE: 229

Trp Tyr Arg Gln Ala Thr Gly Lys Glu Arg Glu Trp Val Ala
1 5 10

<210> SEQ ID NO 230
<211> LENGTH: 16
<212> TYPE: PRT
<213> ORGANISM: Artificial Sequence
<220> FEATURE:
<223> OTHER INFORMATION: Synthetic construct

<400> SEQUENCE: 230

Met Ser Trp Tyr Arg Gln Ala Thr Gly Lys Glu Arg Glu Trp Val Ala
1 5 10 15

<210> SEQ ID NO 231
<211> LENGTH: 19
<212> TYPE: PRT
<213> ORGANISM: Artificial Sequence
<220> FEATURE:
<223> OTHER INFORMATION: Synthetic construct

<400> SEQUENCE: 231

Met Gly Trp Phe Arg Gln Ala Pro Gly Lys Glu Arg Glu Phe Val Ala
1 5 10 15

Ala Ile Arg

<210> SEQ ID NO 232
<211> LENGTH: 18
<212> TYPE: PRT
<213> ORGANISM: Artificial Sequence
<220> FEATURE:
<223> OTHER INFORMATION: Synthetic construct

<400> SEQUENCE: 232

Met Gly Trp Phe Arg Gln Ala Pro Gly Lys Glu Arg Glu Phe Val Ala 1 5 10 15

Ala Ile

<210> SEQ ID NO 233
<211> LENGTH: 16
<212> TYPE: PRT
<213> ORGANISM: Artificial Sequence
<220> FEATURE:
<223> OTHER INFORMATION: Synthetic construct

<400> SEQUENCE: 233

Met Gly Trp Phe Arg Gln Ala Pro Gly Lys Glu Arg Glu Phe Val Ala
1 5 10 15

<210> SEQ ID NO 234
<211> LENGTH: 16
<212> TYPE: PRT
<213> ORGANISM: Artificial Sequence
<220> FEATURE:
<223> OTHER INFORMATION: Synthetic construct

<400> SEQUENCE: 234

Met Gly Trp Tyr Arg Gln Ala Pro Gly Lys Glu Arg Glu Leu Val Ala
1 5 10 15

<210> SEQ ID NO 235
<211> LENGTH: 17
<212> TYPE: PRT
<213> ORGANISM: Artificial Sequence
<220> FEATURE:
<223> OTHER INFORMATION: Synthetic construct

<400> SEQUENCE: 235

Met Gly Trp Tyr Arg Gln Ala Pro Gly Lys Glu Arg Glu Leu Val Ala
1 5 10 15

Ala

<210> SEQ ID NO 236
<211> LENGTH: 19
<212> TYPE: PRT
<213> ORGANISM: Artificial Sequence
<220> FEATURE:
<223> OTHER INFORMATION: Synthetic construct

<400> SEQUENCE: 236

Met Gly Trp Tyr Arg Gln Ala Pro Gly Lys Glu Arg Glu Leu Val Ala
1 5 10 15

Ala Ile Asp

<210> SEQ ID NO 237
<211> LENGTH: 19
<212> TYPE: PRT
<213> ORGANISM: Artificial Sequence
<220> FEATURE:
<223> OTHER INFORMATION: Synthetic construct

<400> SEQUENCE: 237

Met Gly Trp Tyr Arg Gln Ala Pro Gly Lys Glu Arg Glu Leu Val Ala
1 5 10 15

Val Ile Ser

<210> SEQ ID NO 238
<211> LENGTH: 16
<212> TYPE: PRT

<213> ORGANISM: Artificial Sequence
<220> FEATURE:
<223> OTHER INFORMATION: Synthetic construct

<400> SEQUENCE: 238

Met Gly Trp Phe Arg Gln Ala Pro Gly Lys Glu Arg Glu Gly Val Ala
1 5 10 15

<210> SEQ ID NO 239
<211> LENGTH: 14
<212> TYPE: PRT
<213> ORGANISM: Artificial Sequence
<220> FEATURE:
<223> OTHER INFORMATION: Synthetic construct

<400> SEQUENCE: 239

Trp Phe Arg Gln Ala Pro Gly Lys Glu Arg Glu Gly Val Ala
1 5 10

<210> SEQ ID NO 240
<211> LENGTH: 16
<212> TYPE: PRT
<213> ORGANISM: Artificial Sequence
<220> FEATURE:
<223> OTHER INFORMATION: Synthetic construct

<400> SEQUENCE: 240

Met Gly Trp Phe Arg Gln Ala Pro Gly Lys Glu Arg Glu Phe Val Ala
1 5 10 15

<210> SEQ ID NO 241
<211> LENGTH: 14
<212> TYPE: PRT
<213> ORGANISM: Artificial Sequence
<220> FEATURE:
<223> OTHER INFORMATION: Synthetic construct

<400> SEQUENCE: 241

Trp Phe Arg Gln Ala Pro Gly Lys Glu Arg Glu Phe Val Ala
1 5 10

<210> SEQ ID NO 242
<211> LENGTH: 14
<212> TYPE: PRT
<213> ORGANISM: Artificial Sequence
<220> FEATURE:
<223> OTHER INFORMATION: Synthetic construct

<400> SEQUENCE: 242

Trp Val Arg Gln Ala Pro Gly Lys Gly Pro Glu Trp Val Ala
1 5 10

<210> SEQ ID NO 243
<211> LENGTH: 14
<212> TYPE: PRT
<213> ORGANISM: Artificial Sequence
<220> FEATURE:
<223> OTHER INFORMATION: Synthetic construct

<400> SEQUENCE: 243

Trp Phe Arg Gln Ala Pro Gly Lys Glu Arg Glu Phe Val Ser
1 5 10

<210> SEQ ID NO 244
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(19)
<223> OTHER INFORMATION: Xaa can be any naturally occurring amino acid

<400> SEQUENCE: 244

Xaa Xaa Trp Xaa Xaa Xaa Xaa Xaa Xaa Xaa Xaa Xaa Xaa Xaa Xaa Xaa
1               5                   10                  15

Xaa Xaa Xaa

<210> SEQ ID NO 245
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid

<400> SEQUENCE: 245

Xaa Xaa Trp Xaa Arg Gln Ala Xaa Gly Xaa Xaa Xaa Glu Xaa Xaa Xaa
1               5                   10                  15

Xaa Xaa Xaa

<210> SEQ ID NO 246
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(16)

<223> OTHER INFORMATION: Xaa can be any naturally occurring amino acid

<400> SEQUENCE: 246

Xaa Xaa Trp Xaa Arg Gln Ala Xaa Gly Xaa Xaa Xaa Glu Xaa Xaa Xaa
1 5 10 15

<210> SEQ ID NO 247
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid

<400> SEQUENCE: 247

Met Xaa Trp Phe Arg Gln Ala Pro Gly Lys Glu Arg Glu Trp Val Ala
1 5 10 15

Xaa Xaa Xaa

<210> SEQ ID NO 248
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 248

Met Xaa Trp Phe Arg Gln Ala Pro Gly Lys Glu Arg Glu Trp Val Ala
1 5 10 15

<210> SEQ ID NO 249

<400> SEQUENCE: 249

000

<210> SEQ ID NO 250
<211> LENGTH: 38
<212> TYPE: PRT
<213> ORGANISM: Artificial Sequence
<220> FEATURE:
<223> OTHER INFORMATION: Synthetic construct

<400> SEQUENCE: 250

Tyr Ala Asp Ser Val Lys Gly Arg Phe Thr Ile Ser Arg Asp Asn Ala
1 5 10 15

Lys Asn Thr Val Tyr Leu Gln Met Asn Ser Leu Lys Pro Glu Asp Thr
20 25 30

Ala Thr Tyr Tyr Cys Ala
35

<210> SEQ ID NO 251
<211> LENGTH: 39
<212> TYPE: PRT
<213> ORGANISM: Artificial Sequence
<220> FEATURE:

<223> OTHER INFORMATION: Synthetic construct

<400> SEQUENCE: 251

Tyr Tyr Ala Asp Ser Val Lys Gly Arg Phe Thr Ile Ser Arg Asp Asn
1 5 10 15

Ala Lys Asn Thr Val Tyr Leu Gln Met Asn Ser Leu Lys Pro Glu Asp
20 25 30

Thr Ala Thr Tyr Tyr Cys Ala
35

<210> SEQ ID NO 252
<211> LENGTH: 38
<212> TYPE: PRT
<213> ORGANISM: Artificial Sequence
<220> FEATURE:
<223> OTHER INFORMATION: Synthetic construct

<400> SEQUENCE: 252

Tyr Ala Asp Ser Val Lys Gly Arg Phe Thr Ile Ser Arg Asp Asn Ser
1 5 10 15

Lys Asn Thr Val Tyr Leu Gln Met Asn Ser Leu Arg Ala Glu Asp Thr
20 25 30

Ala Thr Tyr Tyr Cys Ala
35

<210> SEQ ID NO 253
<211> LENGTH: 39
<212> TYPE: PRT
<213> ORGANISM: Artificial Sequence
<220> FEATURE:
<223> OTHER INFORMATION: Synthetic construct

<400> SEQUENCE: 253

Tyr Tyr Ala Asp Ser Val Lys Gly Arg Phe Thr Ile Ser Arg Asp Asn
1 5 10 15

Ser Lys Asn Thr Val Tyr Leu Gln Met Asn Ser Leu Arg Ala Glu Asp
20 25 30

Thr Ala Thr Tyr Tyr Cys Ala
35

<210> SEQ ID NO 254
<211> LENGTH: 31
<212> TYPE: PRT
<213> ORGANISM: Artificial Sequence
<220> FEATURE:
<223> OTHER INFORMATION: Synthetic construct

<400> SEQUENCE: 254

Arg Phe Thr Ile Ser Arg Asp Asn Ala Lys Asn Thr Val Thr Leu Gln
1 5 10 15

Met Asn Asn Leu Lys Pro Glu Asp Thr Ala Ile Tyr Tyr Cys Ala
20 25 30

<210> SEQ ID NO 255
<211> LENGTH: 32
<212> TYPE: PRT
<213> ORGANISM: Artificial Sequence
<220> FEATURE:
<223> OTHER INFORMATION: Synthetic construct

<400> SEQUENCE: 255

Arg Phe Thr Ile Ser Arg Asp Asn Ala Lys Asn Thr Val Thr Leu Gln
1 5 10 15

Met Asn Asn Leu Lys Pro Glu Asp Thr Ala Ile Tyr Tyr Cys Ala Ala
20 25 30

<210> SEQ ID NO 256
<211> LENGTH: 31
<212> TYPE: PRT
<213> ORGANISM: Artificial Sequence
<220> FEATURE:
<223> OTHER INFORMATION: Synthetic construct

<400> SEQUENCE: 256

Arg Leu Thr Ile Thr Arg Asp Ile Ser Lys Ser Gln Val Ser Leu Ser
1 5 10 15

Leu Ser Ser Val Thr Leu Glu Asp Thr Ala Glu Tyr Tyr Cys Val
20 25 30

<210> SEQ ID NO 257
<211> LENGTH: 32
<212> TYPE: PRT
<213> ORGANISM: Artificial Sequence
<220> FEATURE:
<223> OTHER INFORMATION: Synthetic construct

<400> SEQUENCE: 257

Arg Leu Thr Ile Thr Arg Asp Ile Ser Lys Ser Gln Val Ser Leu Ser
1 5 10 15

Leu Ser Ser Val Thr Leu Glu Asp Thr Ala Glu Tyr Tyr Cys Val Tyr
20 25 30

<210> SEQ ID NO 258
<211> LENGTH: 31
<212> TYPE: PRT
<213> ORGANISM: Artificial Sequence
<220> FEATURE:
<223> OTHER INFORMATION: Synthetic construct

<400> SEQUENCE: 258

Arg Phe Thr Ile Ser Arg Asp Ile Ala Lys Asn Thr Val Thr Leu Gln
1 5 10 15

Met Asn Asn Leu Lys Pro Glu Asp Thr Ala Ile Tyr Tyr Val Tyr
20 25 30

<210> SEQ ID NO 259
<211> LENGTH: 32
<212> TYPE: PRT
<213> ORGANISM: Artificial Sequence
<220> FEATURE:
<223> OTHER INFORMATION: Synthetic construct

<400> SEQUENCE: 259

Arg Phe Thr Ile Ser Arg Asp Ile Ala Lys Asn Thr Val Thr Leu Gln
1 5 10 15

Met Asn Asn Leu Lys Pro Glu Asp Thr Ala Ile Tyr Tyr Val Tyr Ala
20 25 30

<210> SEQ ID NO 260
<211> LENGTH: 39
<212> TYPE: PRT
<213> ORGANISM: Artificial Sequence
<220> FEATURE:
<223> OTHER INFORMATION: Synthetic construct

<400> SEQUENCE: 260

Tyr Tyr Ala Asp Ser Val Lys Gly Arg Phe Thr Ile Ser Arg Asp Asn

```
1               5                   10                  15

Ala Lys Asn Thr Val Thr Leu Gln Met Asn Asn Leu Lys Pro Glu Asp
            20                  25                  30

Thr Ala Ile Tyr Tyr Cys Ala
        35


<210> SEQ ID NO 261
<211> LENGTH: 40
<212> TYPE: PRT
<213> ORGANISM: Artificial Sequence
<220> FEATURE:
<223> OTHER INFORMATION: Synthetic construct

<400> SEQUENCE: 261

Tyr Tyr Ala Asp Ser Val Lys Gly Arg Phe Thr Ile Ser Arg Asp Asn
1               5                   10                  15

Ala Lys Asn Thr Val Thr Leu Gln Met Asn Asn Leu Lys Pro Glu Asp
            20                  25                  30

Thr Ala Ile Tyr Tyr Cys Ala Ala
        35                  40


<210> SEQ ID NO 262
<211> LENGTH: 39
<212> TYPE: PRT
<213> ORGANISM: Artificial Sequence
<220> FEATURE:
<223> OTHER INFORMATION: Synthetic construct

<400> SEQUENCE: 262

Tyr Glu Asp Ser Val Lys Gly Arg Phe Cys Ile Ser Arg Asp Asp Ala
1               5                   10                  15

Arg Asn Thr Val Tyr Leu Gln Met Asn Ser Leu Lys Pro Glu Asp Thr
            20                  25                  30

Ala Val Tyr Tyr Cys Asn Val
        35


<210> SEQ ID NO 263
<211> LENGTH: 38
<212> TYPE: PRT
<213> ORGANISM: Artificial Sequence
<220> FEATURE:
<223> OTHER INFORMATION: Synthetic construct

<400> SEQUENCE: 263

Tyr Glu Asp Ser Val Lys Gly Arg Phe Cys Ile Ser Arg Asp Asp Ala
1               5                   10                  15

Arg Asn Thr Val Tyr Leu Gln Met Asn Ser Leu Lys Pro Glu Asp Thr
            20                  25                  30

Ala Val Tyr Tyr Cys Asn
        35


<210> SEQ ID NO 264
<211> LENGTH: 39
<212> TYPE: PRT
<213> ORGANISM: Artificial Sequence
<220> FEATURE:
<223> OTHER INFORMATION: Synthetic construct

<400> SEQUENCE: 264

Tyr Ala Asp Ser Val Lys Gly Arg Phe Thr Ile Ser Arg Asp Asn Ala
1               5                   10                  15

Lys Asn Ser Val Tyr Leu Gln Met Asn Ser Leu Arg Val Glu Asp Thr
```

```
            20                  25                  30

Ala Val Tyr Tyr Cys Ala Arg
        35


<210> SEQ ID NO 265
<211> LENGTH: 38
<212> TYPE: PRT
<213> ORGANISM: Artificial Sequence
<220> FEATURE:
<223> OTHER INFORMATION: Synthetic construct

<400> SEQUENCE: 265

Tyr Ala Asp Ser Val Lys Gly Arg Phe Thr Ile Ser Arg Asp Asn Ala
1               5                   10                  15

Lys Asn Ser Val Tyr Leu Gln Met Asn Ser Leu Arg Val Glu Asp Thr
            20                  25                  30

Ala Val Tyr Tyr Cys Ala
        35


<210> SEQ ID NO 266
<211> LENGTH: 39
<212> TYPE: PRT
<213> ORGANISM: Artificial Sequence
<220> FEATURE:
<223> OTHER INFORMATION: Synthetic construct

<400> SEQUENCE: 266

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala Arg
        35


<210> SEQ ID NO 267
<211> LENGTH: 38
<212> TYPE: PRT
<213> ORGANISM: Artificial Sequence
<220> FEATURE:
<223> OTHER INFORMATION: Synthetic construct

<400> SEQUENCE: 267

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala
        35


<210> SEQ ID NO 268
<211> LENGTH: 39
<212> TYPE: PRT
<213> ORGANISM: Artificial Sequence
<220> FEATURE:
<223> OTHER INFORMATION: Synthetic construct

<400> SEQUENCE: 268

Tyr Ala Asp Ser Val Lys Gly Arg Phe Thr Ile Ser Arg Asp Asn Ala
1               5                   10                  15

Arg Asn Thr Val Tyr Leu Gln Met Asn Ser Leu Lys Pro Glu Asp Thr
            20                  25                  30

Ala Val Tyr Tyr Cys Ala Arg
```

35

<210> SEQ ID NO 269
<211> LENGTH: 32
<212> TYPE: PRT
<213> ORGANISM: Artificial Sequence
<220> FEATURE:
<223> OTHER INFORMATION: Synthetic construct

<400> SEQUENCE: 269

Arg Phe Thr Ile Ser Arg Asp Asn Ala Arg Asn Thr Val Tyr Leu Gln
1 5 10 15

Met Asn Ser Leu Lys Pro Glu Asp Thr Ala Val Tyr Tyr Cys Ala Arg
20 25 30

<210> SEQ ID NO 270
<211> LENGTH: 39
<212> TYPE: PRT
<213> ORGANISM: Artificial Sequence
<220> FEATURE:
<223> OTHER INFORMATION: Synthetic construct

<400> SEQUENCE: 270

Tyr Ala Asp Ser Val Lys Gly Arg Phe Thr Ile Ser Arg Asp Lys Gly
1 5 10 15

Lys Asn Thr Val Tyr Leu Gln Met Asp Ser Leu Lys Pro Glu Asp Thr
20 25 30

Ala Thr Tyr Tyr Cys Ala Ala
35

<210> SEQ ID NO 271
<211> LENGTH: 32
<212> TYPE: PRT
<213> ORGANISM: Artificial Sequence
<220> FEATURE:
<223> OTHER INFORMATION: Synthetic construct

<400> SEQUENCE: 271

Arg Phe Thr Ile Ser Arg Asp Lys Gly Lys Asn Thr Val Tyr Leu Gln
1 5 10 15

Met Asp Ser Leu Lys Pro Glu Asp Thr Ala Thr Tyr Tyr Cys Ala Ala
20 25 30

<210> SEQ ID NO 272
<211> LENGTH: 38
<212> TYPE: PRT
<213> ORGANISM: Artificial Sequence
<220> FEATURE:
<223> OTHER INFORMATION: Synthetic construct

<400> SEQUENCE: 272

Tyr Ala Asp Ser Val Lys Gly Arg Phe Thr Ile Ser Arg Asp Lys Gly
1 5 10 15

Lys Asn Thr Val Tyr Leu Gln Met Asp Ser Leu Lys Pro Glu Asp Thr
20 25 30

Ala Thr Tyr Tyr Cys Ala
35

<210> SEQ ID NO 273
<211> LENGTH: 31
<212> TYPE: PRT
<213> ORGANISM: Artificial Sequence
<220> FEATURE:
<223> OTHER INFORMATION: Synthetic construct

<400> SEQUENCE: 273

Arg Phe Thr Ile Ser Arg Asp Lys Gly Lys Asn Thr Val Tyr Leu Gln
1 5 10 15

Met Asp Ser Leu Lys Pro Glu Asp Thr Ala Thr Tyr Tyr Cys Ala
20 25 30

<210> SEQ ID NO 274
<211> LENGTH: 39
<212> TYPE: PRT
<213> ORGANISM: Artificial Sequence
<220> FEATURE:
<223> OTHER INFORMATION: Synthetic construct

<400> SEQUENCE: 274

Tyr Tyr Ala Asp Ser Val Lys Gly Arg Phe Thr Ile Ser Arg Asp Lys
1 5 10 15

Ala Lys Asn Thr Val Tyr Leu Gln Met Asn Ser Leu Lys Tyr Glu Asp
20 25 30

Thr Ala Val Tyr Tyr Cys Ala
35

<210> SEQ ID NO 275
<211> LENGTH: 38
<212> TYPE: PRT
<213> ORGANISM: Artificial Sequence
<220> FEATURE:
<223> OTHER INFORMATION: Synthetic construct

<400> SEQUENCE: 275

Tyr Ala Asp Ser Val Lys Gly Arg Phe Thr Ile Ser Arg Asp Lys Ala
1 5 10 15

Lys Asn Thr Val Tyr Leu Gln Met Asn Ser Leu Lys Tyr Glu Asp Thr
20 25 30

Ala Val Tyr Tyr Cys Ala
35

<210> SEQ ID NO 276
<211> LENGTH: 39
<212> TYPE: PRT
<213> ORGANISM: Artificial Sequence
<220> FEATURE:
<223> OTHER INFORMATION: Synthetic construct

<400> SEQUENCE: 276

Tyr Tyr Ala Asp Ser Val Lys Gly Arg Phe Thr Ile Ser Arg Asp Asn
1 5 10 15

Ala Lys Asn Thr Val Tyr Leu Gln Met Asn Ser Leu Lys Pro Glu Asp
20 25 30

Thr Ala Val Tyr Tyr Cys Ala
35

<210> SEQ ID NO 277
<211> LENGTH: 39
<212> TYPE: PRT
<213> ORGANISM: Artificial Sequence
<220> FEATURE:
<223> OTHER INFORMATION: Synthetic construct

<400> SEQUENCE: 277

Leu His Asn Pro Ala Leu Lys Ser Arg Leu Thr Ile Thr Arg Asp Ile
1 5 10 15

```
Ser Lys Ser Gln Val Ser Leu Ser Leu Ser Ser Val Thr Leu Glu Asp
            20                  25                  30

Thr Ala Glu Tyr Tyr Cys Val
        35


<210> SEQ ID NO 278
<211> LENGTH: 40
<212> TYPE: PRT
<213> ORGANISM: Artificial Sequence
<220> FEATURE:
<223> OTHER INFORMATION: Synthetic construct

<400> SEQUENCE: 278

Leu His Asn Pro Ala Leu Lys Ser Arg Leu Thr Ile Thr Arg Asp Ile
1               5                   10                  15

Ser Lys Ser Gln Val Ser Leu Ser Leu Ser Ser Val Thr Leu Glu Asp
            20                  25                  30

Thr Ala Glu Tyr Tyr Cys Val Tyr
        35                  40


<210> SEQ ID NO 279
<211> LENGTH: 40
<212> TYPE: PRT
<213> ORGANISM: Artificial Sequence
<220> FEATURE:
<223> OTHER INFORMATION: Synthetic construct

<400> SEQUENCE: 279

Leu His Asn Pro Ala Leu Lys Ser Arg Phe Thr Ile Ser Arg Asp Ile
1               5                   10                  15

Ala Lys Asn Thr Val Thr Leu Gln Met Asn Asn Leu Lys Pro Glu Asp
            20                  25                  30

Thr Ala Ile Tyr Tyr Val Tyr Ala
        35                  40


<210> SEQ ID NO 280
<211> LENGTH: 39
<212> TYPE: PRT
<213> ORGANISM: Artificial Sequence
<220> FEATURE:
<223> OTHER INFORMATION: Synthetic construct

<400> SEQUENCE: 280

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Ala
        35


<210> SEQ ID NO 281
<211> LENGTH: 38
<212> TYPE: PRT
<213> ORGANISM: Artificial Sequence
<220> FEATURE:
<223> OTHER INFORMATION: Synthetic construct

<400> SEQUENCE: 281

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30
```

Ala Val Tyr Tyr Cys Ala
        35

<210> SEQ ID NO 282
<211> LENGTH: 40
<212> TYPE: PRT
<213> ORGANISM: Artificial Sequence
<220> FEATURE:
<223> OTHER INFORMATION: Synthetic construct

<400> SEQUENCE: 282

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Ala
        35                  40

<210> SEQ ID NO 283
<211> LENGTH: 32
<212> TYPE: PRT
<213> ORGANISM: Artificial Sequence
<220> FEATURE:
<223> OTHER INFORMATION: Synthetic construct

<400> SEQUENCE: 283

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 284
<211> LENGTH: 32
<212> TYPE: PRT
<213> ORGANISM: Artificial Sequence
<220> FEATURE:
<223> OTHER INFORMATION: Synthetic construct

<400> SEQUENCE: 284

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Asp Tyr Tyr Cys Ala Ala
            20                  25                  30

<210> SEQ ID NO 285
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(14)
<223> OTHER INFORMATION: Xaa can be any naturally occurring amino acid
<220> FEATURE:
<221> NAME/KEY: misc_feature
<222> LOCATION: (16)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid

<400> SEQUENCE: 285

Xaa Xaa Xaa Xaa Xaa Xaa Xaa Xaa Xaa Xaa Xaa Xaa Xaa Xaa Asp Xaa
1               5                   10                  15

Xaa Xaa Xaa Xaa Xaa Xaa Xaa Xaa Xaa Xaa Xaa Xaa Xaa Xaa Xaa Asp
            20                  25                  30

Xaa Xaa Xaa Tyr Xaa Cys Xaa Xaa
        35                  40

<210> SEQ ID NO 286
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(40)
<223> OTHER INFORMATION: Xaa can be any naturally occurring amino acid

<400> SEQUENCE: 286

Xaa Xaa Xaa Xaa Xaa Xaa Xaa Xaa Arg Xaa Xaa Ile Xaa Arg Asp Xaa
1               5                   10                  15

Xaa Xaa Xaa Xaa Val Xaa Leu Xaa Xaa Xaa Xaa Xaa Xaa Xaa Glu Asp
            20                  25                  30

Thr Ala Xaa Tyr Tyr Xaa Xaa Xaa
        35                  40

<210> SEQ ID NO 287
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(11)

<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid

<400> SEQUENCE: 287

```
Xaa Xaa Xaa Xaa Xaa Xaa Xaa Xaa Arg Xaa Xaa Ile Xaa Arg Asp Xaa
1               5                   10                  15

Xaa Xaa Xaa Xaa Val Xaa Leu Xaa Xaa Xaa Xaa Xaa Xaa Xaa Glu Asp
            20                  25                  30

Thr Ala Xaa Tyr Tyr Xaa Xaa
        35
```

<210> SEQ ID NO 288
<211> LENGTH: 40
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 288

```
Xaa Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Xaa
        35                  40
```

<210> SEQ ID NO 289
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 289

```
Xaa Tyr Ala Asp Ser Val Lys Gly Arg Phe Thr Ile Ser Arg Asp Asn
```

-continued

```
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala
        35


<210> SEQ ID NO 290
<211> LENGTH: 12
<212> TYPE: PRT
<213> ORGANISM: Artificial Sequence
<220> FEATURE:
<223> OTHER INFORMATION: Synthetic construct

<400> SEQUENCE: 290

Tyr Trp Gly Gln Gly Thr Gln Val Thr Val Ser Ser
1               5                   10


<210> SEQ ID NO 291
<211> LENGTH: 11
<212> TYPE: PRT
<213> ORGANISM: Artificial Sequence
<220> FEATURE:
<223> OTHER INFORMATION: Synthetic construct

<400> SEQUENCE: 291

Trp Gly Gln Gly Thr Gln Val Thr Val Ser Ser
1               5                   10


<210> SEQ ID NO 292
<211> LENGTH: 12
<212> TYPE: PRT
<213> ORGANISM: Artificial Sequence
<220> FEATURE:
<223> OTHER INFORMATION: Synthetic construct

<400> SEQUENCE: 292

Val Trp Gly Pro Gly Leu Leu Leu Thr Val Ser Ser
1               5                   10


<210> SEQ ID NO 293
<211> LENGTH: 11
<212> TYPE: PRT
<213> ORGANISM: Artificial Sequence
<220> FEATURE:
<223> OTHER INFORMATION: Synthetic construct

<400> SEQUENCE: 293

Trp Gly Pro Gly Leu Leu Leu Thr Val Ser Ser
1               5                   10


<210> SEQ ID NO 294
<211> LENGTH: 10
<212> TYPE: PRT
<213> ORGANISM: Artificial Sequence
<220> FEATURE:
<223> OTHER INFORMATION: Synthetic construct

<400> SEQUENCE: 294

Trp Gly Gln Gly Thr Leu Val Thr Val Ser
1               5                   10


<210> SEQ ID NO 295
<211> LENGTH: 11
<212> TYPE: PRT
<213> ORGANISM: Artificial Sequence
<220> FEATURE:
```

<223> OTHER INFORMATION: Synthetic construct

<400> SEQUENCE: 295

Trp Gly Gln Gly Thr Leu Val Thr Val Ser Ser
1 5 10

<210> SEQ ID NO 296
<211> LENGTH: 10
<212> TYPE: PRT
<213> ORGANISM: Artificial Sequence
<220> FEATURE:
<223> OTHER INFORMATION: Synthetic construct

<400> SEQUENCE: 296

Trp Gly Gln Gly Thr Gln Val Thr Val Ser
1 5 10

<210> SEQ ID NO 297
<211> LENGTH: 11
<212> TYPE: PRT
<213> ORGANISM: Artificial Sequence
<220> FEATURE:
<223> OTHER INFORMATION: Synthetic construct

<400> SEQUENCE: 297

Trp Gly Gln Gly Thr Gln Val Thr Val Ser Ser
1 5 10

<210> SEQ ID NO 298
<211> LENGTH: 12
<212> TYPE: PRT
<213> ORGANISM: Artificial Sequence
<220> FEATURE:
<223> OTHER INFORMATION: Synthetic construct

<400> SEQUENCE: 298

Gln Trp Gly Gln Gly Thr Gln Val Thr Val Ser Ser
1 5 10

<210> SEQ ID NO 299
<211> LENGTH: 11
<212> TYPE: PRT
<213> ORGANISM: Artificial Sequence
<220> FEATURE:
<223> OTHER INFORMATION: Synthetic construct

<400> SEQUENCE: 299

Tyr Trp Gly Gln Gly Thr Gln Val Thr Val Ser
1 5 10

<210> SEQ ID NO 300
<211> LENGTH: 11
<212> TYPE: PRT
<213> ORGANISM: Artificial Sequence
<220> FEATURE:
<223> OTHER INFORMATION: Synthetic construct

<400> SEQUENCE: 300

Trp Gly Gln Gly Thr Thr Val Val Val Ser Ser
1 5 10

<210> SEQ ID NO 301
<211> LENGTH: 11
<212> TYPE: PRT
<213> ORGANISM: Artificial Sequence
<220> FEATURE:
<223> OTHER INFORMATION: Synthetic construct

<400> SEQUENCE: 301

Trp Gly Lys Gly Thr Gln Val Thr Val Ser Ser
1 5 10

<210> SEQ ID NO 302
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 302

Xaa Trp Gly Xaa Gly Xaa Xaa Xaa Thr Val Ser Xaa
1 5 10

<210> SEQ ID NO 303
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 303

Xaa Trp Gly Xaa Gly Xaa Xaa Xaa Thr Val Ser
1 5 10

<210> SEQ ID NO 304
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 304

Trp Gly Xaa Gly Xaa Xaa Xaa Thr Val Ser Xaa
1 5 10

<210> SEQ ID NO 305
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 305

Xaa Xaa Gly Xaa Gly Thr Xaa Xaa Xaa Val Ser Xaa
1 5 10

<210> SEQ ID NO 306
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 306

Xaa Trp Gly Gln Gly Thr Gln Val Thr Val Ser Ser
1 5 10

<210> SEQ ID NO 307
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 307

Xaa Trp Gly Gln Gly Thr Gln Val Thr Val Ser
1 5 10

<210> SEQ ID NO 308

<400> SEQUENCE: 308

000

<210> SEQ ID NO 309

<400> SEQUENCE: 309

000

<210> SEQ ID NO 310
<211> LENGTH: 3
<212> TYPE: PRT
<213> ORGANISM: Artificial Sequence
<220> FEATURE:
<223> OTHER INFORMATION: Synthetic construct

<400> SEQUENCE: 310

Gly Gly Gly
1

<210> SEQ ID NO 311
<211> LENGTH: 4
<212> TYPE: PRT
<213> ORGANISM: Artificial Sequence
<220> FEATURE:
<223> OTHER INFORMATION: Synthetic construct

<400> SEQUENCE: 311

Gly Gly Gly Ser
1

<210> SEQ ID NO 312
<211> LENGTH: 4
<212> TYPE: PRT
<213> ORGANISM: Artificial Sequence
<220> FEATURE:
<223> OTHER INFORMATION: Synthetic construct

<400> SEQUENCE: 312

Gly Gly Gly Gly
1

<210> SEQ ID NO 313
<211> LENGTH: 5
<212> TYPE: PRT
<213> ORGANISM: Artificial Sequence
<220> FEATURE:
<223> OTHER INFORMATION: Synthetic construct

<400> SEQUENCE: 313

Gly Gly Gly Gly Ser
1               5

<210> SEQ ID NO 314
<211> LENGTH: 4
<212> TYPE: PRT
<213> ORGANISM: Artificial Sequence
<220> FEATURE:
<223> OTHER INFORMATION: Synthetic construct

<400> SEQUENCE: 314

Gly Gly Ser Gly
1

<210> SEQ ID NO 315
<211> LENGTH: 10
<212> TYPE: PRT
<213> ORGANISM: Artificial Sequence
<220> FEATURE:
<223> OTHER INFORMATION: Synthetic construct

<400> SEQUENCE: 315

Gly Gly Gly Gly Ser Gly Gly Gly Gly Ser
1 5 10

<210> SEQ ID NO 316
<211> LENGTH: 15
<212> TYPE: PRT
<213> ORGANISM: Artificial Sequence
<220> FEATURE:
<223> OTHER INFORMATION: Synthetic construct

<400> SEQUENCE: 316

Gly Gly Gly Gly Ser Gly Gly Gly Gly Ser Gly Gly Gly Gly Ser
1 5 10 15

<210> SEQ ID NO 317
<211> LENGTH: 20
<212> TYPE: PRT
<213> ORGANISM: Artificial Sequence
<220> FEATURE:
<223> OTHER INFORMATION: Synthetic construct

<400> SEQUENCE: 317

Gly Gly Gly Gly Ser Gly Gly Gly Gly Ser Gly Gly Gly Gly Ser Gly
1 5 10 15

Gly Gly Gly Ser
20

<210> SEQ ID NO 318
<211> LENGTH: 8
<212> TYPE: PRT
<213> ORGANISM: Artificial Sequence
<220> FEATURE:
<223> OTHER INFORMATION: Synthetic construct

<400> SEQUENCE: 318

Gly Gly Ser Gly Gly Gly Ser Gly
1 5

<210> SEQ ID NO 319
<211> LENGTH: 12
<212> TYPE: PRT
<213> ORGANISM: Artificial Sequence
<220> FEATURE:
<223> OTHER INFORMATION: Synthetic construct

<400> SEQUENCE: 319

Gly Gly Ser Gly Gly Gly Ser Gly Gly Gly Ser Gly
1 5 10

<210> SEQ ID NO 320
<211> LENGTH: 1273
<212> TYPE: PRT
<213> ORGANISM: Artificial Sequence
<220> FEATURE:
<223> OTHER INFORMATION: Synthetic construct

<400> SEQUENCE: 320

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

```
Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480
```

-continued

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
```

```
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

<210> SEQ ID NO 321
<211> LENGTH: 1269
<212> TYPE: PRT
<213> ORGANISM: Artificial Sequence -continued
<220> FEATURE:
<223> OTHER INFORMATION: Synthetic construct

<400> SEQUENCE: 321

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Ser
            20                  25                  30

Thr Arg Gly Val Tyr Tyr Pro Asp Lys Val Phe Arg Ser Ser Val Leu
        35                  40                  45

His Leu Thr Gln Asp Leu Phe Leu Pro Phe Phe Ser Asn Val Thr Trp
    50                  55                  60

Phe His Ala Ile His Val Ser Gly Thr Asn Gly Ile Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Pro Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Asp Ser Ile Val Arg Phe Pro Asn Ile Thr Asn Leu Cys
                325                 330                 335

Pro Phe Gly Glu Val Phe Asn Ala Thr Thr Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Thr Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

```
Val Ile Thr Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Lys His Ile Asp Ala Lys Glu Gly Gly Asn
        435                 440                 445

Phe Asn Tyr Leu Tyr Arg Leu Phe Arg Lys Ala Asn Leu Lys Pro Phe
    450                 455                 460

Glu Arg Asp Ile Ser Thr Glu Ile Tyr Gln Ala Gly Ser Lys Pro Cys
465                 470                 475                 480

Asn Gly Gln Thr Gly Leu Asn Cys Tyr Tyr Pro Leu Tyr Arg Tyr Gly
                485                 490                 495

Phe Tyr Pro Thr Asp Gly Val Gly His Gln Pro Tyr Arg Val Val Val
            500                 505                 510

Leu Ser Phe Glu Leu Leu Asn Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Ala Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Arg Ser Val Ala Ser Gln Ser Ile
        675                 680                 685

Ile Ala Tyr Thr Met Ser Leu Gly Ala Glu Asn Ser Val Ala Tyr Ser
    690                 695                 700

Asn Asn Ser Ile Ala Ile Pro Thr Asn Phe Thr Ile Ser Val Thr Thr
705                 710                 715                 720

Glu Ile Leu Pro Val Ser Met Thr Lys Thr Ser Val Asp Cys Thr Met
                725                 730                 735

Tyr Ile Cys Gly Asp Ser Thr Glu Cys Ser Asn Leu Leu Leu Gln Tyr
            740                 745                 750

Gly Ser Phe Cys Thr Gln Leu Asn Arg Ala Leu Thr Gly Ile Ala Val
        755                 760                 765

Glu Gln Asp Lys Asn Thr Gln Glu Val Phe Ala Gln Val Lys Gln Ile
    770                 775                 780

Tyr Lys Thr Pro Pro Ile Lys Asp Phe Gly Gly Phe Asn Phe Ser Gln
785                 790                 795                 800

Ile Leu Pro Asp Pro Ser Lys Pro Ser Lys Arg Ser Phe Ile Glu Asp
                805                 810                 815
```

-continued

```
Leu Leu Phe Asn Lys Val Thr Leu Ala Asp Ala Gly Phe Ile Lys Gln
            820                 825                 830

Tyr Gly Asp Cys Leu Gly Asp Ile Ala Ala Arg Asp Leu Ile Cys Ala
        835                 840                 845

Gln Lys Phe Asn Gly Leu Thr Val Leu Pro Pro Leu Leu Thr Asp Glu
    850                 855                 860

Met Ile Ala Gln Tyr Thr Ser Ala Leu Leu Ala Gly Thr Ile Thr Ser
865                 870                 875                 880

Gly Trp Thr Phe Gly Ala Gly Ala Ala Leu Gln Ile Pro Phe Ala Met
                885                 890                 895

Gln Met Ala Tyr Arg Phe Asn Gly Ile Gly Val Thr Gln Asn Val Leu
            900                 905                 910

Tyr Glu Asn Gln Lys Leu Ile Ala Asn Gln Phe Asn Ser Ala Ile Gly
        915                 920                 925

Lys Ile Gln Asp Ser Leu Ser Ser Thr Ala Ser Ala Leu Gly Lys Leu
    930                 935                 940

Gln Asp Val Val Asn Gln Asn Ala Gln Ala Leu Asn Thr Leu Val Lys
945                 950                 955                 960

Gln Leu Ser Ser Asn Phe Gly Ala Ile Ser Ser Val Leu Asn Asp Ile
                965                 970                 975

Leu Ser Arg Leu Asp Lys Val Glu Ala Glu Val Gln Ile Asp Arg Leu
            980                 985                 990

Ile Thr Gly Arg Leu Gln Ser Leu  Gln Thr Tyr Val Thr  Gln Gln Leu
        995                 1000                1005

Ile Arg  Ala Ala Glu Ile Arg  Ala Ser Ala Asn Leu  Ala Ala Thr
    1010                1015                1020

Lys Met  Ser Glu Cys Val Leu  Gly Gln Ser Lys Arg  Val Asp Phe
    1025                1030                1035

Cys Gly  Lys Gly Tyr His Leu  Met Ser Phe Pro Gln  Ser Ala Pro
    1040                1045                1050

His Gly  Val Val Phe Leu His  Val Thr Tyr Val Pro  Ala Gln Glu
    1055                1060                1065

Lys Asn  Phe Thr Thr Ala Pro  Ala Ile Cys His Asp  Gly Lys Ala
    1070                1075                1080

His Phe  Pro Arg Glu Gly Val  Phe Val Ser Asn Gly  Thr His Trp
    1085                1090                1095

Phe Val  Thr Gln Arg Asn Phe  Tyr Glu Pro Gln Ile  Ile Thr Thr
    1100                1105                1110

Asp Asn  Thr Phe Val Ser Gly  Ser Cys Asp Val Val  Ile Gly Ile
    1115                1120                1125

Val Asn  Asn Thr Val Tyr Asp  Pro Leu Gln Pro Glu  Leu Asp Ser
    1130                1135                1140

Phe Lys  Glu Glu Leu Asp Lys  Tyr Phe Lys Asn His  Thr Ser Pro
    1145                1150                1155

Asp Val  Asp Leu Gly Asp Ile  Ser Gly Ile Asn Ala  Ser Val Val
    1160                1165                1170

Asn Ile  Gln Lys Glu Ile Asp  Arg Leu Asn Glu Val  Ala Lys Asn
    1175                1180                1185

Leu Asn  Glu Ser Leu Ile Asp  Leu Gln Glu Leu Gly  Lys Tyr Glu
    1190                1195                1200

Gln Tyr  Ile Lys Trp Pro Trp  Tyr Ile Trp Leu Gly  Phe Ile Ala
    1205                1210                1215

Gly Leu  Ile Ala Ile Ile Met  Val Thr Ile Met Leu  Cys Cys Met
```

```
    1220                1225                1230

Thr Ser  Cys Cys Ser Cys Leu  Lys Gly Cys Cys Ser  Cys Gly Ser
    1235                1240                1245

Cys Cys  Lys Phe Asp Glu Asp  Asp Ser Glu Pro Val  Leu Lys Gly
    1250                1255                1260

Val Lys  Leu His Tyr Thr
    1265


<210> SEQ ID NO 322
<211> LENGTH: 1255
<212> TYPE: PRT
<213> ORGANISM: Artificial Sequence
<220> FEATURE:
<223> OTHER INFORMATION: Synthetic construct

<400> SEQUENCE: 322

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
```

-continued

```
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735
```

Gln Tyr Gly Ser Phe Cys Thr Gln Leu Asn Arg Ala Leu Ser Gly Ile
740 745 750

Ala Ala Glu Gln Asp Arg Asn Thr Arg Glu Val Phe Ala Gln Val Lys
755 760 765

Gln Met Tyr Lys Thr Pro Thr Leu Lys Tyr Phe Gly Gly Phe Asn Phe
770 775 780

Ser Gln Ile Leu Pro Asp Pro Leu Lys Pro Thr Lys Arg Ser Phe Ile
785 790 795 800

Glu Asp Leu Leu Phe Asn Lys Val Thr Leu Ala Asp Ala Gly Phe Met
805 810 815

Lys Gln Tyr Gly Glu Cys Leu Gly Asp Ile Asn Ala Arg Asp Leu Ile
820 825 830

Cys Ala Gln Lys Phe Asn Gly Leu Thr Val Leu Pro Pro Leu Leu Thr
835 840 845

Asp Asp Met Ile Ala Ala Tyr Thr Ala Ala Leu Val Ser Gly Thr Ala
850 855 860

Thr Ala Gly Trp Thr Phe Gly Ala Gly Ala Ala Leu Gln Ile Pro Phe
865 870 875 880

Ala Met Gln Met Ala Tyr Arg Phe Asn Gly Ile Gly Val Thr Gln Asn
885 890 895

Val Leu Tyr Glu Asn Gln Lys Gln Ile Ala Asn Gln Phe Asn Lys Ala
900 905 910

Ile Ser Gln Ile Gln Glu Ser Leu Thr Thr Thr Ser Thr Ala Leu Gly
915 920 925

Lys Leu Gln Asp Val Val Asn Gln Asn Ala Gln Ala Leu Asn Thr Leu
930 935 940

Val Lys Gln Leu Ser Ser Asn Phe Gly Ala Ile Ser Ser Val Leu Asn
945 950 955 960

Asp Ile Leu Ser Arg Leu Asp Lys Val Glu Ala Glu Val Gln Ile Asp
965 970 975

Arg Leu Ile Thr Gly Arg Leu Gln Ser Leu Gln Thr Tyr Val Thr Gln
980 985 990

Gln Leu Ile Arg Ala Ala Glu Ile Arg Ala Ser Ala Asn Leu Ala Ala
995 1000 1005

Thr Lys Met Ser Glu Cys Val Leu Gly Gln Ser Lys Arg Val Asp
1010 1015 1020

Phe Cys Gly Lys Gly Tyr His Leu Met Ser Phe Pro Gln Ala Ala
1025 1030 1035

Pro His Gly Val Val Phe Leu His Val Thr Tyr Val Pro Ser Gln
1040 1045 1050

Glu Arg Asn Phe Thr Thr Ala Pro Ala Ile Cys His Glu Gly Lys
1055 1060 1065

Ala Tyr Phe Pro Arg Glu Gly Val Phe Val Phe Asn Gly Thr Ser
1070 1075 1080

Trp Phe Ile Thr Gln Arg Asn Phe Phe Ser Pro Gln Ile Ile Thr
1085 1090 1095

Thr Asp Asn Thr Phe Val Ser Gly Asn Cys Asp Val Val Ile Gly
1100 1105 1110

Ile Ile Asn Asn Thr Val Tyr Asp Pro Leu Gln Pro Glu Leu Asp
1115 1120 1125

Ser Phe Lys Glu Glu Leu Asp Lys Tyr Phe Lys Asn His Thr Ser
1130 1135 1140

-continued

```
Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

```
<210> SEQ ID NO 323
<211> LENGTH: 1255
<212> TYPE: PRT
<213> ORGANISM: Artificial Sequence
<220> FEATURE:
<223> OTHER INFORMATION: Synthetic construct

<400> SEQUENCE: 323

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Asp Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Val Val Ser Lys Pro Met
    130                 135                 140

Gly Thr Arg Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240
```

-continued

```
Ala Gln Asp Thr Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Arg Ile Ser Asn Cys Val Ala Asp Tyr
            340                 345                 350

Ser Val Leu Tyr Asn Ser Thr Ser Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Pro Asn Cys Tyr Trp Pro Leu Asn Gly
465                 470                 475                 480

Tyr Gly Phe Tyr Thr Thr Ser Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Leu Ile His Ala Glu Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Ser Leu Arg Ser Thr Ser Gln Lys
```

-continued

```
        660                 665                 670

Ser Ile Val Ala Tyr Thr Met Ser Leu Gly Ala Asp Ser Ser Ile Ala
    675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Arg Gln Leu Asn Arg Ala Leu Ser Gly Ile
            740                 745                 750

Ala Ala Glu Gln Asp Arg Asn Thr Arg Glu Val Phe Val Gln Val Lys
        755                 760                 765

Gln Met Tyr Lys Thr Pro Thr Leu Lys Asp Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080
```

-continued

```
Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Glu Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255


<210> SEQ ID NO 324
<211> LENGTH: 1242
<212> TYPE: PRT
<213> ORGANISM: Artificial Sequence
<220> FEATURE:
<223> OTHER INFORMATION: Synthetic construct

<400> SEQUENCE: 324

Met Lys Ile Leu Ile Phe Ala Phe Leu Ala Asn Leu Ala Lys Ala Gln
1               5                   10                  15

Glu Gly Cys Gly Ile Ile Ser Arg Lys Pro Gln Pro Lys Met Ala Gln
            20                  25                  30

Val Ser Ser Ser Arg Arg Gly Val Tyr Tyr Asn Asp Asp Ile Phe Arg
        35                  40                  45

Ser Asp Val Leu His Leu Thr Gln Asp Tyr Phe Leu Pro Phe Asp Ser
    50                  55                  60

Asn Leu Thr Gln Tyr Phe Ser Leu Asn Val Asp Ser Asp Arg Tyr Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Ser
            100                 105                 110

Phe Asp Asn Thr Thr Gln Ser Ala Val Ile Val Asn Asn Ser Thr His
        115                 120                 125

Ile Ile Ile Arg Val Cys Asn Phe Asn Leu Cys Lys Glu Pro Met Tyr
    130                 135                 140

Thr Val Ser Arg Gly Thr Gln Gln Asn Ala Trp Val Tyr Gln Ser Ala
145                 150                 155                 160

Phe Asn Cys Thr Tyr Asp Arg Val Glu Lys Ser Phe Gln Leu Asp Thr
                165                 170                 175
```

```
Thr Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Leu Pro Thr Gly Phe Ser Val Leu Lys Pro Ile Leu
    210                 215                 220

Lys Leu Pro Phe Gly Ile Asn Ile Thr Ser Tyr Arg Val Val Met Ala
225                 230                 235                 240

Met Phe Ser Gln Thr Thr Ser Asn Phe Leu Pro Glu Ser Ala Ala Tyr
                245                 250                 255

Tyr Val Gly Asn Leu Lys Tyr Ser Thr Phe Met Leu Arg Phe Asn Glu
            260                 265                 270

Asn Gly Thr Ile Thr Asp Ala Val Asp Cys Ser Gln Asn Pro Leu Ala
        275                 280                 285

Glu Leu Lys Cys Thr Ile Lys Asn Phe Asn Val Asp Lys Gly Ile Tyr
    290                 295                 300

Gln Thr Ser Asn Phe Arg Val Ser Pro Thr Gln Glu Val Ile Arg Phe
305                 310                 315                 320

Pro Asn Ile Thr Asn Arg Cys Pro Phe Asp Lys Val Phe Asn Ala Thr
                325                 330                 335

Arg Phe Pro Asn Val Tyr Ala Trp Glu Arg Thr Lys Ile Ser Asp Cys
            340                 345                 350

Val Ala Asp Tyr Thr Val Leu Tyr Asn Ser Thr Ser Phe Ser Thr Phe
        355                 360                 365

Lys Cys Tyr Gly Val Ser Pro Ser Lys Leu Ile Asp Leu Cys Phe Thr
    370                 375                 380

Ser Val Tyr Ala Asp Thr Phe Leu Ile Arg Ser Ser Glu Val Arg Gln
385                 390                 395                 400

Val Ala Pro Gly Glu Thr Gly Val Ile Ala Asp Tyr Asn Tyr Lys Leu
                405                 410                 415

Pro Asp Asp Phe Thr Gly Cys Val Ile Ala Trp Asn Thr Ala Lys His
            420                 425                 430

Asp Thr Gly Asn Tyr Tyr Tyr Arg Ser His Arg Lys Thr Lys Leu Lys
        435                 440                 445

Pro Phe Glu Arg Asp Leu Ser Ser Asp Asp Gly Asn Gly Val Tyr Thr
    450                 455                 460

Leu Ser Thr Tyr Asp Phe Asn Pro Asn Val Pro Val Ala Tyr Gln Ala
465                 470                 475                 480

Thr Arg Val Val Val Leu Ser Phe Glu Leu Leu Asn Ala Pro Ala Thr
                485                 490                 495

Val Cys Gly Pro Lys Leu Ser Thr Glu Leu Val Lys Asn Gln Cys Val
            500                 505                 510

Asn Phe Asn Phe Asn Gly Leu Lys Gly Thr Gly Val Leu Thr Ser Ser
        515                 520                 525

Ser Lys Arg Phe Gln Ser Phe Gln Gln Phe Gly Arg Asp Thr Ser Asp
    530                 535                 540

Phe Thr Asp Ser Val Arg Asp Pro Gln Thr Leu Glu Ile Leu Asp Ile
545                 550                 555                 560

Ser Pro Cys Ser Phe Gly Gly Val Ser Val Ile Thr Pro Gly Thr Asn
                565                 570                 575

Ala Ser Ser Glu Val Ala Val Leu Tyr Gln Asp Val Asn Cys Thr Asp
            580                 585                 590
```

-continued

```
Val Pro Thr Ala Ile Arg Ala Asp Gln Leu Thr Pro Ala Trp Arg Val
        595                 600                 605

Tyr Ser Thr Gly Val Asn Val Phe Gln Thr Gln Ala Gly Cys Leu Ile
    610                 615                 620

Gly Ala Glu His Val Asn Ala Ser Tyr Glu Cys Asp Ile Pro Ile Gly
625                 630                 635                 640

Ala Gly Ile Cys Ala Ser Tyr His Thr Ala Ser Val Leu Arg Ser Thr
                645                 650                 655

Gly Gln Lys Ser Ile Val Ala Tyr Thr Met Ser Leu Gly Ala Glu Asn
            660                 665                 670

Ser Ile Ala Tyr Ala Asn Asn Ser Ile Ala Ile Pro Thr Asn Phe Ser
        675                 680                 685

Ile Ser Val Thr Thr Glu Val Met Pro Val Ser Met Ala Lys Thr Ala
    690                 695                 700

Val Asp Cys Thr Met Tyr Ile Cys Gly Asp Ser Leu Glu Cys Ser Asn
705                 710                 715                 720

Leu Leu Leu Gln Tyr Gly Ser Phe Cys Thr Gln Leu Asn Arg Ala Leu
                725                 730                 735

Thr Gly Ile Ala Ile Glu Gln Asp Lys Asn Thr Gln Glu Val Phe Ala
            740                 745                 750

Gln Val Lys Gln Met Tyr Lys Thr Pro Ala Ile Lys Asp Phe Gly Gly
        755                 760                 765

Phe Asn Phe Ser Gln Ile Leu Pro Asp Pro Ser Lys Pro Thr Lys Arg
    770                 775                 780

Ser Phe Ile Glu Asp Leu Leu Phe Asn Lys Val Thr Leu Ala Asp Ala
785                 790                 795                 800

Gly Phe Met Lys Gln Tyr Gly Asp Cys Leu Gly Asp Val Ser Ala Arg
                805                 810                 815

Asp Leu Ile Cys Ala Gln Lys Phe Asn Gly Leu Thr Val Leu Pro Pro
            820                 825                 830

Leu Leu Thr Asp Glu Met Val Ala Ala Tyr Thr Ala Ala Leu Val Ser
        835                 840                 845

Gly Thr Ala Thr Ala Gly Trp Thr Phe Gly Ala Gly Ala Ala Leu Gln
    850                 855                 860

Ile Pro Phe Ala Met Gln Met Ala Tyr Arg Phe Asn Gly Ile Gly Val
865                 870                 875                 880

Thr Gln Asn Val Leu Tyr Glu Asn Gln Lys Leu Ile Ala Asn Gln Phe
                885                 890                 895

Asn Ser Ala Ile Gly Lys Ile Gln Glu Ser Leu Ser Ser Thr Ala Ser
            900                 905                 910

Ala Leu Gly Lys Leu Gln Asp Val Val Asn Gln Asn Ala Gln Ala Leu
        915                 920                 925

Asn Thr Leu Val Lys Gln Leu Ser Ser Asn Phe Gly Ala Ile Ser Ser
    930                 935                 940

Val Leu Asn Asp Ile Leu Ser Arg Leu Asp Lys Val Glu Ala Glu Val
945                 950                 955                 960

Gln Ile Asp Arg Leu Ile Thr Gly Arg Leu Gln Ser Leu Gln Thr Tyr
                965                 970                 975

Val Thr Gln Gln Leu Ile Arg Ala Ala Glu Ile Arg Ala Ser Ala Asn
            980                 985                 990

Leu Ala Ala Thr Lys Met Ser Glu  Cys Val Leu Gly Gln  Ser Lys Arg
        995                 1000                1005

Val Asp  Phe Cys Gly Lys Gly  Tyr His Leu Met Ser  Phe Pro Gln
```

```
    1010                1015                1020

Ser Ala  Pro His Gly Val Val  Phe Leu His Val Thr  Tyr Val Pro
    1025                1030                1035

Ser Gln  Glu Lys Asn Phe Thr  Thr Ala Pro Ala Ile  Cys His Glu
    1040                1045                1050

Gly Lys  Ala Tyr Phe Pro Arg  Glu Gly Val Phe Val  Ser Asn Gly
    1055                1060                1065

Thr Ser  Trp Phe Ile Thr Gln  Arg Asn Phe Tyr Ser  Pro Gln Leu
    1070                1075                1080

Ile Thr  Thr Asp Asn Thr Phe  Val Ser Gly Asn Cys  Asp Val Val
    1085                1090                1095

Ile Gly  Ile Ile Asn Asn Thr  Val Tyr Asp Pro Leu  Gln Pro Glu
    1100                1105                1110

Leu Asp  Ser Phe Lys Glu Glu  Leu Asp Lys Tyr Phe  Lys Asn His
    1115                1120                1125

Thr Ser  Pro Asp Val Asp Leu  Gly Asp Ile Ser Gly  Ile Asn Ala
    1130                1135                1140

Ser Val  Val Asn Ile Gln Lys  Glu Ile Asp Arg Leu  Asn Glu Val
    1145                1150                1155

Ala Lys  Asn Leu Asn Glu Ser  Leu Ile Asp Leu Gln  Glu Leu Gly
    1160                1165                1170

Lys Tyr  Glu Gln Tyr Ile Lys  Trp Pro Trp Tyr Val  Trp Leu Gly
    1175                1180                1185

Phe Ile  Ala Gly Leu Ile Ala  Ile Val Met Val Thr  Ile Leu Leu
    1190                1195                1200

Cys Cys  Met Thr Ser Cys Cys  Ser Cys Leu Lys Gly  Ala Cys Ser
    1205                1210                1215

Cys Gly  Ser Cys Cys Lys Phe  Asp Glu Asp Asp Ser  Glu Pro Val
    1220                1225                1230

Leu Lys  Gly Val Lys Leu His  Tyr Thr
    1235                1240


<210> SEQ ID NO 325
<211> LENGTH: 1241
<212> TYPE: PRT
<213> ORGANISM: Artificial Sequence
<220> FEATURE:
<223> OTHER INFORMATION: Synthetic construct

<400> SEQUENCE: 325

Met Lys Ile Leu Ile Leu Ala Phe Leu Ala Ser Leu Ala Lys Ala Gln
1               5                   10                  15

Glu Gly Cys Gly Ile Ile Ser Arg Lys Pro Gln Pro Lys Met Ala Gln
            20                  25                  30

Val Ser Ser Ser Arg Arg Gly Val Tyr Tyr Asn Asp Asp Ile Phe Arg
        35                  40                  45

Ser Asn Val Leu His Leu Thr Gln Asp Tyr Phe Leu Pro Phe Asp Ser
    50                  55                  60

Asn Leu Thr Gln Tyr Phe Ser Leu Asn Val Asp Ser Asp Arg Phe Thr
65                  70                  75                  80

Tyr Phe Asp Asn Pro Ile Leu Asp Phe Gly Asp Gly Val Tyr Phe Ala
                85                  90                  95

Ala Thr Glu Lys Ser Asn Val Ile Arg Gly Trp Ile Phe Gly Ser Thr
            100                 105                 110

Phe Asp Asn Thr Thr Gln Ser Ala Val Ile Val Asn Asn Ser Thr His
```

-continued

```
        115                 120                 125

Ile Ile Ile Arg Val Cys Asn Phe Asn Leu Cys Lys Glu Pro Met Tyr
    130                 135                 140

Thr Val Ser Arg Gly Ala Gln Gln Ser Ser Trp Val Tyr Gln Ser Ala
145                 150                 155                 160

Phe Asn Cys Thr Tyr Asp Arg Val Glu Lys Ser Phe Gln Leu Asp Thr
                165                 170                 175

Ala Pro Lys Thr Gly Asn Phe Lys Asp Leu Arg Glu Tyr Val Phe Lys
            180                 185                 190

Asn Arg Asp Gly Phe Leu Ser Val Tyr Gln Thr Tyr Thr Ala Val Asn
        195                 200                 205

Leu Pro Arg Gly Leu Pro Ile Gly Phe Ser Val Leu Arg Pro Ile Leu
    210                 215                 220

Lys Leu Pro Phe Gly Ile Asn Ile Thr Ser Tyr Arg Val Val Met Ala
225                 230                 235                 240

Met Phe Ser Gln Thr Thr Ser Asn Phe Leu Pro Glu Ser Ala Ala Tyr
                245                 250                 255

Tyr Val Gly Asn Leu Lys Tyr Thr Thr Phe Met Leu Ser Phe Asn Glu
            260                 265                 270

Asn Gly Thr Ile Thr Asn Ala Ile Asp Cys Ala Gln Asn Pro Leu Ala
        275                 280                 285

Glu Leu Lys Cys Thr Ile Lys Asn Phe Asn Val Ser Lys Gly Ile Tyr
    290                 295                 300

Gln Thr Ser Asn Phe Arg Val Ser Pro Thr Gln Glu Val Ile Arg Phe
305                 310                 315                 320

Pro Asn Ile Thr Asn Arg Cys Pro Phe Asp Lys Val Phe Asn Ala Thr
                325                 330                 335

Arg Phe Pro Asn Val Tyr Ala Trp Glu Arg Thr Lys Ile Ser Asp Cys
            340                 345                 350

Val Ala Asp Tyr Thr Val Leu Tyr Asn Ser Thr Ser Phe Ser Thr Phe
        355                 360                 365

Lys Cys Tyr Gly Val Ser Pro Ser Lys Leu Ile Asp Leu Cys Phe Thr
    370                 375                 380

Ser Val Tyr Ala Asp Thr Phe Leu Ile Arg Ser Ser Glu Val Arg Gln
385                 390                 395                 400

Val Ala Pro Gly Glu Thr Gly Val Ile Ala Asp Tyr Asn Tyr Lys Leu
                405                 410                 415

Pro Asp Asp Phe Thr Gly Cys Val Ile Ala Trp Asn Thr Ala Lys Gln
            420                 425                 430

Asp Gln Gly Gln Tyr Tyr Tyr Arg Ser His Arg Lys Thr Lys Leu Lys
        435                 440                 445

Pro Phe Glu Arg Asp Leu Ser Ser Asp Glu Asn Gly Val Arg Thr Leu
    450                 455                 460

Ser Thr Tyr Asp Phe Tyr Pro Ser Val Pro Val Ala Tyr Gln Ala Thr
465                 470                 475                 480

Arg Val Val Val Leu Ser Phe Glu Leu Leu Asn Ala Pro Ala Thr Val
                485                 490                 495

Cys Gly Pro Lys Leu Ser Thr Gln Leu Val Lys Asn Gln Cys Val Asn
            500                 505                 510

Phe Asn Phe Asn Gly Leu Lys Gly Thr Gly Val Leu Thr Glu Ser Ser
        515                 520                 525

Lys Arg Phe Gln Ser Phe Gln Gln Phe Gly Arg Asp Thr Ser Asp Phe
    530                 535                 540
```

```
Thr Asp Ser Val Arg Asp Pro Gln Thr Leu Glu Ile Leu Asp Ile Ser
545                 550                 555                 560

Pro Cys Ser Phe Gly Gly Val Ser Val Ile Thr Pro Gly Thr Asn Ala
                565                 570                 575

Ser Ser Glu Val Ala Val Leu Tyr Gln Asp Val Asn Cys Thr Asp Val
            580                 585                 590

Pro Ala Ala Ile His Ala Asp Gln Leu Thr Pro Ala Trp Arg Val Tyr
        595                 600                 605

Ser Thr Gly Thr Asn Val Phe Gln Thr Gln Ala Gly Cys Leu Ile Gly
    610                 615                 620

Ala Glu His Val Asn Ala Ser Tyr Glu Cys Asp Ile Pro Ile Gly Ala
625                 630                 635                 640

Gly Ile Cys Ala Ser Tyr His Thr Ala Ser Thr Leu Arg Ser Val Gly
                645                 650                 655

Gln Lys Ser Ile Val Ala Tyr Thr Met Ser Leu Gly Ala Glu Asn Ser
            660                 665                 670

Ile Ala Tyr Ala Asn Asn Ser Ile Ala Ile Pro Thr Asn Phe Ser Ile
        675                 680                 685

Ser Val Thr Thr Glu Val Met Pro Val Ser Met Ala Lys Thr Ser Val
    690                 695                 700

Asp Cys Thr Met Tyr Ile Cys Gly Asp Ser Leu Glu Cys Ser Asn Leu
705                 710                 715                 720

Leu Leu Gln Tyr Gly Ser Phe Cys Thr Gln Leu Asn Arg Ala Leu Ser
                725                 730                 735

Gly Ile Ala Ile Glu Gln Asp Lys Asn Thr Gln Glu Val Phe Ala Gln
            740                 745                 750

Val Lys Gln Met Tyr Lys Thr Pro Ala Ile Lys Asp Phe Gly Gly Phe
        755                 760                 765

Asn Phe Ser Gln Ile Leu Pro Asp Pro Ser Lys Pro Thr Lys Arg Ser
    770                 775                 780

Phe Ile Glu Asp Leu Leu Phe Asn Lys Val Thr Leu Ala Asp Ala Gly
785                 790                 795                 800

Phe Met Lys Gln Tyr Gly Glu Cys Leu Gly Asp Ile Ser Ala Arg Asp
                805                 810                 815

Leu Ile Cys Ala Gln Lys Phe Asn Gly Leu Thr Val Leu Pro Pro Leu
            820                 825                 830

Leu Thr Asp Glu Met Ile Ala Ala Tyr Thr Ala Ala Leu Val Ser Gly
        835                 840                 845

Thr Ala Thr Ala Gly Trp Thr Phe Gly Ala Gly Ser Ala Leu Gln Ile
    850                 855                 860

Pro Phe Ala Met Gln Met Ala Tyr Arg Phe Asn Gly Ile Gly Val Thr
865                 870                 875                 880

Gln Asn Val Leu Tyr Glu Asn Gln Lys Gln Ile Ala Asn Gln Phe Asn
                885                 890                 895

Lys Ala Ile Ser Gln Ile Gln Glu Ser Leu Thr Thr Thr Ser Thr Ala
            900                 905                 910

Leu Gly Lys Leu Gln Asp Val Val Asn Gln Asn Ala Gln Ala Leu Asn
        915                 920                 925

Thr Leu Val Lys Gln Leu Ser Ser Asn Phe Gly Ala Ile Ser Ser Val
    930                 935                 940

Leu Asn Asp Ile Leu Ser Arg Leu Asp Lys Val Glu Ala Glu Val Gln
945                 950                 955                 960
```

```
Ile Asp Arg Leu Ile Thr Gly Arg Leu Gln Ser Leu Gln Thr Tyr Val
                965                 970                 975

Thr Gln Gln Leu Ile Arg Ala Ala Glu Ile Arg Ala Ser Ala Asn Leu
            980                 985                 990

Ala Ala Thr Lys Met Ser Glu Cys  Val Leu Gly Gln Ser  Lys Arg Val
        995                 1000                 1005

Asp Phe  Cys Gly Lys Gly Tyr  His Leu Met Ser Phe  Pro Gln Ala
    1010                 1015                 1020

Ala Pro  His Gly Val Val Phe  Leu His Val Thr Tyr  Val Pro Ser
    1025                 1030                 1035

Gln Glu  Arg Asn Phe Thr Thr  Ala Pro Ala Ile Cys  His Glu Gly
    1040                 1045                 1050

Lys Ala  Tyr Phe Pro Arg Glu  Gly Val Phe Val Ser  Asn Gly Thr
    1055                 1060                 1065

Ser Trp  Phe Ile Thr Gln Arg  Asn Phe Tyr Ser Pro  Gln Ile Ile
    1070                 1075                 1080

Thr Thr  Asp Asn Thr Phe Val  Ala Gly Ser Cys Asp  Val Val Ile
    1085                 1090                 1095

Gly Ile  Ile Asn Asn Thr Val  Tyr Asp Pro Leu Gln  Pro Glu Leu
    1100                 1105                 1110

Asp Ser  Phe Lys Glu Glu Leu  Asp Lys Tyr Phe Lys  Asn His Thr
    1115                 1120                 1125

Ser Pro  Asp Val Asp Leu Gly  Asp Ile Ser Gly Ile  Asn Ala Ser
    1130                 1135                 1140

Val Val  Asn Ile Gln Lys Glu  Ile Asp Arg Leu Asn  Glu Val Ala
    1145                 1150                 1155

Lys Asn  Leu Asn Glu Ser Leu  Ile Asp Leu Gln Glu  Leu Gly Lys
    1160                 1165                 1170

Tyr Glu  Gln Tyr Ile Lys Trp  Pro Trp Tyr Val Trp  Leu Gly Phe
    1175                 1180                 1185

Ile Ala  Gly Leu Ile Ala Ile  Val Met Val Thr Ile  Leu Leu Cys
    1190                 1195                 1200

Cys Met  Thr Ser Cys Cys Ser  Cys Leu Lys Gly Ala  Cys Ser Cys
    1205                 1210                 1215

Gly Ser  Cys Cys Lys Phe Asp  Glu Asp Asp Ser Glu  Pro Val Leu
    1220                 1225                 1230

Lys Gly  Val Lys Leu His Tyr  Thr
    1235                 1240


<210> SEQ ID NO 326
<211> LENGTH: 1241
<212> TYPE: PRT
<213> ORGANISM: Artificial Sequence
<220> FEATURE:
<223> OTHER INFORMATION: Synthetic construct

<400> SEQUENCE: 326

Met Lys Val Leu Ile Phe Ala Leu Leu Phe Ser Leu Ala Lys Ala Gln
1               5                   10                  15

Glu Gly Cys Gly Ile Ile Ser Arg Lys Pro Gln Pro Lys Met Glu Lys
            20                  25                  30

Val Ser Ser Ser Arg Arg Gly Val Tyr Tyr Asn Asp Asp Ile Phe Arg
        35                  40                  45

Ser Asp Val Leu His Leu Thr Gln Asp Tyr Phe Leu Pro Phe Asp Ser
    50                  55                  60
```

-continued

Asn Leu Thr Gln Tyr Phe Ser Leu Asn Ile Asp Ser Asn Lys Tyr Thr
65 70 75 80

Tyr Phe Asp Asn Pro Ile Leu Asp Phe Gly Asp Gly Val Tyr Phe Ala
85 90 95

Ala Thr Glu Lys Ser Asn Val Ile Arg Gly Trp Ile Phe Gly Ser Ser
100 105 110

Phe Asp Asn Thr Thr Gln Ser Ala Ile Ile Val Asn Asn Ser Thr His
115 120 125

Ile Ile Ile Arg Val Cys Asn Phe Asn Leu Cys Lys Glu Pro Met Tyr
130 135 140

Thr Val Ser Lys Gly Thr Gln Gln Ser Ser Trp Val Tyr Gln Ser Ala
145 150 155 160

Phe Asn Cys Thr Tyr Asp Arg Val Glu Lys Ser Phe Gln Leu Asp Thr
165 170 175

Ala Pro Lys Thr Gly Asn Phe Lys Asp Leu Arg Glu Tyr Val Phe Lys
180 185 190

Asn Arg Asp Gly Phe Leu Ser Val Tyr Gln Thr Tyr Thr Ala Val Asn
195 200 205

Leu Pro Arg Gly Phe Pro Ala Gly Phe Ser Val Leu Arg Pro Ile Leu
210 215 220

Lys Leu Pro Phe Gly Ile Asn Ile Thr Ser Tyr Arg Val Val Met Thr
225 230 235 240

Met Phe Ser Gln Phe Asn Ser Asn Phe Leu Pro Glu Ser Ala Ala Tyr
245 250 255

Tyr Val Gly Asn Leu Lys Tyr Thr Thr Phe Met Leu Ser Phe Asn Glu
260 265 270

Asn Gly Thr Ile Thr Asp Ala Val Asp Cys Ser Gln Asn Pro Leu Ala
275 280 285

Glu Leu Lys Cys Thr Ile Lys Asn Phe Asn Val Ser Lys Gly Ile Tyr
290 295 300

Gln Thr Ser Asn Phe Arg Val Thr Pro Thr Gln Glu Val Val Arg Phe
305 310 315 320

Pro Asn Ile Thr Asn Arg Cys Pro Phe Asp Lys Val Phe Asn Ala Ser
325 330 335

Arg Phe Pro Asn Val Tyr Ala Trp Glu Arg Thr Lys Ile Ser Asp Cys
340 345 350

Val Ala Asp Tyr Thr Val Leu Tyr Asn Ser Thr Ser Phe Ser Thr Phe
355 360 365

Lys Cys Tyr Gly Val Ser Pro Ser Lys Leu Ile Asp Leu Cys Phe Thr
370 375 380

Ser Val Tyr Ala Asp Thr Phe Leu Ile Arg Ser Ser Glu Val Arg Gln
385 390 395 400

Val Ala Pro Gly Glu Thr Gly Val Ile Ala Asp Tyr Asn Tyr Lys Leu
405 410 415

Pro Asp Asp Phe Thr Gly Cys Val Ile Ala Trp Asn Thr Ala Gln Gln
420 425 430

Asp Gln Gly Gln Tyr Tyr Tyr Arg Ser Tyr Arg Lys Glu Lys Leu Lys
435 440 445

Pro Phe Glu Arg Asp Leu Ser Ser Asp Glu Asn Gly Val Tyr Thr Leu
450 455 460

Ser Thr Tyr Asp Phe Tyr Pro Ser Ile Pro Val Glu Tyr Gln Ala Thr
465 470 475 480

Arg Val Val Val Leu Ser Phe Glu Leu Leu Asn Ala Pro Ala Thr Val

-continued

```
                485                 490                 495

Cys Gly Pro Lys Leu Ser Thr Gln Leu Val Lys Asn Gln Cys Val Asn
            500                 505                 510

Phe Asn Phe Asn Gly Leu Arg Gly Thr Gly Val Leu Thr Thr Ser Ser
        515                 520                 525

Lys Arg Phe Gln Ser Phe Gln Gln Phe Gly Arg Asp Thr Ser Asp Phe
    530                 535                 540

Thr Asp Ser Val Arg Asp Pro Gln Thr Leu Glu Ile Leu Asp Ile Ser
545                 550                 555                 560

Pro Cys Ser Phe Gly Gly Val Ser Val Ile Thr Pro Gly Thr Asn Ala
                565                 570                 575

Ser Ser Glu Val Ala Val Leu Tyr Gln Asp Val Asn Cys Thr Asp Val
            580                 585                 590

Pro Thr Ser Ile His Ala Asp Gln Leu Thr Pro Ala Trp Arg Val Tyr
        595                 600                 605

Ser Thr Gly Val Asn Val Phe Gln Thr Gln Ala Gly Cys Leu Ile Gly
    610                 615                 620

Ala Glu His Val Asn Ala Ser Tyr Glu Cys Asp Ile Pro Ile Gly Ala
625                 630                 635                 640

Gly Ile Cys Ala Ser Tyr His Thr Ala Ser Val Leu Arg Ser Thr Gly
                645                 650                 655

Gln Lys Ser Ile Val Ala Tyr Thr Met Ser Leu Gly Ala Glu Asn Ser
            660                 665                 670

Ile Ala Tyr Ala Asn Asn Ser Ile Ala Ile Pro Thr Asn Phe Ser Ile
        675                 680                 685

Ser Val Thr Thr Glu Val Met Pro Val Ser Ile Ala Lys Thr Ser Val
    690                 695                 700

Asp Cys Thr Met Tyr Ile Cys Gly Asp Ser Leu Glu Cys Ser Asn Leu
705                 710                 715                 720

Leu Leu Gln Tyr Gly Ser Phe Cys Thr Gln Leu Asn Arg Ala Leu Thr
                725                 730                 735

Gly Ile Ala Ile Glu Gln Asp Lys Asn Thr Gln Glu Val Phe Ala Gln
            740                 745                 750

Val Lys Gln Met Tyr Lys Thr Pro Ala Ile Lys Asp Phe Gly Gly Phe
        755                 760                 765

Asn Phe Ser Gln Ile Leu Pro Asp Pro Ser Lys Pro Thr Lys Arg Ser
    770                 775                 780

Phe Ile Glu Asp Leu Leu Phe Asn Lys Val Thr Leu Ala Asp Ala Gly
785                 790                 795                 800

Phe Met Lys Gln Tyr Gly Glu Cys Leu Gly Asp Ile Ser Ala Arg Asp
                805                 810                 815

Leu Ile Cys Ala Gln Lys Phe Asn Gly Leu Thr Val Leu Pro Pro Leu
            820                 825                 830

Leu Thr Asp Glu Met Ile Ala Ala Tyr Thr Ala Ala Leu Val Ser Gly
        835                 840                 845

Thr Ala Thr Ala Gly Trp Thr Phe Gly Ala Gly Ser Ala Leu Gln Ile
    850                 855                 860

Pro Phe Ala Met Gln Met Ala Tyr Arg Phe Asn Gly Ile Gly Val Thr
865                 870                 875                 880

Gln Asn Val Leu Tyr Glu Asn Gln Lys Gln Ile Ala Asn Gln Phe Asn
                885                 890                 895

Lys Ala Ile Ser Gln Ile Gln Glu Ser Leu Thr Thr Thr Ser Thr Ala
            900                 905                 910
```

```
Leu Gly Lys Leu Gln Asp Val Val Asn Asp Asn Ala Gln Ala Leu Asn
        915                 920                 925

Thr Leu Val Lys Gln Leu Ser Ser Asn Phe Gly Ala Ile Ser Ser Val
    930                 935                 940

Leu Asn Asp Ile Leu Ser Arg Leu Asp Lys Val Glu Ala Glu Val Gln
945                 950                 955                 960

Ile Asp Arg Leu Ile Thr Gly Arg Leu Gln Ser Leu Gln Thr Tyr Val
                965                 970                 975

Thr Gln Gln Leu Ile Arg Ala Ala Glu Ile Arg Ala Ser Ala Asn Leu
            980                 985                 990

Ala Ala Thr Lys Met Ser Glu Cys  Val Leu Gly Gln Ser  Lys Arg Val
        995                 1000                1005

Asp Phe  Cys Gly Lys Gly Tyr  His Leu Met Ser Phe  Pro Gln Ala
    1010                1015                1020

Ala Pro  His Gly Val Val Phe  Leu His Val Thr Tyr  Val Pro Ser
    1025                1030                1035

Gln Glu  Arg Asn Phe Thr Thr  Ala Pro Ala Ile Cys  His Glu Gly
    1040                1045                1050

Lys Ala  Tyr Phe Pro Arg Glu  Gly Val Phe Val Ser  Asn Gly Thr
    1055                1060                1065

Ser Trp  Phe Ile Thr Gln Arg  Asn Phe Tyr Ser Pro  Gln Ile Ile
    1070                1075                1080

Thr Thr  Asp Asn Thr Phe Val  Ala Gly Asn Cys Asp  Val Val Ile
    1085                1090                1095

Gly Ile  Ile Asn Asn Thr Val  Tyr Asp Pro Leu Gln  Pro Glu Leu
    1100                1105                1110

Asp Ser  Phe Lys Glu Glu Leu  Asp Lys Tyr Phe Lys  Asn His Thr
    1115                1120                1125

Ser Pro  Asp Val Asp Leu Gly  Asp Ile Ser Gly Ile  Asn Ala Ser
    1130                1135                1140

Val Val  Asn Ile Gln Lys Glu  Ile Asp Arg Leu Asn  Glu Val Ala
    1145                1150                1155

Lys Asn  Leu Asn Glu Ser Leu  Ile Asp Leu Gln Glu  Leu Gly Lys
    1160                1165                1170

Tyr Glu  Gln Tyr Ile Lys Trp  Pro Trp Tyr Val Trp  Leu Gly Phe
    1175                1180                1185

Ile Ala  Gly Leu Ile Ala Ile  Val Met Val Thr Ile  Leu Leu Cys
    1190                1195                1200

Cys Met  Thr Ser Cys Cys Ser  Cys Leu Lys Gly Ala  Cys Ser Cys
    1205                1210                1215

Gly Ser  Cys Cys Lys Phe Asp  Glu Asp Asp Ser Glu  Pro Val Leu
    1220                1225                1230

Lys Gly  Val Lys Leu His Tyr  Thr
    1235                1240
```

<210> SEQ ID NO 327
<211> LENGTH: 1264
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: Xaa can be any naturally occurring amino acid
<220> FEATURE:

<221> NAME/KEY: misc_feature
<222> LOCATION: (7)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(105)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (128)..(129)
<223> OTHER INFORMATION: Xaa can be any naturally occurring amino acid
<220> FEATURE:
<221> NAME/KEY: misc_feature
<222> LOCATION: (131)..(133)
<223> OTHER INFORMATION: Xaa can be any naturally occurring amino acid
<220> FEATURE:
<221> NAME/KEY: misc_feature
<222> LOCATION: (135)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (159)..(165)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (170)..(172)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (191)..(194)
<223> OTHER INFORMATION: Xaa can be any naturally occurring amino acid
<220> FEATURE:
<221> NAME/KEY: misc_feature
<222> LOCATION: (196)..(204)
<223> OTHER INFORMATION: Xaa can be any naturally occurring amino acid
<220> FEATURE:
<221> NAME/KEY: misc_feature
<222> LOCATION: (206)..(207)
<223> OTHER INFORMATION: Xaa can be any naturally occurring amino acid
<220> FEATURE:
<221> NAME/KEY: misc_feature
<222> LOCATION: (209)..(209)

<223> OTHER INFORMATION: Xaa can be any naturally occurring amino acid
<220> FEATURE:
<221> NAME/KEY: misc_feature
<222> LOCATION: (212)..(213)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (217)..(219)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (228)..(253)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (262)..(264)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (283)..(285)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (293)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (298)..(300)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid
<220> FEATURE:
<221> NAME/KEY: misc_feature
<222> LOCATION: (314)..(318)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (330)..(331)
<223> OTHER INFORMATION: Xaa can be any naturally occurring amino acid
<220> FEATURE:
<221> NAME/KEY: misc_feature
<222> LOCATION: (336)..(337)
<223> OTHER INFORMATION: Xaa can be any naturally occurring amino acid
<220> FEATURE:
<221> NAME/KEY: misc_feature
<222> LOCATION: (339)..(340)
<223> OTHER INFORMATION: Xaa can be any naturally occurring amino acid
<220> FEATURE:
<221> NAME/KEY: misc_feature
<222> LOCATION: (345)..(345)
<223> OTHER INFORMATION: Xaa can be any naturally occurring amino acid
<220> FEATURE:
<221> NAME/KEY: misc_feature
<222> LOCATION: (347)..(348)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (357)..(357)
<223> OTHER INFORMATION: Xaa can be any naturally occurring amino acid
<220> FEATURE:
<221> NAME/KEY: misc_feature
<222> LOCATION: (363)..(364)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (384)..(385)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (392)..(397)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (408)..(408)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:

<221> NAME/KEY: misc_feature
<222> LOCATION: (429)..(432)
<223> OTHER INFORMATION: Xaa can be any naturally occurring amino acid
<220> FEATURE:
<221> NAME/KEY: misc_feature
<222> LOCATION: (434)..(437)
<223> OTHER INFORMATION: Xaa can be any naturally occurring amino acid
<220> FEATURE:
<221> NAME/KEY: misc_feature
<222> LOCATION: (439)..(441)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (446)..(447)
<223> OTHER INFORMATION: Xaa can be any naturally occurring amino acid
<220> FEATURE:
<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (461)..(477)
<223> OTHER INFORMATION: Xaa can be any naturally occurring amino acid
<220> FEATURE:
<221> NAME/KEY: misc_feature
<222> LOCATION: (479)..(482)
<223> OTHER INFORMATION: Xaa can be any naturally occurring amino acid
<220> FEATURE:
<221> NAME/KEY: misc_feature
<222> LOCATION: (484)..(485)
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (489)..(496)
<223> OTHER INFORMATION: Xaa can be any naturally occurring amino acid
<220> FEATURE:
<221> NAME/KEY: misc_feature
<222> LOCATION: (498)..(499)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (523)..(523)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (538)..(538)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (549)..(549)
<223> OTHER INFORMATION: Xaa can be any naturally occurring amino acid
<220> FEATURE:
<221> NAME/KEY: misc_feature
<222> LOCATION: (551)..(552)
<223> OTHER INFORMATION: Xaa can be any naturally occurring amino acid
<220> FEATURE:
<221> NAME/KEY: misc_feature
<222> LOCATION: (560)..(561)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (566)..(566)
<223> OTHER INFORMATION: Xaa can be any naturally occurring amino acid
<220> FEATURE:
<221> NAME/KEY: misc_feature
<222> LOCATION: (571)..(571)
<223> OTHER INFORMATION: Xaa can be any naturally occurring amino acid
<220> FEATURE:
<221> NAME/KEY: misc_feature
<222> LOCATION: (573)..(573)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (595)..(595)
<223> OTHER INFORMATION: Xaa can be any naturally occurring amino acid
<220> FEATURE:
<221> NAME/KEY: misc_feature
<222> LOCATION: (597)..(598)
<223> OTHER INFORMATION: Xaa can be any naturally occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (612)..(614)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (618)..(618)
<223> OTHER INFORMATION: Xaa can be any naturally occurring amino acid
<220> FEATURE:
<221> NAME/KEY: misc_feature
<222> LOCATION: (623)..(623)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (637)..(637)

<223> OTHER INFORMATION: Xaa can be any naturally occurring amino acid
<220> FEATURE:
<221> NAME/KEY: misc_feature
<222> LOCATION: (648)..(649)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(675)
<223> OTHER INFORMATION: Xaa can be any naturally occurring amino acid
<220> FEATURE:
<221> NAME/KEY: misc_feature
<222> LOCATION: (678)..(681)
<223> OTHER INFORMATION: Xaa can be any naturally occurring amino acid
<220> FEATURE:
<221> NAME/KEY: misc_feature
<222> LOCATION: (684)..(684)
<223> OTHER INFORMATION: Xaa can be any naturally occurring amino acid
<220> FEATURE:
<221> NAME/KEY: misc_feature
<222> LOCATION: (693)..(694)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
<221> NAME/KEY: misc_feature
<222> LOCATION: (699)..(699)
<223> OTHER INFORMATION: Xaa can be any naturally occurring amino acid
<220> FEATURE:
<221> NAME/KEY: misc_feature
<222> LOCATION: (702)..(702)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (713)..(713)
<223> OTHER INFORMATION: Xaa can be any naturally occurring amino acid
<220> FEATURE:
<221> NAME/KEY: misc_feature
<222> LOCATION: (717)..(718)
<223> OTHER INFORMATION: Xaa can be any naturally occurring amino acid
<220> FEATURE:
<221> NAME/KEY: misc_feature
<222> LOCATION: (722)..(723)
<223> OTHER INFORMATION: Xaa can be any naturally occurring amino acid
<220> FEATURE:
<221> NAME/KEY: misc_feature
<222> LOCATION: (726)..(726)
<223> OTHER INFORMATION: Xaa can be any naturally occurring amino acid
<220> FEATURE:
<221> NAME/KEY: misc_feature
<222> LOCATION: (730)..(730)
<223> OTHER INFORMATION: Xaa can be any naturally occurring amino acid
<220> FEATURE:
<221> NAME/KEY: misc_feature
<222> LOCATION: (738)..(738)
<223> OTHER INFORMATION: Xaa can be any naturally occurring amino acid
<220> FEATURE:
<221> NAME/KEY: misc_feature
<222> LOCATION: (741)..(741)
<223> OTHER INFORMATION: Xaa can be any naturally occurring amino acid
<220> FEATURE:
<221> NAME/KEY: misc_feature
<222> LOCATION: (752)..(752)
<223> OTHER INFORMATION: Xaa can be any naturally occurring amino acid
<220> FEATURE:
<221> NAME/KEY: misc_feature
<222> LOCATION: (759)..(759)
<223> OTHER INFORMATION: Xaa can be any naturally occurring amino acid
<220> FEATURE:
<221> NAME/KEY: misc_feature
<222> LOCATION: (763)..(763)
<223> OTHER INFORMATION: Xaa can be any naturally occurring amino acid
<220> FEATURE:
<221> NAME/KEY: misc_feature
<222> LOCATION: (767)..(767)
<223> OTHER INFORMATION: Xaa can be any naturally occurring amino acid
<220> FEATURE:
<221> NAME/KEY: misc_feature
<222> LOCATION: (770)..(770)
<223> OTHER INFORMATION: Xaa can be any naturally occurring amino acid
<220> FEATURE:
<221> NAME/KEY: misc_feature
<222> LOCATION: (774)..(774)
<223> OTHER INFORMATION: Xaa can be any naturally occurring amino acid
<220> FEATURE:
<221> NAME/KEY: misc_feature
<222> LOCATION: (779)..(779)
<223> OTHER INFORMATION: Xaa can be any naturally occurring amino acid
<220> FEATURE:
<221> NAME/KEY: misc_feature
<222> LOCATION: (784)..(785)
<223> OTHER INFORMATION: Xaa can be any naturally occurring amino acid
<220> FEATURE:
<221> NAME/KEY: misc_feature
<222> LOCATION: (787)..(787)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (825)..(825)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
<222> LOCATION: (835)..(836)
<223> OTHER INFORMATION: Xaa can be any naturally occurring amino acid
<220> FEATURE:
<221> NAME/KEY: misc_feature
<222> LOCATION: (859)..(859)
<223> OTHER INFORMATION: Xaa can be any naturally occurring amino acid
<220> FEATURE:
<221> NAME/KEY: misc_feature
<222> LOCATION: (861)..(861)
<223> OTHER INFORMATION: Xaa can be any naturally occurring amino acid
<220> FEATURE:
<221> NAME/KEY: misc_feature
<222> LOCATION: (863)..(863)
<223> OTHER INFORMATION: Xaa can be any naturally occurring amino acid
<220> FEATURE:
<221> NAME/KEY: misc_feature
<222> LOCATION: (866)..(866)
<223> OTHER INFORMATION: Xaa can be any naturally occurring amino acid
<220> FEATURE:
<221> NAME/KEY: misc_feature
<222> LOCATION: (869)..(870)
<223> OTHER INFORMATION: Xaa can be any naturally occurring amino acid
<220> FEATURE:
<221> NAME/KEY: misc_feature
<222> LOCATION: (873)..(873)
<223> OTHER INFORMATION: Xaa can be any naturally occurring amino acid
<220> FEATURE:
<221> NAME/KEY: misc_feature
<222> LOCATION: (875)..(875)
<223> OTHER INFORMATION: Xaa can be any naturally occurring amino acid
<220> FEATURE:
<221> NAME/KEY: misc_feature
<222> LOCATION: (883)..(883)
<223> OTHER INFORMATION: Xaa can be any naturally occurring amino acid
<220> FEATURE:

<221> NAME/KEY: misc_feature
<222> LOCATION: (913)..(913)
<223> OTHER INFORMATION: Xaa can be any naturally occurring amino acid
<220> FEATURE:
<221> NAME/KEY: misc_feature
<222> LOCATION: (920)..(920)
<223> OTHER INFORMATION: Xaa can be any naturally occurring amino acid
<220> FEATURE:
<221> NAME/KEY: misc_feature
<222> LOCATION: (923)..(924)
<223> OTHER INFORMATION: Xaa can be any naturally occurring amino acid
<220> FEATURE:
<221> NAME/KEY: misc_feature
<222> LOCATION: (927)..(927)
<223> OTHER INFORMATION: Xaa can be any naturally occurring amino acid
<220> FEATURE:
<221> NAME/KEY: misc_feature
<222> LOCATION: (930)..(931)
<223> OTHER INFORMATION: Xaa can be any naturally occurring amino acid
<220> FEATURE:
<221> NAME/KEY: misc_feature
<222> LOCATION: (933)..(934)
<223> OTHER INFORMATION: Xaa can be any naturally occurring amino acid
<220> FEATURE:
<221> NAME/KEY: misc_feature
<222> LOCATION: (945)..(945)
<223> OTHER INFORMATION: Xaa can be any naturally occurring amino acid
<220> FEATURE:
<221> NAME/KEY: misc_feature
<222> LOCATION: (1046)..(1046)
<223> OTHER INFORMATION: Xaa can be any naturally occurring amino acid
<220> FEATURE:
<221> NAME/KEY: misc_feature
<222> LOCATION: (1061)..(1061)
<223> OTHER INFORMATION: Xaa can be any naturally occurring amino acid
<220> FEATURE:
<221> NAME/KEY: misc_feature
<222> LOCATION: (1064)..(1064)
<223> OTHER INFORMATION: Xaa can be any naturally occurring amino acid
<220> FEATURE:
<221> NAME/KEY: misc_feature
<222> LOCATION: (1075)..(1075)
<223> OTHER INFORMATION: Xaa can be any naturally occurring amino acid
<220> FEATURE:
<221> NAME/KEY: misc_feature
<222> LOCATION: (1079)..(1079)
<223> OTHER INFORMATION: Xaa can be any naturally occurring amino acid
<220> FEATURE:
<221> NAME/KEY: misc_feature
<222> LOCATION: (1088)..(1088)
<223> OTHER INFORMATION: Xaa can be any naturally occurring amino acid
<220> FEATURE:
<221> NAME/KEY: misc_feature
<222> LOCATION: (1092)..(1092)
<223> OTHER INFORMATION: Xaa can be any naturally occurring amino acid
<220> FEATURE:
<221> NAME/KEY: misc_feature
<222> LOCATION: (1095)..(1095)
<223> OTHER INFORMATION: Xaa can be any naturally occurring amino acid
<220> FEATURE:
<221> NAME/KEY: misc_feature
<222> LOCATION: (1101)..(1102)
<223> OTHER INFORMATION: Xaa can be any naturally occurring amino acid
<220> FEATURE:
<221> NAME/KEY: misc_feature
<222> LOCATION: (1105)..(1105)
<223> OTHER INFORMATION: Xaa can be any naturally occurring amino acid
<220> FEATURE:
<221> NAME/KEY: misc_feature
<222> LOCATION: (1114)..(1114)
<223> OTHER INFORMATION: Xaa can be any naturally occurring amino acid
<220> FEATURE:
<221> NAME/KEY: misc_feature
<222> LOCATION: (1116)..(1116)
<223> OTHER INFORMATION: Xaa can be any naturally occurring amino acid
<220> FEATURE:
<221> NAME/KEY: misc_feature
<222> LOCATION: (1124)..(1124)
<223> OTHER INFORMATION: Xaa can be any naturally occurring amino acid
<220> FEATURE:
<221> NAME/KEY: misc_feature
<222> LOCATION: (1172)..(1172)
<223> OTHER INFORMATION: Xaa can be any naturally occurring amino acid
<220> FEATURE:
<221> NAME/KEY: misc_feature
<222> LOCATION: (1207)..(1207)
<223> OTHER INFORMATION: Xaa can be any naturally occurring amino acid
<220> FEATURE:
<221> NAME/KEY: misc_feature
<222> LOCATION: (1219)..(1219)
<223> OTHER INFORMATION: Xaa can be any naturally occurring amino acid
<220> FEATURE:
<221> NAME/KEY: misc_feature
<222> LOCATION: (1224)..(1224)
<223> OTHER INFORMATION: Xaa can be any naturally occurring amino acid
<220> FEATURE:
<221> NAME/KEY: misc_feature
<222> LOCATION: (1238)..(1238)
<223> OTHER INFORMATION: Xaa can be any naturally occurring amino acid

<400> SEQUENCE: 327

```
Xaa Xaa Xaa Xaa Xaa Cys Xaa Xaa Xaa Xaa Xaa Xaa Xaa Xaa Xaa Xaa
1               5                   10                  15

Xaa Xaa Xaa Xaa Xaa Ser Xaa Xaa Arg Gly Val Tyr Tyr Xaa Asp Xaa
            20                  25                  30

Xaa Phe Arg Ser Xaa Xaa Leu Xaa Xaa Thr Gln Asp Xaa Phe Leu Pro
        35                  40                  45

Phe Xaa Ser Asn Xaa Thr Xaa Xaa Xaa Xaa Xaa Xaa Xaa Xaa Xaa Xaa
    50                  55                  60

Xaa Xaa Xaa Xaa Xaa Phe Xaa Asn Pro Xaa Xaa Xaa Phe Xaa Asp Gly
65                  70                  75                  80

Xaa Tyr Phe Ala Xaa Thr Glu Lys Ser Asn Xaa Xaa Arg Gly Trp Xaa
                85                  90                  95

Phe Gly Xaa Xaa Xaa Xaa Xaa Xaa Xaa Gln Ser Xaa Xaa Ile Xaa Asn
            100                 105                 110

Asn Xaa Thr Xaa Xaa Xaa Ile Xaa Xaa Cys Xaa Phe Xaa Xaa Cys Xaa
        115                 120                 125

Xaa Pro Xaa Xaa Xaa Val Xaa Xaa Xaa Xaa Xaa Xaa Xaa Xaa Xaa Xaa
    130                 135                 140

Xaa Xaa Xaa Xaa Xaa Xaa Xaa Xaa Xaa Ala Xaa Asn Cys Thr Xaa Xaa
145                 150                 155                 160

Xaa Xaa Xaa Xaa Xaa Phe Xaa Xaa Asp Xaa Xaa Xaa Lys Xaa Gly Asn
                165                 170                 175

Phe Lys Xaa Leu Arg Glu Xaa Val Phe Lys Asn Xaa Asp Gly Xaa Xaa
            180                 185                 190

Xaa Xaa Tyr Xaa Xaa Xaa Xaa Xaa Xaa Xaa Xaa Xaa Arg Xaa Xaa Pro
        195                 200                 205

Xaa Gly Phe Xaa Xaa Leu Xaa Pro Xaa Xaa Xaa Leu Pro Xaa Gly Ile
    210                 215                 220

Asn Ile Thr Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Ala Ala Tyr
                245                 250                 255

Xaa Val Gly Xaa Leu Xaa Xaa Xaa Thr Phe Xaa Leu Xaa Xaa Xaa Glu
            260                 265                 270

Asn Gly Thr Ile Thr Xaa Ala Xaa Asp Cys Xaa Xaa Xaa Pro Leu Xaa
        275                 280                 285

Glu Xaa Lys Cys Xaa Xaa Lys Xaa Phe Xaa Xaa Xaa Lys Gly Ile Tyr
    290                 295                 300
```

-continued

```
Gln Thr Ser Asn Phe Arg Val Xaa Pro Xaa Xaa Xaa Xaa Xaa Arg Phe
305                 310                 315                 320

Pro Asn Ile Thr Asn Xaa Cys Pro Phe Xaa Xaa Val Phe Asn Ala Xaa
                325                 330                 335

Xaa Phe Xaa Xaa Val Tyr Ala Trp Xaa Arg Xaa Xaa Ile Ser Xaa Cys
            340                 345                 350

Val Ala Asp Tyr Xaa Val Leu Tyr Asn Ser Xaa Xaa Phe Ser Thr Phe
        355                 360                 365

Lys Cys Tyr Gly Val Ser Xaa Xaa Lys Leu Xaa Asp Leu Cys Phe Xaa
    370                 375                 380

Xaa Val Tyr Ala Asp Xaa Phe Xaa Xaa Xaa Xaa Xaa Xaa Val Arg Gln
385                 390                 395                 400

Xaa Ala Pro Gly Xaa Thr Gly Xaa Ile Ala Asp Tyr Asn Tyr Lys Leu
                405                 410                 415

Pro Asp Asp Phe Xaa Gly Cys Val Xaa Ala Trp Asn Xaa Xaa Xaa Xaa
            420                 425                 430

Asp Xaa Xaa Xaa Xaa Gly Xaa Xaa Xaa Tyr Xaa Tyr Arg Xaa Xaa Arg
        435                 440                 445

Xaa Xaa Xaa Leu Xaa Pro Phe Glu Arg Asp Xaa Ser Xaa Xaa Xaa Xaa
    450                 455                 460

Xaa Xaa Xaa Xaa Xaa Xaa Xaa Xaa Xaa Xaa Xaa Xaa Xaa Asn Xaa Xaa
465                 470                 475                 480

Xaa Xaa Leu Xaa Xaa Tyr Xaa Phe Xaa Xaa Xaa Xaa Xaa Xaa Xaa Xaa
                485                 490                 495

Gln Xaa Xaa Arg Val Val Val Leu Ser Phe Glu Leu Leu Xaa Ala Pro
            500                 505                 510

Ala Thr Val Cys Gly Pro Lys Xaa Ser Thr Xaa Leu Xaa Lys Asn Xaa
        515                 520                 525

Cys Val Asn Phe Asn Phe Asn Gly Leu Xaa Gly Thr Gly Val Leu Thr
    530                 535                 540

Xaa Ser Xaa Lys Xaa Phe Xaa Xaa Phe Gln Gln Phe Gly Arg Asp Xaa
545                 550                 555                 560

Xaa Asp Xaa Thr Asp Xaa Val Arg Asp Pro Xaa Thr Xaa Glu Ile Leu
                565                 570                 575

Asp Ile Xaa Pro Cys Ser Phe Gly Gly Val Ser Val Ile Thr Pro Gly
            580                 585                 590

Thr Asn Xaa Ser Xaa Xaa Val Ala Val Leu Tyr Gln Asp Val Asn Cys
        595                 600                 605

Thr Xaa Val Xaa Xaa Xaa Ile Xaa Ala Xaa Gln Leu Thr Pro Xaa Trp
    610                 615                 620

Arg Xaa Tyr Ser Thr Gly Xaa Asn Val Phe Gln Thr Xaa Ala Gly Cys
625                 630                 635                 640

Leu Ile Gly Ala Glu His Val Xaa Xaa Ser Tyr Glu Cys Asp Ile Pro
                645                 650                 655

Ile Gly Ala Gly Ile Cys Ala Ser Tyr Xaa Thr Xaa Xaa Xaa Xaa Xaa
            660                 665                 670

Xaa Xaa Xaa Arg Ser Xaa Xaa Xaa Xaa Ser Ile Xaa Ala Tyr Thr Met
        675                 680                 685

Ser Leu Gly Ala Xaa Xaa Ser Xaa Ala Tyr Xaa Asn Asn Xaa Ile Ala
    690                 695                 700

Ile Pro Thr Asn Phe Xaa Ile Ser Xaa Thr Thr Glu Xaa Xaa Pro Val
705                 710                 715                 720
```

-continued

```
Ser Xaa Xaa Lys Thr Xaa Val Asp Cys Xaa Met Tyr Ile Cys Gly Asp
                725                 730                 735

Ser Xaa Glu Cys Xaa Asn Leu Leu Leu Gln Tyr Gly Ser Phe Cys Xaa
            740                 745                 750

Gln Leu Asn Arg Ala Leu Xaa Gly Ile Ala Xaa Glu Gln Asp Xaa Asn
        755                 760                 765

Thr Xaa Glu Val Phe Xaa Gln Val Lys Gln Xaa Tyr Lys Thr Pro Xaa
    770                 775                 780

Xaa Lys Xaa Phe Gly Gly Phe Asn Phe Ser Gln Ile Leu Pro Asp Pro
785                 790                 795                 800

Xaa Lys Pro Xaa Lys Arg Ser Phe Ile Glu Asp Leu Leu Phe Asn Lys
                805                 810                 815

Val Thr Leu Ala Asp Ala Gly Phe Xaa Lys Gln Tyr Gly Xaa Cys Leu
            820                 825                 830

Gly Asp Xaa Xaa Ala Arg Asp Leu Ile Cys Ala Gln Lys Phe Asn Gly
        835                 840                 845

Leu Thr Val Leu Pro Pro Leu Leu Thr Asp Xaa Met Xaa Ala Xaa Tyr
    850                 855                 860

Thr Xaa Ala Leu Xaa Xaa Gly Thr Xaa Thr Xaa Gly Trp Thr Phe Gly
865                 870                 875                 880

Ala Gly Xaa Ala Leu Gln Ile Pro Phe Ala Met Gln Met Ala Tyr Arg
                885                 890                 895

Phe Asn Gly Ile Gly Val Thr Gln Asn Val Leu Tyr Glu Asn Gln Lys
            900                 905                 910

Xaa Ile Ala Asn Gln Phe Asn Xaa Ala Ile Xaa Xaa Ile Gln Xaa Ser
        915                 920                 925

Leu Xaa Xaa Thr Xaa Xaa Ala Leu Gly Lys Leu Gln Asp Val Val Asn
    930                 935                 940

Xaa Asn Ala Gln Ala Leu Asn Thr Leu Val Lys Gln Leu Ser Ser Asn
945                 950                 955                 960

Phe Gly Ala Ile Ser Ser Val Leu Asn Asp Ile Leu Ser Arg Leu Asp
                965                 970                 975

Lys Val Glu Ala Glu Val Gln Ile Asp Arg Leu Ile Thr Gly Arg Leu
            980                 985                 990

Gln Ser Leu Gln Thr Tyr Val Thr  Gln Gln Leu Ile Arg  Ala Ala Glu
        995                 1000                1005

Ile Arg  Ala Ser Ala Asn Leu  Ala Ala Thr Lys Met  Ser Glu Cys
    1010                1015                1020

Val Leu  Gly Gln Ser Lys Arg  Val Asp Phe Cys Gly  Lys Gly Tyr
    1025                1030                1035

His Leu  Met Ser Phe Pro Gln  Xaa Ala Pro His Gly  Val Val Phe
    1040                1045                1050

Leu His  Val Thr Tyr Val Pro  Xaa Gln Glu Xaa Asn  Phe Thr Thr
    1055                1060                1065

Ala Pro  Ala Ile Cys His Xaa  Gly Lys Ala Xaa Phe  Pro Arg Glu
    1070                1075                1080

Gly Val  Phe Val Xaa Asn Gly  Thr Xaa Trp Phe Xaa  Thr Gln Arg
    1085                1090                1095

Asn Phe  Xaa Xaa Pro Gln Xaa  Ile Thr Thr Asp Asn  Thr Phe Val
    1100                1105                1110

Xaa Gly  Xaa Cys Asp Val Val  Ile Gly Ile Xaa Asn  Asn Thr Val
    1115                1120                1125

Tyr Asp  Pro Leu Gln Pro Glu  Leu Asp Ser Phe Lys  Glu Glu Leu
```

```
    1130                 1135                 1140

Asp Lys  Tyr Phe Lys Asn His  Thr Ser Pro Asp Val  Asp Leu Gly
    1145                 1150                 1155

Asp Ile  Ser Gly Ile Asn Ala  Ser Val Val Asn Ile  Gln Xaa Glu
    1160                 1165                 1170

Ile Asp  Arg Leu Asn Glu Val  Ala Lys Asn Leu Asn  Glu Ser Leu
    1175                 1180                 1185

Ile Asp  Leu Gln Glu Leu Gly  Lys Tyr Glu Gln Tyr  Ile Lys Trp
    1190                 1195                 1200

Pro Trp  Tyr Xaa Trp Leu Gly  Phe Ile Ala Gly Leu  Ile Ala Ile
    1205                 1210                 1215

Xaa Met  Val Thr Ile Xaa Leu  Cys Cys Met Thr Ser  Cys Cys Ser
    1220                 1225                 1230

Cys Leu  Lys Gly Xaa Cys Ser  Cys Gly Ser Cys Cys  Lys Phe Asp
    1235                 1240                 1245

Glu Asp  Asp Ser Glu Pro Val  Leu Lys Gly Val Lys  Leu His Tyr
    1250                 1255                 1260

Thr


<210> SEQ ID NO 328
<211> LENGTH: 223
<212> TYPE: PRT
<213> ORGANISM: Artificial Sequence
<220> FEATURE:
<223> OTHER INFORMATION: Synthetic construct

<400> SEQUENCE: 328

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 329
<211> LENGTH: 223
<212> TYPE: PRT
<213> ORGANISM: Artificial Sequence
<220> FEATURE:
<223> OTHER INFORMATION: Synthetic construct

<400> SEQUENCE: 329

```
Arg Val Gln Pro Thr Asp Ser Ile Val Arg Phe Pro Asn Ile Thr Asn
1               5                   10                  15

Leu Cys Pro Phe Gly Glu Val Phe Asn Ala Thr Thr Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Thr Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Thr Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Lys His Ile Asp Ala Lys Glu Gly
        115                 120                 125

Gly Asn Phe Asn Tyr Leu Tyr Arg Leu Phe Arg Lys Ala Asn Leu Lys
    130                 135                 140

Pro Phe Glu Arg Asp Ile Ser Thr Glu Ile Tyr Gln Ala Gly Ser Lys
145                 150                 155                 160

Pro Cys Asn Gly Gln Thr Gly Leu Asn Cys Tyr Tyr Pro Leu Tyr Arg
                165                 170                 175

Tyr Gly Phe Tyr Pro Thr Asp Gly Val Gly His Gln Pro Tyr Arg Val
            180                 185                 190

Val Val Leu Ser Phe Glu Leu Leu Asn Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 330
<211> LENGTH: 222
<212> TYPE: PRT
<213> ORGANISM: Artificial Sequence
<220> FEATURE:
<223> OTHER INFORMATION: Synthetic construct

<400> SEQUENCE: 330

```
Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
```

-continued

```
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220


<210> SEQ ID NO 331
<211> LENGTH: 222
<212> TYPE: PRT
<213> ORGANISM: Artificial Sequence
<220> FEATURE:
<223> OTHER INFORMATION: Synthetic construct

<400> SEQUENCE: 331

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Arg Ile Ser Asn Cys Val Ala Asp Tyr Ser
        35                  40                  45

Val Leu Tyr Asn Ser Thr Ser Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Pro Asn Cys Tyr Trp Pro Leu Asn Gly Tyr
                165                 170                 175

Gly Phe Tyr Thr Thr Ser Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220
```

<210> SEQ ID NO 332
<211> LENGTH: 205
<212> TYPE: PRT
<213> ORGANISM: Artificial Sequence
<220> FEATURE:
<223> OTHER INFORMATION: Synthetic construct

<400> SEQUENCE: 332

```
Arg Val Ser Pro Thr Gln Glu Val Ile Arg Phe Pro Asn Ile Thr Asn
1               5                   10                  15

Arg Cys Pro Phe Asp Lys Val Phe Asn Ala Thr Arg Phe Pro Asn Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Ser Ser Glu Val Arg Gln Val Ala Pro Gly Glu
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys His Asp Thr Gly Asn Tyr
        115                 120                 125

Tyr Tyr Arg Ser His Arg Lys Thr Lys Leu Lys Pro Phe Glu Arg Asp
    130                 135                 140

Leu Ser Ser Asp Asp Gly Asn Gly Val Tyr Thr Leu Ser Thr Tyr Asp
145                 150                 155                 160

Phe Asn Pro Asn Val Pro Val Ala Tyr Gln Ala Thr Arg Val Val Val
                165                 170                 175

Leu Ser Phe Glu Leu Leu Asn Ala Pro Ala Thr Val Cys Gly Pro Lys
            180                 185                 190

Leu Ser Thr Glu Leu Val Lys Asn Gln Cys Val Asn Phe
        195                 200                 205
```

<210> SEQ ID NO 333
<211> LENGTH: 204
<212> TYPE: PRT
<213> ORGANISM: Artificial Sequence
<220> FEATURE:
<223> OTHER INFORMATION: Synthetic construct

<400> SEQUENCE: 333

```
Arg Val Ser Pro Thr Gln Glu Val Ile Arg Phe Pro Asn Ile Thr Asn
1               5                   10                  15

Arg Cys Pro Phe Asp Lys Val Phe Asn Ala Thr Arg Phe Pro Asn Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Ser Ser Glu Val Arg Gln Val Ala Pro Gly Glu
                85                  90                  95

Thr Gly Val Ile Ala Asp Tyr Asn Tyr Lys Leu Pro Asp Asp Phe Thr
            100                 105                 110
```

```
Gly Cys Val Ile Ala Trp Asn Thr Ala Lys Gln Asp Gln Gly Gln Tyr
        115                 120                 125

Tyr Tyr Arg Ser His Arg Lys Thr Lys Leu Lys Pro Phe Glu Arg Asp
    130                 135                 140

Leu Ser Ser Asp Glu Asn Gly Val Arg Thr Leu Ser Thr Tyr Asp Phe
145                 150                 155                 160

Tyr Pro Ser Val Pro Val Ala Tyr Gln Ala Thr Arg Val Val Val Leu
                165                 170                 175

Ser Phe Glu Leu Leu Asn Ala Pro Ala Thr Val Cys Gly Pro Lys Leu
            180                 185                 190

Ser Thr Gln Leu Val Lys Asn Gln Cys Val Asn Phe
        195                 200


<210> SEQ ID NO 334
<211> LENGTH: 204
<212> TYPE: PRT
<213> ORGANISM: Artificial Sequence
<220> FEATURE:
<223> OTHER INFORMATION: Synthetic construct

<400> SEQUENCE: 334

Arg Val Thr Pro Thr Gln Glu Val Val Arg Phe Pro Asn Ile Thr Asn
1               5                   10                  15

Arg Cys Pro Phe Asp Lys Val Phe Asn Ala Ser Arg Phe Pro Asn Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Ser Ser Glu Val Arg Gln Val Ala Pro Gly Glu
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Gln Gln Asp Gln Gly Gln Tyr
        115                 120                 125

Tyr Tyr Arg Ser Tyr Arg Lys Glu Lys Leu Lys Pro Phe Glu Arg Asp
    130                 135                 140

Leu Ser Ser Asp Glu Asn Gly Val Tyr Thr Leu Ser Thr Tyr Asp Phe
145                 150                 155                 160

Tyr Pro Ser Ile Pro Val Glu Tyr Gln Ala Thr Arg Val Val Val Leu
                165                 170                 175

Ser Phe Glu Leu Leu Asn Ala Pro Ala Thr Val Cys Gly Pro Lys Leu
            180                 185                 190

Ser Thr Gln Leu Val Lys Asn Gln Cys Val Asn Phe
        195                 200


<210> SEQ ID NO 335
<211> LENGTH: 223
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
```

<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (83)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (120)..(123)
<223> OTHER INFORMATION: Xaa can be any naturally occurring amino acid
<220> FEATURE:
<221> NAME/KEY: misc_feature
<222> LOCATION: (125)..(128)
<223> OTHER INFORMATION: Xaa can be any naturally occurring amino acid
<220> FEATURE:
<221> NAME/KEY: misc_feature
<222> LOCATION: (130)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (137)..(138)
<223> OTHER INFORMATION: Xaa can be any naturally occurring amino acid
<220> FEATURE:
<221> NAME/KEY: misc_feature
<222> LOCATION: (140)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(168)
<223> OTHER INFORMATION: Xaa can be any naturally occurring amino acid
<220> FEATURE:
<221> NAME/KEY: misc_feature
<222> LOCATION: (170)..(173)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (180)..(187)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid

<400> SEQUENCE: 335

-continued

```
Arg Val Xaa Pro Xaa Xaa Xaa Xaa Xaa Arg Phe Pro Asn Ile Thr Asn
1               5                   10                  15

Xaa Cys Pro Phe Xaa Xaa Xaa Phe Asn Ala Xaa Xaa Phe Xaa Xaa Val
            20                  25                  30

Tyr Ala Trp Xaa Arg Xaa Xaa Ile Ser Xaa Cys Val Ala Asp Tyr Xaa
        35                  40                  45

Val Leu Tyr Asn Ser Xaa Xaa Phe Ser Thr Phe Lys Cys Tyr Gly Val
    50                  55                  60

Ser Xaa Xaa Lys Leu Xaa Asp Leu Cys Phe Xaa Xaa Val Tyr Ala Asp
65                  70                  75                  80

Xaa Phe Xaa Xaa Xaa Xaa Xaa Xaa Val Arg Gln Xaa Ala Pro Gly Xaa
                85                  90                  95

Thr Gly Xaa Ile Ala Asp Tyr Asn Tyr Lys Leu Pro Asp Asp Phe Xaa
            100                 105                 110

Gly Cys Val Xaa Xaa Trp Asn Xaa Xaa Xaa Xaa Asp Xaa Xaa Xaa Xaa
        115                 120                 125

Gly Xaa Xaa Xaa Tyr Xaa Tyr Arg Xaa Xaa Arg Xaa Xaa Xaa Leu Xaa
    130                 135                 140

Pro Phe Glu Arg Asp Xaa Ser Xaa Xaa Xaa Xaa Xaa Xaa Xaa Xaa Xaa
145                 150                 155                 160

Xaa Xaa Xaa Xaa Xaa Xaa Xaa Xaa Asn Xaa Xaa Xaa Xaa Leu Xaa Xaa
                165                 170                 175

Tyr Xaa Phe Xaa Xaa Xaa Xaa Xaa Xaa Xaa Xaa Gln Xaa Xaa Arg Val
            180                 185                 190

Val Val Leu Ser Phe Glu Leu Leu Xaa Ala Pro Ala Thr Val Cys Gly
        195                 200                 205

Pro Lys Xaa Ser Thr Xaa Leu Xaa Lys Asn Xaa Cys Val Asn Phe
    210                 215                 220
```

<210> SEQ ID NO 336
<211> LENGTH: 72
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(50)
<223> OTHER INFORMATION: Xaa can be any naturally occurring amino acid
<220> FEATURE:
<221> NAME/KEY: misc_feature
<222> LOCATION: (52)..(55)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(69)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid

<400> SEQUENCE: 336

```
Asn Xaa Xaa Xaa Xaa Asp Xaa Xaa Xaa Xaa Gly Xaa Xaa Xaa Tyr Xaa
1               5                   10                  15

Tyr Arg Xaa Xaa Arg Xaa Xaa Xaa Leu Xaa Pro Phe Glu Arg Asp Xaa
            20                  25                  30

Ser Xaa Xaa Xaa Xaa Xaa Xaa Xaa Xaa Xaa Xaa Xaa Xaa Xaa Xaa Xaa
        35                  40                  45

Xaa Xaa Asn Xaa Xaa Xaa Xaa Leu Xaa Xaa Tyr Xaa Phe Xaa Xaa Xaa
    50                  55                  60

Xaa Xaa Xaa Xaa Xaa Gln Xaa Xaa
65                  70
```

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340
<211> LENGTH: 121
<212> TYPE: PRT
<213> ORGANISM: Artificial Sequence
<220> FEATURE:
<223> OTHER INFORMATION: Synthetic

<400> SEQUENCE: 340

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Ser Gly Glu Tyr
```

```
            20                  25                  30

Asp Met Gly Trp Phe Arg Gln Ala Pro Gly Lys Glu Arg Glu Phe Val
        35                  40                  45

Ser Ala Ile Ser His Trp Asp Gly Lys Ala Thr Ala Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ala Arg Leu Asp Asp Glu Ile Asp Phe Tyr Trp Gly Gln
            100                 105                 110

Gly Thr Gln Val Thr Val Ser Ser Ala
        115                 120


<210> SEQ ID NO 341
<211> LENGTH: 121
<212> TYPE: PRT
<213> ORGANISM: Artificial Sequence
<220> FEATURE:
<223> OTHER INFORMATION: Synthetic

<400> SEQUENCE: 341

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Ser Phe Ser Thr Tyr
            20                  25                  30

Tyr Met Gly Trp Phe Arg Gln Ala Pro Gly Lys Glu Arg Glu Phe Val
        35                  40                  45

Ser Ala Ile Ser Ala Phe Gly Ala Gly Glu Gln Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ala Tyr Thr Thr Thr Thr Val Pro Gln Tyr Trp Gly Gln
            100                 105                 110

Gly Thr Gln Val Thr Val Ser Ser Ala
        115                 120


<210> SEQ ID NO 342
<211> LENGTH: 121
<212> TYPE: PRT
<213> ORGANISM: Artificial Sequence
<220> FEATURE:
<223> OTHER INFORMATION: Synthetic

<400> SEQUENCE: 342

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Ser Asp Gly Arg Phe
            20                  25                  30

His Met Gly Trp Phe Arg Gln Ala Pro Gly Lys Glu Arg Glu Phe Val
        35                  40                  45

Ser Ala Ile Ser Gln Thr Thr Asp Glu Asp Thr Tyr Tyr Tyr Ala Asp
    50                  55                  60

Ser Val Lys Gly Arg Phe Thr Ile Ser Arg Asp Asn Ser Lys Asn Thr
65                  70                  75                  80
```

```
Val Tyr Leu Gln Met Asn Ser Leu Arg Ala Glu Asp Thr Ala Thr Tyr
                85                  90                  95

Tyr Cys Ala Ala Tyr Thr Thr Thr Thr Val Pro Gln Tyr Trp Gly Gln
            100                 105                 110

Gly Thr Gln Val Thr Val Ser Ser Ala
        115                 120


<210> SEQ ID NO 343
<211> LENGTH: 124
<212> TYPE: PRT
<213> ORGANISM: Artificial Sequence
<220> FEATURE:
<223> OTHER INFORMATION: Synthetic

<400> SEQUENCE: 343

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Pro Phe Asp His Tyr
            20                  25                  30

Val Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ile Phe Asp Asn Ile Arg Ala Ser Leu Gln Asp Pro Tyr
            100                 105                 110

Trp Gly Gln Gly Thr Gln Val Thr Val Ser Ser Ala
        115                 120


<210> SEQ ID NO 344
<211> LENGTH: 121
<212> TYPE: PRT
<213> ORGANISM: Artificial Sequence
<220> FEATURE:
<223> OTHER INFORMATION: Synthetic

<400> SEQUENCE: 344

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Thr Asp Ser Gln Tyr
            20                  25                  30

Asp Met Gly Trp Phe Arg Gln Ala Pro Gly Lys Glu Arg Glu Phe Val
        35                  40                  45

Ser Ala Ile Ser Ser Trp Ala Asp Thr Thr Val Ser Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ile Gln Ser Arg Lys Gln Val Gly Phe Tyr Trp Gly Gln
            100                 105                 110

Gly Thr Gln Val Thr Val Ser Ser Ala
        115                 120


<210> SEQ ID NO 345
```

```
<211> LENGTH: 124
<212> TYPE: PRT
<213> ORGANISM: Artificial Sequence
<220> FEATURE:
<223> OTHER INFORMATION: Synthetic

<400> SEQUENCE: 345

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Tyr Phe Ser Gly Gln
            20                  25                  30

Tyr Met Gly Trp Phe Arg Gln Ala Pro Gly Lys Glu Arg Glu Phe Val
        35                  40                  45

Ser Ala Ile Ser Thr Ala Tyr Asp Gly Glu Thr Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Leu Lys Asp Pro Val Arg Ile Ile Asp Ala Ile Trp Tyr
            100                 105                 110

Trp Gly Gln Gly Thr Gln Val Thr Val Ser Ser Ala
        115                 120


<210> SEQ ID NO 346
<211> LENGTH: 124
<212> TYPE: PRT
<213> ORGANISM: Artificial Sequence
<220> FEATURE:
<223> OTHER INFORMATION: Synthetic

<400> SEQUENCE: 346

Glu Val Gln Leu Gln Ala Ser Gly Gly Gly Phe Val Gln Pro Gly Gly
1               5                   10                  15

Ser Leu Arg Leu Ser Cys Ala Ala Ser Gly His Thr Phe Gly Phe Ser
            20                  25                  30

His Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Leu Trp Pro Tyr Ser Asp Asp Arg Leu Asp Ser Tyr Tyr
            100                 105                 110

Trp Gly Gln Gly Thr Gln Val Thr Val Ser Ser Ala
        115                 120


<210> SEQ ID NO 347
<211> LENGTH: 121
<212> TYPE: PRT
<213> ORGANISM: Artificial Sequence
<220> FEATURE:
<223> OTHER INFORMATION: Synthetic

<400> SEQUENCE: 347

Glu Val Gln Leu Gln Ala Ser Gly Gly Gly Phe Val Gln Pro Gly Gly
1               5                   10                  15
```

-continued

```
Ser Leu Arg Leu Ser Cys Ala Ala Ser Gly Arg Thr Phe Ser Gly Tyr
            20                  25                  30

Ile Met Gly Trp Phe Arg Gln Ala Pro Gly Lys Glu Arg Glu Phe Val
        35                  40                  45

Ser Ala Ile Ser His Gly Asp Ser Tyr Ala Ser Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Leu Tyr Asp Ile Asn Thr Val Pro Tyr Tyr Trp Gly Gln
            100                 105                 110

Gly Thr Gln Val Thr Val Ser Ser Ala
        115                 120


<210> SEQ ID NO 348
<211> LENGTH: 121
<212> TYPE: PRT
<213> ORGANISM: Artificial Sequence
<220> FEATURE:
<223> OTHER INFORMATION: Synthetic

<400> SEQUENCE: 348

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Ile Phe Gly Asp Leu
            20                  25                  30

Gln Met Gly Trp Phe Arg Gln Ala Pro Gly Lys Glu Arg Glu Phe Val
        35                  40                  45

Ser Ala Ile Ser Ala Trp Tyr Asp Asp Thr Thr Gln Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Pro Tyr Phe Gly Glu Ala Asp Ile Ala Tyr Trp Gly Gln
            100                 105                 110

Gly Thr Gln Val Thr Val Ser Ser Ala
        115                 120


<210> SEQ ID NO 349
<211> LENGTH: 124
<212> TYPE: PRT
<213> ORGANISM: Artificial Sequence
<220> FEATURE:
<223> OTHER INFORMATION: Synthetic

<400> SEQUENCE: 349

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Ala Phe Ser Gln Tyr
            20                  25                  30

His Met Gly Trp Phe Arg Gln Ala Pro Gly Lys Glu Arg Glu Phe Val
        35                  40                  45

Ser Ala Ile Ser Ser Gln Ala Gly Ala Thr Thr Gln Tyr Tyr Ala Asp
    50                  55                  60

Ser Val Lys Gly Arg Phe Thr Ile Ser Arg Asp Asn Ser Lys Asn Thr
65                  70                  75                  80
```

Val Tyr Leu Gln Met Asn Ser Leu Arg Ala Glu Asp Thr Ala Thr Tyr
85 90 95

Tyr Cys Ala Val Trp Tyr Gly His Thr Asp Pro Gln His Asp Arg Tyr
100 105 110

Trp Gly Gln Gly Thr Gln Val Thr Val Ser Ser Ala
115 120

<210> SEQ ID NO 350
<211> LENGTH: 121
<212> TYPE: PRT
<213> ORGANISM: Artificial Sequence
<220> FEATURE:
<223> OTHER INFORMATION: Synthetic

<400> SEQUENCE: 350

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Tyr Ser Gln Asp Tyr
20 25 30

Arg Met Gly Trp Phe Arg Gln Ala Pro Gly Lys Glu Arg Glu Phe Val
35 40 45

Ser Ala Ile Ser Asp Arg Gly Gly Thr Thr Thr Asp Tyr Tyr Ala Asp
50 55 60

Ser Val Lys Gly Arg Phe Thr Ile Ser Arg Asp Asn Ser Lys Asn Thr
65 70 75 80

Val Tyr Leu Gln Met Asn Ser Leu Arg Ala Glu Asp Thr Ala Thr Tyr
85 90 95

Tyr Cys Ala Tyr Phe Gln His Arg Glu Pro Phe Leu Tyr Trp Gly Gln
100 105 110

Gly Thr Gln Val Thr Val Ser Ser Ala
115 120

<210> SEQ ID NO 351
<211> LENGTH: 124
<212> TYPE: PRT
<213> ORGANISM: Artificial Sequence
<220> FEATURE:
<223> OTHER INFORMATION: Synthetic

<400> SEQUENCE: 351

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Thr Ser Gln Asp Tyr
20 25 30

Arg Met Gly Trp Phe Arg Gln Ala Pro Gly Lys Glu Arg Glu Phe Val
35 40 45

Ser Ala Ile Ser Ala Trp Ser Gly Asp Ser Phe Arg Tyr Tyr Ala Asp
50 55 60

Ser Val Lys Gly Arg Phe Thr Ile Ser Arg Asp Asn Ser Lys Asn Thr
65 70 75 80

Val Tyr Leu Gln Met Asn Ser Leu Arg Ala Glu Asp Thr Ala Thr Tyr
85 90 95

Tyr Cys Ala Ala Phe Gly Pro Ala Gln Asp Gly Lys Gly Arg Trp Tyr
100 105 110

Trp Gly Gln Gly Thr Gln Val Thr Val Ser Ser Ala
115 120

<210> SEQ ID NO 352
<211> LENGTH: 121
<212> TYPE: PRT
<213> ORGANISM: Artificial Sequence
<220> FEATURE:
<223> OTHER INFORMATION: Synthetic

<400> SEQUENCE: 352

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Tyr Asp His Thr
            20                  25                  30

Ala Met Gly Trp Phe Arg Gln Ala Pro Gly Lys Glu Arg Glu Phe Val
        35                  40                  45

Ser Ala Ile Ser Ser Thr Gln Gly Arg Thr Val Arg Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ala Ile Asp Arg Trp Asn Thr Arg Val Tyr Trp Gly Gln
            100                 105                 110

Gly Thr Gln Val Thr Val Ser Ser Ala
        115                 120
```

<210> SEQ ID NO 353
<211> LENGTH: 121
<212> TYPE: PRT
<213> ORGANISM: Artificial Sequence
<220> FEATURE:
<223> OTHER INFORMATION: Synthetic

<400> SEQUENCE: 353

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly His Ala Phe Asp Gln Asp
            20                  25                  30

Arg Met Gly Trp Phe Arg Gln Ala Pro Gly Lys Glu Arg Glu Phe Val
        35                  40                  45

Ser Ala Ile Ser Thr Trp Ala Gly Asp Ser Ala Arg Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala His Leu Pro Leu Val Arg Gly Lys Asn Tyr Trp Gly Gln
            100                 105                 110

Gly Thr Gln Val Thr Val Ser Ser Ala
        115                 120
```

<210> SEQ ID NO 354
<211> LENGTH: 124
<212> TYPE: PRT
<213> ORGANISM: Artificial Sequence
<220> FEATURE:
<223> OTHER INFORMATION: Synthetic

<400> SEQUENCE: 354

```
Glu Val Gln Leu Gln Ala Ser Gly Gly Gly Phe Val Gln Pro Gly Gly
1               5                   10                  15
```

```
Ser Leu Arg Leu Ser Cys Ala Ala Ser Gly Phe Tyr Phe Ser Ala His
            20                  25                  30

Arg Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Leu Tyr Asn Gln Ser Val Arg Pro Trp Phe Thr His Tyr
            100                 105                 110

Trp Gly Gln Gly Thr Gln Val Thr Val Ser Ser Ala
        115                 120
```

<210> SEQ ID NO 355
<211> LENGTH: 121
<212> TYPE: PRT
<213> ORGANISM: Artificial Sequence
<220> FEATURE:
<223> OTHER INFORMATION: Synthetic

<400> SEQUENCE: 355

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Ser Phe His Asp Tyr
            20                  25                  30

Arg Met Gly Trp Phe Arg Gln Ala Pro Gly Lys Glu Arg Glu Phe Val
        35                  40                  45

Ser Ala Ile Ser Asp Arg Gly Gly Thr Thr Thr Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Tyr Phe Gln His Arg Glu Pro Phe Leu Tyr Trp Gly Gln
            100                 105                 110

Gly Thr Gln Val Thr Val Ser Ser Ala
        115                 120
```

<210> SEQ ID NO 356
<211> LENGTH: 127
<212> TYPE: PRT
<213> ORGANISM: Artificial Sequence
<220> FEATURE:
<223> OTHER INFORMATION: Synthetic

<400> SEQUENCE: 356

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Pro Phe Gly Thr Tyr
            20                  25                  30

Arg Met Gly Trp Phe Arg Gln Ala Pro Gly Lys Glu Arg Glu Phe Val
        35                  40                  45

Ser Ala Ile Ser Ser Trp Ser Gly Gly Ser Ala Arg Tyr Tyr Ala Asp
    50                  55                  60

Ser Val Lys Gly Arg Phe Thr Ile Ser Arg Asp Asn Ser Lys Asn Thr
```

```
65                  70                  75                  80

Val Tyr Leu Gln Met Asn Ser Leu Arg Ala Glu Asp Thr Ala Thr Tyr
                85                  90                  95

Tyr Cys Ala Ser Trp Phe Val Asp Gln Ser Asp Ala His Thr Ser Ile
            100                 105                 110

Phe Arg Tyr Trp Gly Gln Gly Thr Gln Val Thr Val Ser Ser Ala
        115                 120                 125


<210> SEQ ID NO 357
<211> LENGTH: 124
<212> TYPE: PRT
<213> ORGANISM: Artificial Sequence
<220> FEATURE:
<223> OTHER INFORMATION: Synthetic

<400> SEQUENCE: 357

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Thr Tyr Ser Glu Arg
            20                  25                  30

Val Met Gly Trp Phe Arg Gln Ala Pro Gly Lys Glu Arg Glu Phe Val
        35                  40                  45

Ser Ala Ile Ser Ser Gly Gln Ser Asp Gln Thr Tyr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Pro Phe Ala Gly Asp Ala Asn Leu Pro Arg Glu Trp Tyr
            100                 105                 110

Trp Gly Gln Gly Thr Gln Val Thr Val Ser Ser Ala
        115                 120


<210> SEQ ID NO 358
<211> LENGTH: 124
<212> TYPE: PRT
<213> ORGANISM: Artificial Sequence
<220> FEATURE:
<223> OTHER INFORMATION: Synthetic

<400> SEQUENCE: 358

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Phe Asp Gln Arg Ser
            20                  25                  30

Arg Met Gly Trp Phe Arg Gln Ala Pro Gly Lys Glu Arg Glu Phe Val
        35                  40                  45

Ser Ala Ile Ser Ala Trp Gly Gly Gly Ser Ala Lys Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ser Trp Ile Leu Asp Ala Asn Thr Phe Leu Gln Glu Tyr
            100                 105                 110

Trp Gly Gln Gly Thr Gln Val Thr Val Ser Ser Ala
        115                 120
```

<210> SEQ ID NO 359
<211> LENGTH: 119
<212> TYPE: PRT
<213> ORGANISM: Artificial Sequence
<220> FEATURE:
<223> OTHER INFORMATION: Synthetic

<400> SEQUENCE: 359

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Thr Ser Gly Gln Tyr
20 25 30

Arg Met Gly Trp Phe Arg Gln Ala Pro Gly Lys Glu Arg Glu Phe Val
35 40 45

Ser Ala Ile Ser Ser Trp Ser Gly Gly Ser Ala Arg Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Ala Trp Lys Ser Asp Ile Ala Glu Trp Tyr Trp Gly Gln Gly
100 105 110

Thr Gln Val Thr Val Ser Ser
115

<210> SEQ ID NO 360
<211> LENGTH: 119
<212> TYPE: PRT
<213> ORGANISM: Artificial Sequence
<220> FEATURE:
<223> OTHER INFORMATION: Synthetic

<400> SEQUENCE: 360

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Thr Phe Arg Ala Tyr
20 25 30

Thr Met Gly Trp Phe Arg Gln Ala Pro Gly Lys Glu Arg Glu Phe Val
35 40 45

Ser Ala Ile Ser Gly Gly Thr Gly Glu Ala Thr Tyr Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Ala Tyr Thr Thr Thr Thr Val Pro Gln Tyr Trp Gly Gln Gly
100 105 110

Thr Gln Val Thr Val Ser Ser
115

<210> SEQ ID NO 361
<211> LENGTH: 119
<212> TYPE: PRT
<213> ORGANISM: Artificial Sequence
<220> FEATURE:
<223> OTHER INFORMATION: Synthetic

<400> SEQUENCE: 361

Glu Val Gln Leu Gln Ala Ser Gly Gly Gly Phe Val Gln Pro Gly Gly

```
1               5                   10                  15

Ser Leu Arg Leu Ser Cys Ala Ala Ser Gly Arg Thr Phe Thr Ser Phe
            20                  25                  30

His Met Gly Trp Phe Arg Gln Ala Pro Gly Lys Glu Arg Glu Phe Val
        35                  40                  45

Ser Ala Ile Ser Ser Gly Asp Asp Gly Thr Gln Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Tyr Thr Thr Thr Thr Val Pro Gln Tyr Trp Gly Gln Gly
            100                 105                 110

Thr Gln Val Thr Val Ser Ser
        115


<210> SEQ ID NO 362
<211> LENGTH: 119
<212> TYPE: PRT
<213> ORGANISM: Artificial Sequence
<220> FEATURE:
<223> OTHER INFORMATION: Synthetic

<400> SEQUENCE: 362

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Ser Phe Gly Ala Tyr
            20                  25                  30

Ile Met Gly Trp Phe Arg Gln Ala Pro Gly Lys Glu Arg Glu Phe Val
        35                  40                  45

Ser Ala Ile Ser Thr Thr Thr Asp Ala Glu Tyr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Tyr Thr Thr Thr Thr Val Pro Tyr Tyr Trp Gly Gln Gly
            100                 105                 110

Thr Gln Val Thr Val Ser Ser
        115


<210> SEQ ID NO 363
<211> LENGTH: 122
<212> TYPE: PRT
<213> ORGANISM: Artificial Sequence
<220> FEATURE:
<223> OTHER INFORMATION: Synthetic

<400> SEQUENCE: 363

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Tyr Phe Asp Arg Arg
            20                  25                  30

Trp Met Gly Trp Phe Arg Gln Ala Pro Gly Lys Glu Arg Glu Phe Val
        35                  40                  45

Ser Ala Ile Ser Ser Ala Tyr Gly Phe Ala Thr Tyr Tyr Ala Asp Ser
    50                  55                  60
```

```
Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Glu Ile Glu Ala Trp Gly His Arg Glu Val Arg Pro Tyr Trp
            100                 105                 110

Gly Gln Gly Thr Gln Val Thr Val Ser Ser
        115                 120


<210> SEQ ID NO 364
<211> LENGTH: 122
<212> TYPE: PRT
<213> ORGANISM: Artificial Sequence
<220> FEATURE:
<223> OTHER INFORMATION: Synthetic

<400> SEQUENCE: 364

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Ser Ala Tyr
            20                  25                  30

Ser Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala His Tyr Tyr Thr Thr Ser Ala Thr Leu Asp Tyr Ala Tyr Trp
            100                 105                 110

Gly Gln Gly Thr Gln Val Thr Val Ser Ser
        115                 120


<210> SEQ ID NO 365
<211> LENGTH: 119
<212> TYPE: PRT
<213> ORGANISM: Artificial Sequence
<220> FEATURE:
<223> OTHER INFORMATION: Synthetic

<400> SEQUENCE: 365

Glu Val Gln Leu Gln Ala Ser Gly Gly Gly Phe Val Gln Pro Gly Gly
1               5                   10                  15

Ser Leu Arg Leu Ser Cys Ala Ala Ser Gly Thr Ser Phe Asp Asp Gln
            20                  25                  30

Pro Met Gly Trp Phe Arg Gln Ala Pro Gly Lys Glu Arg Glu Phe Val
        35                  40                  45

Ser Ala Ile Ser Gly Gly Gly Asp Lys Ser Thr Trp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ile Ala Gln Asp Arg Phe Arg Asn Pro Tyr Trp Gly Gln Gly
            100                 105                 110

Thr Gln Val Thr Val Ser Ser
        115
```

<210> SEQ ID NO 366
<211> LENGTH: 119
<212> TYPE: PRT
<213> ORGANISM: Artificial Sequence
<220> FEATURE:
<223> OTHER INFORMATION: Synthetic

<400> SEQUENCE: 366

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Thr Phe Arg Ser Leu
            20                  25                  30

Thr Met Gly Trp Phe Arg Gln Ala Pro Gly Lys Glu Arg Glu Phe Val
        35                  40                  45

Ser Ala Ile Ser Ser Gly Asp Gly Gly Pro Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ile Phe Gln Gln Arg Ala Val Pro Ile Tyr Trp Gly Gln Gly
            100                 105                 110

Thr Gln Val Thr Val Ser Ser
        115
```

<210> SEQ ID NO 367
<211> LENGTH: 119
<212> TYPE: PRT
<213> ORGANISM: Artificial Sequence
<220> FEATURE:
<223> OTHER INFORMATION: Synthetic

<400> SEQUENCE: 367

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Thr Phe Ser His Tyr
            20                  25                  30

Ile Met Gly Trp Phe Arg Gln Ala Pro Gly Lys Glu Arg Glu Phe Val
        35                  40                  45

Ser Ala Ile Ser Ala Gly Gln Gly His Ala Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Lys Tyr Gln Asp Thr Ile Ala Pro Leu Tyr Trp Gly Gln Gly
            100                 105                 110

Thr Gln Val Thr Val Ser Ser
        115
```

<210> SEQ ID NO 368
<211> LENGTH: 122
<212> TYPE: PRT
<213> ORGANISM: Artificial Sequence
<220> FEATURE:
<223> OTHER INFORMATION: Synthetic

<400> SEQUENCE: 368

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Ser Phe Gly Ile Arg
            20                  25                  30

Arg Met Gly Trp Phe Arg Gln Ala Pro Gly Lys Glu Arg Glu Phe Val
        35                  40                  45

Ser Ala Ile Ser Arg Trp Ser Asp Trp Ala Val Trp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Lys Tyr Trp Thr Gly Lys Tyr Asp Arg Gln Trp Trp Tyr Trp
            100                 105                 110

Gly Gln Gly Thr Gln Val Thr Val Ser Ser
        115                 120


<210> SEQ ID NO 369
<211> LENGTH: 119
<212> TYPE: PRT
<213> ORGANISM: Artificial Sequence
<220> FEATURE:
<223> OTHER INFORMATION: Synthetic

<400> SEQUENCE: 369

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Asp Ala Tyr
            20                  25                  30

Ser Met Gly Trp Phe Arg Gln Ala Pro Gly Lys Glu Arg Glu Phe Val
        35                  40                  45

Ser Ala Ile Ser Ser Trp Ser Asp Asp Trp Thr Ala Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Leu Gln Asn Thr Lys Glu Asp Arg Leu Tyr Trp Gly Gln Gly
            100                 105                 110

Thr Gln Val Thr Val Ser Ser
        115


<210> SEQ ID NO 370
<211> LENGTH: 122
<212> TYPE: PRT
<213> ORGANISM: Artificial Sequence
<220> FEATURE:
<223> OTHER INFORMATION: Synthetic

<400> SEQUENCE: 370

Glu Val Gln Leu Gln Ala Ser Gly Gly Gly Phe Val Gln Pro Gly Gly
1               5                   10                  15

Ser Leu Arg Leu Ser Cys Ala Ala Ser Gly His Thr Phe Gly Phe Asn
            20                  25                  30

His Met Gly Trp Phe Arg Gln Ala Pro Gly Lys Glu Arg Glu Phe Val
        35                  40                  45

Ser Ala Ile Ser Pro Gly Asp Cys Ala Ala Ser Tyr Tyr Ala Asp Ser
    50                  55                  60
```

```
Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Leu Trp Ala Cys Ser Asp Asp Pro Leu Asp Ser Tyr Tyr Trp
            100                 105                 110

Gly Gln Gly Thr Gln Val Thr Val Ser Ser
        115                 120


<210> SEQ ID NO 371
<211> LENGTH: 119
<212> TYPE: PRT
<213> ORGANISM: Artificial Sequence
<220> FEATURE:
<223> OTHER INFORMATION: Synthetic

<400> SEQUENCE: 371

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Ser Gly Tyr
            20                  25                  30

Ile Met Gly Trp Phe Arg Gln Ala Pro Gly Lys Glu Arg Glu Phe Val
        35                  40                  45

Ser Ala Ile Ser Gln Gly Asp Ser Tyr Ala Ser Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Leu Tyr Asp Ile Asn Thr Val Pro Tyr Tyr Trp Gly Gln Gly
            100                 105                 110

Thr Gln Val Thr Val Ser Ser
        115


<210> SEQ ID NO 372
<211> LENGTH: 119
<212> TYPE: PRT
<213> ORGANISM: Artificial Sequence
<220> FEATURE:
<223> OTHER INFORMATION: Synthetic

<400> SEQUENCE: 372

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Ala Phe Ser Asp Tyr
            20                  25                  30

Gly Met Gly Trp Phe Arg Gln Ala Pro Gly Lys Glu Arg Glu Phe Val
        35                  40                  45

Ser Ala Ile Ser Thr Ala Gly Ser Trp Tyr Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Asn Lys Glu Thr Trp Asn Thr His Trp Tyr Trp Gly Gln Gly
            100                 105                 110

Thr Gln Val Thr Val Ser Ser
```

115

<210> SEQ ID NO 373
<211> LENGTH: 122
<212> TYPE: PRT
<213> ORGANISM: Artificial Sequence
<220> FEATURE:
<223> OTHER INFORMATION: Synthetic

<400> SEQUENCE: 373

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Phe Phe Thr Asp Arg
20 25 30

Thr Met Gly Trp Phe Arg Gln Ala Pro Gly Lys Glu Arg Glu Phe Val
35 40 45

Ser Ala Ile Ser Asp Arg Ser Gly Lys His Thr Tyr Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Pro Phe Ala Gly Asp Ala Asn Leu Pro Arg Glu Trp Tyr Trp
100 105 110

Gly Gln Gly Thr Gln Val Thr Val Ser Ser
115 120

<210> SEQ ID NO 374
<211> LENGTH: 122
<212> TYPE: PRT
<213> ORGANISM: Artificial Sequence
<220> FEATURE:
<223> OTHER INFORMATION: Synthetic

<400> SEQUENCE: 374

Glu Val Gln Leu Gln Ala Ser Gly Gly Gly Phe Val Gln Pro Gly Gly
1 5 10 15

Ser Leu Arg Leu Ser Cys Ala Ala Ser Gly His Tyr Phe Gly Glu Tyr
20 25 30

Arg Met Gly Trp Phe Arg Gln Ala Pro Gly Lys Glu Arg Glu Phe Val
35 40 45

Ser Ala Ile Ser Ser Trp Ser Gly Gly Ser Ala Arg Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Pro Leu Val Gly Pro Glu Asp Ser Gly Leu Ile Arg Tyr Trp
100 105 110

Gly Gln Gly Thr Gln Val Thr Val Ser Ser
115 120

<210> SEQ ID NO 375
<211> LENGTH: 119
<212> TYPE: PRT
<213> ORGANISM: Artificial Sequence
<220> FEATURE:
<223> OTHER INFORMATION: Synthetic

<400> SEQUENCE: 375

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Met Phe Thr Asp Val
            20                  25                  30

Ala Met Gly Trp Phe Arg Gln Ala Pro Gly Lys Glu Arg Glu Phe Val
        35                  40                  45

Ser Ala Ile Ser Ser Trp Ala Gly Gly Arg Ser Leu Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Tyr Phe Glu Val Asp Asp Asn Pro Tyr Trp Gly Gln Gly
            100                 105                 110

Thr Gln Val Thr Val Ser Ser
        115

<210> SEQ ID NO 376
<211> LENGTH: 122
<212> TYPE: PRT
<213> ORGANISM: Artificial Sequence
<220> FEATURE:
<223> OTHER INFORMATION: Synthetic

<400> SEQUENCE: 376

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Tyr Asp Asp Phe Gln
            20                  25                  30

Val Met Gly Trp Phe Arg Gln Ala Pro Gly Lys Glu Arg Glu Phe Val
        35                  40                  45

Ser Ala Ile Ser Asp Gly Tyr Gln Glu Ser Thr Ala Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Tyr Phe Gly Glu Ala Asp Glu His Ile Lys Ser Tyr Trp
            100                 105                 110

Gly Gln Gly Thr Gln Val Thr Val Ser Ser
        115                 120

<210> SEQ ID NO 377
<211> LENGTH: 122
<212> TYPE: PRT
<213> ORGANISM: Artificial Sequence
<220> FEATURE:
<223> OTHER INFORMATION: Synthetic

<400> SEQUENCE: 377

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Thr Tyr Asp Gln Tyr
            20                  25                  30

Val Met Gly Trp Phe Arg Gln Ala Pro Gly Lys Glu Arg Glu Phe Val
        35                  40                  45

Ser Ala Ile Ser Asp Arg Gly Gly Thr Thr Thr Asp Tyr Ala Asp Ser

```
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Pro Tyr Phe Gly Glu Ala Asp Pro Tyr Pro Asp Ala Tyr Trp
            100                 105                 110

Gly Gln Gly Thr Gln Val Thr Val Ser Ser
        115                 120


<210> SEQ ID NO 378
<211> LENGTH: 122
<212> TYPE: PRT
<213> ORGANISM: Artificial Sequence
<220> FEATURE:
<223> OTHER INFORMATION: Synthetic

<400> SEQUENCE: 378

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Ala Phe Gln Ser Tyr
            20                  25                  30

Arg Met Gly Trp Phe Arg Gln Ala Pro Gly Lys Glu Arg Glu Phe Val
        35                  40                  45

Ser Ala Ile Ser Ala Gly Asp Gly Ala Ala Ser Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Gln Phe His Gln Ser Pro Ile Asp Lys Gly Leu Arg Tyr Trp
            100                 105                 110

Gly Gln Gly Thr Gln Val Thr Val Ser Ser
        115                 120


<210> SEQ ID NO 379
<211> LENGTH: 119
<212> TYPE: PRT
<213> ORGANISM: Artificial Sequence
<220> FEATURE:
<223> OTHER INFORMATION: Synthetic

<400> SEQUENCE: 379

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Asp Thr Gly Tyr
            20                  25                  30

Val Met Gly Trp Phe Arg Gln Ala Pro Gly Lys Glu Arg Glu Phe Val
        35                  40                  45

Ser Ala Ile Ser Gly Gln Ser Gly His Thr Thr Leu Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Gln Gly Asp Trp Gly Arg His Pro Thr Tyr Trp Gly Gln Gly
            100                 105                 110
```

Thr Gln Val Thr Val Ser Ser
115

<210> SEQ ID NO 380
<211> LENGTH: 119
<212> TYPE: PRT
<213> ORGANISM: Artificial Sequence
<220> FEATURE:
<223> OTHER INFORMATION: Synthetic

<400> SEQUENCE: 380

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Thr Ala Asp His His
20 25 30

Val Met Gly Trp Phe Arg Gln Ala Pro Gly Lys Glu Arg Glu Phe Val
35 40 45

Ser Ala Ile Ser Ala Gln Ala Gly Gly Ser Ser Ala Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Gln Gly Asp Trp Gly Arg His Pro Thr Tyr Trp Gly Gln Gly
100 105 110

Thr Gln Val Thr Val Ser Ser
115

<210> SEQ ID NO 381
<211> LENGTH: 119
<212> TYPE: PRT
<213> ORGANISM: Artificial Sequence
<220> FEATURE:
<223> OTHER INFORMATION: Synthetic

<400> SEQUENCE: 381

Glu Val Gln Leu Gln Ala Ser Gly Gly Gly Phe Val Gln Pro Gly Gly
1 5 10 15

Ser Leu Arg Leu Ser Cys Ala Ala Ser Gly His Thr Phe Asp Ala His
20 25 30

Arg Met Gly Trp Phe Arg Gln Ala Pro Gly Lys Glu Arg Glu Phe Val
35 40 45

Ser Ala Ile Ser Ser Trp Gly Gln Ser Ser Thr Tyr Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Gln Thr Asp Glu Gly Asn Gln Tyr Val Tyr Trp Gly Gln Gly
100 105 110

Thr Gln Val Thr Val Ser Ser
115

<210> SEQ ID NO 382
<211> LENGTH: 119
<212> TYPE: PRT
<213> ORGANISM: Artificial Sequence
<220> FEATURE:
<223> OTHER INFORMATION: Synthetic

<400> SEQUENCE: 382

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Ala Phe Arg Ile Tyr
20 25 30

Thr Met Gly Trp Phe Arg Gln Ala Pro Gly Lys Glu Arg Glu Phe Val
35 40 45

Ser Ala Ile Ser Ala Gly Asp Gly Ala Ala Ser Tyr Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Gln Tyr Trp Gln Ser Ile Asn Pro Ile Tyr Trp Gly Gln Gly
100 105 110

Thr Gln Val Thr Val Ser Ser
115

<210> SEQ ID NO 383
<211> LENGTH: 125
<212> TYPE: PRT
<213> ORGANISM: Artificial Sequence
<220> FEATURE:
<223> OTHER INFORMATION: Synthetic

<400> SEQUENCE: 383

Glu Val Gln Leu Gln Ala Ser Gly Gly Gly Phe Val Gln Pro Gly Gly
1 5 10 15

Ser Leu Arg Leu Ser Cys Ala Ala Ser Gly Thr Thr Phe Ser Asp His
20 25 30

Thr Met Gly Trp Phe Arg Gln Ala Pro Gly Lys Glu Arg Glu Phe Val
35 40 45

Ser Ala Ile Ser Gln Ser Asp Gly Trp Asp Thr Tyr Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Thr Phe Asn His Ser Leu Ala Ser Lys Leu Phe Asn Asp Ile
100 105 110

Lys Tyr Trp Gly Gln Gly Thr Gln Val Thr Val Ser Ser
115 120 125

<210> SEQ ID NO 384
<211> LENGTH: 125
<212> TYPE: PRT
<213> ORGANISM: Artificial Sequence
<220> FEATURE:
<223> OTHER INFORMATION: Synthetic

<400> SEQUENCE: 384

Glu Val Gln Leu Gln Ala Ser Gly Gly Gly Phe Val Gln Pro Gly Gly
1 5 10 15

Ser Leu Arg Leu Ser Cys Ala Ala Ser Gly Arg Thr Phe Asp Ala Tyr
20 25 30

Ser Met Gly Trp Phe Arg Gln Ala Pro Gly Lys Glu Arg Glu Phe Val
35 40 45

```
Ser Ala Ile Ser Thr Gln Ser Gly Tyr Ser Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Thr Phe Asn His Ser Leu Ala Ser Lys Leu Phe Asn Asp Ile
            100                 105                 110

Lys Tyr Trp Gly Gln Gly Thr Gln Val Thr Val Ser Ser
        115                 120                 125


<210> SEQ ID NO 385
<211> LENGTH: 119
<212> TYPE: PRT
<213> ORGANISM: Artificial Sequence
<220> FEATURE:
<223> OTHER INFORMATION: Synthetic

<400> SEQUENCE: 385

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Pro Ser Asp Arg Tyr
            20                  25                  30

Ile Met Gly Trp Phe Arg Gln Ala Pro Gly Lys Glu Arg Glu Phe Val
        35                  40                  45

Ser Ala Ile Ser Gln Gly Ala Ala Asn Lys Thr Ala Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Thr His Phe Asn Trp Gln Asn Tyr Ser Tyr Trp Gly Gln Gly
            100                 105                 110

Thr Gln Val Thr Val Ser Ser
        115


<210> SEQ ID NO 386
<211> LENGTH: 122
<212> TYPE: PRT
<213> ORGANISM: Artificial Sequence
<220> FEATURE:
<223> OTHER INFORMATION: Synthetic

<400> SEQUENCE: 386

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Phe Phe Ser Trp Tyr
            20                  25                  30

Ala Met Gly Trp Phe Arg Gln Ala Pro Gly Lys Glu Arg Glu Phe Val
        35                  40                  45

Ser Ala Ile Ser Gly Ala Ser Gly Phe Gln Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Thr Ser Gly Lys Ala Ala Leu Pro Phe Val Ser Lys Tyr Trp
            100                 105                 110
```

```
Gly Gln Gly Thr Gln Val Thr Val Ser Ser
        115                 120


<210> SEQ ID NO 387
<211> LENGTH: 122
<212> TYPE: PRT
<213> ORGANISM: Artificial Sequence
<220> FEATURE:
<223> OTHER INFORMATION: Synthetic

<400> SEQUENCE: 387

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Thr Phe Asp Trp Ser
            20                  25                  30

Ala Met Gly Trp Phe Arg Gln Ala Pro Gly Lys Glu Arg Glu Phe Val
        35                  40                  45

Ser Ala Ile Ser Ser Ser Thr Ser Glu Ser Thr Thr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Thr Tyr Tyr Gly Gly Lys Thr Val Glu Gln Asp Phe Tyr Trp
            100                 105                 110

Gly Gln Gly Thr Gln Val Thr Val Ser Ser
        115                 120


<210> SEQ ID NO 388
<211> LENGTH: 125
<212> TYPE: PRT
<213> ORGANISM: Artificial Sequence
<220> FEATURE:
<223> OTHER INFORMATION: Synthetic

<400> SEQUENCE: 388

Glu Val Gln Leu Gln Ala Ser Gly Gly Gly Phe Val Gln Pro Gly Gly
1               5                   10                  15

Ser Leu Arg Leu Ser Cys Ala Ala Ser Gly Phe Pro Phe Ser Ser His
            20                  25                  30

Trp Met Gly Trp Phe Arg Gln Ala Pro Gly Lys Glu Arg Glu Phe Val
        35                  40                  45

Ser Ala Ile Ser Asp Trp Arg Asp His Lys Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Val Ala Phe Gly Ile His Trp Phe Ala Pro His Ser Asp His
            100                 105                 110

Ile Tyr Trp Gly Gln Gly Thr Gln Val Thr Val Ser Ser
        115                 120                 125


<210> SEQ ID NO 389
<211> LENGTH: 125
<212> TYPE: PRT
<213> ORGANISM: Artificial Sequence
<220> FEATURE:
<223> OTHER INFORMATION: Synthetic
```

<400> SEQUENCE: 389

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Ala Phe Gln Ile Tyr
            20                  25                  30

Ala Met Gly Trp Phe Arg Gln Ala Pro Gly Lys Glu Arg Glu Phe Val
        35                  40                  45

Ser Ala Ile Ser Ser Thr Asp Ser Glu Thr Asp His Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Val Asn Gly Phe Asp Tyr Ala His Ser Lys Ala Gly Pro Gln
            100                 105                 110

Val Tyr Trp Gly Gln Gly Thr Gln Val Thr Val Ser Ser
        115                 120                 125

<210> SEQ ID NO 390
<211> LENGTH: 118
<212> TYPE: PRT
<213> ORGANISM: Artificial Sequence
<220> FEATURE:
<223> OTHER INFORMATION: Synthetic

<400> SEQUENCE: 390

Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Ile Phe Thr His Val
            20                  25                  30

Pro Met Gly Trp Phe Arg Gln Ala Pro Gly Lys Glu Arg Glu Phe Val
        35                  40                  45

Ser Ala Ile Ser His Ala Asn Gly Gly Ser Gln Thr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Trp Ala Tyr Asp His Phe Asn Asn Tyr Trp Gly Gln Gly Thr
            100                 105                 110

Gln Val Thr Val Ser Ser
        115

<210> SEQ ID NO 391
<211> LENGTH: 119
<212> TYPE: PRT
<213> ORGANISM: Artificial Sequence
<220> FEATURE:
<223> OTHER INFORMATION: Synthetic

<400> SEQUENCE: 391

Glu Val Gln Leu Gln Ala Ser Gly Gly Gly Phe Val Gln Pro Gly Gly
1               5                   10                  15

Ser Leu Arg Leu Ser Cys Ala Ala Ser Gly His Thr Phe Thr His Tyr
            20                  25                  30

Arg Met Gly Trp Phe Arg Gln Ala Pro Gly Lys Glu Arg Glu Phe Val
        35                  40                  45

```
Ser Ala Ile Ser Gly Ala Gly Gly Thr Ser Phe Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Trp Ala Tyr Asp Gln Phe Asn Trp Asn Tyr Trp Gly Gln Gly
            100                 105                 110

Thr Gln Val Thr Val Ser Ser
        115


<210> SEQ ID NO 392
<211> LENGTH: 119
<212> TYPE: PRT
<213> ORGANISM: Artificial Sequence
<220> FEATURE:
<223> OTHER INFORMATION: Synthetic

<400> SEQUENCE: 392

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gln Thr Phe Thr His Val
            20                  25                  30

Pro Met Gly Trp Phe Arg Gln Ala Pro Gly Lys Glu Arg Glu Phe Val
        35                  40                  45

Ser Ala Ile Ser Asp Thr Ser Gly Phe Glu Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Trp Ala Tyr Asp Gln Phe Asn Trp Asn Tyr Trp Gly Gln Gly
            100                 105                 110

Thr Gln Val Thr Val Ser Ser
        115


<210> SEQ ID NO 393
<211> LENGTH: 119
<212> TYPE: PRT
<213> ORGANISM: Artificial Sequence
<220> FEATURE:
<223> OTHER INFORMATION: Synthetic

<400> SEQUENCE: 393

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Lys Glu Arg Glu Phe Val
        35                  40                  45

Ser Ala Ile Ser Ser Trp Ser Asp Asp Trp Thr Ala Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Trp Gln Tyr Ile Asp Glu Ile Gln Tyr Tyr Trp Gly Gln Gly
```

100 105 110

Thr Gln Val Thr Val Ser Ser
115

<210> SEQ ID NO 394
<211> LENGTH: 122
<212> TYPE: PRT
<213> ORGANISM: Artificial Sequence
<220> FEATURE:
<223> OTHER INFORMATION: Synthetic

<400> SEQUENCE: 394

Glu Val Gln Leu Gln Ala Ser Gly Gly Gly Phe Val Gln Pro Gly Gly
1 5 10 15

Ser Leu Arg Leu Ser Cys Ala Ala Ser Gly Ser Thr Ala Ser His Tyr
20 25 30

Thr Met Gly Trp Phe Arg Gln Ala Pro Gly Lys Glu Arg Glu Phe Val
35 40 45

Ser Ala Ile Ser Ser Gly Arg Asp His Ala Lys Gln Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Tyr Glu Glu Ile Asn Ala Thr Gln Lys Asp Thr Leu Tyr Trp
100 105 110

Gly Gln Gly Thr Gln Val Thr Val Ser Ser
115 120

<210> SEQ ID NO 395
<211> LENGTH: 121
<212> TYPE: PRT
<213> ORGANISM: Artificial Sequence
<220> FEATURE:
<223> OTHER INFORMATION: Synthetic

<400> SEQUENCE: 395

Glu Val Gln Leu Gln Ala Ser Gly Gly Gly Phe Val Gln Pro Gly Gly
1 5 10 15

Ser Leu Arg Leu Ser Cys Ala Ala Ser Gly Phe Thr Ala Gln Glu Tyr
20 25 30

Ser Met Gly Trp Phe Arg Gln Ala Pro Gly Lys Glu Arg Glu Phe Val
35 40 45

Ser Ala Ile Ser Thr Phe Ala Gly His Asp Lys Gln Tyr Ala Asp Ser
50 55 60

Val Lys Gly Arg Phe Thr Ile Ser Arg Asp Asn Ser Lys Asn Thr Val
65 70 75 80

Tyr Leu Gln Met Asn Ser Leu Arg Ala Glu Asp Thr Ala Thr Tyr Tyr
85 90 95

Cys Ala Tyr Glu Ile Asn Ala Asp Pro His Gly Ser Ile Tyr Trp Gly
100 105 110

Gln Gly Thr Gln Val Thr Val Ser Ser
115 120

<210> SEQ ID NO 396
<211> LENGTH: 119
<212> TYPE: PRT
<213> ORGANISM: Artificial Sequence
<220> FEATURE:

<223> OTHER INFORMATION: Synthetic

<400> SEQUENCE: 396

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly His Thr Phe Ser Phe Trp
            20                  25                  30

Arg Met Gly Trp Phe Arg Gln Ala Pro Gly Lys Glu Arg Glu Phe Val
        35                  40                  45

Ser Ala Ile Ser Ser Gly Tyr Gly Gly Ser Ser Lys Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Tyr Leu Ser Gln Glu Arg Thr Pro Val Tyr Trp Gly Gln Gly
            100                 105                 110

Thr Gln Val Thr Val Ser Ser
        115
```

<210> SEQ ID NO 397
<211> LENGTH: 119
<212> TYPE: PRT
<213> ORGANISM: Artificial Sequence
<220> FEATURE:
<223> OTHER INFORMATION: Synthetic

<400> SEQUENCE: 397

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Phe Gln Asp Phe
            20                  25                  30

Ala Met Gly Trp Phe Arg Gln Ala Pro Gly Lys Glu Arg Glu Phe Val
        35                  40                  45

Ser Ala Ile Ser Arg Phe Thr Gly Trp Ser Thr Asp Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Tyr Gln Thr His Asn Asn Glu Trp Val Tyr Trp Gly Gln Gly
            100                 105                 110

Thr Gln Val Thr Val Ser Ser
        115
```

<210> SEQ ID NO 398
<211> LENGTH: 125
<212> TYPE: PRT
<213> ORGANISM: Artificial Sequence
<220> FEATURE:
<223> OTHER INFORMATION: Synthetic

<400> SEQUENCE: 398

```
Glu Val Gln Leu Gln Ala Ser Gly Gly Gly Phe Val Gln Pro Gly Gly
1               5                   10                  15

Ser Leu Arg Leu Ser Cys Ala Ala Ser Gly Ser Tyr Phe Arg Trp Tyr
            20                  25                  30

Tyr Met Gly Trp Phe Arg Gln Ala Pro Gly Lys Glu Arg Glu Phe Val
```

-continued

```
        35                  40                  45

Ser Ala Ile Ser Ser Gly Arg Ala Glu Arg Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Tyr Trp Asn Pro Val Ala Tyr Arg Phe Arg Phe Pro Thr Pro
            100                 105                 110

Thr Tyr Trp Gly Gln Gly Thr Gln Val Thr Val Ser Ser
        115                 120                 125


<210> SEQ ID NO 399

<400> SEQUENCE: 399

000


<210> SEQ ID NO 400
<211> LENGTH: 353
<212> TYPE: PRT
<213> ORGANISM: Artificial Sequence
<220> FEATURE:
<223> OTHER INFORMATION: Synthetic

<400> SEQUENCE: 400

Glu Val Gln Leu Gln Ala Ser Gly Gly Gly Phe Val Gln Pro Gly Gly
1               5                   10                  15

Ser Leu Arg Leu Ser Cys Ala Ala Ser Gly Gly Thr Ser Gly Glu Tyr
            20                  25                  30

Asp Met Gly Trp Phe Arg Gln Ala Pro Gly Lys Glu Arg Glu Phe Val
        35                  40                  45

Ser Ala Ile Ser His Trp Asp Gly Lys Ala Thr Ala Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Thr Tyr
                85                  90                  95

Tyr Cys Ala Ala Arg Leu Asp Asp Glu Ile Asp Phe Tyr Trp Gly Gln
            100                 105                 110

Gly Thr Gln Val Thr Val Ser Ser Ala Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240
```

Thr Ile Ser Lys Ala Lys Gly Gln Pro Arg Glu Pro Gln Val Tyr Thr
245 250 255

Leu Pro Pro Ser Arg Asp Glu Leu Thr Lys Asn Gln Val Ser Leu Thr
260 265 270

Cys Leu Val Lys Gly Phe Tyr Pro Ser Asp Ile Ala Val Glu Trp Glu
275 280 285

Ser Asn Gly Gln Pro Glu Asn Asn Tyr Lys Thr Thr Pro Pro Val Leu
290 295 300

Asp Ser Asp Gly Ser Phe Phe Leu Tyr Ser Lys Leu Thr Val Asp Lys
305 310 315 320

Ser Arg Trp Gln Gln Gly Asn Val Phe Ser Cys Ser Val Met His Glu
325 330 335

Ala Leu His Asn His Tyr Thr Gln Lys Ser Leu Ser Leu Ser Pro Gly
340 345 350

Lys

<210> SEQ ID NO 401
<211> LENGTH: 10
<212> TYPE: PRT
<213> ORGANISM: Artificial Sequence
<220> FEATURE:
<223> OTHER INFORMATION: Synthetic

<400> SEQUENCE: 401

Glu Pro Lys Ser Cys Asp Lys Thr His Thr
1 5 10

<210> SEQ ID NO 402
<211> LENGTH: 4
<212> TYPE: PRT
<213> ORGANISM: Artificial Sequence
<220> FEATURE:
<223> OTHER INFORMATION: Synthetic

<400> SEQUENCE: 402

Cys Pro Pro Cys
1

<210> SEQ ID NO 403
<211> LENGTH: 9
<212> TYPE: PRT
<213> ORGANISM: Artificial Sequence
<220> FEATURE:
<223> OTHER INFORMATION: Synthetic

<400> SEQUENCE: 403

Pro Ala Pro Glu Leu Leu Gly Gly Pro
1 5

<210> SEQ ID NO 404
<211> LENGTH: 209
<212> TYPE: PRT
<213> ORGANISM: Artificial Sequence
<220> FEATURE:
<223> OTHER INFORMATION: Synthetic

<400> SEQUENCE: 404

Ser Val Phe Leu Phe Pro Pro Lys Pro Lys Asp Thr Leu Met Ile Ser
1 5 10 15

Arg Thr Pro Glu Val Thr Cys Val Val Val Asp Val Ser His Glu Asp
20 25 30

Pro Glu Val Lys Phe Asn Trp Tyr Val Asp Gly Val Glu Val His Asn

```
        35                  40                  45

Ala Lys Thr Lys Pro Arg Glu Glu Gln Tyr Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Arg Asp Glu Leu Thr Lys Asn Gln Val Ser Leu Thr
        115                 120                 125

Cys Leu Val Lys Gly Phe Tyr Pro Ser Asp Ile Ala Val Glu Trp Glu
    130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Lys Leu Thr Val Asp Lys
                165                 170                 175

Ser Arg Trp Gln Gln Gly Asn Val Phe Ser Cys Ser Val Met His Glu
            180                 185                 190

Ala Leu His Asn His Tyr Thr Gln Lys Ser Leu Ser Leu Ser Pro Gly
        195                 200                 205

Lys


<210> SEQ ID NO 405
<211> LENGTH: 26
<212> TYPE: PRT
<213> ORGANISM: Artificial Sequence
<220> FEATURE:
<223> OTHER INFORMATION: Synthetic

<400> SEQUENCE: 405

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25


<210> SEQ ID NO 406
<211> LENGTH: 19
<212> TYPE: PRT
<213> ORGANISM: Artificial Sequence
<220> FEATURE:
<223> OTHER INFORMATION: Synthetic

<400> SEQUENCE: 406

Met Gly Trp Phe Arg Gln Ala Pro Gly Lys Glu Arg Glu Phe Val Ser
1               5                   10                  15

Ala Ile Ser


<210> SEQ ID NO 407
<211> LENGTH: 38
<212> TYPE: PRT
<213> ORGANISM: Artificial Sequence
<220> FEATURE:
<223> OTHER INFORMATION: Synthetic

<400> SEQUENCE: 407

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Ala Glu Asp Thr
```

-continued

```
          20                  25                  30

Ala Thr Tyr Tyr Cys Ala
        35


<210> SEQ ID NO 408
<211> LENGTH: 12
<212> TYPE: PRT
<213> ORGANISM: Artificial Sequence
<220> FEATURE:
<223> OTHER INFORMATION: Synthetic

<400> SEQUENCE: 408

Tyr Trp Gly Gln Gly Thr Gln Val Thr Val Ser Ser
1               5                   10
```